US012116577B2

(12) United States Patent
Venditti et al.

(10) Patent No.: US 12,116,577 B2
(45) Date of Patent: Oct. 15, 2024

(54) CODON-OPTIMIZED HUMAN NPC1 GENES FOR THE TREATMENT OF NIEMANN-PICK TYPE C1 DEFICIENCY AND RELATED CONDITIONS

(71) Applicant: The United State of America, as represented by the Secretary, Department of Health and Human Services, Bethesda, MD (US)

(72) Inventors: Charles P. Venditti, Potomac, MD (US); William J. Pavan, Derwood, MD (US); Randy J. Chandler, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 361 days.

(21) Appl. No.: 16/623,863

(22) PCT Filed: Jun. 20, 2018

(86) PCT No.: PCT/US2018/038584

§ 371 (c)(1),
(2) Date: Dec. 18, 2019

(87) PCT Pub. No.: WO2018/237066

PCT Pub. Date: Dec. 27, 2018

(65) Prior Publication Data

US 2020/0377906 A1 Dec. 3, 2020

Related U.S. Application Data

(60) Provisional application No. 62/522,677, filed on Jun. 20, 2017.

(51) Int. Cl.

| | |
|---|---|
| ***C12N 15/67*** | (2006.01) |
| ***C12N 15/52*** | (2006.01) |
| ***C12N 15/62*** | (2006.01) |
| ***C12N 15/86*** | (2006.01) |

(52) U.S. Cl.

CPC ............. *C12N 15/67* (2013.01); *C12N 15/52* (2013.01); *C12N 15/62* (2013.01); *C12N 15/86* (2013.01); *C07K 2319/10* (2013.01); *C12N 2710/10243* (2013.01); *C12N 2799/022* (2013.01)

(58) Field of Classification Search

CPC ........ C12N 15/67; C12N 15/52; C12N 15/62; C07K 2319/10

See application file for complete search history.

(56) References Cited

U.S. PATENT DOCUMENTS

| | | | | |
|---|---|---|---|---|
| 6,426,198 | B1 * | 7/2002 | Carstea | C07K 14/47 435/325 |
| 9,719,080 | B2 * | 8/2017 | Venditti | A61K 38/52 |
| 9,983,200 | B2 | 5/2018 | Pavan et al. | |
| 2004/0071659 | A1 * | 4/2004 | Chang | C12Y 304/21007 435/235.1 |
| 2012/0232133 | A1 * | 9/2012 | Balazs | C07K 16/1045 536/23.53 |
| 2015/0050302 | A1 * | 2/2015 | Thess | C12N 15/85 424/185.1 |
| 2017/0067042 | A1 | 3/2017 | Venditti et al. | |
| 2018/0104289 | A1 * | 4/2018 | Venditti | A61K 48/005 |

FOREIGN PATENT DOCUMENTS

| | | | |
|---|---|---|---|
| WO | WO 99/01555 | A1 | 1/1999 |
| WO | WO 2007/092563 | A2 | 8/2007 |
| WO | WO 2008/154198 | A1 | 12/2008 |
| WO | WO 2012/103081 | A1 * | 8/2012 |
| WO | WO 2014/153083 | A1 | 9/2014 |
| WO | WO 2016/164642 | A1 | 10/2016 |

OTHER PUBLICATIONS

Daniel, E., et al., 2015, ATGme: Open-source web application for rare codon identification and custom DNA sequence optimization, BMV Bionformatics 16:303, pp. 1-6.*

Chandler, R. J., et al., 2017, Systemic AAV9 gene therapy improves the lifespan of mice with Niemann-Pick disease, type C1, Hum. Mol. Genetics 26(1):52-64, published online Oct. 25, 2016.*

Daniel, E., et al., 2015, ATGme: Open-source web application for rare codon identification and custom DNA sequence optimization, BMC Bioinformatics 16:303, pp. 1-6.*

Veldhoen, S., et al., 2008, Recent developments in peptide-based nucleic acid delivery, Int. J. Mol. Sci. 9:1276-1320.*

Kauffman, W. B., et al., Dec. 2015, Feature Review: Mechanism Matters: A Taxonomy of Cell Penetrating Peptides, Trends Biochem. Sci. 40(12):749-764.*

Foust, K. D., et al., Jan. 2009, Intravascular AAV9 preferentially targets neonatal neurons and adult astrocytes, Nat. Biotech. 27(1):59-65.*

Mauro et al., "A Critical Analysis of Codon Optimization in Human Therapeutics," *Trends Mol Med.* 20(11): 604-613 (Nov. 2014); author manuscript as published in PubMed.

"AAV Vector Biology," Abstracts, $20^{th}$ Annual Meeting of the American Society of Gene an Cell Therapy, *Molecular Therapy*, 25 (5S1): 1-363 (2017).

Carstea et al., "Niemann-Pick C1 Disease Gene: Homology to Mediators of Cholesterol Homeostasis," *Science*, 227(5323): 228-231 (1997).

(Continued)

*Primary Examiner* — Jeffrey S Parkin

(74) *Attorney, Agent, or Firm* — Leydig, Voit & Mayer, Ltd.

(57) ABSTRACT

The present disclosure provides compositions for viral gene therapy, e.g. Adeno-Associated virus-directed gene therapy, and methods of using the same for the treatment and/or prevention of cholesterol storage diseases or disorders, such as Niemann-Pick disease, Type C.

11 Claims, 33 Drawing Sheets

Specification includes a Sequence Listing.

(56) References Cited

OTHER PUBLICATIONS

Chandler et al., "Systemic AAV9 gene therapy improves the lifespan of mice with Niemann-Pick disease, type C1," HMG Advance Access Oxford Journals, Oxford University Press, 1-31 (2016).
Chandler et al., "Systemic AAV9 gene therapy improves the lifespan of mice with Niemann-Pick disease, type C1," *Human Molecular Genetics*, 26(1): 52-64 (2017).
Chauhan et al., "The Taming of the Cell Penetrating Domain of the HIV Tat: Myths and Realities," *J. Control Release*, 117(2): 148-162 (2007).
Cruz et al., "A Membrane-Translocating Peptide Penetrates into Bilayers without Significant Bilayer Perturbations," *Biophysical Journal*, 104: 2419-2428 (2013).
European Patent Office, International Search Report in International Patent Application No. PCT/US2018/038584 (Aug. 24, 2018).
European Patent Office, Written Opinion in International Patent Application No. PCT/US2018/038584 (Aug. 24, 2018).
GenBank Accession No. AF258783.1, "Felis catus Niemann-Pick type C1 disease protein (NPC1) mRNA, complete cds" (2000).
GenBank Accession No. BC054539, "Mus musculus Niemann Pick type C1, mRNA (cDNA clone MGC:62352 Image:6405214), complete cds" (2006).
GenBank Accession No. BC063302, "*Homo sapiens* Niemann-Pick disease, type C1, mRNA (cDNA clone MGC:71703 Image:30340517), complete cds" (2006).
GenBank Accession No. BC090541, "Danio rerio Niemann-Pick disease, type C1, mRNA (cDNA clone Image:7149020), partial cds" (2016).
GenBank Accession No. BC117178, "*Homo sapiens* NPC1 (Niemann-Pick disease, type C1, gene)-like 1, mRNA (cDNA clone MGC:150787 Image:40125729), complete cds" (2006).
GenBank Accession No. BC143756, "*Homo sapiens* NPC1 (Niemann-Pick disease, type C1, gene)-like 1, mRNA (cDNA clone MGC:177287 Image:9052270), complete cds" (2009).
GenBank Accession No. BC151276, "Bos taurus Niemann-Pick disease, type C1, mRNA (cDNA clone MGC:152602 Image:8433293), complete cds" (2007).
GenBank Accession No. NM_000271.4, "*Homo sapiens* NPC intracellular cholesterol transporter 1 (NPC1), mRNA" (2017).
GenBank Accession No. NM_006432.3, "*Homo sapiens* NPC intracellular cholesterol transporter 2 (NPC2), mRNA" (2017).
GenBank Accession No. NM_008720.2, "Mus musculus NPC intracellular cholesterol transporter 1 (Npc1), mRNA" (2017).
GenBank Accession No. NM_023409.4, "Mus musculus NPC intracellular cholesterol transporter 2 (Npc2), mRNA" (2017).
GenBank Accession No. NP_000262.2, "NPC intracellular cholesterol transporter 1 precursor [*Homo sapiens*]" (2019).
GenBank Accession No. NP_006423.1, "NPC intracellular cholesterol transporter 2 isoform 2 precursor [*Homo sapiens*]" (2019).
GenBank Accession No. NP_032746.2, "NPC intracellular cholesterol transporter 1 precursor [Mus musculus]" (2019).
GenBank Accession No. NP_075898.1, "NPC intracellular cholesterol transporter 2 precursor [Mus musculus]" (2019).
Ho et al., "Synthetic Protein Transduction Domains: Enhanced Transduction Potential in Vitro and in Vivo," *Cancer Research*, 61: 474-477 (2001).
Hughes et al., "AAV9 intracerebroventricular gene therapy improves lifespan, locomotor function and pathology in a mouse model of Niemann-Pick type C1 disease," *Human Molecular Genetics*, 0(0): 1-20 (2018).
Kauffman et al., "Mechanism Matters: A Taxonomy of Cell Penetrating Peptides," *Trends in Biochemical Sciences*, 40(12): 749-764 (2015).
Loftus et al., "Murine Model of Niemann-Pick C Disease: Mutation in a Cholesterol Homeostasis Gene," *Science*, 227(5323): 232-235 (1997).
Meng et al., "HIV Tat Domain Improves Cross-correction of Human Galactocerebrosidase in a Gene- and Flanking Sequence-dependent Manner," *Molecular Therapy-Nucleic Acids*, 2: e130 (2013).
Rastall et al., "Recent advances in gene therapy for lysosomal storage disorders," *The Application of Clinical Genetics*, 8: 157-169 (2015).
Wassif et al., "High incidence of unrecognized visceral/neurological late-onset Niemann-Pick disease, type C1, predicted by analysis of massively parallel sequencing data sets," *Genetics in Medicine*, 18(1): 41-48 (2015).
Xia et al., "The HIV Tat protein transduction domain improves the biodistribution of β-glucuronidase expressed from recombinant viral vectors," *Nature Biotechnology*, 19: 640-644 (2001).
Yandek et al., "Mechanism of the Cell-Penetrating Peptide Transportan 10 Permeation of Lipid Bilayers," *Biophysical Journal*, 92: 2434-2444 (2007).

* cited by examiner

FIG. 1A

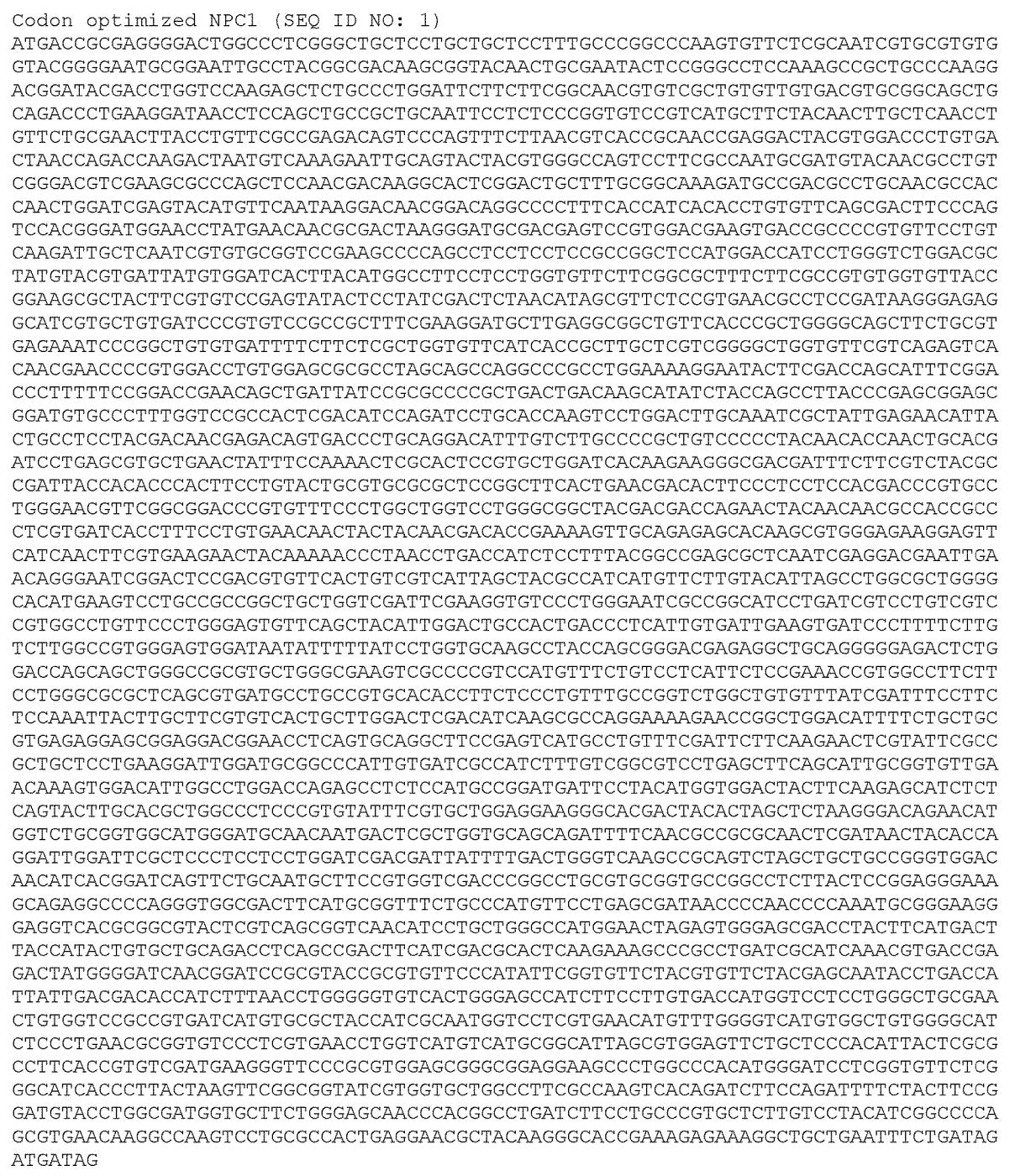

Codon optimized NPC1 (SEQ ID NO: 1)

```
ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAGATTTTCTACTTCCG
GATGTACCTGGCGATGGTGCTTCTGGGAGCAACCCACGGCCTGATCTTCCTGCCCGTGCTCTTGTCCTACATCGGCCCCA
GCGTGAACAAGGCCAAGTCCTGCGCCACTGAGGAACGCTACAAGGGCACCGAAAGAGAAAGGCTGCTGAATTTCTGATAG
ATGATAG
```

FIG. 1B

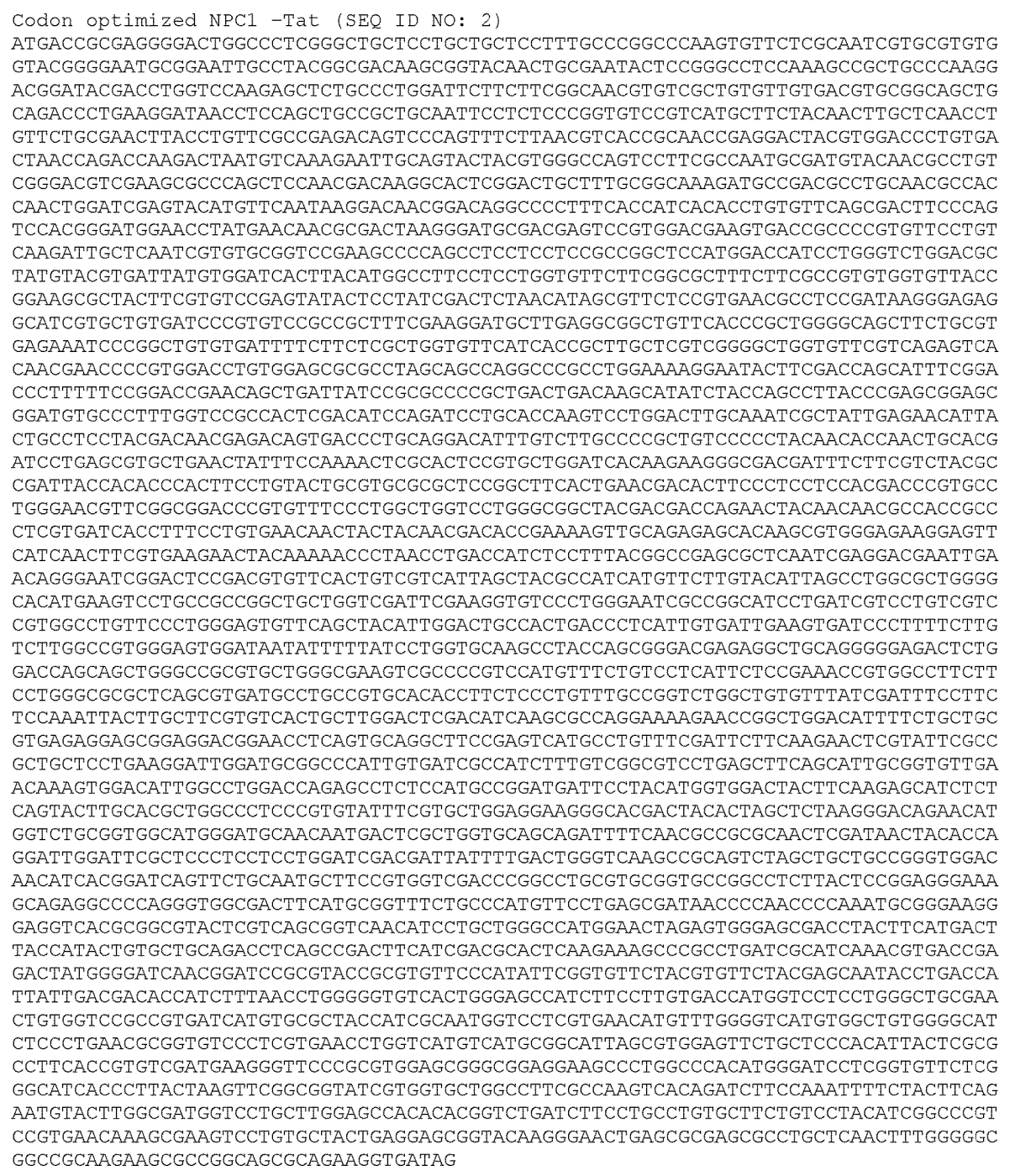

Codon optimized NPC1 -Tat (SEQ ID NO: 2)

ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTTCTGTCCTACATCGGCCCGT
CCGTGAACAAAGCGAAGTCCTGTGCTACTGAGGAGCGGTACAAGGGAACTGAGCGCGAGCGCCTGCTCAACTTTGGGGGC
GGCCGCAAGAAGCGCCGGCAGCGCAGAAGGTGATAG

FIG. 1C

Codon optimized NPC1 -3xFLAG (SEQ ID NO: 3)

ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTGCTGAGCTACATCGGTCCCA
GCGTGAACAAGGCTAAGTCCTGCGCGACGGAGGAAAGGTACAAGGGAACCGAGAGGGAGCGCCTTCTCAACTTCGGAGGA
GATTATAAAGACGATGATGACAAGGGGGACTACAAGGACGACGATGACAAGGGCGATTACAAAGACGACGACGACAAGTT
GATAG

FIG. 1D

Codon optimized NPC1 -TP10 (SEQ ID NO: 4)

ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTGCTGAGCTACATCGGTCCCA
GCGTGAACAAGGCTAAGTCCTGCGCGACGGAGGAAAGGTACAAGGGGACTGAACGCGAACGGCTGCTGAACTTTGGCGGC
GCTGGGTACCTGCTCGGAAAGATCAACCTCAAAGCGCTGGCGGCCCTGGCCAAGAAGATCCTGTTGATAG

FIG. 1E

Codon optimized NPC1 -TP2 (SEQ ID NO: 5)

ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTGCTGAGCTACATCGGTCCCA
GCGTGAACAAGGCTAAGTCCTGCGCGACGGAGGAAAGGTACAAGGGTACTGAAAGAGAGCGGCTGCTCAACTTCGGTGGC
CCCCTGATCTACCTGCGCCTCCTGCGGGGTCAGTTCTTGATAG

FIG. 1F

Codon optimized NPC1 -3xFLAG-TAT (SEQ ID NO: 6)

ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTGCTGAGCTACATCGGTCCCA
GCGTGAACAAGGCTAAGTCCTGCGCGACGGAGGAAAGGTACAAGGGAACCGAGAGGGAGCGCCTTCTCAACTTCGGAGGA
GATTATAAAGACGATGATGACAAGGGGGACTACAAGGACGACGATGACAAGGGCGATTACAAAGACGACGACGACAAGGG
CGGCCGGAAGAAGCGCCGCCAGCGGCGGAGATTGATAG

FIG. 1G

Codon optimized NPC1-3xFLAG-TP10 (SEQ ID NO: 7)

ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTGCTGAGCTACATCGGTCCCA
GCGTGAACAAGGCTAAGTCCTGCGCGACGGAGGAAAGGTACAAGGGAACCGAGAGGGAGCGCCTTCTCAACTTCGGAGGA
GATTATAAAGACGATGATGACAAGGGGGACTACAAGGACGACGATGACAAGGGCGATTACAAAGACGACGACGACAAGGG
CGGCGCCGGCTACCTCCTGGGGAAGATTAACCTGAAGGCCCTGGCAGCCCTCGCCAAGAAGATCCTGTTGATAG

FIG. 1H

Codon optimized NPC1_3xFLAG-TP2 (SEQ ID NO: 8)
ATGACCGCGAGGGGACTGGCCCTCGGGCTGCTCCTGCTGCTCCTTTGCCCGGCCCAAGTGTTCTCGCAATCGTGCGTGTG
GTACGGGGAATGCGGAATTGCCTACGGCGACAAGCGGTACAACTGCGAATACTCCGGGCCTCCAAAGCCGCTGCCCAAGG
ACGGATACGACCTGGTCCAAGAGCTCTGCCCTGGATTCTTCTTCGGCAACGTGTCGCTGTGTTGTGACGTGCGGCAGCTG
CAGACCCTGAAGGATAACCTCCAGCTGCCGCTGCAATTCCTCTCCCGGTGTCCGTCATGCTTCTACAACTTGCTCAACCT
GTTCTGCGAACTTACCTGTTCGCCGAGACAGTCCCAGTTTCTTAACGTCACCGCAACCGAGGACTACGTGGACCCTGTGA
CTAACCAGACCAAGACTAATGTCAAAGAATTGCAGTACTACGTGGGCCAGTCCTTCGCCAATGCGATGTACAACGCCTGT
CGGGACGTCGAAGCGCCCAGCTCCAACGACAAGGCACTCGGACTGCTTTGCGGCAAAGATGCCGACGCCTGCAACGCCAC
CAACTGGATCGAGTACATGTTCAATAAGGACAACGGACAGGCCCCTTTCACCATCACACCTGTGTTCAGCGACTTCCCAG
TCCACGGGATGGAACCTATGAACAACGCGACTAAGGGATGCGACGAGTCCGTGGACGAAGTGACCGCCCCGTGTTCCTGT
CAAGATTGCTCAATCGTGTGCGGTCCGAAGCCCCAGCCTCCTCCTCCGCCGGCTCCATGGACCATCCTGGGTCTGGACGC
TATGTACGTGATTATGTGGATCACTTACATGGCCTTCCTCCTGGTGTTCTTCGGCGCTTTCTTCGCCGTGTGGTGTTACC
GGAAGCGCTACTTCGTGTCCGAGTATACTCCTATCGACTCTAACATAGCGTTCTCCGTGAACGCCTCCGATAAGGGAGAG
GCATCGTGCTGTGATCCCGTGTCCGCCGCTTTCGAAGGATGCTTGAGGCGGCTGTTCACCCGCTGGGGCAGCTTCTGCGT
GAGAAATCCCGGCTGTGTGATTTTCTTCTCGCTGGTGTTCATCACCGCTTGCTCGTCGGGGCTGGTGTTCGTCAGAGTCA
CAACGAACCCCGTGGACCTGTGGAGCGCGCCTAGCAGCCAGGCCCGCCTGGAAAAGGAATACTTCGACCAGCATTTCGGA
CCCTTTTTCCGGACCGAACAGCTGATTATCCGCGCCCCGCTGACTGACAAGCATATCTACCAGCCTTACCCGAGCGGAGC
GGATGTGCCCTTTGGTCCGCCACTCGACATCCAGATCCTGCACCAAGTCCTGGACTTGCAAATCGCTATTGAGAACATTA
CTGCCTCCTACGACAACGAGACAGTGACCCTGCAGGACATTTGTCTTGCCCCGCTGTCCCCCTACAACACCAACTGCACG
ATCCTGAGCGTGCTGAACTATTTCCAAAACTCGCACTCCGTGCTGGATCACAAGAAGGGCGACGATTTCTTCGTCTACGC
CGATTACCACACCCACTTCCTGTACTGCGTGCGCGCTCCGGCTTCACTGAACGACACTTCCCTCCTCCACGACCCGTGCC
TGGGAACGTTCGGCGGACCCGTGTTTCCCTGGCTGGTCCTGGGCGGCTACGACGACCAGAACTACAACAACGCCACCGCC
CTCGTGATCACCTTTCCTGTGAACAACTACTACAACGACACCGAAAAGTTGCAGAGAGCACAAGCGTGGGAGAAGGAGTT
CATCAACTTCGTGAAGAACTACAAAAACCCTAACCTGACCATCTCCTTTACGGCCGAGCGCTCAATCGAGGACGAATTGA
ACAGGGAATCGGACTCCGACGTGTTCACTGTCGTCATTAGCTACGCCATCATGTTCTTGTACATTAGCCTGGCGCTGGGG
CACATGAAGTCCTGCCGCCGGCTGCTGGTCGATTCGAAGGTGTCCCTGGGAATCGCCGGCATCCTGATCGTCCTGTCGTC
CGTGGCCTGTTCCCTGGGAGTGTTCAGCTACATTGGACTGCCACTGACCCTCATTGTGATTGAAGTGATCCCTTTTCTTG
TCTTGGCCGTGGGAGTGGATAATATTTTTATCCTGGTGCAAGCCTACCAGCGGGACGAGAGGCTGCAGGGGGAGACTCTG
GACCAGCAGCTGGGCCGCGTGCTGGGCGAAGTCGCCCCGTCCATGTTTCTGTCCTCATTCTCCGAAACCGTGGCCTTCTT
CCTGGGCGCGCTCAGCGTGATGCCTGCCGTGCACACCTTCTCCCTGTTTGCCGGTCTGGCTGTGTTTATCGATTTCCTTC
TCCAAATTACTTGCTTCGTGTCACTGCTTGGACTCGACATCAAGCGCCAGGAAAAGAACCGGCTGGACATTTTCTGCTGC
GTGAGAGGAGCGGAGGACGGAACCTCAGTGCAGGCTTCCGAGTCATGCCTGTTTCGATTCTTCAAGAACTCGTATTCGCC
GCTGCTCCTGAAGGATTGGATGCGGCCCATTGTGATCGCCATCTTTGTCGGCGTCCTGAGCTTCAGCATTGCGGTGTTGA
ACAAAGTGGACATTGGCCTGGACCAGAGCCTCTCCATGCCGGATGATTCCTACATGGTGGACTACTTCAAGAGCATCTCT
CAGTACTTGCACGCTGGCCCTCCCGTGTATTTCGTGCTGGAGGAAGGGCACGACTACACTAGCTCTAAGGGACAGAACAT
GGTCTGCGGTGGCATGGGATGCAACAATGACTCGCTGGTGCAGCAGATTTTCAACGCCGCGCAACTCGATAACTACACCA
GGATTGGATTCGCTCCCTCCTCCTGGATCGACGATTATTTTGACTGGGTCAAGCCGCAGTCTAGCTGCTGCCGGGTGGAC
AACATCACGGATCAGTTCTGCAATGCTTCCGTGGTCGACCCGGCCTGCGTGCGGTGCCGGCCTCTTACTCCGGAGGGAAA
GCAGAGGCCCCAGGGTGGCGACTTCATGCGGTTTCTGCCCATGTTCCTGAGCGATAACCCCAACCCCAAATGCGGGAAGG
GAGGTCACGCGGCGTACTCGTCAGCGGTCAACATCCTGCTGGGCCATGGAACTAGAGTGGGAGCGACCTACTTCATGACT
TACCATACTGTGCTGCAGACCTCAGCCGACTTCATCGACGCACTCAAGAAAGCCCGCCTGATCGCATCAAACGTGACCGA
GACTATGGGGATCAACGGATCCGCGTACCGCGTGTTCCCATATTCGGTGTTCTACGTGTTCTACGAGCAATACCTGACCA
TTATTGACGACACCATCTTTAACCTGGGGGTGTCACTGGGAGCCATCTTCCTTGTGACCATGGTCCTCCTGGGCTGCGAA
CTGTGGTCCGCCGTGATCATGTGCGCTACCATCGCAATGGTCCTCGTGAACATGTTTGGGGTCATGTGGCTGTGGGGCAT
CTCCCTGAACGCGGTGTCCCTCGTGAACCTGGTCATGTCATGCGGCATTAGCGTGGAGTTCTGCTCCCACATTACTCGCG
CCTTCACCGTGTCGATGAAGGGTTCCCGCGTGGAGCGGGCGGAGGAAGCCCTGGCCCACATGGGATCCTCGGTGTTCTCG
GGCATCACCCTTACTAAGTTCGGCGGTATCGTGGTGCTGGCCTTCGCCAAGTCACAGATCTTCCAAATTTTCTACTTCAG
AATGTACTTGGCGATGGTCCTGCTTGGAGCCACACACGGTCTGATCTTCCTGCCTGTGCTGCTGAGCTACATCGGTCCCA
GCGTGAACAAGGCTAAGTCCTGCGCGACGGAGGAAAGGTACAAGGGAACCGAGAGGGAGCGCCTTCTCAACTTCGGAGGA
GATTATAAAGACGATGATGACAAGGGGGACTACAAGGACGACGATGACAAGGGCGATTACAAAGACGACGACGACAAGGG
GGGCCCGCTCATCTACCTCCGGCTGCTGCGGGGCCAGTTTTTGATAG

FIG. 2A

BLASTN WT NPC1 vs codon optimized NPC1

Alignment statistics for:
Query 1 = WT NPC1 (SEQ ID NO: 9)
Subject 1= codon optimized NPC1 (SEQ ID NO: 1)

| Score | Expect | Identities | Gaps | Strand |
|---|---|---|---|---|
| 2895 bits(3210) | 0.0 | 2943/3835(77%) | 0/3835(0%) | Plus/Plus |

```
Query  1    ATGACCGCTCGCGGCCTGGCCCTTGGCCTCCTCCTGCTGCTACTGTGTCCAGCGCAGGTG  60
            ||||||||  | || |||||||| || || ||||||||||| || || || || || |||
Sbjct  1    ATGACCGCGAGGGGACTGGCCCTCGGGCTGCTCCTGCTGCTCCTTTGCCCGGCCCAAGTG  60

Query  61   TTTTCACAGTCCTGTGTTTGGTATGGAGAGTGTGGAATTGCATATGGGGACAAGAGGTAC  120
            || || || || || || ||||| || || || |||||||| || || |||||| |||||
Sbjct  61   TTCTCGCAATCGTGCGTGTGGTACGGGGAATGCGGAATTGCCTACGGCGACAAGCGGTAC  120

Query  121  AATTGCGAATATTCTGGCCCACCAAAACCATTGCCAAAGGATGGATATGACTTAGTGCAG  180
            || |||||||| || || || ||||| ||  |||| ||||| ||||| ||| | || ||
Sbjct  121  AACTGCGAATACTCCGGGCCTCCAAAGCCGCTGCCCAAGGACGGATACGACCTGGTCCAA  180

Query  181  GAACTCTGTCCAGGATTCTTCTTTGGCAATGTCAGTCTCTGTTGTGATGTTCGGCAGCTT  240
            || ||||| || ||||||||||| ||||| ||    || |||||||| || ||||||||
Sbjct  181  GAGCTCTGCCCTGGATTCTTCTTCGGCAACGTGTCGCTGTGTTGTGACGTGCGGCAGCTG  240

Query  241  CAGACACTAAAAGACAACCTGCAGCTGCCTCTACAGTTTCTGTCCAGATGTCCATCCTGT  300
            ||||| || || || ||||| |||||||| || || || || ||| | ||||| || ||
Sbjct  241  CAGACCCTGAAGGATAACCTCCAGCTGCCGCTGCAATTCCTCTCCCGGTGTCCGTCATGC  300

Query  301  TTTTATAACCTACTGAACCTGTTTTGTGAGCTGACATGTAGCCCTCGACAGAGTCAGTTT  360
            || || ||| | || |||||||| || || || || |||   ||  |||||   ||||||
Sbjct  301  TTCTACAACTTGCTCAACCTGTTCTGCGAACTTACCTGTTCGCCGAGACAGTCCCAGTTT  360

Query  361  TTGAATGTTACAGCTACTGAAGATTATGTTGATCCTGTTACAAACCAGACGAAAACAAAT  420
             | || || || || || || || || || || ||||| || |||||||| || || |||
Sbjct  361  CTTAACGTCACCGCAACCGAGGACTACGTGGACCCTGTGACTAACCAGACCAAGACTAAT  420

Query  421  GTGAAAGAGTTACAATACTACGTCGGACAGAGTTTTGCCAATGCAATGTACAATGCCTGC  480
            || ||||| || || |||||||| || |||   || |||||||| |||||||| |||||
Sbjct  421  GTCAAAGAATTGCAGTACTACGTGGGCCAGTCCTTCGCCAATGCGATGTACAACGCCTGT  480

Query  481  CGGGATGTGGAGGCCCCCTCAAGTAATGACAAGGCCCTGGGACTCCTGTGTGGGAAGGAC  540
            ||||| || || |||      || |||||||| || ||||| || || || || || ||
Sbjct  481  CGGGACGTCGAAGCGCCCAGCTCCAACGACAAGGCACTCGGACTGCTTTGCGGCAAAGAT  540

Query  541  GCTGACGCCTGTAATGCCACCAACTGGATTGAATACATGTTCAATAAGGACAATGGACAG  600
            || |||||||| || |||||||||||||| || |||||||||||||||||||| ||||||
Sbjct  541  GCCGACGCCTGCAACGCCACCAACTGGATCGAGTACATGTTCAATAAGGACAACGGACAG  600

Query  601  GCACCTTTTACCATCACTCCTGTGTTTTCAGATTTTCCAGTCCATGGGATGGAGCCCATG  660
            || ||||| |||||||| ||||||||    || || |||||||| |||||||| || |||
Sbjct  601  GCCCCTTTCACCATCACACCTGTGTTCAGCGACTTCCCAGTCCACGGGATGGAACCTATG  660

Query  661  AACAATGCCACCAAAGGCTGTGACGAGTCTGTGGATGAGGTCACAGCACCATGTAGCTGC  720
            ||||| || || || || || |||||||| ||||| || || || || || |||  |||
Sbjct  661  AACAACGCGACTAAGGGATGCGACGAGTCCGTGGACGAAGTGACCGCCCCGTGTTCCTGT  720

Query  721  CAAGACTGCTCTATTGTCTGTGGCCCCAAGCCCCAGCCCCCACCTCCTCCTGCTCCCTGG  780
            ||||| ||||| || || || || || ||||||||||| || ||||| || ||||| |||
Sbjct  721  CAAGATTGCTCAATCGTGTGCGGTCCGAAGCCCCAGCCTCCTCCTCCGCCGGCTCCATGG  780

Query  781  ACGATCCTTGGCTTGGACGCCATGTATGTCATCATGTGGATCACCTACATGGCGttgttg  840
            || ||||| ||  ||||||| ||||| || || ||||||||||| |||||||| ||  |
Sbjct  781  ACCATCCTGGGTCTGGACGCTATGTACGTGATTATGTGGATCACTTACATGGCCTTCCTC  840
```

FIG. 2B

```
Query  841   cttgtgttttttggagcattttttgCAGTGTGGTGCTACAGAAAACGGTATTTTGTCTCC  900
             || ||||| || || || || || || |||||||| ||| | || || || || || |||
Sbjct  841   CTGGTGTTCTTCGGCGCTTTCTTCGCCGTGTGGTGTTACCGGAAGCGCTACTTCGTGTCC  900

Query  901   GAGTACACTCCCATCGATAGCAATATAGCTTTTTCTGTTAATGCAAGTGACAAAGGAGAG  960
             ||||| ||||| |||||    || ||||| || || || || ||    || || ||||||
Sbjct  901   GAGTATACTCCTATCGACTCTAACATAGCGTTCTCCGTGAACGCCTCCGATAAGGGAGAG  960

Query  961   GCGTCCTGCTGTGACCCTGTCAGCGCAGCATTTGAGGGCTGCTTGAGGCGGCTGTTCACA  1020
             || || |||||||| || ||    ||| || || || || ||||||||||||||||||| 
Sbjct  961   GCATCGTGCTGTGATCCCGTGTCCGCCGCTTTCGAAGGATGCTTGAGGCGGCTGTTCACC  1020

Query  1021  CGCTGGGGGTCTTTCTGCGTCCGAAACCCTGGCTGTGTCATTTTCTTCTCGCTGGTCTTC  1080
             ||||||||    ||||||||  |||| || |||||||| |||||||||||||||| |||
Sbjct  1021  CGCTGGGGCAGCTTCTGCGTGAGAAATCCCGGCTGTGTGATTTTCTTCTCGCTGGTGTTC  1080

Query  1081  ATTACTGCGTGTTCGTCAGGCCTGGTGTTTGTCCGGGTCACAACCAATCCAGTTGACCTC  1140
             || || || || ||||| || |||||||| ||| | |||||||  |  || || ||||| 
Sbjct  1081  ATCACCGCTTGCTCGTCGGGGCTGGTGTTCGTCAGAGTCACAACGAACCCCGTGGACCTG  1140

Query  1141  TGGTCAGCCCCCAGCAGCCAGGCTCGCCTGGAAAAAGAGTACTTTGACCAGCACTTTGGG  1200
             |||   || || ||||||||||| |||||||||| || ||||| ||||||||| || || 
Sbjct  1141  TGGAGCGCGCCTAGCAGCCAGGCCCGCCTGGAAAAGGAATACTTCGACCAGCATTTCGGA  1200

Query  1201  CCTTTCTTCCGGACGGAGCAGCTCATCATCCGGGCCCCTCTCACTGACAAACACATTTAC  1260
             || || |||||||| || ||||| || |||||| ||||| || |||||||| || || |||
Sbjct  1201  CCCTTTTTCCGGACCGAACAGCTGATTATCCGCGCCCCGCTGACTGACAAGCATATCTAC  1260

Query  1261  CAGCCATACCCTTCGGGAGCTGATGTACCCTTTGGACCTCCGCTTGACATACAGATACTG  1320
             ||||| |||||    ||||| ||||| |||||||| || || || ||||| ||||| |||
Sbjct  1261  CAGCCTTACCCGAGCGGAGCGGATGTGCCCTTTGGTCCGCCACTCGACATCCAGATCCTG  1320

Query  1321  CACCAGGTTCTTGACTTACAAATAGCCATCGAAAACATTACTGCCTCTTATGACAATGAG  1380
             ||||| || || ||||| ||||| || || || ||||||||||||| || ||||| |||
Sbjct  1321  CACCAAGTCCTGGACTTGCAAATCGCTATTGAGAACATTACTGCCTCCTACGACAACGAG  1380

Query  1381  ACTGTGACACTTCAAGACATCTGCTTGGCCCCTCTTTCACCGTATAACACGAACTGCACC  1440
             || ||||| || || ||||| ||  | ||||| || || || || ||||| |||||||| 
Sbjct  1381  ACAGTGACCCTGCAGGACATTTGTCTTGCCCCGCTGTCCCCCTACAACACCAACTGCACG  1440

Query  1441  ATTTTGAGTGTGTTAAATTACTTCCAGAACAGCCATTCCGTGCTGGACCACAAGAAAGGG  1500
             ||  |||| ||| | || || ||||| |||    || ||||||||||| ||||||||| || 
Sbjct  1441  ATCCTGAGCGTGCTGAACTATTTCCAAAACTCGCACTCCGTGCTGGATCACAAGAAGGGC  1500

Query  1501  GACGACTTCTTTGTGTATGCCGATTACCACACGCACTTTCTGTACTGCGTACGGGCTCCT  1560
             ||||| ||||| || || |||||||||||||| ||||| ||||||||||| || ||||| 
Sbjct  1501  GACGATTTCTTCGTCTACGCCGATTACCACACCCACTTCCTGTACTGCGTGCGCGCTCCG  1560

Query  1561  GCCTCTCTGAATGATACAAGTTTGCTCCATGACCCTTGTCTGGGTACGTTTGGTGGACCA  1620
             || || ||||| || ||      | ||||| ||||| || ||||| ||||| || ||||| 
Sbjct  1561  GCTTCACTGAACGACACTTCCCTCCTCCACGACCCGTGCCTGGGAACGTTCGGCGGACCC  1620

Query  1621  GTGTTCCCGTGGCTTGTGTTGGGAGGCTATGATGATCAAAACTACAATAACGCCACTGCC  1680
             ||||| || ||||| ||  |||| ||||| || || || |||||||| |||||| |||
Sbjct  1621  GTGTTTCCCTGGCTGGTCCTGGGCGGCTACGACGACCAGAACTACAACAACGCCACCGCC  1680

Query  1681  CTTGTGATTACCTTCCCTGTCAATAATTACTATAATGATACAGAGAAGCTCCAGAGGGCC  1740
             || ||||| ||||| ||||| || || ||||| || || || || ||| | ||||| || 
Sbjct  1681  CTCGTGATCACCTTTCCTGTGAACAACTACTACAACGACACCGAAAAGTTGCAGAGAGCA  1740

Query  1741  CAGGCCTGGGAAAAAGAGTTTATTAATTTTGTGAAAAACTACAAGAATCCCAATCTGACC  1800
             || || ||||| || ||||| || || || ||||| |||||||| || || || ||||||
Sbjct  1741  CAAGCGTGGGAGAAGGAGTTCATCAACTTCGTGAAGAACTACAAAAACCCTAACCTGACC  1800

Query  1801  ATTTCCTTCACTGCTGAACGAAGTATTGAAGATGAACTAAATCGTGAAAGTGACAGTGAT  1860
             || ||||| || || || ||    || || || ||| | ||  | |||   |||   || 
Sbjct  1801  ATCTCCTTTACGGCCGAGCGCTCAATCGAGGACGAATTGAACAGGGAATCGGACTCCGAC  1860
```

FIG. 2C

```
Query  1861  GTCTTCACCGTTGTAATTAGCTATGCCATCATGTTTCTATATATTTCCCTAGCCTTGGGG  1920
             || ||||| || || |||||||| |||||||||||  | || |||  ||| ||  |||||
Sbjct  1861  GTGTTCACTGTCGTCATTAGCTACGCCATCATGTTCTTGTACATTAGCCTGGCGCTGGGG  1920

Query  1921  CACATCAAAAGCTGTCGCAGGCTTCTGGTGGATTCGAAGGTCTCACTAGGCATCGCGGGC  1980
             ||||| ||   ||| ||| |||| ||||| ||||||||||| || || || ||||| |||
Sbjct  1921  CACATGAAGTCCTGCCGCCGGCTGCTGGTCGATTCGAAGGTGTCCCTGGGAATCGCCGGC  1980

Query  1981  ATCTTGATCGTGCTGAGCTCGGTGGCTTGCTCCTTGGGTGTCTTCAGCTACATTGGGTTG  2040
             ||| ||||||| |||   || ||||| || ||| |||| || ||||||||||||||  ||
Sbjct  1981  ATCCTGATCGTCCTGTCGTCCGTGGCCTGTTCCCTGGGAGTGTTCAGCTACATTGGACTG  2040

Query  2041  CCCTTGACCCTCATTGTGATTGAAGTCATCCCGTTCCTGGTGCTGGCTGTTGGAGTGGAC  2100
             ||  |||||||||||||||||||||| ||||| || || ||  |||| || |||||||| 
Sbjct  2041  CCACTGACCCTCATTGTGATTGAAGTGATCCCTTTTCTTGTCTTGGCCGTGGGAGTGGAT  2100

Query  2101  AACATCTTCATTCTGGTGCAGGCCTACCAGAGAGATGAACGTCTTCAAGGGGAAACCCTG  2160
             || || || || |||||||| ||||||||| | || ||  | || || ||||| || |||
Sbjct  2101  AATATTTTTATCCTGGTGCAAGCCTACCAGCGGGACGAGAGGCTGCAGGGGGAGACTCTG  2160

Query  2161  GATCAGCAGCTGGGCAGGGTCCTAGGAGAAGTGGCTCCCAGTATGTTCCTGTCATCCTTT  2220
             || |||||||||||| | || || || ||||| || ||    ||||| ||||| || || 
Sbjct  2161  GACCAGCAGCTGGGCCGCGTGCTGGGCGAAGTCGCCCCGTCCATGTTTCTGTCCTCATTC  2220

Query  2221  TCTGAGACTGTAGCATTTTTCTTAGGAGCATTGTCCGTGATGCCAGCCGTGCACACCTTC  2280
             || || || || || || ||| | || ||  |   ||||||||| |||||||||||||||
Sbjct  2221  TCCGAAACCGTGGCCTTCTTCCTGGGCGCGCTCAGCGTGATGCCTGCCGTGCACACCTTC  2280

Query  2281  TCTCTCTTTGCGGGATTGGCAGTCTTCATTGACTTTCTTCTGCAGATTACCTGTTTCGTG  2340
             || || ||||| ||  |||| || || || || || ||||| || ||||| || ||||||
Sbjct  2281  TCCCTGTTTGCCGGTCTGGCTGTGTTTATCGATTTCCTTCTCCAAATTACTTGCTTCGTG  2340

Query  2341  AGTCTCTTGGGGTTAGACATTAAACGTCAAGAGAAAAATCGGCTAGACATCTTTTGCTGT  2400
                ||  | ||  | ||||| || || || || || ||||| ||||| || ||||| 
Sbjct  2341  TCACTGCTTGGACTCGACATCAAGCGCCAGGAAAAGAACCGGCTGGACATTTTCTGCTGC  2400

Query  2401  GTCAGAGGTGCTGAAGATGGAACAAGCGTCCAGGCCTCAGAGAGCTGTTTGTTTCGCTTC  2460
             || ||||| || || || |||||    || ||||| || |||   ||  ||||||| |||
Sbjct  2401  GTGAGAGGAGCGGAGGACGGAACCTCAGTGCAGGCTTCCGAGTCATGCCTGTTTCGATTC  2460

Query  2461  TTCAAAAACTCCTATTCTCCACTTCTGCTAAAGGACTGGATGAGACCAATTGTGATAGCA  2520
             ||||| ||||| ||||| || || || || ||||| |||||| | || |||||||| || 
Sbjct  2461  TTCAAGAACTCGTATTCGCCGCTGCTCCTGAAGGATTGGATGCGGCCCATTGTGATCGCC  2520

Query  2521  ATATTTGTGGGTGTTCTGTCATTCAGCATCGCAGTCCTGAACAAAGTAGATATTGGATTG  2580
             || ||||| || || |||   |||||||| || ||  |||||||||| || |||||  ||
Sbjct  2521  ATCTTTGTCGGCGTCCTGAGCTTCAGCATTGCGGTGTTGAACAAAGTGGACATTGGCCTG  2580

Query  2581  GATCAGTCTCTTTCGATGCCAGATGACTCCTACATGGTGGATTATTTCAAATCCATCAGT  2640
             || |||   || || ||||| ||||| |||||||||||||| || |||||   ||||  |
Sbjct  2581  GACCAGAGCCTCTCCATGCCGGATGATTCCTACATGGTGGACTACTTCAAGAGCATCTCT  2640

Query  2641  CAGTACCTGCATGCGGGTCCGCCTGTGTACTTTGTCCTGGAGGAAGGGCACGACTACACT  2700
             |||||| |||| || || || ||||| || || ||||||||||||||||||||||||
Sbjct  2641  CAGTACTTGCACGCTGGCCCTCCCGTGTATTTCGTGCTGGAGGAAGGGCACGACTACACT  2700

Query  2701  TCTTCCAAGGGGCAGAACATGGTGTGCGGCGGCATGGGCTGCAACAATGATTCCCTGGTG  2760
                || ||||| ||||||||||| ||||| |||||||| ||||||||||| || ||||||
Sbjct  2701  AGCTCTAAGGGACAGAACATGGTCTGCGGTGGCATGGGATGCAACAATGACTCGCTGGTG  2760

Query  2761  CAGCAGATATTTAACGCGGCGCAGCTGGACAACTATACCCGAATAGGCTTCGCCCCCTCG  2820
             |||||||| || ||||| ||||| || || ||||| ||| | || || ||||| ||||| 
Sbjct  2761  CAGCAGATTTTCAACGCCGCGCAACTCGATAACTACACCAGGATTGGATTCGCTCCCTCC  2820

Query  2821  TCCTGGATCGACGATTATTTCGACTGGGTGAAGCCACAGTCGTCTTGCTGTCGAGTGGAC  2880
             |||||||||||||||||||| |||||||| ||||| |||||    ||||| || ||||||
Sbjct  2821  TCCTGGATCGACGATTATTTTGACTGGGTCAAGCCGCAGTCTAGCTGCTGCCGGGTGGAC  2880
```

FIG. 2D

```
Query  2881  AATATCACTGACCAGTTCTGCAATGCTTCAGTGGTTGACCCTGCCTGCGTTCGCTGCAGG  2940
             || ||||| || ||||||||||||||||| ||||| ||||| |||||||| || ||| ||
Sbjct  2881  AACATCACGGATCAGTTCTGCAATGCTTCCGTGGTCGACCCGGCCTGCGTGCGGTGCCGG  2940

Query  2941  CCTCTGACTCCGGAAGGCAAACAGAGGCCTCAGGGGGGAGACTTCATGAGATTCCTGCCC  3000
             ||||| |||||||| || || |||||||| ||||| || ||||||||| | || ||||||
Sbjct  2941  CCTCTTACTCCGGAGGGAAAGCAGAGGCCCCAGGGTGGCGACTTCATGCGGTTTCTGCCC  3000

Query  3001  ATGTTCCTTTCGGATAACCCTAACCCCAAGTGTGGCAAAGGGGGACATGCTGCCTATAGT  3060
             ||||||||    |||||||| |||||||| || || || || || || || || ||
Sbjct  3001  ATGTTCCTGAGCGATAACCCCAACCCCAAATGCGGGAAGGGAGGTCACGCGGCGTACTCG  3060

Query  3061  TCTGCAGTTAACATCCTCCTTGGCCATGGCACCAGGGTCGGAGCCACGTACTTCATGACC  3120
             || || || |||||||| || |||||||| || || || ||||| || |||||||||||
Sbjct  3061  TCAGCGGTCAACATCCTGCTGGGCCATGGAACTAGAGTGGGAGCGACCTACTTCATGACT  3120

Query  3121  TACCACACCGTGCTGCAGACCTCTGCTGACTTTATTGACGCTCTGAAGAAAGCCCGACTT  3180
             ||||| || |||||||||||||| || ||||| || ||||| || ||||||||||| ||
Sbjct  3121  TACCATACTGTGCTGCAGACCTCAGCCGACTTCATCGACGCACTCAAGAAAGCCCGCCTG  3180

Query  3181  ATAGCCAGTAATGTCACCGAAACCATGGGCATTAACGGCAGTGCCTACCGAGTATTTCCT  3240
             || ||    || || ||||| || ||||| || |||||    || ||||| || || ||
Sbjct  3181  ATCGCATCAAACGTGACCGAGACTATGGGGATCAACGGATCCGCGTACCGCGTGTTCCCA  3240

Query  3241  TACAGTGTGTTTTATGTCTTCTACGAACAGTACCTGACCATCATTGACGACACTATCTTC  3300
             ||    ||||| || || |||||||| || ||||||||||| ||||||||||| |||||
Sbjct  3241  TATTCGGTGTTCTACGTGTTCTACGAGCAATACCTGACCATTATTGACGACACCATCTTT  3300

Query  3301  AACCTCGGTGTGTCCCTGGGCGCGATATTTCTGGTGACCATGGTCCTCCTGGGCTGTGAG  3360
             ||||| || ||||| ||||| || || || || ||||||||||||||||||||||| ||
Sbjct  3301  AACCTGGGGGTGTCACTGGGAGCCATCTTCCTTGTGACCATGGTCCTCCTGGGCTGCGAA  3360

Query  3361  CTCTGGTCTGCAGTCATCATGTGTGCCACCATCGCCATGGTCTTGGTCAACATGTTTGGA  3420
             || ||||| || || |||||||| || |||||||| |||||| | || |||||||||||
Sbjct  3361  CTGTGGTCCGCCGTGATCATGTGCGCTACCATCGCAATGGTCCTCGTGAACATGTTTGGG  3420

Query  3421  GTTATGTGGCTCTGGGGCATCAGTCTGAACGCTGTATCCTTGGTCAACCTGGTGATGAGC  3480
             || |||||||| |||||||||   |||||||| || ||| | || |||||||| |||
Sbjct  3421  GTCATGTGGCTGTGGGGCATCTCCCTGAACGCGGTGTCCCTCGTGAACCTGGTCATGTCA  3480

Query  3481  TGTGGCATCTCCGTGGAGTTCTGCAGCCACATAACCAGAGCGTTCACGGTGAGCATGAAA  3540
             || |||||   |||||||||||||  |||||| ||  | || ||||| |||   |||||
Sbjct  3481  TGCGGCATTAGCGTGGAGTTCTGCTCCCACATTACTCGCGCCTTCACCGTGTCGATGAAG  3540

Query  3541  GGCAGCCGCGTGGAGCGCGCGGAAGAGGCACTTGCCCACATGGGCAGCTCCGTGTTCAGT  3600
             ||   |||||||||||| ||||| || || || |||||||||||   ||| ||||||
Sbjct  3541  GGTTCCCGCGTGGAGCGGGCGGAGGAAGCCCTGGCCCACATGGGATCCTCGGTGTTCTCG  3600

Query  3601  GGAATCACACTTACAAAATTTGGAGGGATTGTGGTGTTGGCTTTTGCCAAATCTCAAATT  3660
             || ||||| ||||| || || || || || |||||| |||| || ||||| || || ||
Sbjct  3601  GGCATCACCCTTACTAAGTTCGGCGGTATCGTGGTGCTGGCCTTCGCCAAGTCACAGATC  3660

Query  3661  TTCCAGATATTCTACTTCAGGATGTATTTGGCCATGGTCTTACTGGGAGCCACTCACGGA  3720
             |||||||| ||||||||| |||||||  |||| |||||  | |||||||| || |||||
Sbjct  3661  TTCCAGATTTTCTACTTCCGGATGTACCTGGCGATGGTGCTTCTGGGAGCAACCCACGGC  3720

Query  3721  TTAATATTTCTCCCTGTCTTACTCAGTTACATAGGGCCATCAGTAAATAAAGCCAAAAGT  3780
              | || || || || ||  |  |    ||||| || ||    || || || |||||
Sbjct  3721  CTGATCTTCCTGCCCGTGCTCTTGTCCTACATCGGCCCCAGCGTGAACAAGGCCAAGTCC  3780

Query  3781  TGTGCCACTGAAGAGCGATACAAAGGAACAGAGCGCGAACGGCTTCTAAATTTCT  3835
             || |||||||| || || ||||| || || ||  | ||| |||| || |||||||
Sbjct  3781  TGCGCCACTGAGGAACGCTACAAGGGCACCGAAAGAGAAAGGCTGCTGAATTTCT  3835
```

| EF1α mini | coNPC1 | globin Poly A |

| EF1α mini | coNPC1 | 3X FLAG globin Poly A |

| EF1α mini | coNPC1 | TAT/TP2/TP10 globin Poly A |

| EF1α mini | coNPC1 | 3X FLAG-PTD globin Poly A |

| EF1α S | Intron S | coNPC1 | globin Poly A |

| EF1α S | Intron S | coNPC1 | 3X FLAG | globin Poly A |

| EF1α S | Intron S | coNPC1 | TAT | globin Poly A |

CODON-OPTIMIZED HUMAN NPC1 GENES FOR THE TREATMENT OF NIEMANN-PICK TYPE C1 DEFICIENCY AND RELATED CONDITIONS

CROSS-REFERENCE TO RELATED APPLICATION

This application is the U.S. National Phase of International Patent Application No. PCT/US2018/038584, filed Jun. 20, 2018, which claims the benefit of U.S. Provisional Patent Application No. 62/522,677, filed Jun. 20, 2017, each of which is incorporated herein by reference in its entirety for all purposes.

STATEMENT REGARDING FEDERALLY SPONSORED RESEARCH OR DEVELOPMENT

This invention was made with Government support under project numbers HG-200318-11 and HG-000064-14, by the National Institutes of Health, National Human Genome Research Institute. The Government has certain rights in the invention.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 279,738 Byte ASCII (Text) file named "744687 ST25.txt" created on Dec. 3, 2019.

BACKGROUND OF THE INVENTION

Niemann-Pick disease, type C (NPC) is a rare and fatal, autosomal recessive, neurodegenerative disease that can present in infants, children, or adults. Its incidence in persons of Western European descent is 1/90,000 (Wassif C A et al., "High incidence of unrecognized visceral/neurological late-onset Niemann-Pick disease, type C1, predicted by analysis of massively parallel sequencing data sets," Genet Med. 2015 Mar. 12). Approximately 95% of patients with NPC have mutations in NPC1, a gene implicated in intracellular cholesterol trafficking. Mutation of NPC1 causes intracellular accumulation of unesterified cholesterol in late endosomal/lysosomal structures and marked accumulation of glycosphingolipids, especially in neuronal tissue. Thus, NPC patients generally present with hepatosplenomegaly (enlargement of liver and spleen) and neurological degeneration.

A prenatal syndrome of nonimmune fetal hydrops can be the first symptom of NPC disease. Neonates can present with severe liver disease from infiltration of the liver and/or respiratory failure. Other infants, without liver or pulmonary disease, have hypotonia and developmental delay. The classic presentation occurs in mid-to-late childhood with the insidious onset of ataxia, vertical supranuclear gaze palsy (VSGP), and dementia. Regression is common. Seizures are frequent and neurological symptoms become disabling, making oral feeding impossible; death usually occurs in the late second or third decade from aspiration pneumonia. Adults can be more mildly affected and are more likely to present with dementia or psychiatric symptoms. There are no proven treatments for NPC, and after the diagnosis, fatal neurodegeneration is inevitable. The fact that most patients have disease onset in childhood makes the search for effective therapies urgent.

The diagnosis of NPC disease is confirmed by specialized biochemical testing that demonstrates cholesterol storage and is detected by filipin staining in cultured fibroblasts. Most individuals with NPC disease have NPC type 1, caused by mutations in NPC1; fewer than 20 individuals have been diagnosed with NPC type 2, caused by mutations in NPC2. Molecular genetic testing of NPC1 and NPC2 detects disease-causing mutations in approximately 94% of individuals with NPC disease, almost all of whom have mutations in NPC1. NPC disease, regardless of the locus and allele(s), is a recessive metabolic condition and the mutations are loss of function or reduced function. Therefore, providing and expressing a single copy of the wild type gene can completely restore NPC1 or 2 enzymatic function.

A series of landmark studies conducted by the research group of Dr. William Pavan of the NHGRI/NIH led to the identification of both the mouse and human genes for NPC1 (Loftus et al. Science 277: 232-35; Carstea et al. Science 277: 228-31). A murine model of NPC, $Npc^{nih}$ (also called BALB/cNctr-$Npc1^{m1N}$/J), arising from a spontaneous frame-shift mutation in the Npc1 gene has been described and extensively characterized during these research efforts (Loftus et al. Science 277: 232-35). $Npc^{nih}$ homozygotes have an early, severe, and rapidly progressing disease, which is characterized by weight loss, ataxia, and lethality by 9 weeks of age. The mutation carried by this mouse is a null, and $Npc^{nih}$ homozygous mice fail to make Npc1 protein or mRNA. This animal model also displays neurological symptoms and early lethality: $Npc^{nih}$ homozygous mice uniformly begin losing weight by 6 weeks of age and do not survive past 9 weeks. Thus, these animals represent an ideal model of human NPC disease caused by loss of function mutations in the gene NPC1.

Over the years, other mouse models of NPC disease, specifically caused by varied natural or engineered mutations in the mouse Npc1 gene, have been generated but display less severe of a disease phenotype. All mouse models of NPC disease caused by mutation or other malfunction of the Npc1 gene in any mouse strain are treatable by the vector and derivatives described herein and are encompassed in the claims. Such models, as a group including $Npc^{nih}$ homozygous animals, are generally considered Npc designating homozygous Npc loss-of-function alleles, of which $Npc^{nih}$ is paradigmatic.

Notwithstanding the development of such mouse models, no curative therapy for NPC yet exists. A strategy or methodology for clinically treating NPC and/or providing a curative therapy for NPC and/or its symptoms is urgently needed in the art. The present disclosure fulfills such a need.

BRIEF SUMMARY OF THE INVENTION

The present disclosure provides gene therapy vectors (e.g., Adeno-Associated Virus (AAV) gene therapy vectors) comprising a therapeutic human nucleic acid molecule which is able to ameliorate, treat, and/or correct the cellular defect characteristic of certain cholesterol storage diseases or disorders, such as, Niemann-Pick disease type C ("NPC"). The gene therapy vectors of the present disclosure comprise NPC1 alleles that are codon optimized in order to maximize human expression (coNPC1).

The alleles may be a fusion protein that includes a tag (e.g., a FLAG® tag, such as a 3×FLAG® tag (Sigma, St. Louis, MO), which can afford facile detection, for example to determine biodistribution of the $_{co}$NPC1. The alleles may be part of a fusion protein that includes a protein transduction domain peptide (PTD), which allows trans-cellular correction (i.e., the transfer of the allele and/or expressed therapeutic protein to neighboring cells that have not received or been infected with the therapy vector; a/k/a “cross correction”). In certain embodiments, the alleles are part of a fusion protein that comprises a PTD (Tat, TP2, and/or TP10) and a tag (e.g., FLAG® tag).

The gene therapy vectors in accordance with the present disclosure may include a truncated Elongation Factor alpha (EF1α) promoter (EF1$\alpha_t$) (SEQ ID NO: 10) at the 5' end of NPC1. The EF1$\alpha_t$ promoter is a 227 base pair truncated EF1α promoter that retains activity. Additional promoters that are suitable for the inventive gene therapy vectors include the 231 base pair mini EF1α promoter (mini EF1α) (SEQ ID NO: 51) and the 231 base pair short EF1α promoter, also called EF1α S (SEQ ID NO: 52).

The gene therapy vector may include at least one of: a strong translation initiation site; multiple stop signals/codons at the end of the NCP1 allele or the fusion protein (e.g., coNCP1-PTD, coNCP1-3×FLAG® tag, coNCP1-PTD-3× FLAG® tag, wherein the PTD can be any protein transduction domain, such as Tat, TP2, or TP10); or both. The use of multiple stop signals/codons ensures maximal NPC1 gene or fusion protein expression and protein production in the cell and prevents aberrant read-through.

The vector constructs of the present disclosure may be utilized for gene therapy of certain cholesterol storage diseases or disorders, for example Niemann-Pick disease, type C (NPC).

Examples provided herein demonstrate the reduction of practice and the effectiveness of the compositions and methods of the present disclosure in the most established and well-characterized animal model of NPC.

In particular, according to a further aspect, the present disclosure provides compositions and methods for ameliorating, treating and/or preventing at least one symptom of cholesterol storage diseases or disorders (e.g., diseases associated with accumulated cellular cholesterol). In certain aspects, the present disclosure provides compositions and methods for ameliorating, treating, and/or preventing at least one symptom of Niemann-Pick disease, type C. In certain embodiments, the present disclosure relates to compositions and methods for ameliorating, treating, and/or preventing at least one symptom of cholesterol storage diseases or disorders that are characterized by or associated with a risk of diminution of central nervous system (CNS) function, for example NPC. In still other embodiments, the present disclosure relates to nucleic acid molecules encoding therapeutic transgenes, e.g., NPC1, which has been codon optimized for expression in humans and/or human cell lines, and is capable of restoring the function loss to one or more defective genes or polypeptide products thereof, e.g., a mutant NPC1 gene. In yet other embodiments, the disclosure relates to pharmaceutical compositions that are suitable for administering therapeutically effective amounts the nucleic acid molecules of the present disclosure. In still further embodiments, the present disclosure relates to methods for diagnosing NPC and/or monitoring the progress of gene therapy treatment of NPC by monitoring the expression and/or function of a therapeutic gene, e.g., NPC1.

According to yet a further aspect, the present disclosure relates to an engineered cell line that expresses (e.g., overexpresses) NPC1 protein, the cell line comprising the construct or gene therapy vector of the present disclosure comprising the $_{co}$NPC1 or the fusion protein of the present disclosure. In some embodiments, the protein produced from the engineered cell line may be utilized in at least one of: enzyme replacement therapy, to produce exosomes containing the NPC1 protein, or a combination thereof.

The present disclosure, in further embodiments, relates to methods of gene therapy involving administering in an effective amount a nucleic acid molecule comprising a therapeutic transgene, e.g., $_{co}$NPC1, in order to ameliorate, treat, and/or prevent at least one symptom of a cholesterol storage disease or disorder, such as NPC related to an NPC1 mutation. In still other embodiments, the present disclosure relates to methods of gene therapy involving administering, in an effective amount, an expression vector encoding $_{co}$NPC1 in order to ameliorate, treat, and/or prevent at least one symptom of a cholesterol storage disease or disorder, for example NPC disease. In yet other embodiments, the nucleic acid molecule and/or expression vector of the present disclosure may be selectively delivered to a target site or tissue, e.g., the central nervous system.

The nucleic acid molecules or gene therapy constructs in certain embodiments comprise one or more therapeutic transgenes, e.g., NPC1, which is codon optimized for expression in humans and is under the control of at least one genetic regulatory element, such as a promoter. In certain embodiments, the promoter is a tissue-specific promoter that is capable of being expressed in the CNS. In some embodiments, the promoter is a truncated EF1α promoter (EF1$\alpha_t$) (SEQ ID NO: 10). In other embodiments, the promoter is the mini EF1α promoter (SEQ ID NO: 51) or the short EF1α promoter, EF1α S (SEQ ID NO: 52).

The present disclosure also relates to specific nucleic acid molecules comprising a therapeutic transgene, e.g., $_{co}$NPC1, under transcriptional control of a promoter that is capable of being expressed in the CNS. The disclosure also contemplates that such nucleic acid constructs may be engineered into any suitable gene therapy vector, such as a retrovirus, lentivirus adenovirus, or AAV vector (e.g., the AAV vector can be of any serotype, including, but not limited to serotype 9, PHP.B or derivatives thereof, and Anc80 or derivatives thereof), nucleic acid such as plasmid DNA, peptide nucleic acids, or mRNA, including mRNAs that contain modified bases to enhance in vivo expression. All forms of nucleic acids can be delivered without further modification, such as naked DNA, or packaged into nanoparticles or lipid nanoparticles and delivered in an appropriate fashion to produce NPC1 expression. In a particular embodiment, the background gene therapy vector is an AAV. In a particular embodiment, a therapeutic exosome is administered to a subject, wherein the therapeutic exosome comprises at least one of the therapeutic transgene as described herein (e.g., coNPC1 gene, which may be translationally fused with at least one of a PTD, a tag moiety, or a combination thereof), NPC1 protein, or a combination thereof.

The foregoing and other features and advantages of the disclosure will become more apparent from the following detailed description and accompanying drawings. Those skilled in the art will appreciate that the utility of this disclosure is not limited to the specific experimental modes and materials described herein.

In a preferred embodiment, the present disclosure is directed to a nucleic acid construct for the expression of a therapeutic amount of NPC1 in a cell, the construct comprising a human codon-optimized NPC1 gene selected from the group consisting of SEQ ID NOs: 1-8.

In certain embodiments, the NPC1 is translationally fused to a protein transduction domain (PTD) to form a NPC1-

PTD fusion protein, wherein the fusion protein is capable of cross-correcting non-transformed neighboring cells.

The protein transduction domain can be HIV-Tat, transportin 10 (TP10), or TP2.

The $_{co}$NPC1 gene can be under the control of a promoter.

The promoter can be an E a truncated promoter (EF1$\alpha_t$).

The promoter can be a mini EF1α promoter (EF1α promoter).

The promoter can be a short EF1α promoter (EF1α S).

The NPC1 of the nucleic acid construct can be translationally fused to a FLAG®-tag moiety (e.g., 1×-FLAG® tag or 3×-FLAG® tag).

The nucleic acid construct can be expressed in a transduced cell and the neighboring cells, each of which can be neuronal cells.

The nucleic acid construct can comprises a nucleic acid sequence selected from the group consisting of SEQ ID NOS: 1-8.

An expression vector comprising a nucleic acid construct of the present disclosure can be capable of expressing the NPC1 protein, the NPC-PTD fusion protein, the NPC1-FLAG® tag fusion protein, the NPC1-PTD-FLAG® tag fusion protein, or the NPC1-FLAG® tag-PTD fusion protein in a cell.

A cell can comprise the expression vector, e.g., the cell can produce the expression vector and/or the cell can produce NPC1, such as a therapeutic exosome having NPC1 protein.

The expression vector can be used to treat Niemann-Pick disease, type C1 in a subject. The method can comprise administering a therapeutically effective amount of an expression vector comprising a nucleic acid molecule encoding an NPC1-PTD fusion protein, wherein the NPC1 gene is a human codon-optimized NPC1 gene selected from the group consisting of SEQ ID NOs: 1-8 and wherein the fusion protein is capable of cross-correcting non-transformed neighboring cells.

The PTD protein transduction domain can be HIV Tat, TP10, or TP2.

The NPC1 or fusion gene can be under the control of a promoter.

The promoter can be an EF$1_t$ promoter.

The NPC1 can be translationally fused to a FLAG®-tag moiety (e.g., a 1×-FLAG® tag or 3×FLAG® tag) to form a NPC1-FLAG® tag fusion protein, a NPC1-PTD-FLAG® tag fusion protein, or a NPC1-FLAG® tag-PTD fusion protein.

The cell transduced with the NPC1 gene or the fusion gene, and the neighboring cells can be neuronal cells.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the present disclosure may be utilized in numerous combinations, all of which are expressly contemplated by the present description. These additional advantages, objects and embodiments are expressly included within the scope of the present disclosure. The publications and other materials used herein to illuminate the background of the disclosure, and in particular cases, to provide additional details respecting the practice, are incorporated by reference in their entirety for all purposes.

BRIEF DESCRIPTION OF THE DRAWINGS

The following detailed description, given by way of example, but not intended to limit the disclosure solely to the specific embodiments described, may best be understood in conjunction with the accompanying drawings. Reference will now be made, by way of example, to the accompanying drawings which show example embodiments of the present disclosure.

FIG. 1A depicts a nucleotide sequence of codon optimized NPC1 (SEQ ID NO: 1).

FIG. 1B depicts a nucleotide sequence of codon optimized NPC1-Tat (SEQ ID NO: 2).

FIG. 1C depicts a nucleotide sequence of codon optimized NPC1-3×FLAG® tag (SEQ ID NO: 3).

FIG. 1D depicts a nucleotide sequence of codon optimized NPC1-TP10 (SEQ ID NO: 4).

FIG. 1E depicts a nucleotide sequence of codon optimized NPC1-TP2 (SEQ ID NO: 5).

FIG. 1F depicts a nucleotide sequence of codon optimized NPC1-3×FLAG® tag-TAT (SEQ ID NO: 6).

FIG. 1G depicts a nucleotide sequence of codon optimized NPC1-3×FLAG® tag-TP10 (SEQ ID NO: 7).

FIG. 1H depicts a nucleotide sequence of codon optimized NPC1-3×FLAG® tag-TP2) SEQ ID NO: 8.

FIGS. 2A-2D depict the results of a BLASTN sequence comparison between wildtype NPC1 (SEQ ID NO: 9) and the codon optimized NPC1 gene (SEQ ID NO: 1), in consecutive order from the 5' end to the 3' end. The sequence comparison starts at FIG. 2A, which shows the 5' end of the sequences, and continues in order from 5' in the direction of the 3' end of the sequences from FIG. 2A, to FIG. 2B, to FIG. 2C, and the 3' ends of the sequences are shown at the end of FIG. 2D.

FIG. 4C shows both the filipin staining and anti-FLAG tag antibody. Arrows indicate cells showing less accumulated filipin (less white) in cells that have been transfected. This demonstrates that the $_{co}$NPC1 expression via the $_{co}$NPC1-3×FLAG tag plasmid is effective at reducing/removing accumulated cellular cholesterol.

FIG. 4F shows both the filipin staining and anti-FLAG tag antibody. Arrows indicate cells showing less accumulated filipin (less white) in cells that have been transfected. This demonstrates that the $_{co}$NPC1 expression via the $_{co}$NPC1-3×FLAG tag plasmid is effective at reducing/removing accumulated cellular cholesterol.

FIG. 4I shows both the filipin staining and anti-FLAG tag antibody. Arrows indicate cells showing less accumulated filipin (less white) in cells that have been transfected. This demonstrates that the $_{co}$NPC1 expression via the NPC1-3×FLAG tag plasmid is effective at reducing/removing accumulated cellular cholesterol.

FIG. 4L shows both the filipin staining and anti-FLAG tag antibody. Arrows indicate cells showing less accumulated filipin (less white) in cells that have been transfected. This demonstrates that the $_{co}$NPC1 expression via the coNPC1-3×FLAG tag plasmid is effective at reducing/removing accumulated cellular cholesterol.

FIG. 4O shows both the filipin staining and anti-FLAG tag antibody. Arrows indicate cells showing less accumulated filipin (less white) in cells that have been transfected. This demonstrates that the $_{co}$NPC1 expression via the cNPC1-3×FLAG tag plasmid is effective at reducing/removing accumulated cellular cholesterol.

FIG. 4R shows both the filipin staining and anti-FLAG tag antibody. Arrows indicate cells showing less accumulated filipin (less white) in cells that have been transfected. This demonstrates that the $_{co}$NPC1 expression via the NPC1-3×FLAG tag plasmid is effective at reducing/removing accumulated cellular cholesterol.

FIG. 5C shows both showing both the filipin staining and anti-FLAG tag antibody. This shows that filipin is present in cells that have been transfected with hMITF-FLAG tag plasmid.

FIG. 5F shows both the filipin staining and anti-FLAG tag antibody. This shows that filipin is present in cells that have been transfected with hMITF-FLAG tag plasmid.

FIG. 5I shows both showing both the filipin staining and anti-FLAG tag antibody. This shows that filipin is present in cells that have been transfected with hMITF-FLAG tag plasmid.

FIG. 5L shows both the filipin staining and anti-FLAG tag antibody. This shows that filipin is present in cells that have been transfected with hMITF-FLAG tag plasmid.

FIGS. 5M-50 are enlarged microscopic images of the same field of well 3 in FIG. 3: U2OS-NPC1-null cells, four days post-transfection with hMITF-FLAG tag plasmid (as negative control). The areas in FIG. 5M showing accumulation of white particles are areas of filipin accumulation. The areas in FIG. 5N showing light gray and white accumulation are cells that highly expressed the MITF-FLAG tag after transfection with hMITF-FLAG tag plasmid, and the FLAG tag epitope has been detected by the anti-FLAG antibody.

FIG. 5R shows both showing both the filipin staining and anti-FLAG tag antibody. This shows that filipin is present in cells that have been transfected with hMITF-FLAG tag plasmid.

FIG. 6 is an image of a gel that demonstrates that human NPC1 knock-out cells (U2OS c cells) transfected with AAV mini EF1α coNPC1 3×FLAG tag (FIG. 8B), AAV mini EF1α-coNPC1-tat (FIG. 8C), AAV mini EF1α-coNPC1-TP10 (FIG. 8C), AAV mini EF1α-coNPC1-TP2 (FIG. 8C), AAV mini EF1α-coNPC1 3×FLAG tag-tat (FIG. 8D), and AAV mini EF1α-coNPC1 3×FLAG tag-TP2 (FIG. 8D) constructs produced robust expression of NPC1, which was comparable to Npc1 expression in wild-type mouse liver.

FIG. 7C shows less accumulated filipin in cells that express NPC1 protein indicated by arrow. This demonstrates that the $_{co}$NPC1 expression via the pAAV-EF1-intronS-coNPC1 plasmid is effective at reducing/removing accumulated cellular cholesterol.

FIG. 7F shows less accumulated filipin less accumulated filipin in cells that express NPC1 protein indicated by arrow. This demonstrates that the $_{co}$NPC1 expression via the pAAV-EF1-intronS-coNPC1 plasmid is effective at reducing/removing accumulated cellular cholesterol.

FIG. 7I shows less accumulated filipin less accumulated filipin in cells that express NPC1 protein indicated by arrow. This demonstrates that the $_{co}$NPC1 expression via the pAAV-EF1α S-intronS-coNPC1-TAT plasmid is effective at reducing/removing accumulated cellular cholesterol. Cross-correction is shown as bright specks in the top-right quadrant of FIG. 7I.

FIG. 9 is a schematic showing the differences between the first and second generation (top) AAV gene therapy vectors and the third and fourth generation (bottom) AAV gene therapy vectors. In the first and second generation vectors, the duplicated 59 base pair sequence from the wild-type ("WT") AAV2 vector is present, and the Inverted Terminal Repeats (shown as the '5 ITR and the '3 ITR) are 130 base pairs long (SEQ ID NO: 48). In the third and fourth generation vectors, the duplicated 59 base pair sequence (SEQ ID NO: 50) from the wild-type ("WT") AAV2 vector is deleted (shown as dotted lines). The third and fourth generation vectors further include a 30 base pair miscellaneous sequence and a 21 base pair miscellaneous sequence flanking the transgene, and the ITRs (shown as the '5 ITR and the '3 ITR) are 145 base pairs long (SEQ ID NO: 49).

Figure 10A:
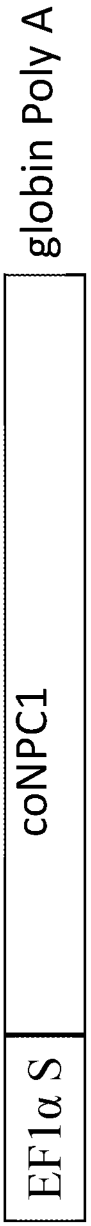
FIG. 10A is a schematic of the experimental design of a "third generation" vector which includes the short EF1α promoter, a codon-optimized NPC1 gene, and a rabbit beta globin gene polyA signal.
Figure 10B:
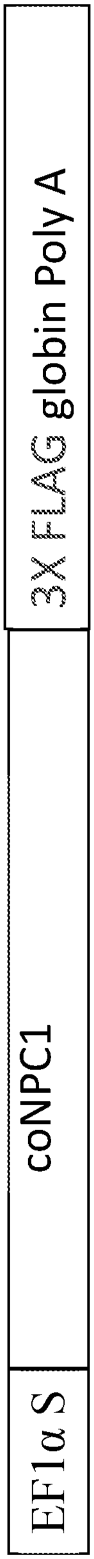
FIG. 10B is a schematic of the experimental design of a "third generation" vector which includes the short EF1α promoter, a codon-optimized NPC1 gene, a 3×FLAG tag moiety, and a rabbit beta globin gene polyA signal.
Figure 10C:
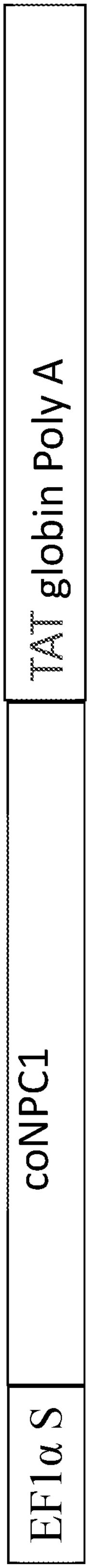
FIG. 10C is a schematic of the experimental design of a "third generation" vector which includes the short EF1α promoter, a codon-optimized NPC1 gene, a TAT protein transduction domain, and a rabbit beta globin gene polyA signal.
Figure 10D:
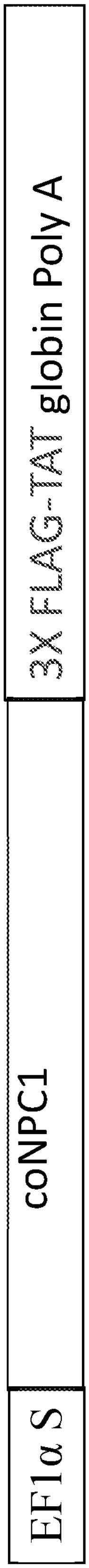

FIG. 10D is a schematic of the experimental design of a "third generation" vector which includes the short EF1α promoter, a codon-optimized NPC1 gene, a 3×FLAG tag moiety, a TAT protein transduction domain, anda rabbit beta globin gene polyA signal.

Figure 11A:
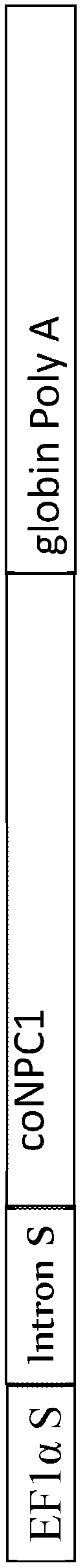

FIG. 11A is a schematic of the experimental design of a "fourth generation" vector which includes the short EF1α promoter, a synthetic intron ("Intron S"), a codon-optimized NPC1 gene, and a rabbit beta globin gene polyA signal.

Figure 11B:
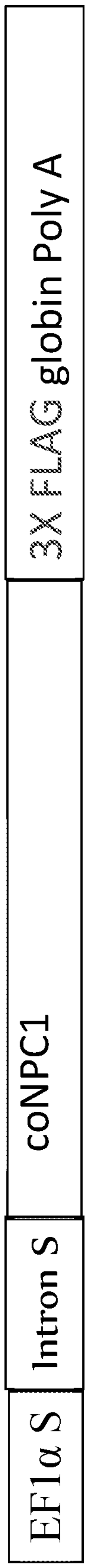

FIG. 11B is a schematic of the experimental design of a "fourth generation" vector which includes the short EF1α promoter, a synthetic intron ("Intron S"), codon-optimized NPC1 gene, a 3×FLAG tag moiety, and a rabbit beta globin gene polyA signal.

Figure 11C:
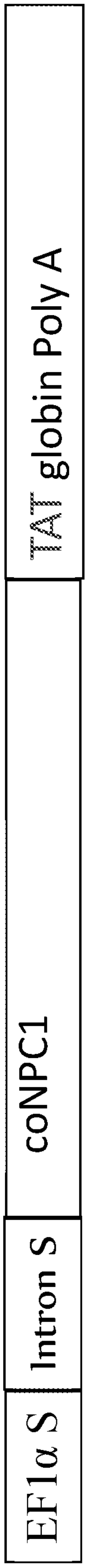

FIG. 11C is a schematic of the experimental design of a "fourth generation" vector which includes the short EF1α promoter, a synthetic intron ("Intron S"), a codon-optimized NPC1 gene, a TAT protein transduction domain, and a rabbit beta globin gene polyA signal.

DETAILED DESCRIPTION OF THE INVENTION

The present disclosure is directed, at least in part, to compositions and methods for ameliorating, treating, and/or preventing at least one symptom of a cholesterol storage disease or disorder, such as Niemann-Pick disease, type C ("NPC") caused by mutation or malfunction of the NPC1 enzyme, which is encoded by the NPC1 gene.

The present disclosure relates to a particular set of newly developed expression constructs for the therapeutic expression of NPC1 for treating Niemann-Pick disease, type C (NPC) caused as a result of mutations in the NPC1 gene.

Niemann-Pick disease, type C (NPC) is a rare and fatal, autosomal recessive, neurodegenerative disease that can present in infants, children, or adults, and which causes progressive neurological degeneration that ultimately leads to disability and premature death.

Approximately 95% of NPC patients have mutations in the NPC1 gene, which is a gene encoding a 1278 amino acid transmembrane protein that is involved in the intracellular trafficking of cholesterol. NPC1 patients typically exhibit an impairment in the esterification of low-density lipoprotein (LDL) cholesterol and reduced trafficking of unesterified cholesterol to the plasma membrane, thereby leading to an accumulation of cholesterol in the cells, and in particular, in neuronal tissues. Intracellular cholesterol levels may be detected/examined by filipin staining. That is, filipin staining is directly related to the level of cholesterol in a cell.

The inventors previously constructed a series of therapeutic adeno-associated virus (AAV) vectors for expressing the human NPC1 gene in cells, such as neurons, as a gene therapy based treatment for NPC1 disease, such as NPC related to an NPC1 mutation. Specifically, the inventors constructed and tested two AAV9-based vectors expressing the human NPC1 gene under control of either the EF1α or CamKII promoters and demonstrated in $Npc1^{-/-}$ mouse models that AAV-based gene therapy corrected mutant NPC1-based cholesterol accumulation and thus "represents a viable and efficacious therapeutic approach for NPC1 disease." See Chandler et al., "Systemic AAV9 gene therapy improves the lifespan of mice with Niemann-Pick disease, type C1," *Hum Mol Genet.* 1; 26(1):52-64 (January 2017), which is incorporated by reference herein.

The present disclosure describes a new set of improved AAV gene therapy vectors that contain a codon optimized NPC1 allele, referred to herein as second, third, and fourth generation vectors. The second and third generation vectors include: (1) codon optimized NPC1 allele to maximize human expression and enable detection of a unique nucleic acid sequence in a human or other specie; (2) a codon optimized NPC1 fused to a 3×FLAG®-tag to facilitate easy analysis of intracellular biodistribution of NPC1; (3) a codon optimized NPC1 fused to a protein transduction domain (e.g., TAT, TP10, and TP2) and a 3×FLAG®-tag to allow for cross-correction; and (4) a codon optimized NPC1 fused only to a protein transduction domain (e.g., TAT, TP10, and TP2) to allow for cross-correction. The fourth generation vectors further include a synthetic intron ("intron S," SEQ ID NO: 25).

The new set of improved AAV gene therapy vectors of the present disclosure may further contain a nucleotide sequence encoding an antibiotic resistance marker. The antibiotic resistance marker may be an ampicillin resistance marker or a kanamycin resistance marker.

In addition, the new vector constructs can utilize a truncated EF1α promoter ($EF1_t$), a mini EF1α promoter, or a short EF1α promoter, a stronger translation initiation site at the 5' end of NPC1 gene, and/or multiple stop signals to ensure maximal NPC1 gene expression and protein production in the cell.

In accordance with the present disclosure, each of the constructs was synthesized and tested for NPC1 expression in a human NPC1-null mutant cell. In addition, the ability of the expressed NPC1 variants to clear disease-associated cholesterol accumulation was tested using a filipin staining assay. At least one construct-mini EF1α-$_{co}$NPC1-3×FLAG® tag—was prepared as an AAV9 virus vector.

The constructs comprising NPC1 fused at their C-terminal ends to protein transduction domains (e.g., TAT, TP10, and TP2) have positive NPC1 expression in cells. According to this aspect, a cell abutting or touching the transduced cell would now also have the vector expressing NPC1 present because the protein transduction domain will pull the fusion protein from the cytosol across the cell membrane and then into contact with other local cells that were not directly transduced to transfer NCP1. In this way, the PTD fusion alleles of NPC1 may allow a cell that has not received the AAV viral genome to nevertheless have the expressed fusion enzyme present.

In accordance with the present disclosure, the "cross correction" or "trans-cellular correction" is aspect is an improvement on earlier NPC1 gene therapy approaches, which require individual cellular correction. The herein disclosed vector embodiments would allow cross correction of local or proximal cells not otherwise directly transformed by an expression vector and thereby increase the potency of the NPC1-based gene therapy approach. Cross-correction or trans-cellular correction can refer to the transfer of the allele and/or expressed therapeutic protein to neighboring cells that have not been directly transformed by an expression vector described here.

The present disclosure provides constructs that represent a new suite of therapeutic agents to treat human NPC1 deficiency and related conditions. The NPC1 alleles may be easily and uniquely detected in preclinical models and patients given that they are synthetic and easily tested. Furthermore, the vectors could be used to treat NPC1 deficiency by systemic or targeted gene delivery, including into the cerebral spinal fluid or brain structures-which are typically affected by NPC1 patients.

In certain aspects, compositions of the instant disclosure include one or more gene therapy vectors (e.g., AAV vectors of various serotypes, including but not limited to serotypes 9, PHP.B, Anc serotypes including Anc80, rh10 and related neuronotrophic capsids) comprising a therapeutic human nucleic acid molecule which is able to correct the cellular defect characteristic of certain cholesterol storage diseases or disorders, such as, Niemann-Pick disease type C ("NPC"). The gene therapy vectors comprise NPC1 alleles that are codon optimized in order to maximize human expression (coNPC1).

The alleles of the present disclosure may also be tagged in order to afford facile detection. For example, the tags can be used in biodistribution analysis. The alleles of the present disclosure may be fused with a tag (e.g., 1×FLAG® tag or 3×FLAG® tag). In other embodiments, the alleles of the present disclosure may be fused with a tag and a protein transduction domain, which allow for trans-cellular correction.

The gene therapy vectors in accordance with the present disclosure may comprise an improved and truncated promoter (EF1α t), and/or a stronger translation initiation site at the 5' end of NPC1. The gene therapy vectors of the present disclosure may comprise multiple stop signals, thereby ensuring maximal NPC1 gene expression and protein production in the cell.

The gene therapy vectors of the present disclosure may further contain a synthetic intron ("intron S," SEQ ID NO: 25), which may increase splicing and expression of the transgene.

The gene therapy vectors of the present disclosure may comprise full-length, wild type AAV inverted terminal repeats (ITRs) that flank the transgene. Besides the ITRs, the nucleic acid construct may be devoid of any other sequence from the wild-type AAV genome, which may lessen or eliminate genotoxicity of the vectors, as described in Logan et al., "Identification of liver-specific enhancer-promoter activity in the 3' untranslated region of the wild-type AAV2 genome," *Nat Genet.* 49(8):1267-1273 (August 2017), which is incorporated by reference herein.

In order to facilitate review of the various embodiments of the disclosure, the following definitions of terms and explanations of abbreviations are provided, as follows:

Definitions

The instant disclosure provides for the therapeutic or prophylactic use of gene therapy vectors to achieve treatment of subjects having or at risk of developing a cholesterol storage disease or disorder. In certain embodiments, the disclosure provides compositions and methods for ameliorating, treating, and/or preventing Niemann-Pick disease, type C1, either by delivery of the vector to the CNS in a targeted manner, or systemically, using a recombinant AAV viral vector (such as, but not limited to, serotypes 9, PHP.B, Anc80, and related capsids) that contain an NPC1 allele as described herein. In related embodiments, the codon optimized NPC1 allele as described herein is used to maximize human expression. In another embodiment, the codon optimized NPC1 described herein is fused to a tag, such as a 3×FLAG®-tag, which can be used to examine intracellular biodistribution of NPC1. In a further embodiment, the codon optimized NPC1 described herein may be fused to a protein transduction domain (e.g., Tat, TP10, and TP2) and/or a 3×FLAG®-tag to allow for cross-correction. In another embodiment, the codon optimized NPC1 of the present disclosure is fused to a protein transduction domain (e.g., Tat, TP10, and TP2) to allow for cross-correction.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

General Terms

In the claims, as well as in the specification above, all transitional phrases such as "comprising," "including," "carrying," "having," "containing," "involving," "holding," "composed of," and the like are to be understood to be open-ended, i.e., to mean including but not limited to. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or", as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "obtaining" is understood herein as manufacturing, purchasing, or otherwise coming into possession of.

As used herein, "kits" are understood to contain at least the non-standard laboratory reagents of the present disclosure and one or more non-standard laboratory reagents for use in the methods of the disclosure.

The terms "about" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Terms Relating to NPC

The term Niemann-Pick disease, Type C or abbreviated as "NPC," refers to the disorder as it is known in the medical art, and is distinct from Type A or B. NPC patients are not able to metabolize cholesterol and other lipids properly within the cell. Consequently, excessive amounts of cholesterol accumulate within the liver and spleen and excessive amounts of other lipids accumulate in the brain. NPC causes a secondary reduction of ASM (acid sphingomyelinase) activity such as is characteristic of Type A and B. Type C Niemann-Pick disease has an estimated 500 cases diagnosed worldwide. It is believed, however, that the number of people affected by NPC is much higher, but diagnostic difficulties do not allow an accurate assessment of the population indicence. NPC has been initially diagnosed as a learning disability, mild retardation, "clumsiness," and delayed development of fine motor skills. It is not uncommon for a family to spend several years seeking a diagnosis before NPC is identified. NPC is always fatal. The majority of children with NPC die before age 20 (many die before the age of 10). Late onset of symptoms can lead to longer life spans, but it is extremely rare for any person with NPC to reach age 40. A recent study based on genomic analyses suggests the incidence of infantile onset NPC is 1:90,000, but when all forms are considered, including the adult onset variants, the disease may be as common as 1/19,000-1/36,000. There is currently no curative therapy for any form of NPC disease.

The term "NPC1" refers to the wildtype NPC1 gene or protein, various mutant forms of which are associated with Niemann-Pick Type C disease by leading to the accumulation of intracellular unesterified cholesterol. For convenience, the human gene is referred to as hNPC1 or NPC1 and the murine gene as mNPC1 or Npc1 (this same nomenclature is also used to distinguish between the human and murine cDNAs and proteins). Where no "h" or "m" designation is given, reference to the human NPC1 gene generally is intended. The definition of an NPC1 gene includes the various sequence polymorphisms that exist in the species in question, i.e., the term "hNPC1" or a wildtype hNPC1 encompasses all various sequence polymorphisms in humans.

The NPC1 protein or a derivative may be functionally characterized by its ability, when expressed in NPC cells, to correct the lysosomal cholesterol accumulation phenotype that is characteristic of such cells. Thus, "NPC1 protein biological activity" refers to the ability of a protein to correct the lysosomal cholesterol accumulation phenotype that is characteristic of NPC cells.

A "wildtype NPC1 protein" refers to any protein encoded by a wild-type gene that is capable of having normal (level of function absent disease or disorder) biological activity when expressed or introduced in vivo. Such functionality can be tested by any means known to establish functionality of a protein.

The term "NPC1 derivative gene," which can include a "mutant NPC1 gene" or a codon optimized NPC1", refers to any non-wildtype NPC1 sequence. Typically, a "mutant NPC1 gene" refers to a non-wildtype sequence that results in an aberrant functioning NPC1 protein, and thus, NPC disease. However, the term "NPC1 derivative gene" is meant to be broad enough to encompass an NPC1 mutant gene, but also any other NPC1 gene carrying a genetic change that may result an NPC1 protein having any of an increase, a decrease, or no change in activity as compared to the wildtype protein.

The term "NPC1 protein, derivative, or functional variant thereof," which can include a "mutant NPC1 protein" or a "codon optimized NPC", refers to any non-wildtype NPC1 sequence or fragment thereof. Typically, a "mutant NPC1 protein" refers to a non-wildtype NPC1 polypeptide that has an aberrant function as compared to a wildtype NPC1 protein, and which results in NPC1 disease. However, the term "NPC1 protein, derivative, or functional variant thereof" is meant to be broad enough to encompass an NPC1 mutant protein, but also any other NPC1 protein carrying a genetic change (including a fragment) that may result an NPC1 protein having any of an increase, a decrease, or no change in activity as compared to the wildtype NPC1 protein. In the case of the present disclosure, the "NPC1 protein, derivative, or functional variant thereof" can also refer to homologous NPC1 proteins from non-human sources, e.g., mouse, monkey, horse, rabbit, and the like.

"Codon optimization" refers to the process of altering a naturally occurring polynucleotide sequence to enhance expression in the target organism, e.g., humans. As described herein, the human NPC1 gene can be altered to replace codons that occur less frequently in human genes with those that occur more frequently and/or with codons that are frequently found in highly expressed human genes. This method involves determining the relative frequency of a codon in the protein-encoding genes in the human genome. For example, isoleucine can be encoded by AUU, AUC, or AUA, but in the human genome, AUC (47%), AUU (36%), and AUA (17%) are variably used to encode isoleucine in proteins. Therefore, in the proper sequence context, AUA would be changed to AUC to allow this codon to be more efficiently translated in human cells. However, any known technique for codon optimization for expression may be utilized.

The term "NPC sufferer" or "NPC homozygote" refers to a person who carries a mutant NPC1 or NPC2 gene, such that the person exhibits clinical symptoms of Niemann-Pick type C disease.

The term "NPC carrier" or "NPC heterozygote" refers to a person who does not exhibit clinical symptoms of NPC, but who carries one mutant form of the NPC1 or NPC2 gene and may transmit this mutant gene to progeny.

As used herein, the term "cholesterol storage disease or disorder" is meant to refer to a disease or disorder of or related to cholesterol metabolism, optionally that is treatable via use of gene therapy for delivery of NPC to a subject. Exemplary "cholesterol storage disease or disorders" include but are not limited to Niemann-Pick disease, type C1. Whether cholesterol storage and related pathophysiology may be impacted by NPC1 function in other conditions is certain and extends the utility of NPC directed therapies, specifically NPC1 gene therapy, toward other more common disorders in the future. For example, a subset of neuropsychiatric disorders, such as dementia, seizures, and atherosclerotic brain disease might to be influenced by or improved after cholesterol reduction mediated by NPC1 activity and as such, these groups of patients might be candidates for NPC1 viral gene therapy.

Terms Relating to Molecular Biology

In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization; B. D. Hames & S. J. Higgins eds. (1985); Transcription And Translation; [B. D. Hames & S. J. Higgins, eds. (1984); Animal Cell Culture; R. I. Freshney, ed. (1986); Immobilized Cells And Enzymes; IRL Press, (1986); B. Perbal, A Practical Guide To Molecular Cloning (1984); F. M. Ausubel et al. (eds.), Current Protocols in Molecular Biology, John Wiley & Sons, Inc. (1994).

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein, may be associated with other proteins or nucleic acids, or both, with which it associates in the cell, or with cellular membranes if it is a membrane-associated protein. In a specific embodiment, an isolated NPC1 protein is a recombinant NPC1 protein expressed from an expression vector. An isolated material may be, but need not be, purified.

As used herein, the term "cDNA" (complementary DNA) refers to a piece of DNA lacking internal, non-coding segments (introns) and regulatory sequences that determine transcription. cDNA can be synthesized in the laboratory by reverse transcription from messenger RNA extracted from cells.

As used herein, the term "ORF" (open reading frame) refers to a series of nucleotide triplets (codons) coding for amino acids without any termination codons. These sequences are usually translatable into a peptide, such as $_{co}$NPC1 or a fusion protein comprising the same.

As used herein, the term "ortholog" refers to two nucleotide sequences that share a common ancestral sequence and diverged when a species carrying that ancestral sequence split into two species. Ortholgous sequences are also homologous sequences.

As used herein, the terms "probes" and "primers" refers to oligonucleotide sequences that may readily be prepared based on the nucleic acids provided by this disclosure. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987). "Primers" are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the human NPC1 cDNA or gene will anneal to a-target sequence such as an NPC1 gene homolog from rat contained within a genomic rat genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the NPC1 cDNA or gene sequences.

The present disclosure thus includes isolated nucleic acid molecules that comprise specified lengths of the disclosed NPC1 DNA (or cDNA) or gene sequences. Such molecules may comprise at least 20, 25, 30, 35, 40 or 50 consecutive nucleotides of these sequences and may be obtained from any region of the disclosed sequences.

As used herein, a "vector" nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. A vector may include a "gene transfer vector," "gene therapy vector," or "gene therapy construct," or similar terms, which refer to specific vector constructs that are suitable to conduct gene transfer to administer a desired gene.

The terms "vector," "cloning vector," and "expression vector" mean the vehicle by which an ASM DNA or RNA sequence (e.g., a foreign gene) can be introduced into a host cell so as to transform the host and promote expression (e.g., transcription and translation) of the introduced sequence. Vectors include any genetic element, such as a plasmid, phage, transposon, cosmid, chromosome, virus, virion, etc., which is capable of replication when associated with the proper control elements and which can transfer ASM gene sequences between cells. Thus, the term includes cloning and expression vehicles, as well as viral vectors.

As used herein, the term "expression system" means a host cell and compatible vector under suitable conditions, e.g., for the expression of a coNPC1 protein coded for by foreign DNA carried by the vector and introduced to the host cell. Common expression systems include *E. coli* host cells and plasmid vectors, insect host cells such as Sf9, Hi5 or S2 cells and Baculovirus vectors, and expression systems, and mammalian host cells and vectors. The term "expression system" also may refer to a suitable gene therapy vector, which may be delivered by any means, including ex vivo and in vivo methods.

The term "host cell" means any cell of any organism that is selected, modified, transformed, grown, or used or manipulated in any way, for the production of a substance by the cell, for example the expression by the cell of a human ASM gene, including a DNA or RNA sequence, or the NPC1 enzyme. Host cells can further be used for preliminary evaluation of other assays. A "recombinant DNA molecule" is a DNA molecule that has undergone a molecular biological manipulation or engineering. In one embodiment of the disclosure, the host cell is a fibroblast.

A "gene" is a sequence of nucleotides that code for a "gene product". Generally, a gene product is a protein. However, a gene product can also be another type of molecule in a cell, such as an RNA (e.g., a tRNA or a rRNA). For the purposes of the present disclosure, a gene product also refers to an mRNA sequence which may be found in a cell. As used herein, a gene can refer to the nucleotide sequences encoding wild-type or mutant or codon-optimized NPC1 gene.

As used herein, a "transformed cell" is a cell into which has been introduced a nucleic acid molecule by molecular biology techniques or gene therapy techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration and includes both in vitro and in vivo conditions.

As used herein, the term "purified" does not require absolute purity; rather, it is intended as a relative term. Thus, for example, a purified NPC1 protein preparation is one in which the NPC1 protein is more pure than the protein in its natural environment within a cell. Preferably, a preparation of an NPC1 protein is purified such that the NPC1 protein represents at least 50% of the total protein content of the preparation.

As used herein, the term "operably linked" refers to where a first nucleic acid sequence (e.g., an NPC1 gene) is operably linked with a second nucleic acid sequence (e.g., a promoter sequence, protein transduction domain gene, and/or a tag, such as a 3×FLAG®-tag) when the first nucleic acid sequence is placed in a functional relationship with the second nucleic acid sequence. For instance, a promoter is operably linked to a coding sequence if the promoter affects the transcription or expression of the coding sequence and two genes are operably linked when they are expressed together to make a fusion protein. Generally, operably linked DNA sequences are contiguous and, where necessary to join two protein coding regions, in the same reading frame.

As used herein, the term "recombinant nucleic acid" is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

As used herein, the term "sequence identity" refers to the similarity between two nucleic acid sequences, or two amino acid sequences and is expressed in terms of the similarity between the sequences, otherwise referred to as sequence identity. Sequence identity is frequently measured in terms of percentage identity (or similarity or homology); the higher the percentage, the more similar the two sequences are. Homologs of the human and mouse NPC1 proteins will possess a relatively high degree of sequence identity when aligned using standard methods.

Methods of alignment of sequences for comparison are well-known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI online site under the "BLAST" heading. A description of how to determine sequence identity using this program is available at the NCBI online site under the "BLAST overview" subheading.

Homologs of the disclosed NPC1 and NPC2 proteins are typically characterized by possession of at least 70% sequence identity counted over the full length alignment with the disclosed amino acid sequence of either the human or mouse NPC1/NPC2 sequences using the NCBI Blast 2.0, gapped blastp set to default parameters. Proteins with even greater similarity to the reference sequences will show increasing percentage identities when assessed by this method, such as at least 75%, at least 80%, at least 90% or at least 95% sequence identity. When less than the entire sequence is being compared for sequence identity, homologs will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI online site under the "Frequently Asked Questions" subheading. One of skill in the art will appreciate that these sequence identity ranges are provided for guidance only; it is entirely possible that strongly significant homologs could be obtained that fall outside of the ranges provided. The present disclosure provides not only the peptide homologs are described above, but also nucleic acid molecules that encode such homologs, such as those generated by codon optimization. In an embodiment, changing the nucleotide sequence on the corresponding codons will generate a synthetic NPC1 or NPC2 gene that would have improved translation efficiency and detection in the presence of the endogenous gene.

One indication that two nucleic acid sequences are substantially identical is that the polypeptide which the first nucleic acid encodes is immunologically cross reactive with the polypeptide encoded by the second nucleic acid (e.g., a human NPC1 protein and an NPC1 homolog from another species, or a variant human NPC1 protein).

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993) and are otherwise known in the art.

Terms Relating to Gene Therapy

The term "gene therapy" refers to a method of changing the expression of an endogenous gene by exogenous administration of a gene, i.e., a wildtype or mutant or codon-optimized NPC1 gene. As used herein, gene therapy also refers to the replacement of a defective NPC1 gene, or replacement of a missing NPC1 gene, by introducing a functional gene (e.g., codon-optimized gene) or portion of a gene corresponding to the defective or missing NPC1 gene into somatic or stem cells of an individual in need. Gene therapy can be accomplished by "ex vivo" methods, in which differentiated or somatic stem cells are removed from the individual's body followed by the introduction of a normal copy of the defective gene into the explanted cells using a viral vector as the gene delivery vehicle. In addition, in vivo transfer involves direct gene transfer into cells in the individual in situ using a broad range of viral vectors (e.g., AAV9 or Anc80), liposomes, exosomes, nanoparticles, protein:DNA complexes, modified nucleic acids or naked DNA in order to achieve a therapeutic outcome.

The term "transgene" refers to a polynucleotide that is introduced into a cell and is capable of being expressed under appropriate conditions and confers a desired property to a cell into which it was introduced, or otherwise leads to a desired therapeutic outcome.

The terms "genome particles (gp)," or "genome equivalents," or genome copies (gc) as used in reference to a viral titer, refer to the number of virions containing the recombinant AAV DNA genome, regardless of infectivity or functionality. The number of genome particles in a particular vector preparation can be measured by procedures such as described elsewhere herein, or for example, in Clark et al. (1999) *Hum. Gene Ther.,* 10:1031-1039; Veldwijk et al. (2002) *Mol. Ther.,* 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.,* 62:1963-1973.

The term "transducing unit (tu)" as used in reference to a viral titer, refers to the number of infectious recombinant AAV vector particles that result in the production of a functional transgene product as measured in functional assays such as described elsewhere herein, or for example, in Xiao et al. (1997) *Exp. Neurobiol.,* 144:113-124; or in Fisher et al. (1996) *J. Virol.,* 70:520-532 (LFU assay).

Terms Relating to Therapeutic Application

The present disclosure further provides compositions and methods for ameliorating, treating, and/or preventing at least one symptom of a cholesterol storage disease or disorder, such as Niemann-Pick disease, type C caused by mutation or malfunction of the NPC1 enzyme which are encoded by the NPC1 gene.

The present disclosure relates to a particular set of newly developed expression constructs for the therapeutic expression of NPC1 for ameliorating, treating, and/or preventing at least one symptom of Niemann-Pick disease, type C ("NPC") caused as a result of mutations to the NPC1 gene.

As used herein, the term "administering" is meant to refer to a means of providing the composition (e.g., to the subject in a manner that results in the composition being inside the subject's body. Such an administration can be by any route including, without limitation, subcutaneous, intradermal, intravenous, intra-arterial, intraperitoneal, sublingual, buccal, and intramuscular. In certain embodiments, the delivery may be appropriate for CNS delivery, e.g., epidural, intracerebral, or intracerebroventricular.

The present disclosure provides a number of compositions (e.g., sequences and vectors) that are useful for the development of highly specific drugs or biologics to treat or prevent a disease or disorder in a subject, as further characterized by the methods delineated herein. In addition, the methods of the present disclosure provide a facile means to identify therapies that are safe for use in subjects. Other disorders that can feature cholesterol storage are contemplated, including adult forms of dementia and conditions that may be caused, in part, by diminished activity of NPC1.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.,* 15th Ed. (Mack Publ. Co., Easton (1975)).

A "subject" or "patient" is a human or an animal that has developed, or is likely to develop NPC disease, more particularly a mammal, preferably a rodent or a primate, and most preferably a human. In one embodiment, the patient is a member of the Ashkenazi Jewish population who has been diagnosed with, or who has been identified as having an increased risk of developing NPC disease due to inherited mutations in the NPC1 or NPC2 gene. In another embodiment, the patient is a member of the French Canadian population of Nova Scotia, an inhabitant of the Maghreb region (Tunisia, Morocco, Algeria) of North Africa, or a member of the Spanish-American population of southern New Mexico and Colorado. However, Niemann-Pick disease is pan-ethnic, and the term subject encompasses anyone in the world having, or genetically at risk of developing, NPC disease. The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Ameliorate", "ameliorating", "amelioration", or the like, refers to decreasing, suppressing, attenuating, diminishing, arresting, or stabilizing the development or progression of a disease.

"Treatment", or "treating" as used herein, is defined as the application or administration of a therapeutic agent (e.g., an AAV-coNPC1 vector) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. In the context of the present disclosure, the symptoms that may be alleviated can include, but are not limited to, the accumulation of sphingomyelin in reticuloendothelial lysosomes, which results in hepatosplenomegaly, psychomotor retardation, pulmonary abnormalities, progressive neurodegeneration. In some instances, treatment will prevent death resulting from NPC disease.

The term "prevention" refers to the prevention of the onset of the disease, which means to prophylactically interfere with a pathological mechanism that results in the disease. In the context of the present disclosure, such a pathological mechanism can be an increase expression of mutant NPC1 or NPC2.

The terms "effective dose" or "effective dosage" or "therapeutically effective amount" are defined as an amount sufficient to achieve or at least partially achieve the desired effect. The term "therapeutically effective dose" is defined as an amount sufficient to cure or at least partially arrest the disease and its complications in a patient already suffering from the disease or prevent the disease prophylactically. The term "patient" includes human and other mammalian subjects that receive either prophylactic or therapeutic treatment. As it pertains to the instant disclosure, the term "therapeutically effective amount" also is used herein to mean an amount or dose of a gene therapy vector encoding NPC1 (or a mutant or functional variant thereof) sufficient to increase the level of NPC1 activity over the mutant or defective level to about 3-5%, preferably by about 10%, and more preferably by about 30%, or about 40%, or about 50%, or about 60%, or about 70%, or about 80%, or about 90%, or about 95%, or even up to 100% of the level found in normal cells. Preferably, a therapeutically effective amount can ameliorate or prevent a clinically significant deficit in NPC1 in the subject. Alternatively, a therapeutically effective amount is sufficient to cause an improvement in a clinically significant condition/symptom in the subject, e.g., amelioration of progressive neurodegeneration in Type C NPD patients.

Certain methodologies of the instant disclosure include at least one step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a gene therapy methodology, as described herein. For example, a transcription rate, mRNA level, translation rate, protein level, biological activity, cellular characteristic or property, genotype, phenotype, etc. can be determined prior to introducing an AAV or other vector of the disclosure into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Other definitions appear in context throughout the disclosure.

Gene Therapy Vectors

In one aspect, the present disclosure relates to gene therapy vectors or constructs comprising NPC1 genes, or derivatives and/or mutants thereof (e.g., NPC1 gene that is codon modified to enhance or improve NPC1 protein expression in a subject, such as a human), which are operably linked to at least a promoter element that is capable of being expressed in a tissue of the central nervous system.

In one embodiment, the present disclosure relates nucleic acid constructs for the expression of a therapeutic amount of NPC1 (e.g., $_{co}$NPC1) in a cell.

In another embodiment, the nucleic acid construct or gene therapy vector comprise a human codon-optimized NPC1 gene. For example, the nucleic acid construct or gene therapy vector can comprise a NPC1 codon optimized nucleic acid sequence selected from the group consisting of SEQ ID NOs: 1-8. For example, the nucleic acid construct or gene therapy vector can comprise a nucleic acid sequence selected from the group consisting of SEQ ID NOs: 1-8.

In another embodiment, the NPC1 is translationally fused to a protein transduction domain (PTD) gene (such as, HIV-tat, TP10, or TP2) to form a $_{co}$NPC1-PTD fusion protein. In other embodiments, the $_{co}$NPC1 is translationally fused to a tag (e.g., a 1×FLAG®-tag or a 3×FLAG®-tag) to form a NPC1-tag fusion protein (e.g., coNPC1-1×FLAG® tag or $_{co}$NPC1-3×FLAG® tag). The coNPC1 can be translationally fused to a PTD gene and a tag to form a coNPC1-PTD-FLAG® tag or $_{co}$NPC1-FLAG® tag-PTD fusion protein, wherein the fusion protein is capable of cross-correcting non-transformed neighboring cells.

In an embodiment, at least one of the cell, the neighboring cells, or both, are neuronal cells.

In an embodiment, the NPC1 gene may be under the control of a promoter, wherein the promoter is a truncated EF1 promoter ($EF1_t$ promoter) or a mini EF1 promoter (EF1α promoter), or the EF1 short promoter (EF1α s).

In an embodiment, the nucleic acid construct comprises an expression cassette comprising a nucleotide sequence selected from the group consisting of SEQ ID NOs: 26-38.

In an embodiment, the gene therapy vector may comprise shortened or full-length, wild type AAV inverted terminal repeats (ITRs) that flank the transgene. In an embodiment, besides the ITRs, the nucleic acid construct may be devoid of any other sequence from the wild-type AAV genome.

In an embodiment, the shortened or full-length AAV ITRs are AAV2 ITRs. In a particular embodiment, the shortened or full-length AAV ITRs each comprise the nucleotide sequence of SEQ ID NO: 48. In another particular embodiment, the shortened or full-length AAV ITRs each comprise the nucleotide sequence of SEQ ID NO: 49.

In an embodiment, the coNPC1 protein, the $_W$NPC1-PTD fusion protein and NPC1-tag fusion protein can be included in a vector, more particularly, in an expression cassette, with a synthetic intron sequence (SEQ ID NO: 25) which may enhance expression by providing more effective splicing of the transgene as compared to a vector which does not comprise the synthetic intron sequence.

In an embodiment, the NPC1 gene is under the control of a promoter, and the Intron S is positioned between the promoter and the NPC1 gene. In a particular embodiment, the Intron S comprises the nucleotide sequence of SEQ ID NO: 25.

In an embodiment, the nucleic acid construct may further comprise a nucleotide sequence encoding an antibiotic resistance marker. In an embodiment, the antibiotic resistance marker is an ampicillin resistance marker. In another embodiment, the antibiotic resistance marker is a kanamycin resistance marker.

In an embodiment, the nucleic acid construct comprises an expression vector which is capable of expressing the NPC1 protein, the NPC1-PTD fusion protein, or the NPC1 fusion protein, optionally comprising a tag moiety.

In an embodiment, the invention comprises a cell comprising the expression vector, wherein the cell produces the expression vector and/or the cell expresses the NPC1 protein.

In an embodiment, the invention comprises a method of ameliorating, treating, or preventing Niemann-Pick disease, type C1 in a subject, the method comprising administering a therapeutically effective amount of an expression vector to at least one cell, the expression vector comprising a nucleic acid molecule comprising a human codon-optimized NPC1 gene, wherein the expression vector is effective at of ameliorating, treating, or preventing at least one symptom of Niemann-Pick disease, type C1 in the subject.

In an embodiment, the NPC1 of the inventive method is translationally fused to a PTD to form a NPC1-PTD fusion protein, wherein the NPC1-PTD fusion protein is capable of cross-correcting non-transformed neighboring cells. In particular embodiments, the PTD protein transduction domain may be HIV-Tat, TP10, or TP2.

In an embodiment, the N PCI gene of the inventive method is under the control of a promoter. In embodiments, the promoter may be a truncated EF1α promoter (EF1α promoter) or a mini EF1α promoter (EF1α promoter), or the short EF1α promoter (EF1α S).

In an embodiment, the NPC1 gene of the inventive method may be translationally fused to a tag moiety to form a NPC1-tag fusion protein, a NPC1-PTD-tag fusion protein, or a NPC1-tag-PTD fusion protein.

In an embodiment, the nucleic acid molecule of the inventive method comprises a nucleic acid sequence selected from the group consisting of SEQ ID NO: 1-8.

In an embodiment, the expression vector of the inventive method may comprise an expression cassette, with a synthetic intron sequence (SEQ ID NO: 25), which sequence may enhance expression by providing more effective splicing of the transgene as compared to the gene therapy vector which does not comprise the synthetic intron sequence. In an embodiment, the NPC1 gene of the inventive method is under the control of a promoter, and the Intron S is positioned between the promoter and the NPC1 gene. In a particular embodiment, the Intron S comprises the nucleotide sequence of SEQ ID NO: 25.

In a further embodiment, the inventive method comprises a nucleic acid construct comprising an expression cassette comprising a nucleotide sequence selected from the group consisting of SEQ ID NOs: 26-38.

In an embodiment, the expression vector of the inventive method may comprise first and second full-length, wild type AAV inverted terminal repeats (ITRs) that flank the transgene. In an embodiment, besides the ITRs, the nucleic acid construct may be devoid of any other sequence from the wild-type AAV genome. In an embodiment, the first and second AAV ITRs are AAV2 ITRs. In a particular embodiment, the first and second AAV ITRs each comprise the nucleotide sequence of SEQ ID NO: 48. In another particular embodiment, the first and second AAV ITRs each comprise the nucleotide sequence of SEQ ID NO: 49.

In an embodiment, inventive method may further comprise a nucleotide sequence encoding an antibiotic resistance marker. In an embodiment, the antibiotic resistance marker is an ampicillin resistance marker. In another embodiment, the antibiotic resistance marker is a kanamycin resistance marker.

In an embodiment, the nucleic acid construct may comprise first and second AAV ITRs, the human codon-optimized NPC1 gene, and one or more of a nucleotide sequence encoding a PTD, a promoter, an Intron S, and a nucleotide sequence encoding a tag, wherein the NPC1 gene and all of the one or more of the nucleotide sequence encoding the PTD, the promoter, and the nucleotide sequence encoding the tag are positioned between the first and second AAV ITRs. In another embodiment, the nucleic acid construct may comprise first and second AAV ITRs, the human codon-optimized NPC1 gene, and all of a nucleotide sequence encoding a PTD, a promoter, an Intron S, and a nucleotide sequence encoding a tag, wherein the NPC1 gene and all of the one or more of the nucleotide sequence encoding the PTD, the promoter, and the nucleotide sequence encoding the tag are positioned between the first and second AAV ITRs.

In one embodiment, the fusion protein is capable of cross-correcting non-transformed neighboring cells, such as neuronal cells.

In certain embodiments, the gene therapy vectors or constructs comprise an NPC1 gene, or a derivative and/or mutant NPC1 gene. The NPC1 gene, including any derivatives and/or mutants thereof, can encode a codon optimized NPC1 polypeptide, as described herein, as well as any functional fragment or variants thereof. The variants or functional fragments of the codon optimized NPC1 may have increased or decreased activity as compared to a wildtype NPC1 protein, or the activity may be unchanged.

The NPC1 nucleotide sequences comprising a coding region for NPC1 proteins may be obtained from any source, including human, mouse, horse, pig, monkey, and the like.

The nucleotide sequences encoding NPC1, and NPC1 homologs from species other than human, are generally known in the art and can be obtained from public sequence repositories, including, for example, GenBank. In particular, cDNA sequences encoding NPC1 proteins (or variants thereof) may also be obtained from public sequence repositories such as GenBank.

For example, the following NPC1 sequences (or any variants comprising or genetically modified to comprise any mutations that encode a functional variant NPC1) that have been codon optimized for expression in humans are contemplated for use in the gene therapy constructs of the present disclosure:

- GenBank Accession No. BC063302 (*Homo sapiens* Niemann-Pick disease, type C1, mRNA (cDNA clone), which provides the NPC1 cDNA coding sequence SEQ ID NO: 9) and the NPC1 polypeptide amino acid sequence (SEQ ID NO: 41);
- GenBank Accession No. BC117178 (*Homo sapiens* NPC1 (Niemann-Pick disease, type C1, gene)-like 1 mRNA (cDNA clone), which provides a variant NPC1 cDNA coding sequence (SEQ ID NO: 11) and NPC1 polypeptide amino sequence (SEQ ID NO: 42);
- GenBank Accession No. BC143756 (*Homo sapiens* NPC1 (Niemann-Pick disease, type C1, gene)-like 1, mRNA (cDNA clone), which provides a variant NPC1 cDNA coding sequence (SEQ ID NO: 12) and NPC1 polypeptide amino sequence (SEQ ID NO: 43);
- GenBank Accession No. AF258783.1 (*Felis catus* Niemann-Pick type C1 disease protein (NPC1) mRNA, complete cds) which provides cat NPC1 cDNA coding sequence (SEQ ID NO: 13) and cat NPC1 polypeptide amino sequence (SEQ ID NO: 44);
- GenBank Accession No. BC054539 (Mouse Npc1 (Niemann-Pick disease, type C1, gene) mRNA (cDNA clone), which provides mouse Npc1 cDNA coding sequence and mouse NPC1 polypeptide amino sequence (SEQ ID NO: 45);
- GenBank Accession No. BC151276 (Bovine NPC1 (Niemann-Pick disease, type C1, gene) mRNA (cDNA clone), which provides bovine NPC1 cDNA coding sequence (SEQ ID NO: 15) and bovine NPC1 polypeptide amino sequence (SEQ ID NO: 46); and
- GenBank Accession No. BC090541 (Zebrafish NPC1 (Niemann-Pick disease, type C1, gene) mRNA (cDNA clone), which provides Zebrafish NPC1 cDNA coding sequence (SEQ ID NO: 16) and Zebrafish NPC1 polypeptide amino sequence (SEQ ID NO: 47).

The disclosed subject matter further encompasses any NPC1 gene and/or polypeptide sequence not expressly indicated here, but which is publicly available at the time of the present disclosure, or which becomes available after the time of the disclosure.

In preferred embodiments, the transgene encodes a biologically active molecule, expression of which in the subject, e.g., in the CNS of a subject, results in at least partial correction of the cholesterol storage disease or disorder, for example, Niemann-Pick disease, Type C. In some embodiments, the transgene encodes NPC1 (or a functional variant and/or fragment thereof) that has been codon optimized for expression in a subject, such as a human. The genomic and functional mRNA, cDNA and corresponding polypeptide sequences of human, mouse, or other species NPC1 genes and proteins are known, as indicated above, and in particular are available as GenBank Accession Nos.: NM_000271.4 (SEQ ID NO: 17); NM_008720.2 (SEQ ID NO: 18); NM_006432.3 (SEQ ID NO: 19); NM_023409.4 (SEQ ID NO: 20); and corresponding polypeptides NP_000262.2 (SEQ ID NO: 21); NP_032746.2 (SEQ ID NO: 22); NP_006423.1 (SEQ ID NO: 23); and NP_075898.1 (SEQ ID NO: 24).

Nucleotide sequences encoding NPC1 genes (or variants thereof) may be obtained by any known molecular biology technique, including by cloning, synthesis, or PCR amplification. Oligonucleotides for using in amplification reactions and/or probes for use in gene cloning may be synthesized or otherwise obtained by any known means and based on the nucleotide sequences that flank the desired gene or coding region encoding the NPC1 target genes. Methods and techniques for gene cloning and/or PCR amplification are well known in the art and are discussed elsewhere herein.

The gene therapy constructs described herein also comprise a vector (or gene therapy expression vector) into which the gene of interest (e.g., codon optimized NPC1) is cloned or otherwise which includes the gene of interest in a manner such that the nucleotide sequences of the vector allow for the expression (constitutive or otherwise regulated in some manner) of the gene of interest with or without a PTD gene and/or a tag (e.g., FLAG®-tag). The vector constructs herein described include any suitable gene expression vector that is capable of being delivered to a tissue of interest (e.g., CNS) and which will provide for the expression of the gene of interest in the selected tissue of interest (e.g., CNS). In a preferred embodiment, the gene therapy vector is capable of efficient delivery to a tissue of the central nervous system, including the spine and the brain, and in particular, is capable of crossing the blood-brain barrier of the brain.

In a preferred embodiment, the vector is an adeno-associated virus (AAV) vector because of the capacity of AAV vectors to cross the blood-brain barrier and transduction of neuronal tissue. In the methods disclosed herein, AAV of any serotype can be used, though in certain embodiments, it is advantageous to use a vector that is capable of undergoing retrograde axonal transport in a disease-compromised brain. The serotype of the viral vector used in certain embodiments of the disclosure is selected from the group consisting of AAV1, AAV2, AAV3, AAV4, AAV5, AAV6, AAV7, AAV8, AAV9, AAVrh8, AAVrh10, AAVrh33, AAV rh34, AAV Anc80, AAV PHP.B, and others (see, e.g., Gao et al. (2002) *PNAS*, 99:11854-11859; and Viral Vectors for Gene Therapy: Methods and Protocols, ed. Machida, Humana Press, 2003, incorporated herein by reference). Other serotype besides those listed herein are also contemplated. In certain exemplary embodiments, AAV 2/9 is used. In a particular embodiment AAV2/Anc80 or AAV2/PHP.B is used. The herein disclosed compositions and methods may also use AAV chimeric vectors, whereby portions of AAV are fused with other similar vectors, such as Adenovirus.

AAV vectors are derived from single-stranded (ss) DNA parvoviruses that are nonpathogenic for mammals (reviewed in Muzyscka (1992) *Curr. Top. Microb. Immunol.*, 158:97-129, incorporated herein by reference). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, the AAV backbone, comprising sequences between two AAV inverted terminal repeats (ITRs), is pseudotyped using the serotype 2 capsid to create an AAV2 vector. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003, incorporated herein by reference). Additionally, AAV-based gene therapy targeted to cells of the CNS has been described in U.S. Pat. Nos. 6,180,613 and 6,503,888 (each of which are incorporated herein by reference).

Optionally, the AAV viral capsid is AAV2, AAV9, AAVrh8, AAVrh10, AAV Anc80, or AAV PHP.B.; however, the serotype of the viral capsid used in certain embodiments of the disclosure can be selected from among known viral capsids, including AAV viral capsids of other known serotypes.

Optionally, the gene therapy vector, e.g., AAV or AAV-based vector, can be modified to improve virus uptake into the target tissue of interest (e.g., CNS), viral stability, and tropism. For example, the capsid of an AAV vector may be modified with a ligand (e.g., synthetic or naturally occurring small molecule, peptide, or polypeptide, or other biomolecule) that binds to a receptor at or in the tissue of interest (e.g., CNS). Other modifications are possible to improve and/or enhance the functional properties of the vector being used to both target the tissue of interest and allow the construct to enter and effectively transduce the target cells. Such modifications will be within the skill set of a person having ordinary skill in the art.

Further information regarding the use of AAV vectors can be found in the art, for example, in Kaplitt et al. (1994) *Nat. Genet.,* 8:148-154; Bartlett et al. (1998) *Hum. Gene Ther.,* 9:1181-1186; and Passini et al. (2002) *J. Neurosci.,* 22:6437-6446, each of which are incorporated herein by reference. Furthermore, these viral vectors can transduce a variety of CNS cell types, including neurons, when delivered by the systemic route, intrathecal route or by direct brain injection.

As further contemplated herein, the gene therapy vectors may comprise a transgene (e.g., codon optimized NPC1) that is operably linked to a promoter or other genetic transcriptional and/or translational control elements. Certain AAV vectors pre-engineered with or comprising promoters can be obtained from public sources, including, for example the websites for Vector Laboratories or Addgene.

In certain embodiments, the promoter is a promoter which is capable of efficient inducible expression in the CNS. In still other embodiments, the promoter is constitutively active in the CNS. In certain preferred embodiments, the promoter provides for selective expression in the CNS, and expression outside of the CNS is limited or entirely absent. Promoter sequences having differing characteristics and expression profiles are well known in the art, including those that are tissue-specific, tissue-non-specific, constitutive, and inducible. Reference can be further made to, for example, Papadakis et al., "Promoters and Control Elements: Designing Expression Cassettes for Gene Therapy," Current Gene Therapy, 2004, 4, 89-113, the contents of which are incorporated herein by reference. Promoters contemplated by the present disclosure include, but are not limited to: Apo A-1, ApoE, serpina (TBG), alpha-1-antitrypsin (hAAT) (liver specific); MCK (muscle specific); GFAP, NSE, Synapsin 1, Preproenkephalin, Dopamine b-hydroxylase (dbH), Prolactin, Myelin basic protein (neuronal-specific), GUSB, CBA, CAG and Ankyrin (erythroid specific).

In a particular embodiment, the disclosed compositions and methods utilize an AAV vectors that contain new NPC1 alleles that have been codon optimized to maximize human expression ($_{co}$NPC1).

In another embodiment, the NPC1 alleles may be tagged.

In another embodiment, the NPC1 alleles may be configured with at least one of one or more tags, transduction domain peptides in order to allow trans-cellular correction or with only the native protein transduction domain (PTD) peptides, or a combination thereof.

In another embodiment, the gene therapy vector may comprise a truncated EF1α promoter (EF1$\alpha_t$ promoter), or a mini EF1α promoter (EF1α promoter), or the short EF1α promoter (EF1α S). For example, the coNPC1 or fusion protein may be operationally linked to a EF1$\alpha_t$ promoter. The EF1$\alpha_t$ promoter may be a truncated EF1 promoter, which may be operationally linked to a stronger translation initiation site at the 5' end of the operationally linked nucleic acid, such as the codon optimized NPC1 alone or in the context of a fusion protein, as discussed herein. The gene therapy vector may also include multiple stop signals, which ensures maximal NPC1 gene expression and protein production in the cell.

In an embodiment, at least one of the cell, the neighboring cells, or both, are neuronal cells.

In an embodiment, the nucleic acid construct comprises an expression cassette comprising a nucleotide sequence selected from the group consisting of SEQ ID NOs: 26-38.

In an embodiment, the gene therapy vector may comprise first and second full-length, wild type AAV inverted terminal repeats (ITRs) that flank the transgene. In an embodiment, besides the ITRs, the nucleic acid construct may be devoid of any other sequence from the wild-type AAV genome.

In an embodiment, the first and second AAV ITRs are AAV2 ITRs. In a particular embodiment, the first and second AAV ITRs each comprise the nucleotide sequence of SEQ ID NO: 48. In another particular embodiment, the first and second AAV ITRs each comprise the nucleotide sequence of SEQ ID NO: 49.

In an embodiment, the $_{co}$NPC1 protein, the $_{co}$NPC1-PTD fusion protein and NPC1-tag fusion protein can be included in a vector, more particularly, in an expression cassette, with a synthetic intron sequence (SEQ ID NO: 25) which may enhance expression by providing more effective splicing of the transgene as compared to the vector which does not comprise the synthetic intron sequence.

In an embodiment, the NPC1 gene is under the control of a promoter, and the Intron S is positioned between the promoter and the NPC1 gene. In a particular embodiment, the Intron S comprises the nucleotide sequence of SEQ ID NO: 25.

In an embodiment, the nucleic acid construct may further comprise a nucleotide sequence encoding an antibiotic resistance marker. In an embodiment, the antibiotic resistance marker is an ampicillin resistance marker. In another embodiment, the antibiotic resistance marker is a kanamycin resistance marker.

In an embodiment, the nucleic acid construct comprises an expression vector which is capable of expressing the NPC1 protein, the NPC1-PTD fusion protein, or the NPC1 fusion protein, optionally comprising a tag moiety.

In an embodiment, the invention comprises a cell comprising the expression vector, wherein the cell produces the expression vector and/or the cell expresses the NPC1 protein.

In an embodiment, the invention comprises a method of ameliorating, treating, or preventing Niemann-Pick disease, type C1 in a subject, the method comprising administering a therapeutically effective amount of an expression vector to at least one cell, the expression vector comprising a nucleic acid molecule comprising a human codon-optimized NPC1 gene, wherein the expression vector is effective at of ameliorating, treating, or preventing at least one symptom of Niemann-Pick disease, type C1 in the subject.

In an embodiment, the NPC1 of the inventive method is translationally fused to a PTD to form a NPC1-PTD fusion protein, wherein the NPC1-PTD fusion protein is capable of cross-correcting non-transformed neighboring cells. In particular embodiments, the PTD protein transduction domain may be HIV-Tat, TP10, or TP2.

In an embodiment, the NPC1 gene of the inventive method is under the control of a promoter. In embodiments, the promoter may be a truncated EF1α promoter ($EF1\alpha_T$ promoter) or a mini EF1α promoter (EF1α promoter) or the short EF1α promoter (EF1α S).

In an embodiment, the NPC1 gene of the inventive method may be translationally fused to a tag moiety to form a NPC1-tag fusion protein, a NPC1-PTD-tag fusion protein, or a NPC1-tag-PTD fusion protein.

In an embodiment, the nucleic acid molecule of the inventive method comprises a nucleic acid sequence selected from the group consisting of SEQ ID NO: 1-8.

In an embodiment, the expression vector of the inventive method may comprise an expression cassette, with a synthetic intron sequence (SEQ ID NO: 25), which sequence may enhance expression by providing more effective splicing of the transgene as compared to the gene therapy vector which does not comprise the synthetic intron sequence. In an embodiment, the NPC1 gene of the inventive method is under the control of a promoter, and the Intron S is positioned between the promoter and the NPC1 gene. In a particular embodiment, the Intron S comprises the nucleotide sequence of SEQ ID NO: 25.

In a further embodiment, the inventive method comprises a nucleic acid construct comprising an expression cassette comprising a nucleotide sequence selected from the group consisting of SEQ ID NOs: 26-38.

In an embodiment, the expression vector of the inventive method may comprise first and second full-length, wild type AAV inverted terminal repeats (ITRs) that flank the transgene. In an embodiment, besides the ITRs, the nucleic acid construct may be devoid of any other sequence from the wild-type AAV genome. In an embodiment, the first and second AAV ITRs are AAV2 ITRs. In a particular embodiment, the first and second AAV ITRs each comprise the nucleotide sequence of SEQ ID NO: 48. In another particular embodiment, the first and second AAV ITRs each comprise the nucleotide sequence of SEQ ID NO: 49.

In an embodiment, inventive method may further comprise a nucleotide sequence encoding an antibiotic resistance marker. In an embodiment, the antibiotic resistance marker is an ampicillin resistance marker. In another embodiment, the antibiotic resistance marker is a kanamycin resistance marker.

In an embodiment, the nucleic acid construct may comprise first and second AAV ITRs, the human codon-optimized NPC1 gene, and one or more of a nucleotide sequence encoding a PTD, a promoter, an Intron S, and a nucleotide sequence encoding a tag, wherein the NPC1 gene and all of the one or more of the nucleotide sequence encoding the PTD, the promoter, and the nucleotide sequence encoding the tag are positioned between the first and second AAV ITRs. In another embodiment, the nucleic acid construct may comprise first and second AAV ITRs, the human codon-optimized NPC1 gene, and all of a nucleotide sequence encoding a PTD, a promoter, an Intron S, and a nucleotide sequence encoding a tag, wherein the NPC1 gene and all of the one or more of the nucleotide sequence encoding the PTD, the promoter, and the nucleotide sequence encoding the tag are positioned between the first and second AAV ITRs.

Methods of Treatment, Prevention, and/or Amelioration

In one aspect, the present disclosure provides methods for ameliorating, treating and/or preventing at least one symptom of a cholesterol storage disease or disorder in mammals, such as Niemann-Pick disease, Type C. In preferred embodiments, the populations treated by the methods of the present disclosure include, but are not limited to, patients having or at risk for developing a cholesterol storage disease or disorder, e.g., Niemann-Pick disease, type C1, particularly, if such a disease affects the CNS. In an illustrative embodiment, the disease is Niemann-Pick disease, Type C1.

In certain aspects of the disclosure, the method of treating, ameliorating and/or preventing a cholesterol storage disease or disorder comprises administration of a high titer gene therapy vector described herein (e.g., an AAV-based gene therapy vector) carrying a therapeutic transgene so that the transgene product is expressed at a therapeutic level in the CNS of a subject. In some embodiments, the viral titer of the composition is at least: (a) 5, 6, 7, 8, 8.4, 9, 9.3, 10, 15, 20, 25, or $50\times10^{12}$ gc/ml; (b) 5, 6, 7, 8, 8.4, 9, 9.3, 10, 15, 20, 25, or $50\times10^{9}$ tu/ml; or (c) 5, 6, 7, 8, 8.4, 9, 9.3, 10, 15, 20, 25, or $50\times10^{0}$ iu/ml. In further embodiments, the administration is accomplished by direct intraparenchymal injection of solution comprising a high titer gene therapy vector described herein (e.g., an AAV-based gene therapy vector) into the diseased brain, thereafter the transgene is expressed distally, contralaterally or ipsilaterally, to the administration site at a therapeutic level at least 2, 3, 5, 8 10, 15, 20, 25, 30, 35, 40, 45, or 50 mm from the administration site.

In further embodiments, the administration is accomplished by direct intrathecal injection of a solution comprising a high titer gene therapy vector described herein (e.g., an AAV-based gene therapy vector) into the spinal fluid compartment, as is routine for practioners of the art, and thereafter the transgene is expressed distally, contralaterally, ipsilaterally and globally in the CNS, to the administration site at a therapeutic level at least 2, 3, 5, 8 10, 15, 20, 25, 30, 35, 40, 45, or 50 mm from the administration site. In other embodiments, the administration is accomplished by direct intraventricular injection of a solution (which is routine for practitioners in the art) comprising the gene therapy vector described herein (e.g., a high titer of the gene therapy vector described herein). The administered gene therapy vector is expressed at least one of distally, contralaterally, ipsilaterally, globally, or a combination thereof, in the CNS.

In certain embodiments, the transgene product (e.g., NPC1 polypeptide) is expressed at a therapeutic level in a second site within the CNS distal to the first site. The distance between the first and the second sites is defined as the minimal distance region between the site of administration (first site) and the boundary of the detectable transduction of the distal site (second site) as measured using procedures known in the art, e.g., magnetic resonance imaging including spectroscopy or direct brain biopsy. Some neurons in the CNS of larger mammals may span large distances by virtue of their axonal projections. For example, in humans, some axons may span a distance of 1000 mm or greater. Thus, in various methods of the disclosure, a gene therapy vector of the disclosure can be axonally transported along the entire length of the axon at such a distance to reach and transduce the parent cell body.

A site of vector administration within the CNS can be chosen based on the desired target region of neuropathology and, optionally, the topology of brain circuits involved when an administration site and the target region have axonal connections. In certain embodiments, the target region can be defined, for example, using 3-D sterotaxic coordinates. In some embodiments, the administration site is chosen so that at least 0.1, 0.5, 1, 5, or 10% of the total amount of vector injected is delivered distally at the target region of at least 1, 200, 500, or 1000 $mm^3$. An administration site may be localized in a region innervated by projection neurons connecting distal regions of the brain. For example, the substantia nigra and ventral tegmental area send dense projections to the caudate and putamen (collectively known as the striatum). Neurons within the substantia nigra and ventral tegmentum can be targeted for transduction by retrograde transport of a gene therapy construct described herein (e.g., AAV based vector) following injection into the striatum. As another example, the hippocampus receives well-defined, predictable axonal projections from other regions of the brain. Other administration sites may be localized, for example, in the spinal cord, brainstem (medulla and pons), mesencephalon, cerebellum, diencephalon (thalamus, hypothalamus), telencephalon (corpus striatum, cerebral cortex, or, within the cortex, the occipital, temporal, parietal or frontal lobes), or combinations thereof.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Sterotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000. If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

In certain embodiments, the target site can be located any region of the CNS, including the brain and the spinal cord, that contains neurons that project to the first (administration) site. In some embodiments, the second site is in a region of the CNS chosen from the substantia nigra, the medulla oblongata, or the spinal cord.

To deliver a gene therapy vector described herein specifically to a particular region of the central nervous system, especially to a particular region of the brain, it may be administered by sterotaxic microinjection. For example, on the day of surgery, patients will have the sterotaxic frame base fixed in place (screwed into the skull). The brain with sterotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector in a pharmaceutically acceptable carrier will then be injected. The AAV vector is then administrated by direct injection to the primary target site and retrogradely transported to distal target sites via axons. Additional routes of administration may be used, e.g., superficial cortical application under direct visualization, or other non-stereotaxic application.

Optionally, non-CNS delivery can also be performed, e.g., for cholesterol storage diseases or disorders where non-CNS delivery would also be desirable. Such non-CNS delivery of the compositions (e.g., constructs) of the instant disclosure can be performed in addition to or as an alternative to CNS delivery. In certain such embodiments, injection, e.g., intravenous, intraperitoneal, etc. injection can be performed using the compositions of the instant disclosure. Direct delivery to large peripheral nerves is also considered.

In yet another method, a suitable AAV vector configured to express NPC1 can be encapsidated with a capsid known to afford transduction of the blood brain barrier and further penetration of the CNS and its elements. In this embodiment, the AAV vector can be delivered systemically, by IV infusion, and engender both peripheral and CNS correction, and depending upon the promoter and serotype of the vector, may enable neurovisceral correction.

The total volume of material to be administered, and the total number of vector particles to be administered, will be determined by those skilled in the art based upon known aspects of gene therapy. Therapeutic effectiveness and safety can be tested in an appropriate animal model. For example, for NPC, in any $Npc1^{-/-}$ model mouse such as the $Npc^{nih}$ homozygous mice.

In experimental mice, the total volume of injected vector, e.g., AAV vector, solution is, for example, between 1 to 10 μl. For other mammals, including the human brain, volumes and delivery rates are appropriately scaled. For example, it has been demonstrated that volumes of 150 μl can be safely injected in the primate brain (Janson et al. (2002) *Hum. Gene Ther.,* 13:1391-1412). Treatment may consist of a single injection per target site, or may be repeated along the injection tract, if necessary. Multiple injection sites can be used. For example, in some embodiments, in addition to the first administration site, a composition comprising a gene therapy vector described herein carrying a transgene is administered to another site that can be contralateral or ipsilateral to the first administration site.

In another aspect, the disclosure provides a method of delivering a transgene product to a target cell of the CNS, which is a neuron or a glial cell, in a mammal afflicted with a cholesterol storage disease or disorder, e.g., Niemann-Pick disease, type C. The method comprises contacting an axonal ending of a neuron with a composition of the present disclosure (a nucleic acid construct or gene therapy vector comprising a codon optimized NCP1); allowing the viral particles to be endocytosed and retrogradely transported intracellularly along the axon to the nucleus of the neuron; allowing the transgene product to be expressed and transported within the membrane(s) of the neuron, wherein the transgene product thereby alleviates pathology related to cholesterol storage. In another embodiment, a gene therapy vector encoding a codon optimized NPC1, optionally with tags and/or a PTD, can be infused into a reservoir, such as an Omoyaya reservoir, for direct intracranial delivery. In some embodiments, the concentration of the AAV vector in the composition is at least: (a) 5, 6, 7, 8, 8.4, 9, 9.3, 10, 15, 20, 25, or $50\times10^{12}$ gc/ml; (b) 5, 6, 7, 8, 8.4, 9, 9.3, 10, 15, 20, 25, or $50\times10^{9}$ tu/ml; or (c) 5, 6, 7, 8, 8.4, 9, 9.3, 10, 15, 20, 25, or $50\times10^{10}$ iu/ml.

The present disclosure provides for both prophylactic and therapeutic methods of treating a subject at risk of (or susceptible to) a disease or disorder caused, in whole or in part, by altered cholesterol storage, optionally treatable via selective or systemic delivery of a NPC1-containing gene therapy vector to a subject.

In certain aspects, the disclosure provides a method for preventing in a subject, a disease or disorder as described herein (including, e.g., NPC), by administering to the subject the gene therapy composition of the present disclosure. Subjects at risk for the disease can be identified by, for example, one or a combination of diagnostic or prognostic assays known in the art (e.g., genetic assessment of the subject and/or phenotypic assessment). Administration of a prophylactic agent can occur prior to the detection of, e.g., NPC in a subject, or the manifestation of at least one symptom characteristic of the disease or disorder, such that the disease or disorder is prevented or, alternatively, delayed in its progression.

Another aspect of the disclosure pertains to methods of treating subjects therapeutically, i.e., altering the onset of symptoms of the disease or disorder. These methods can be performed in vitro (e.g., by culturing the cell with the gene therapy composition) or, alternatively, in vivo (e.g., by administering the gene therapy composition to a subject).

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the disclosure provides methods for tailoring an individual's prophylactic or therapeutic treatment with the gene therapy transgene of the present disclosure to that individual's drug response genotype. Pharmacogenomics allows a clinician or physician to target prophylactic or therapeutic treatments to patients who will most benefit from the treatment and to avoid treatment of patients who will experience toxic drug-related side effects.

Gene Therapy Compositions

The disclosure, in part, pertains to a gene therapy composition comprising the NPC1-providing vectors as described herein. The gene therapy composition of the present disclosure can gain entry into a cell or tissue, e.g., a CNS cell or tissue, for ameliorating, treating and/or preventing at least one symptom of NPC disease or mitigating the complications, such as liver disease, neurological decline or seizures.

Advantageously, the gene therapy composition of the disclosure provides for a controlled delivery of an active gene, especially a therapeutic gene, to a site of action at an optimum rate and therapeutic dose. Thus, improvements in therapeutic index may be obtained by modulating the distribution of the active ingredient in the body and/or by modulating the promoter used in such gene therapy construct. Association of the gene therapy vector and/or viral vector containing such gene therapy vector with a delivery system enables, in particular, its specific delivery to the site of action or its controlled expression of a gene after targeting the action site. By reducing the amount of active gene therapy vector distributes to any compartments in which its presence is not desired, it is possible to increase the efficacy of the gene therapy agent, and to reduce any toxic side effects or even modify or restore activity of gene therapy agents. In this application, the capsid serotype can influence route of delivery, cellular transduction efficacy, and dose required for a therapeutic effect. The promoter of the vector further dictates cell type expression i.e., in all cells or only neurons and the degree to which expression occurs at the cellular level. As such, some promoters are stronger than others, and produce higher transgene expression. In another embodiment, microRNA (miRNA) binding sites are embedded in the 3' untranslated region of the therapeutic transgene to provide a cell specific inhibition of translation if the NPC1 transgene product is toxic in one cell type compared to another. This approach would minimize off target expression in cell types other than neurons if needed.

The disclosure also relates to pharmaceutical or diagnostic compositions comprising the NPC1-including vectors or constructs of the disclosure and a pharmaceutically acceptable carrier. As such, direct RNA or DNA or modified forms if such, including peptide or covalently modified nucleic acids, injections in the brain or other locations are considered using the therapeutic transgenes described in this application. In another embodiment, nanoparticles containing codon optimized nucleic acids encoding NPC1 are used for gene delivery. In further embodiments, exosomes containing codon optimized nucleic acids (e.g., codon optimized for expression in human cells) encoding NPC1 are used for gene delivery. In other embodiments, exosomes containing codon optimized nucleic acids (e.g., codon optimized for expression in human cells) encoding NPC1 and NPC1 are used for gene delivery. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

In certain embodiments, the present disclosure provides for a viral vector composition comprising a gene therapy agent (e.g., codon optimized NPC1 operably linked to a tissue-specific or systemic promoter, optionally operably linked to a PTD and/or a tag and within a plasmid corresponding to the form of viral delivery system employed, e.g., AAV viral vector plasmid) of the present disclosure. The active viral vector can be suitably formulated and introduced into the environment of the cell by any means that allows for a sufficient portion of the sample to enter the cell to induce expression of the gene therapy agent, if it is to occur. Many formulations for AAV and other vector-based gene therapy delivery are known in the art and can be used.

Such compositions can include the gene therapy agent and a pharmaceutically acceptable carrier. Supplementary active compounds can also be incorporated into the compositions. The AAV capsid can likewise be modified to improve uptake and viral stability, and alter tropism.

A gene therapy composition can be formulated to be compatible with its intended route of administration. Examples of routes of administration include parenteral, e.g., intravenous, intracranial, intrathecal, intraventricular, intramuscular, intrahepatic, intradermal, subcutaneous, oral (e.g., inhalation, buccal, sublingual, intranasal), transdermal (topical), transmucosal, and rectal administration. Nucleic acids can be delivered using electrical or magnetic stimulation, or direct physical uptake using hydrodynamic pressure. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Gene therapy compositions suitable for injectable use can include sterile aqueous solutions or dispersions and sterile powders for the extemporaneous preparation of sterile injectable solutions or dispersion. For intravenous administration, in certain embodiments, carriers can include physiological saline, bacteriostatic water, Cremophor EL® (BASF, Parsippany, N.J.) or phosphate buffered saline (PBS). However, the art as relates to a specific viral delivery vector will be known to the skilled artisan and will provide appropriate constituents for a gene therapy vector composition. A composition for injection must be sterile (apart from the AAV or other viral vector employed for delivery) and should be fluid to the extent that easy syringability exists. In certain embodiments, such compositions are stable under the conditions of manufacture and storage and are preserved against the contaminating action of microorganisms such as bacteria and fungi. Exemplary carriers can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin or albumin.

Sterile injectable solutions can be prepared by incorporating the gene therapy vectors disclosed herein in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

For administration by inhalation, gene delivery compositions can be delivered in the form of an aerosol spray from pressured container or dispenser which contains a suitable propellant, e.g., a gas such as carbon dioxide, or a nebulizer. Such methods include those described in U.S. Pat. No. 6,468,798, which is incorporated herein by reference.

The data obtained from the cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For a compositions used in the method of the disclosure, the therapeutically effective dose can be estimated initially from cell culture assays. A dose may be formulated in animal models to achieve a circulating plasma concentration range that includes the $IC_{50}$ (i.e., the concentration of the test compositions which achieves a half-maximal inhibition of symptoms) as determined in cell culture. Such information can be used to more accurately determine useful doses in humans. Levels in plasma may be measured, for example, by high performance liquid chromatography.

Expression constructs of the disclosure can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057) or by any aforementioned delivery route. The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The expression constructs may be constructs suitable for use in the appropriate expression system and include, but are not limited to retroviral vectors, linear expression cassettes, modified mRNAs, plasmids and viral or virally-derived vectors, such as the AAV described herein, as known in the art. The nucleic acids can be modified covalently, such as peptide nucleic acids or base modified ribonucleic acids. Such expression constructs may include one or more promoters as detailed elsewhere herein.

Suitable amounts of a gene therapy composition must be introduced and these amounts can be empirically determined using standard methods.

The gene therapy composition can be formulated as a composition which comprises a pharmacologically effective amount of a transgene and/or viral vector containing a transgene, and pharmaceutically acceptable carrier. A pharmacologically or therapeutically effective amount refers to that amount of gene therapy agent effective to produce the intended pharmacological, therapeutic or preventive result. The phrases "pharmacologically effective amount" and "therapeutically effective amount" or simply "effective amount" refer to that amount of a gene therapy transgene effective to produce the intended pharmacological, therapeutic or preventive result. For example, if a given clinical treatment is considered effective when there is at least a 20% increase in a measurable parameter associated with a disease or disorder, a therapeutically effective amount of a gene therapy composition for the treatment of that disease or disorder is the amount necessary to effect at least a 20% increase in that parameter. In another example, if a given clinical treatment is considered effective when there is at least 10%, 20%, 30%, 40%, 50%, 60%, 70%, or 80% or more increase in a measurable parameter associated with a disease or disorder, a therapeutically effective amount of a gene therapy composition for the treatment of that disease or disorder is the amount necessary to effect at least a 10%, 20%, 30%, 40%, 50%, 60%, 70%, or 80% or more increase in that parameter.

Markers of Transgene Expression/Activity

Toxicity and therapeutic efficacy of gene delivery compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Gene therapy compositions which exhibit high therapeutic indices are preferred. While gene therapy compositions that exhibit toxic side effects may be used, care should be taken to design a delivery system that targets such compositions to the site of affected tissue in order to minimize potential damage to uninfected cells and, thereby, reduce side effects.

In certain embodiments, membrane localization, including intracellular localization of a transgene or product thereof, e.g., NPC1, is assessed in the subject and/or in cells of the subject, e.g., using the FLAG-tag. In other embodiments, assessment of the efficacy of NPC1 transgene delivery is performed via measurement of cholesterol uptake (e.g., endocytic cholesterol uptake) of the cells of a subject and/or via phenotypic assessment of a subject before and after administration of the AAV-NPC composition(s). Such assessment can be performed within days of administration of an AAV-NPC composition of the disclosure, or can be performed at a time of, e.g., one week, two weeks, three weeks, one month, two months, three months, four months, five months, six months, one year or more post-administration. The use of previously described biomarkers such as unesterified cholesterol, sphingomyelin, bis(monoacylglycero)phosphate, glucosylceramide, lactosylceramide, globotriaosylceramide, free sphingosine, gangliosides GM2 and GM3; galectin-3 (LGALS3) a pro-inflammatory molecule, and cathepsin D (CTSD), a lysosomal aspartic protease; and cholesterol oxidation products and neurosteroids such as cholestane-3β,5α,6β-triol ('triol'), a cholesterol oxidation product that is elevated 10-fold in the plasma of NPC1 subjects, and 24(S)-hydroxycholesterol (24(S)-HC), an enzymatically generated oxygenated cholesterol that is reduced in the plasma of NPC1 subjects. Untargeted metabolomics are likewise envisioned to monitor the efficacy and activity of AAV gene therapy for NPC.

In certain embodiments, prior to treatment, a subject is assessed for the identity of genetic deficiency that has produced NPC in the subject—whether NPC1 or NPC2—and the subject is then administered is then administered an NPC1 transgene depending upon the outcome of such assessment. In another embodiment, the transgene encodes a transgene that has been codon optimized for human expression designated coNPC1. Methods for diagnosing NP disease can be found, for example, in U.S. Pat. Nos. 4,039,388, 5,686,240, 6,426,198, and 7,045,675 each of which are incorporated by reference.

The disclosure further provides a method to treat related disorders of unesterified cholesterol accumulation, such as atherosclerosis.

The level or activity of a transgene mRNA or polypeptide can be determined by a suitable method now known in the art or that is later developed, e.g., analyzing expression levels by PCR, hybridization, microarrays, or other similar methodologies. Suitable primers, probes, and oligonucleotides capable of performing such detection will be known and readily obtainable in the art. It can be appreciated that the method used to measure a transgenic mRNA and/or the expression of a transgenic protein can depend upon the nature of the transgene. Such measurements can be made on cells, cell extracts, tissues, tissue extracts or other suitable source material.

The determination of whether the expression of a transgene has been increased can be by a suitable method that can reliably detect changes in RNA or protein levels. In certain embodiments, the determination is made by introducing into the environment of a cell a gene therapy composition of the disclosure such that at least a portion of the gene therapy vector enters the cytoplasm (optionally, the nucleus; optionally, with nuclear chromosomal integration), and then measuring the level of the transgene RNA and/or polypeptide. The same measurement is made on identical untreated cells and the results obtained from each measurement are compared.

Combination Therapies

It is contemplated that the compositions of the current disclosure can be combined with other proposed therapies (e.g., for NPC) to slow disease progression and ameliorate symptoms, even in patients with advanced disease. There are no published standards of care for NPC other than symptomatic treatment of disease manifestations—seizures are controlled as possible and supportive care is provided as needed. In one embodiment, AAV gene therapy would be combined with the pharmaceutical excipient 2-hydroxypropyl-β-cyclodextrin (HPβCD), such as VTS 270. In another, AAV gene therapy would be combined therapies shown to have modest efficacy in mouse models or cell culture studies including treatment with antioxidants such as N-acetylcysteine; vitamin E or derivatives such as α-tocepherol or δ-tocepherol; miglustat, a small imino sugar that partially inhibits glucosylceramide synthase and the synthesis of all glucosylceramide-based glycosphingolipids; curcumin to compensates for the lysosomal calcium defect by elevating cytosolic calcium; the non-steroidal anti-inflammatory drug ibuprofen or related compounds to reduce central nervous system inflammation; donepezil, a widely used acetylcholinesterase (AChE) inhibitor; or Histone deacetylase inhibitors (HDACi) such as vorinostat. In another embodiment, AAV gene therapy would be combined with other therapies that have a theoretical basis for efficacy—such as those that influence cholesterol metabolism, but have limited efficacy to date. These include the cholesterol-lowering agents cholestyramine, lovastatin, and nicotinic acid as well as a low-cholesterol diet.

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In certain embodiments, a suitable dosage unit of a transgene vector is in the range of 0.001 to 0.25 milligrams per kilogram body weight of the recipient per day, or in the range of 0.01 to 20 micrograms per kilogram body weight per day, or in the range of 0.001 to 5 micrograms per kilogram of body weight per day, or in the range of 1 to 500 nanograms per kilogram of body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. A gene therapy composition comprising the transgene can be administered once or on multiple occasions.

Data can be obtained from cell culture assays and animal studies to formulate a suitable dosage range for humans. The dosage of compositions of the disclosure can lie within a range of circulating concentrations that include the $ED_{50}$ (as determined by known methods) with little or no toxicity. The dosage may vary within this range depending upon the dosage form employed and the route of administration utilized. For a composition used in the method of the disclosure, the therapeutically effective dose can be estimated initially from cell culture assays. A dose may be formulated in animal models to achieve a circulating plasma concentration range of the composition that includes the $IC_{50}$ (i.e., the concentration of the test compound which achieves a half-maximal inhibition of symptoms) as determined in cell culture. Such information can be used to more accurately determine useful doses in humans. Levels of a gene therapy composition in plasma may be measured by standard methods, for example, by high performance liquid chromatography.

In certain embodiments, the dosage may be in terms of vector concentration. For example, the concentration of gene therapy vector described herein is at least: (a) 5, 6, 7, 8, 8.4, 9, 9.3, 10, 15, 20, 25, or $50\times10^{12}$ gc/ml; (b) 5, 6, 7, 8, 8.4, 9, 9.3, 10, 15, 20, 25, or $50\times10^{9}$ tu/ml ("transducing units per ml"); (c) 5, 6, 7, 8, 8.4, 9, 9.3, 10, 15, 20, 25, or $50\times10^{10}$ iu/ml ("international units per ml"), or (d) 5, 6, 7, 8, 8.4, 9, 9.3, 10, 15, 20, 25, or $50\times10^{10}$ pfu/ml ("plaque forming units per ml").

Kits and/or Pharmaceutical Packages

The gene therapy compositions of the disclosure can be included in a kit and/or pharmaceutical package, container, pack, or dispenser together with instructions for administration.

The disclosure provides kits for the treatment or prevention of disease, e.g., NP disease, Type C. In one embodiment, the kit includes a therapeutic or prophylactic composition containing an effective amount of an agent of the disclosure (e.g., gene therapy vectors) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject having or at risk of developing a disease. The instructions will generally include information about the use of the composition for the treatment or prevention of the disease (e.g., NPC). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

SUMMARY OF SEQUENCE LISTING

The specification includes a Sequence Listing appended herewith, which includes sequences, as follows:

SEQ ID NO: 1 (FIG. 1A—codon optimized NPC1);
SEQ ID NO: 2 (FIG. 1B—codon optimized NPC1-Tat);
SEQ ID NO: 3 (FIG. 1C—codon optimized NPC1-3× FLAG® tag);
SEQ ID NO: 4 (FIG. 1D—codon optimized NPC1-TP10);
SEQ ID NO: 5 (FIG. 1E—codon optimized NPC1-TP2);
SEQ ID NO: 6 (FIG. 1F—codon optimized NPC1-3× FLAG® tag-TAT);
SEQ ID NO: 7 (FIG. 1G—codon optimized NPC1-3× FLAG® tag-TP10);
SEQ ID NO: 8 (FIG. 1H—codon optimized NPC1-3× FLAG® tag-TP2);
SEQ ID NO: 9 (human NPC1 wild-type cDNA);
SEQ ID NO: 10 (truncated EF1α promoter (EF1$\alpha_t$));
SEQ ID NO: 11 (GenBank Accession No. BC17178; cDNA);
SEQ ID NO: 12 (GenBank Accession No. BC143756; cDNA);
SEQ ID NO: 13 (GenBank Accession No. AF258783.1; cDNA);
SEQ ID NO: 14 (GenBank Accession No. BC054539; cDNA);
SEQ ID NO: 15 (GenBank Accession No. BC151276; cDNA);
SEQ ID NO: 16 (GenBank Accession No. BC090541; cDNA);
SEQ ID NO: 17 (GenBank Accession No: NM_000271.4; cDNA);
SEQ ID NO: 18 (GenBank Accession No: NM_008720.2; cDNA);
SEQ ID NO: 19 (GenBank Accession No: NM_006432.3; cDNA);
SEQ ID NO: 20 (GenBank Accession No: NM_023409.4; cDNA);
SEQ ID NO: 21 (GenBank Accession No: NP_000262.2; protein);
SEQ ID NO: 22 (GenBank Accession No: NP_032746.2; protein);
SEQ ID NO: 23 (GenBank Accession No: NP_006423.1; protein);
SEQ ID NO: 24 (GenBank Accession No: NP_075898.1; protein);
SEQ ID NO: 25 (synthetic Intron S);
SEQ ID NO: 26 (Expression cassette for second generation vector miniEF1-coNPC1);
SEQ ID NO: 27 (Expression cassette for second generation vector miniEF1-coNPC1-TAT);
SEQ ID NO: 28 (Expression cassette for second generation vector miniEF1-coNPC1-3×FLAG tag);
SEQ ID NO: 29 (Expression cassette for second generation vector miniEF1-coNPC1-TP10);
SEQ ID NO: 30 (Expression cassette for second generation vector miniEF1-coNPC1-TP2)
SEQ ID NO: 31 (Expression cassette for second generation vector miniEF1-coNPC1-3×FLAG tag-TAT);
SEQ ID NO: 32 (Expression cassette for second generation vector miniEF1-coNPC1-3×FLAG tag-TP10);
SEQ ID NO: 33 (Expression cassette for second generation vector miniEF1-coNPC1-3×FLAG tag-TP2);
SEQ ID NO: 34 (Expression cassette for third generation vector EF1s-coNPC1);
SEQ ID NO: 35 (Expression cassette for third generation vector EF1s-coNPC1-TAT);
SEQ ID NO: 36 (Expression cassette for third generation vector EF1s-coNPC1-3×FLAG tag);
SEQ ID NO: 37 (Expression cassette for third generation vector EF1s-coNPC1-3×FLAG tag-TAT);
SEQ ID NO: 38 (Expression cassette for fourth generation vector EF1s-intronS-coNPC1);
SEQ ID NO: 39 (Expression cassette for fourth generation vector EF1s-intronS-coNPC1-TAT);
SEQ ID NO: 40 (Expression cassette for fourth generation vector EF1s-intronS-coNPC1-3×FLAG tag);
SEQ ID NO: 41 (GenBank Accession No. BC063302; amino acid);
SEQ ID NO: 42 (GenBank Accession No. BC117178; amino acid);
SEQ ID NO: 43 (GenBank Accession No. BC143756; amino acid);
SEQ ID NO: 44 (GenBank Accession No. AF258783.1; amino acid);
SEQ ID NO: 45 (GenBank Accession No. BC054539; amino acid);
SEQ ID NO: 46 (GenBank Accession No. BC151276; amino acid);
SEQ ID NO: 47 (GenBank Accession No. BC090541; amino acid);

SEQ ID NO: 48 (Inverted Terminal Repeat 130 bases);
SEQ ID NO: 49 (Inverted Terminal Repeat 145 bases);
SEQ ID NO: 50 (deleted 59 base pair sequence);
SEQ ID NO: 51 (Mini EF1α promoter); and
SEQ ID NO: 52 (Short EF1α promoter (EF1α S)).

EXAMPLES

The present disclosure is described by reference to the following Examples, which are offered by way of illustration and are not intended to limit the disclosure in any manner. Standard techniques well known in the art or the techniques specifically described below were utilized.

Example 1

Figure 3:
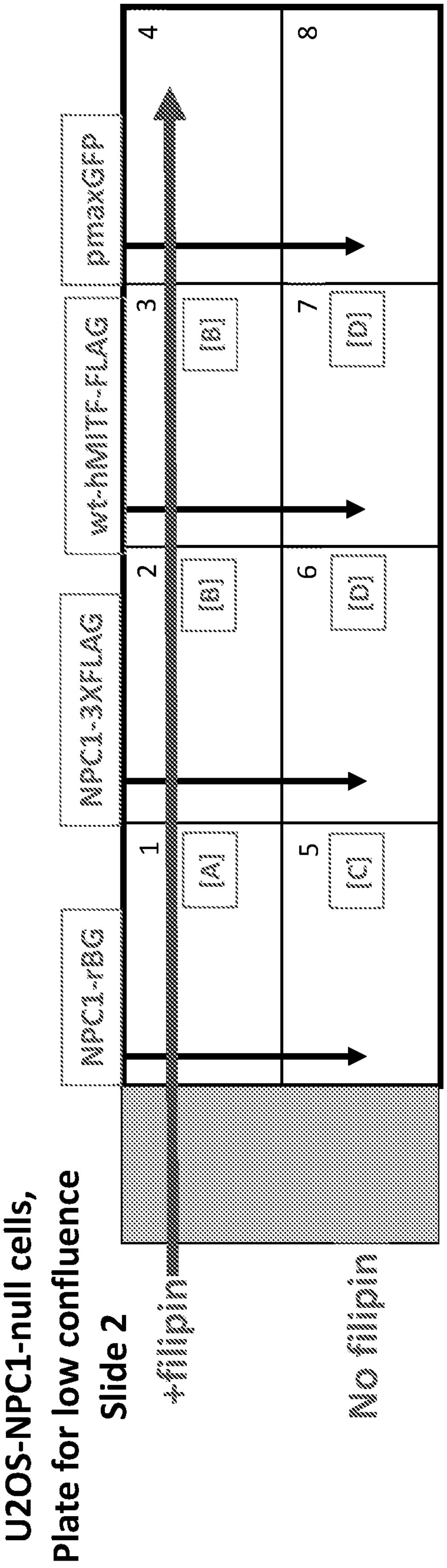
FIG. 3 is a schematic showing the strategy for anti-FLAG tag/Red transfection and filipin staining after transfection with the pAAV-mini EF1α NPC1 plasmid in U2OS-NPC1-null cells. Cells were plated in 8 wells, numbered 1-8, for low confluence and staining was determined four days post-transfection. [A] is no primary; Anti-rabbit-red secondary 1:200. [B] is Anti-FLAG tag primary, 1:200; Anti-rabbit-red secondary 1:200. [C] is No primary; Anti-rabbit-red secondary 1:200. [D] is Anti-FLAG tag primary, 1:200; Anti-rabbit-red secondary, 1:200.
Figure 4A:
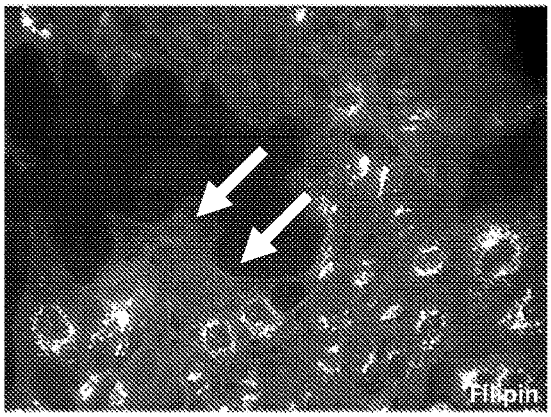
FIGS. 4A-4C are enlarged microscopic images of the same field of well 2 in FIG. 3; U2OS-NPC1-null cells, four days post-transfection with pAAV-mini EF1α coNPC1-3× FLAG tag plasmid, stained with filipin and anti-FLAG tag antibody. The areas showing accumulation of white particles in FIG. 4A are areas of filipin accumulation. The areas in FIG. 4B showing light gray and white accumulation are cells that highly expressed the $_{co}$NPC1-3×FLAG tag after transfection with pAAV-mini EF1α-coNPC1-3×FLAG tag plasmid, and the FLAG tag epitope has been detected by the anti-FLAG tag antibody.
Figure 4B:
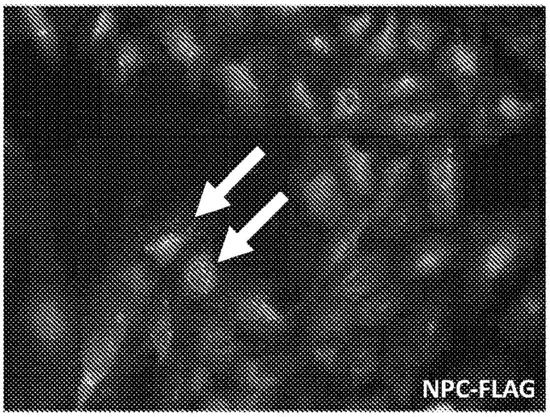
Figure 4C:
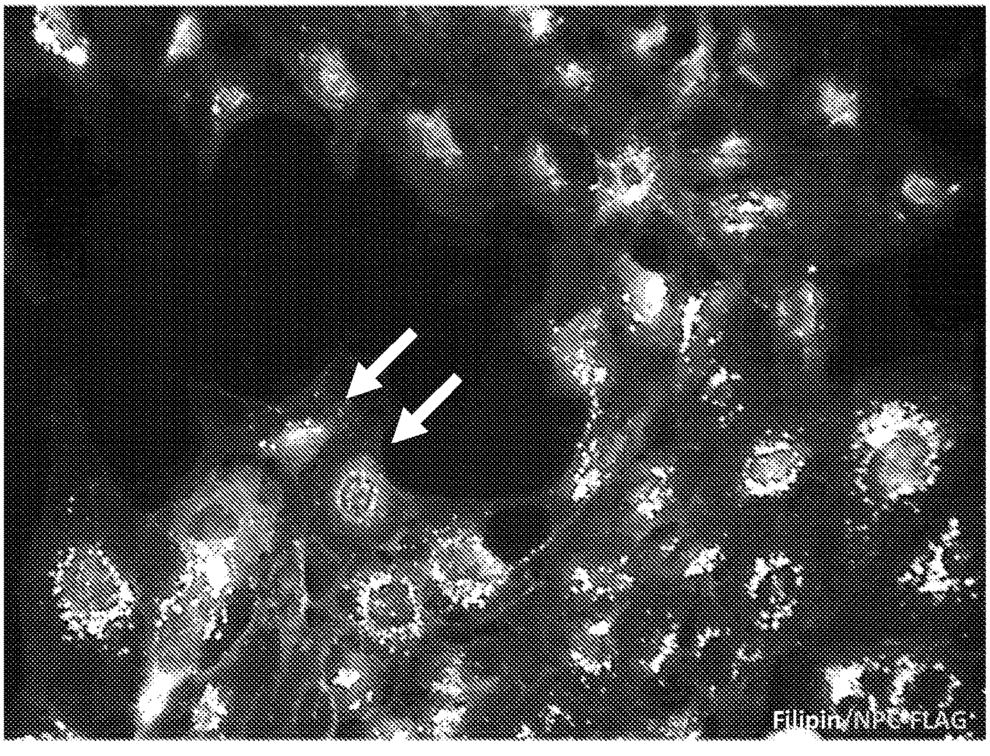
Figure 4D:
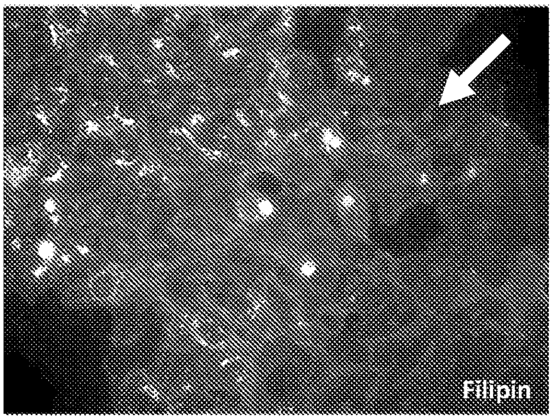
FIGS. 4D-4F are enlarged microscopic images of the same field of well 2 in FIG. 3; U2OS-NPC1-null cells, four days post-transfection with pAAV-mini EF1α-coNPC1-3× FLAG tag plasmid, stained with filipin and anti-FLAG tag antibody. The areas showing accumulation of white particles in FIG. 4D are areas of filipin accumulation. The areas in FIG. 4E showing light gray and white accumulation are cells that highly expressed the coNPC1-3×FLAG tag after transfection with pAAV-coNPC1-3×FLAG tag plasmid, and the FLAG tag epitope has been detected by the anti-FLAG tag antibody.
Figure 4E:
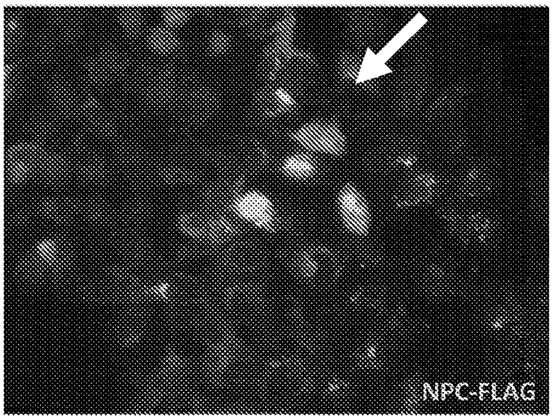
Figure 4F:
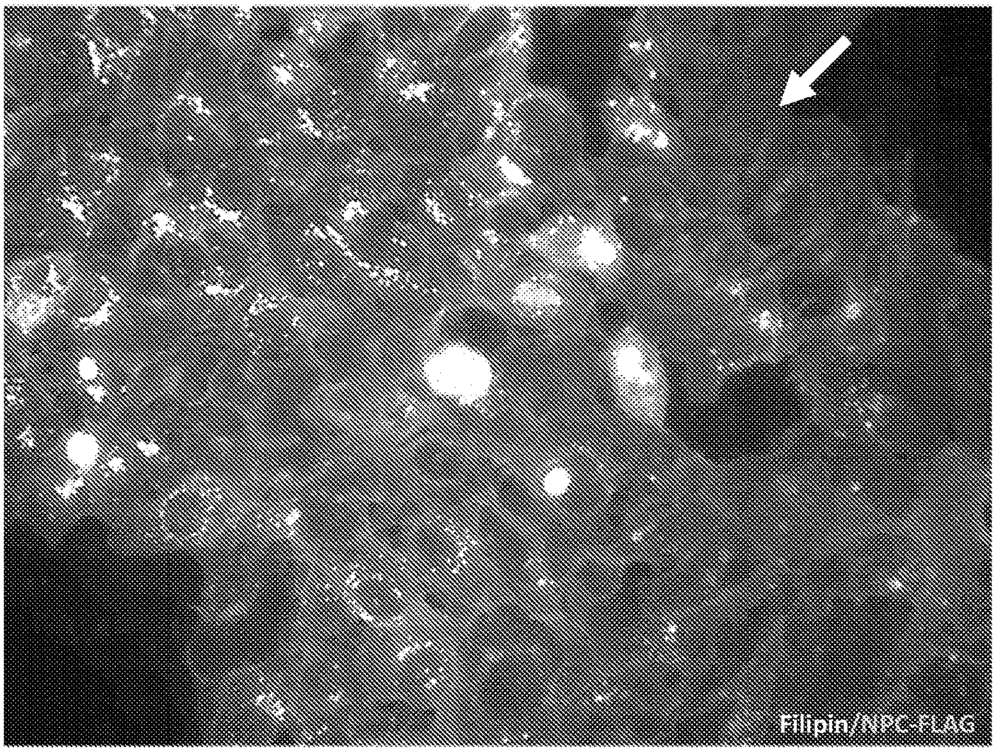
Figure 4G:
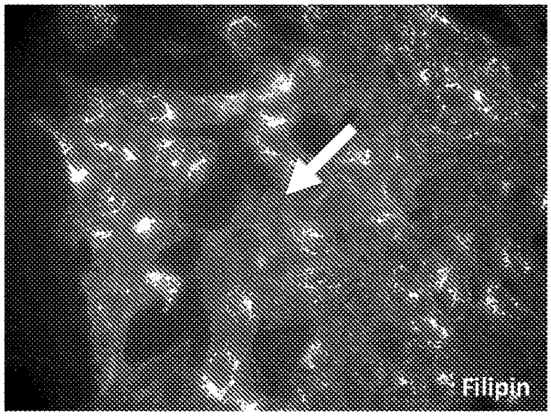
FIGS. 4G-4I are enlarged microscopic images of the same field of well 2 in FIG. 3; U2OS-NPC1-null cells, four days post-transfection with pAAV-mini EF1α coNPC1-3×FLAG tag plasmid, stained with filipin and anti-FLAG tag antibody. The areas showing accumulation of white particles in FIG. 4G are areas of filipin accumulation. The areas in FIG. 4H showing light gray and white accumulation are cells that highly expressed the $_{co}$NPC1-3×FLAG tag after transfection with pAAV-mini EF1α-coNPC1-3×FLAG tag plasmid, and the FLAG tag epitope has been detected by the anti-FLAG tag antibody.
Figure 4H:
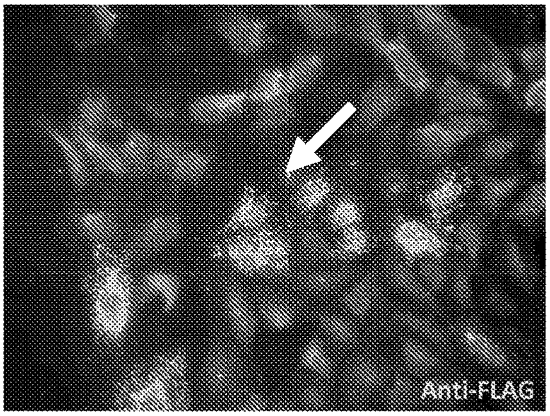
Figure 4I:
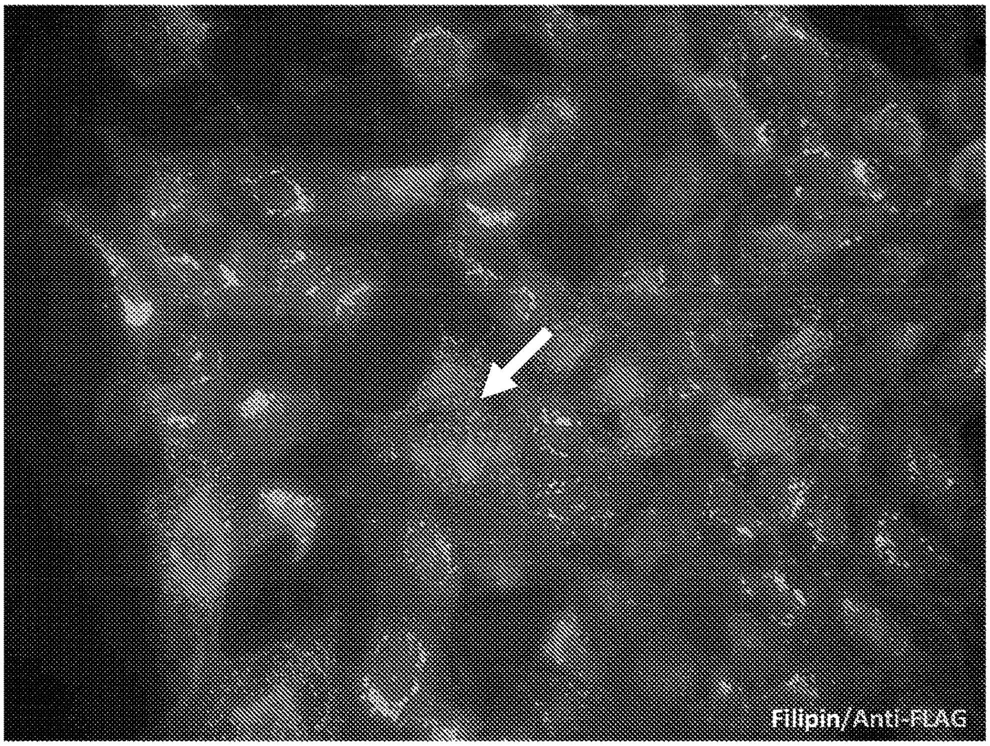
Figure 4J:
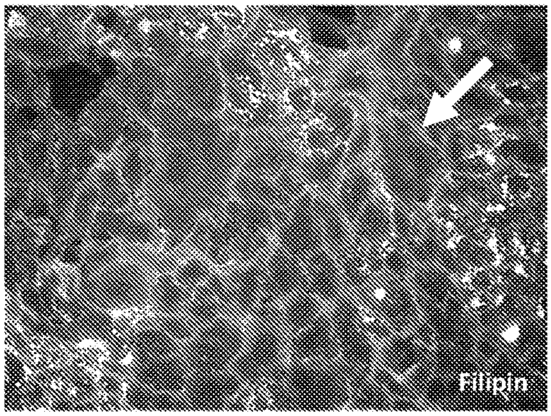
FIGS. 4J-4L are enlarged microscopic images of the same field of well 2 in FIG. 3; U2OS-NPC1-null cells, four days post-transfection with pAAV-mini EF1α coNPC1-3×FLAG tag plasmid, stained with filipin and anti-FLAG tag antibody. The areas showing accumulation of white particles in FIG. 4J are areas of filipin accumulation. The areas in FIG. 4K showing light gray and white accumulation are cells that highly expressed the $_{co}$NPC1-3×FLAG tag after transfection with pAAV-mini EF1α-coNPC1-3×FLAG tag plasmid, and the FLAG tag epitope has been detected by the anti-FLAG tag antibody.
Figure 4K:
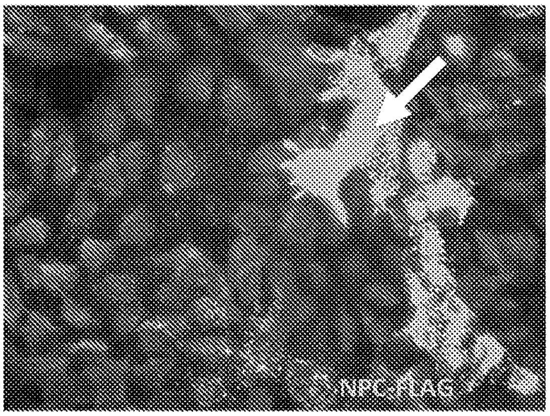
Figure 4L:
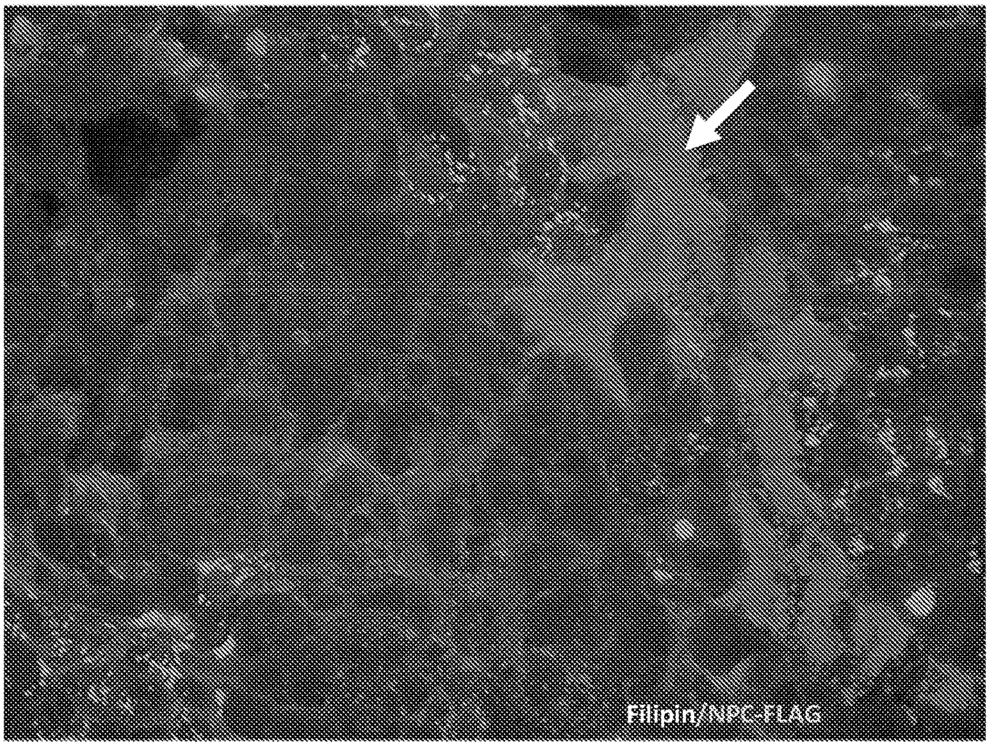
Figure 4M:
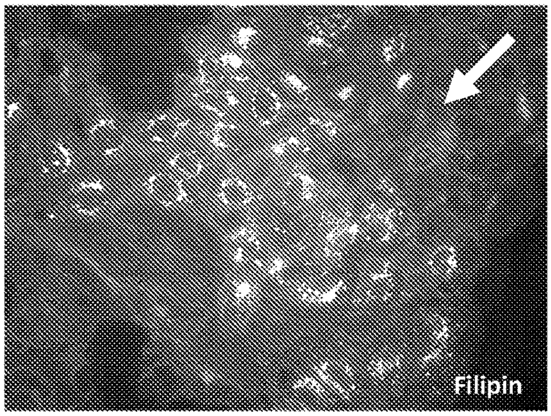
FIGS. 4M-4O are enlarged microscopic images of the same field of well 2 in FIG. 3; U2OS-NPC1-null cells, four days post-transfection with pAAV-mini EF1α-coNPC1-3×FLAG tag plasmid, stained with filipin and anti-FLAG tag antibody. The areas showing accumulation of white particles in FIG. 4M are areas of filipin accumulation. The areas in FIG. 4N showing light gray and white accumulation are cells that highly expressed the $_{co}$NPC1-3×FLAG tag after transfection with pAAV-coNPC1-3×FLAG tag plasmid, and the FLAG tag epitope has been detected by the anti-FLAG tag antibody.
Figure 4N:
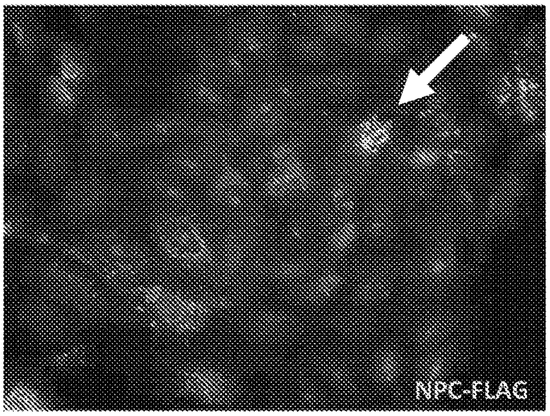
Figure 4O:
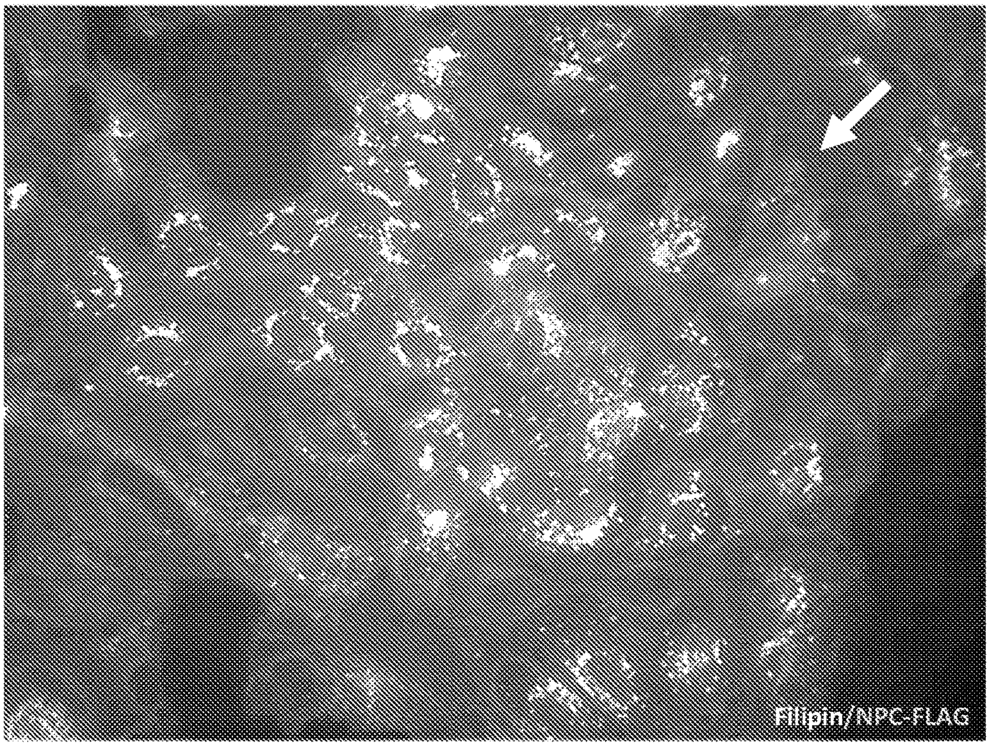
Figure 4P:
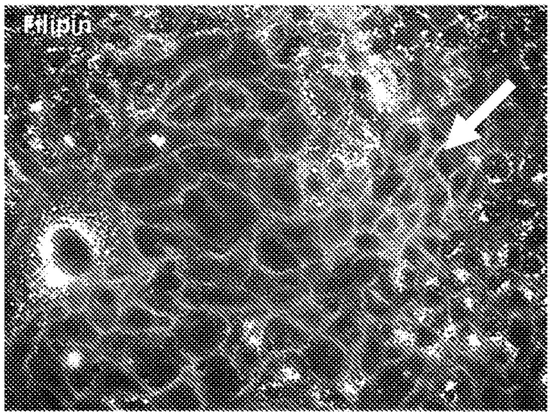
FIGS. 4P-4R are enlarged microscopic images of the same field of well 2 in FIG. 3; U2OS-NPC1-null cells, four days post-transfection with pAAV-mini EF1α coNPC1-3×FLAG tag plasmid, stained with filipin and anti-FLAG tag antibody. The areas showing accumulation of white particles in FIG. 4P are areas of filipin accumulation. The areas in FIG. 4Q showing light gray and white accumulation are cells that highly expressed the $_{co}$NPC1-3×FLAG tag after transfection with pAAV-mini EF1α-coNPC1-3×FLAG tag plasmid, and the FLAG tag epitope has been detected by the anti-FLAG tag antibody.
Figure 4Q:
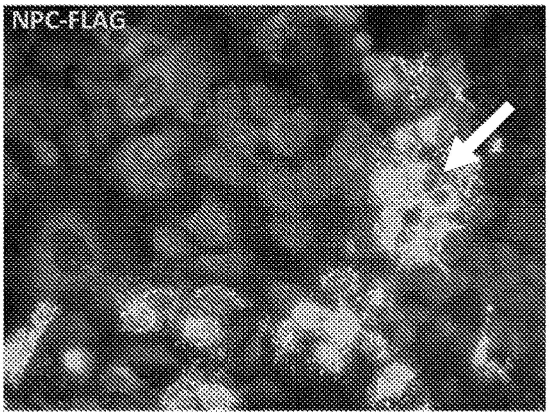
Figure 4R:
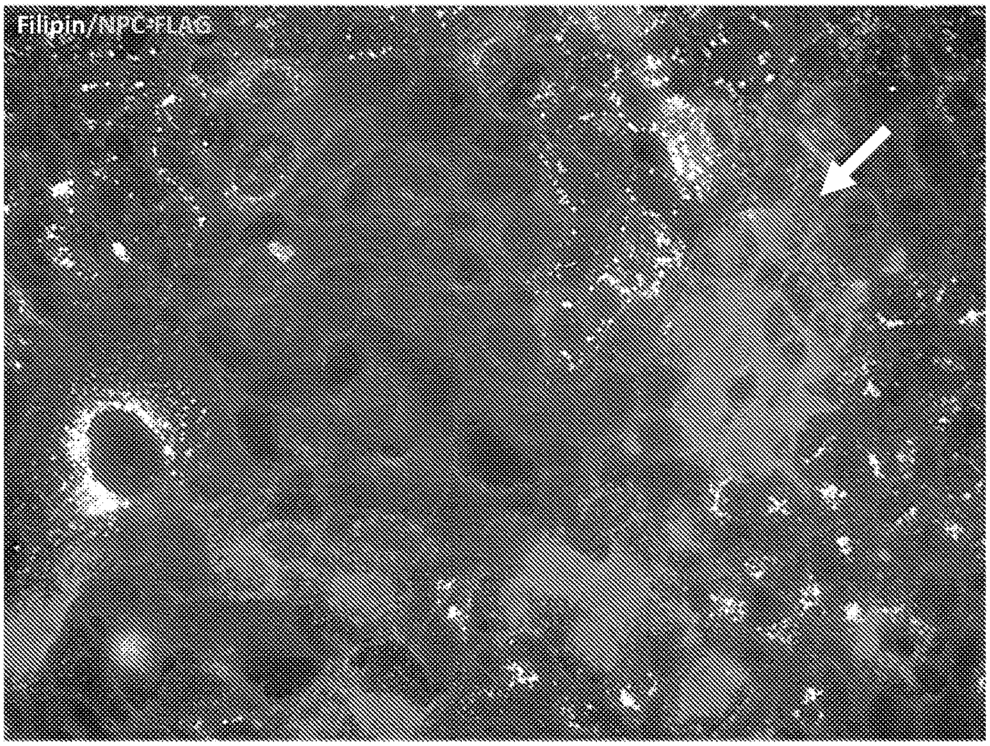
Figure 5A:
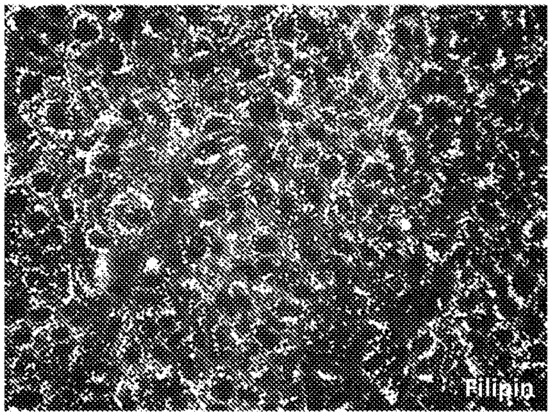
FIGS. 5A-5C are enlarged microscopic images of the same field of well 3 in FIG. 3: U2OS-NPC1-null cells, four days post-transfection with hMITF-FLAG tag plasmid (as negative control). The areas in FIG. 5A showing accumulation of white particles are areas of filipin accumulation. The areas in FIG. 5B showing light gray and white accumulation are cells that highly expressed the MITF-FLAG tag after transfection with hMITF-FLAG tag plasmid, and the FLAG tag epitope has been detected by the anti-FLAG antibody.
Figure 5B:
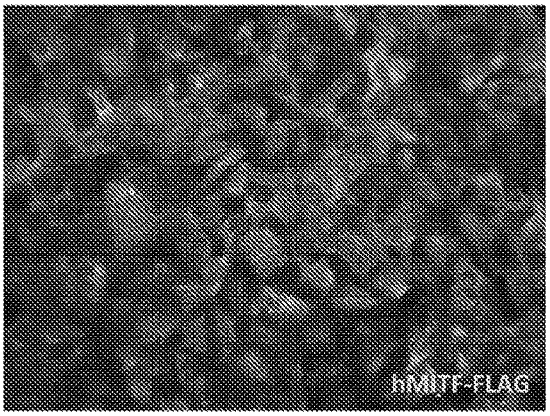
Figure 5C:
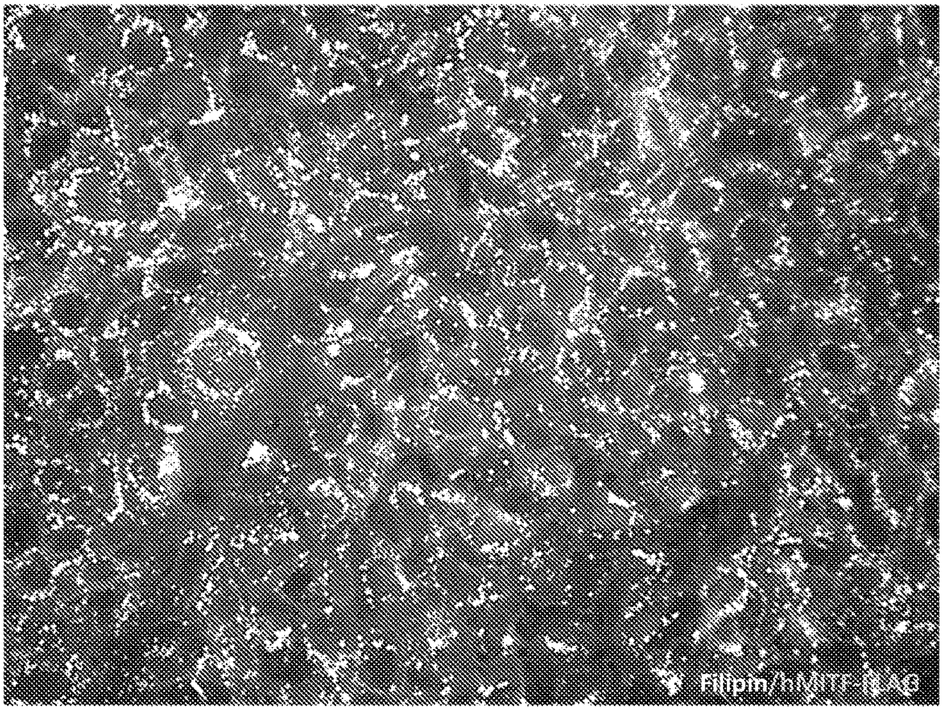
Figure 5D:
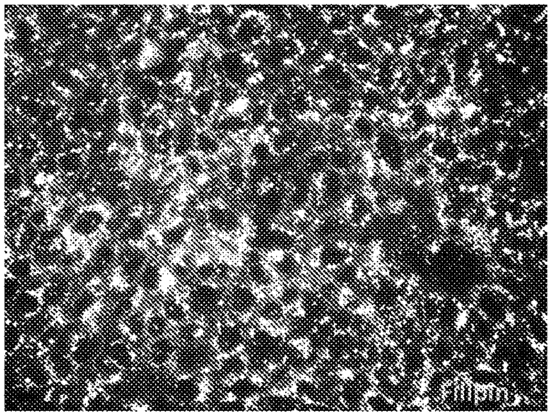
FIGS. 5D-5F are enlarged microscopic images of the same field of well 3 in FIG. 3: U2OS-NPC1-null cells, four days post-transfection with hMITF-FLAG tag plasmid (as negative control). The areas in FIG. 5D showing accumulation of white particles are areas of filipin accumulation. The areas in FIG. 5E showing light gray and white accumulation are cells that highly expressed the MITF-FLAG tag after transfection with hMITF-FLAG tag plasmid, and the FLAG tag epitope has been detected by the anti-FLAG antibody.
Figure 5E:
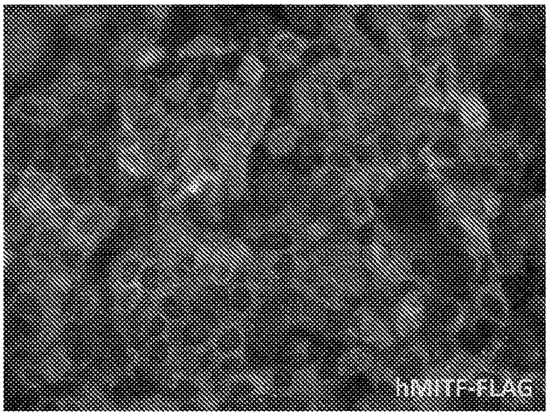
Figure 5F:
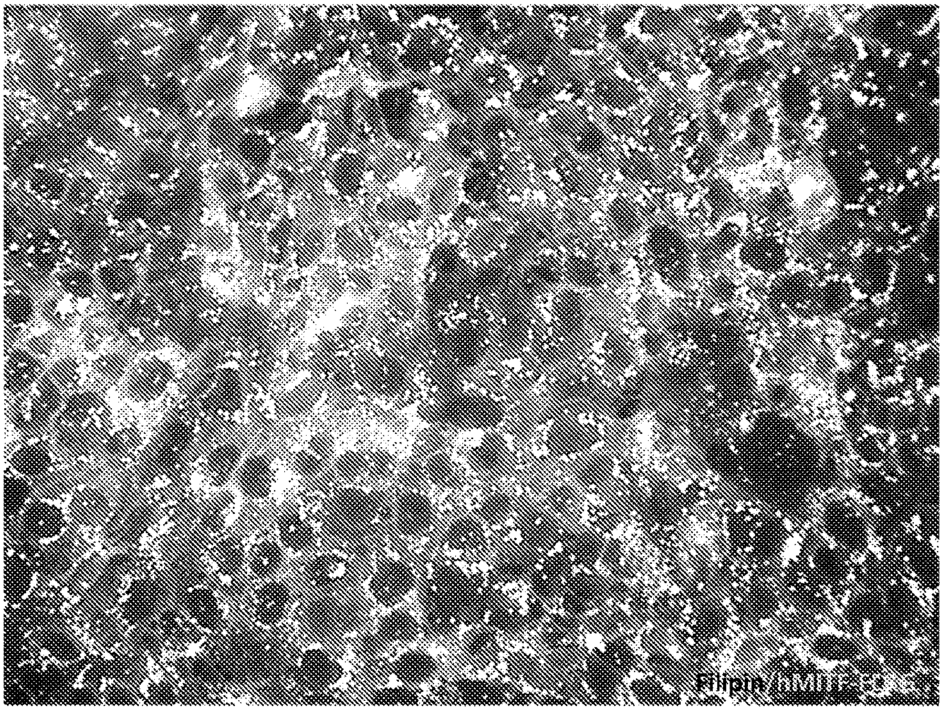
Figure 5G:
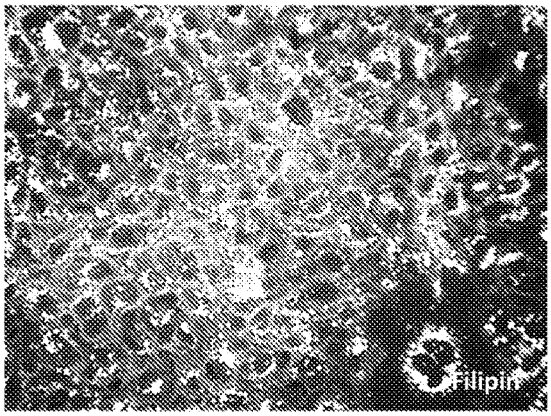
FIGS. 5G-5I are enlarged microscopic images of the same field of well 3 in FIG. 3: U2OS-NPC1-null cells, four days post-transfection with hMITF-FLAG tag plasmid (as negative control). The areas in FIG. 5G showing accumulation of white particles are areas of filipin accumulation. The areas in FIG. 5H showing light gray and white accumulation are cells that highly expressed the MITF-FLAG tag after transfection with hMITF-FLAG tag plasmid, and the FLAG tag epitope has been detected by the anti-FLAG antibody.
Figure 5H:
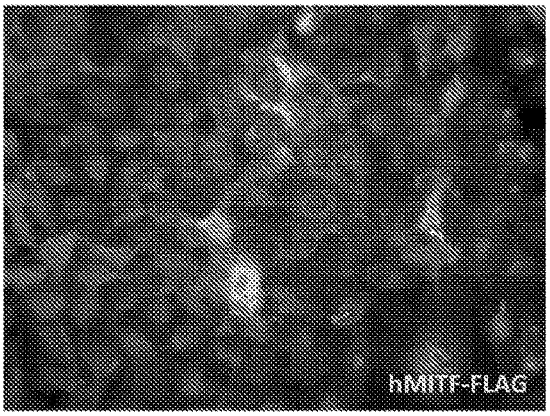
Figure 5I:
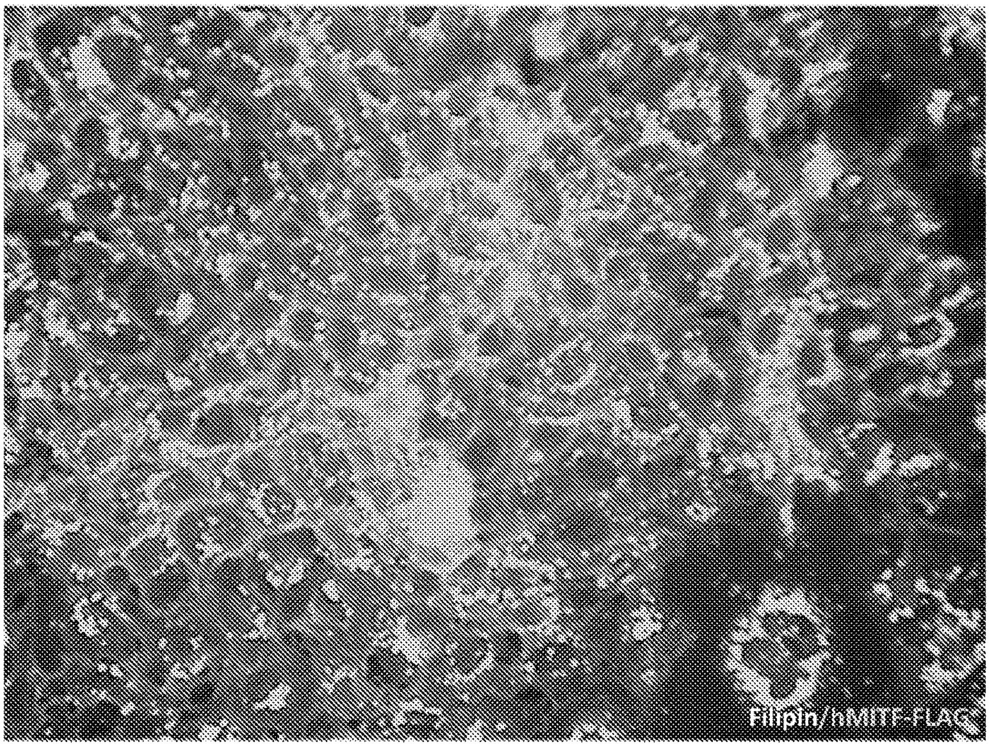
Figure 5J:
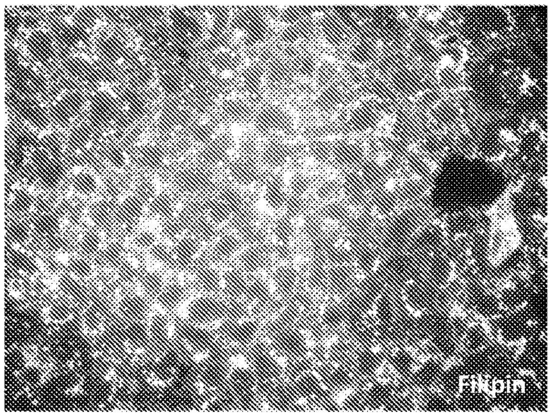
FIGS. 5J-5L are enlarged microscopic images of the same field of well 3 in FIG. 3: U2OS-NPC1-null cells, four days post-transfection with hMITF-FLAG tag plasmid (as negative control). The areas in FIG. 5J showing accumulation of white particles are areas of filipin accumulation. The areas in 5K showing light gray and white accumulation are cells that highly expressed the MITF-FLAG tag after transfection with hMITF-FLAG tag plasmid, and the FLAG tag epitope has been detected by the anti-FLAG antibody.
Figure 5K:
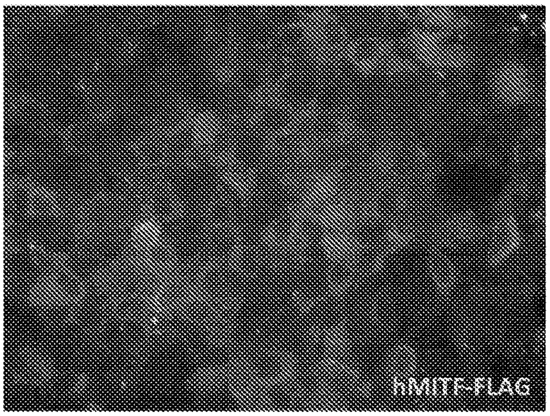
Figure 5L:
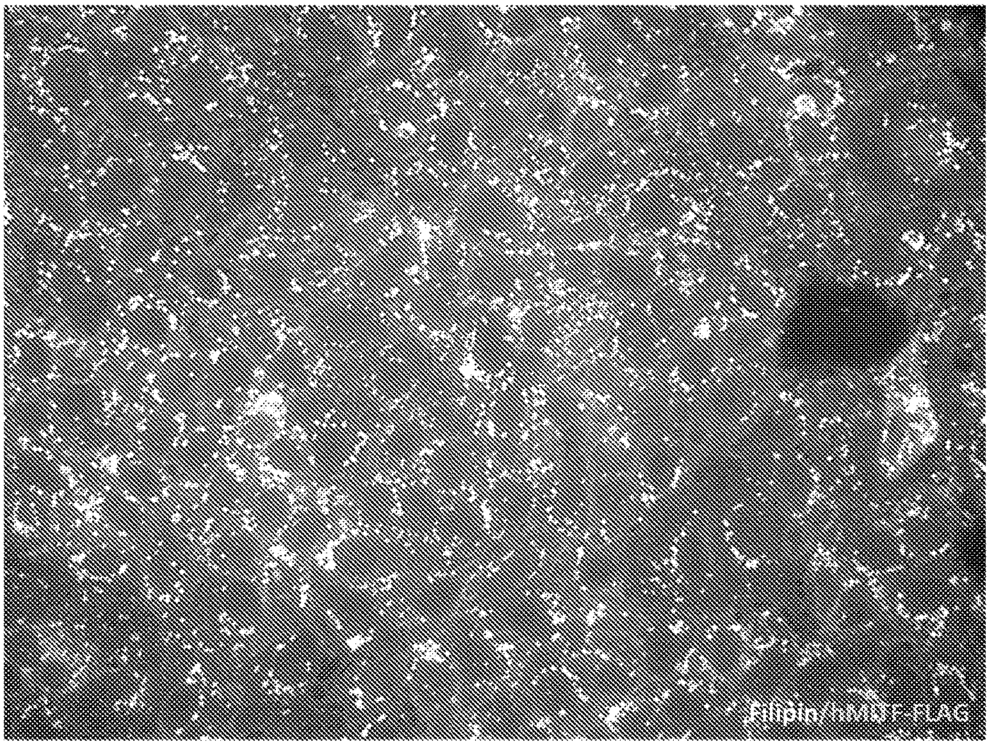
Figure 5M:
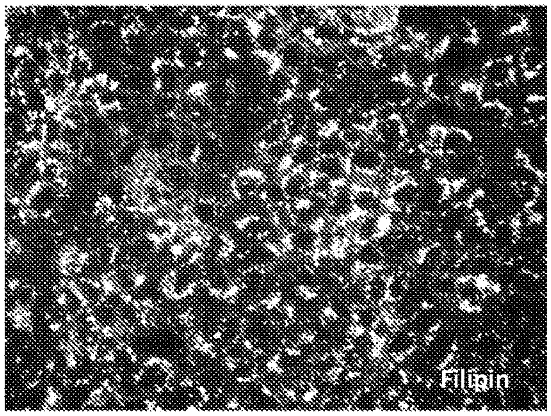
Figure 5N:
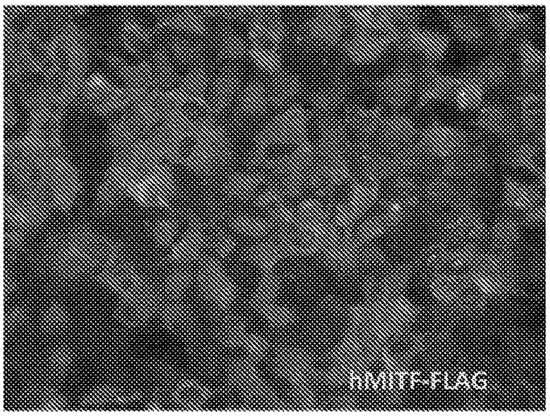
Figure 5O:
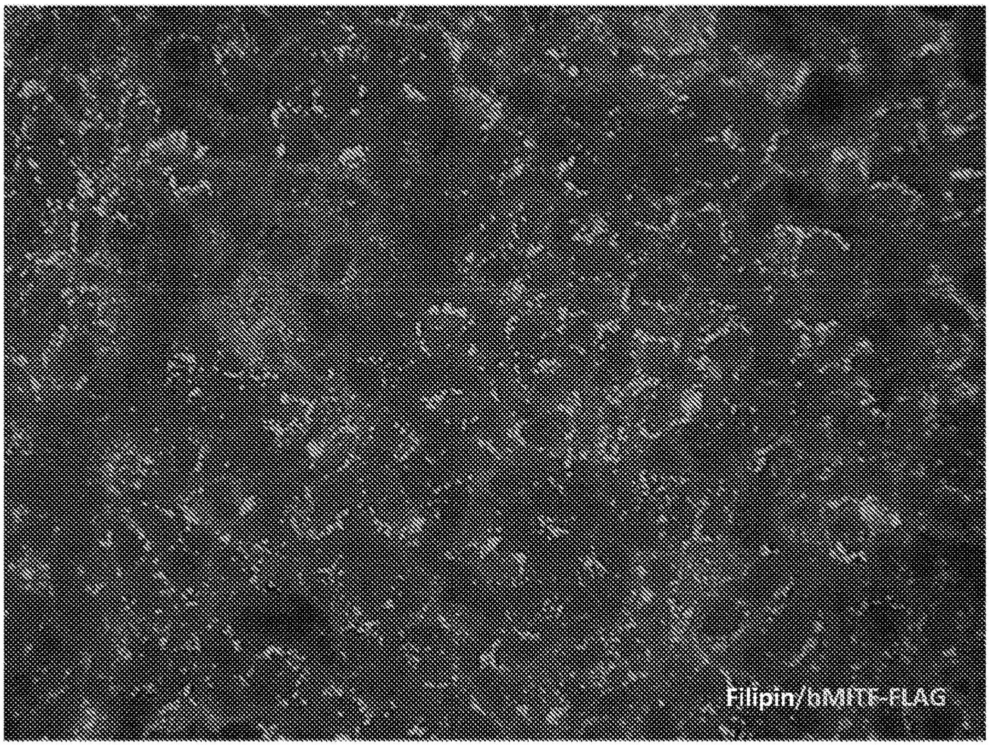
FIG. 5O shows both showing both the filipin staining and anti-FLAG tag antibody. This shows that filipin is present in cells that have been transfected with hMITF-FLAG tag plasmid.
Figure 5P:
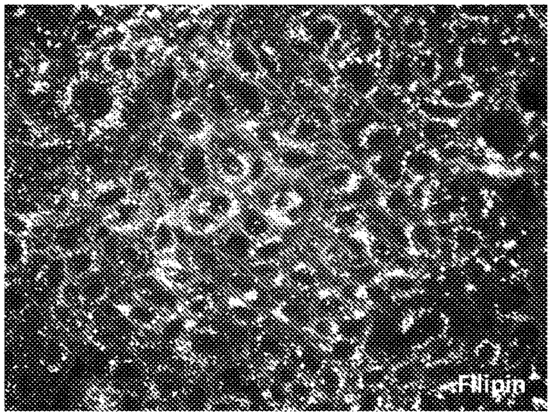
FIGS. 5P-5R are enlarged microscopic images of the same field of well 3 in FIG. 3: U2OS-NPC1-null cells, four days post-transfection with hMITF-FLAG tag plasmid (as negative control). The areas in FIG. 5P showing accumulation of white particles are areas of filipin accumulation. The areas in FIG. 5Q showing light gray and white accumulation are cells that highly expressed the MITF-FLAG tag after transfection with hMITF-FLAG tag plasmid, and the FLAG tag epitope has been detected by the anti-FLAG antibody.
Figure 5Q:
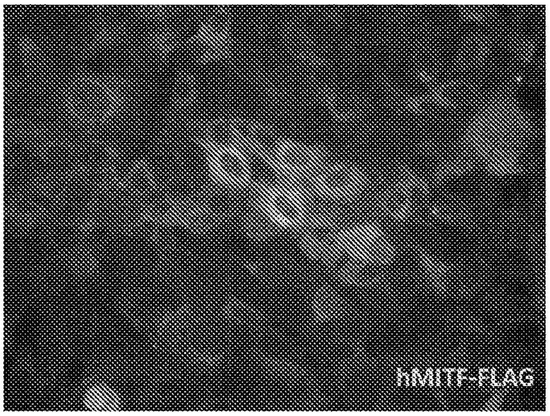
Figure 5R:
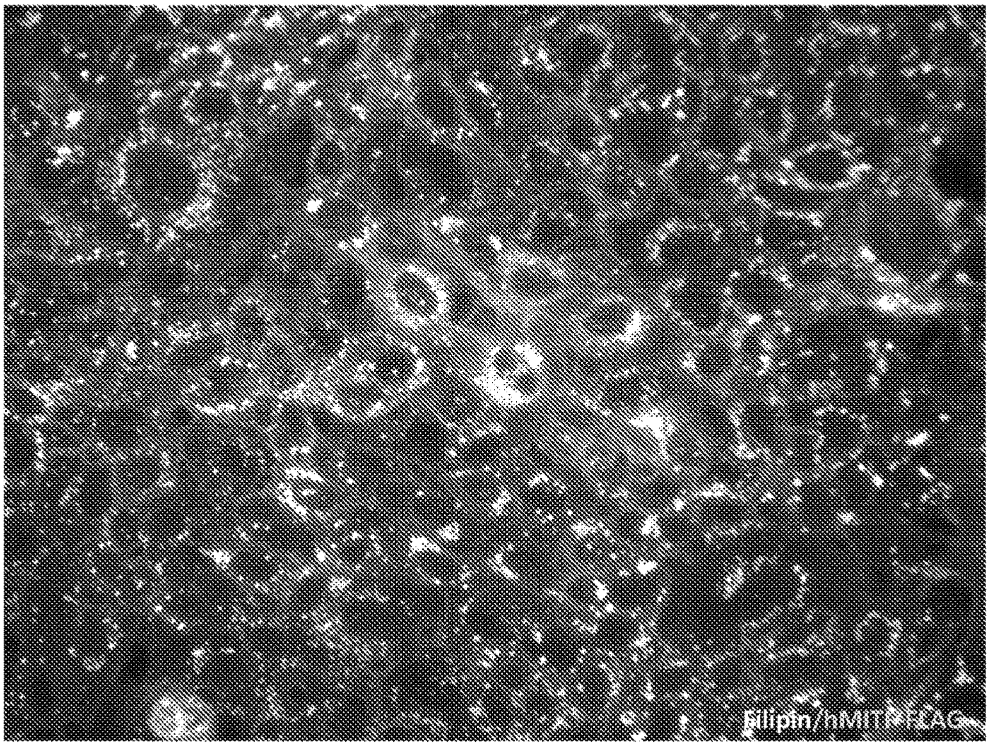
Figure 7A:
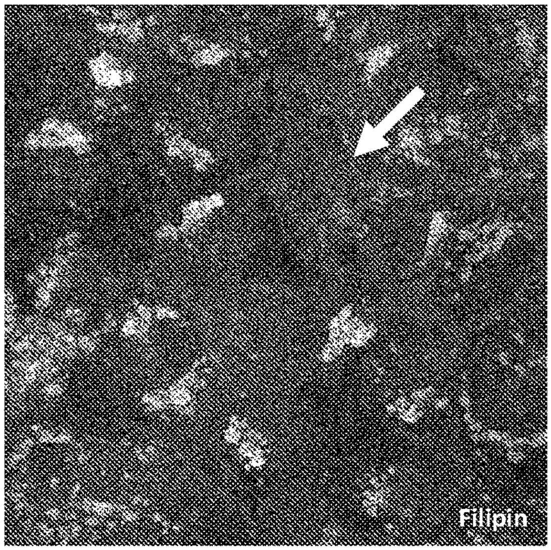
FIG. 7A is an enlarged microscopic image of an area of U2OS-NPC1-null cells, four days post-transfection with the pAAV-EF1α S-intronS-coNPC1 plasmid, stained with filipin. The areas showing accumulation of white particles are areas of filipin accumulation. Arrow indicates cell without accumulation.
Figure 7B:
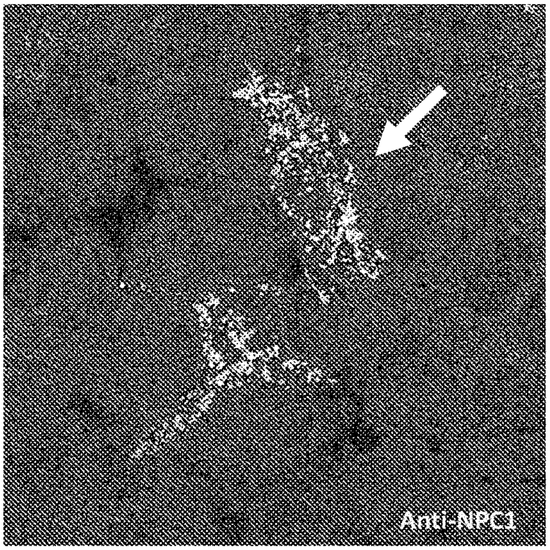
FIG. 7B is an enlarged microspic image of the area shown in FIG. 7A of U2OS-NPC1-null cells, four days post-transfection with the pAAV-EF1α S-intronS-coNPC1 plasmid. The areas showing light gray and white accumulation indicates coNPC1 protein which was detected by the anti-NPC1 antibody. Arrow indicates cell with NPC1 staining.
Figure 7C:
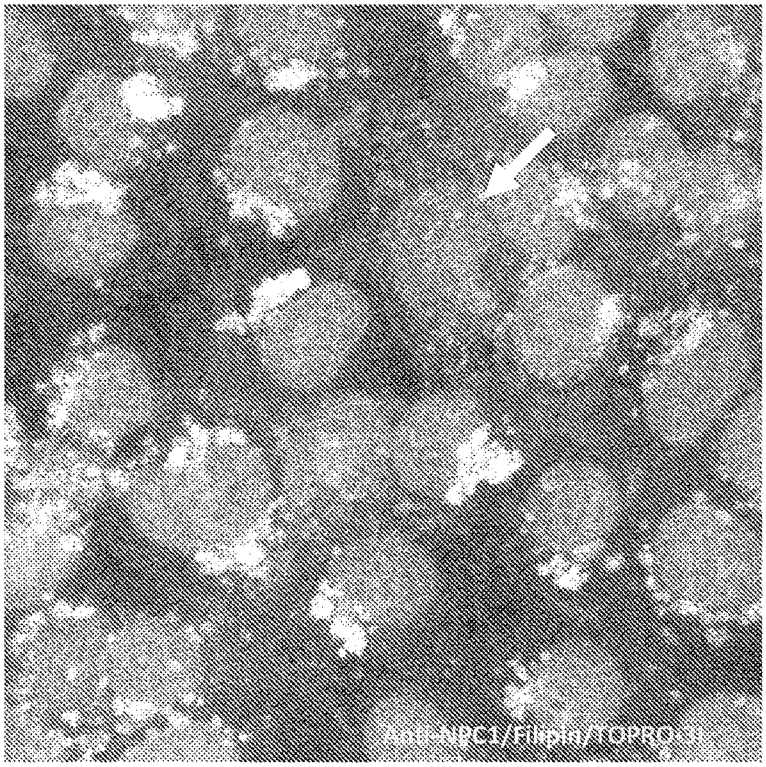
FIG. 7C is an enlarged microscopic image of the area shown in FIGS. 7A and 7B showing the filipin staining, anti-NPC1 antibody, and TOPRO-31 (a nuclear marker).
Figure 7D:
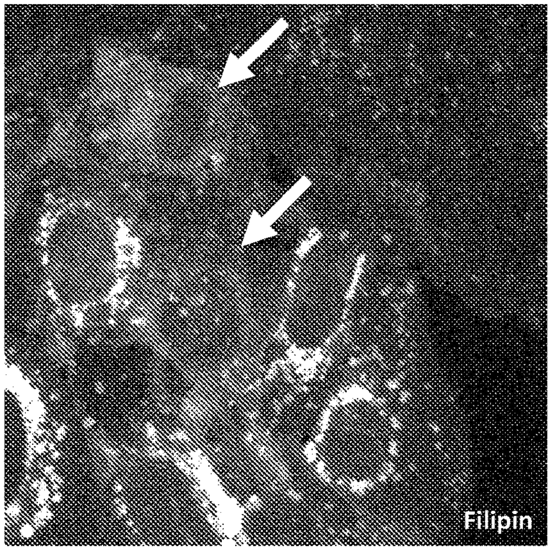
FIG. 7D is an enlarged microscopic image of an area of U2OS-NPC1-null cells, four days post-transfection with pAAV-EF1α S-intronS-coNPC-3×FLAG tag plasmid, stained with filipin. The areas showing accumulation of white particles are areas of filipin accumulation. Arrow indicates cell without accumulation.
Figure 7E:
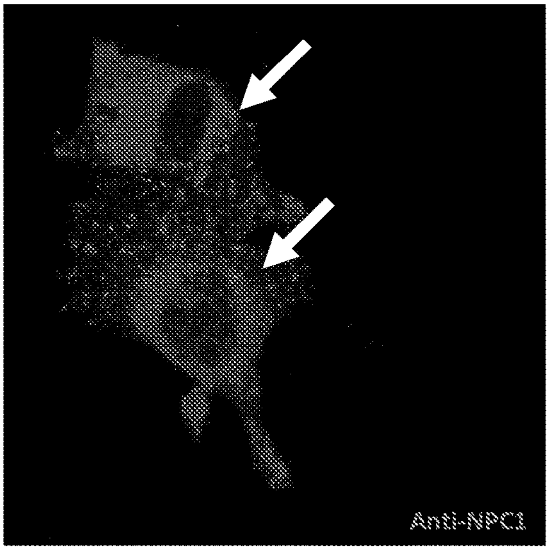
FIG. 7E is an enlarged microscopic image of an area of U2OS-NPC1-null cells, four days post-transfection with the pAAV-EF1α S-intronS-coNPC-3×FLAG tag plasmid. The areas showing light gray and white accumulation are coNPC-3×FLAG tag protein which was detected by the anti-NPC1 antibody. Arrow indicates cell with NPC1 staining.
Figure 7F:
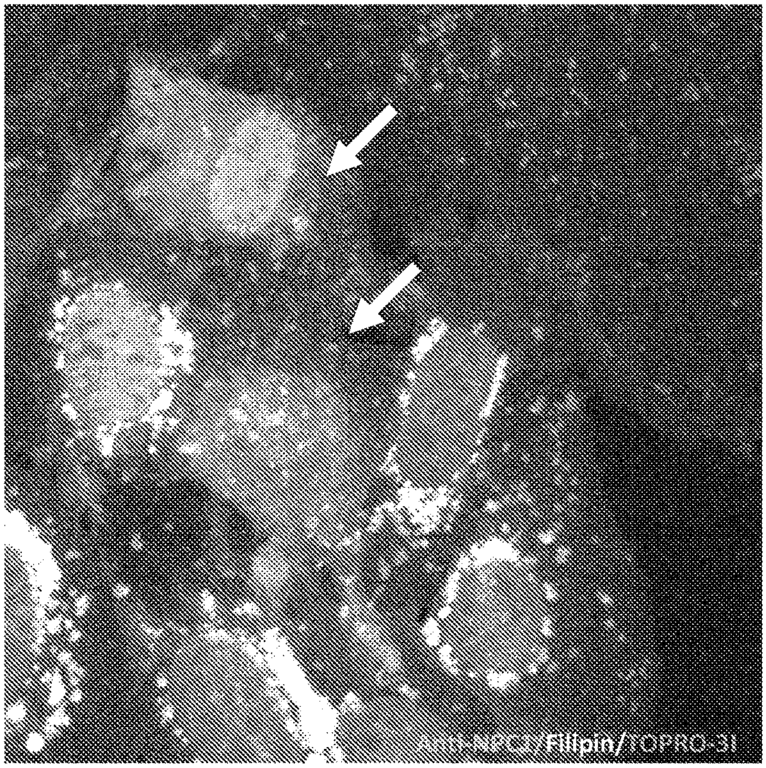
FIG. 7F is an enlarged microscopic image of the area shown in FIGS. 7D and 7E showing both the filipin staining, anti-NPC1 antibody, and TOPRO-31 (a nuclear marker).
Figure 7G:
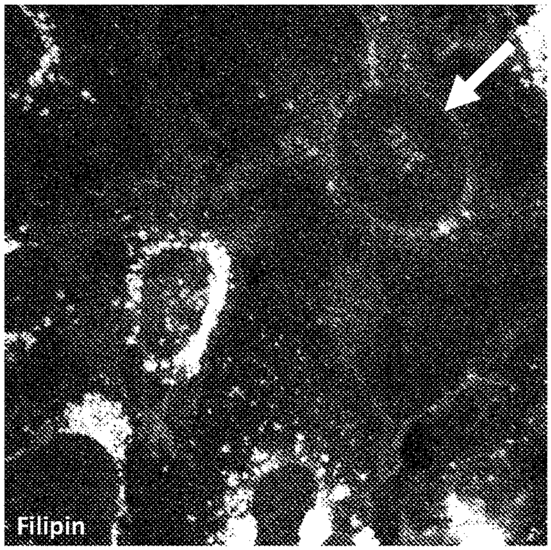
FIG. 7G is an enlarged microscopic image of an area of U2OS-NPC1-null cells, four days post-transfection with the pAAV-EF1α S-intronS-coNPC1-TAT plasmid, stained with filipin. The areas showing accumulation of white particles are areas of filipin accumulation. Arrow indicates cell without accumulation.
Figure 7H:
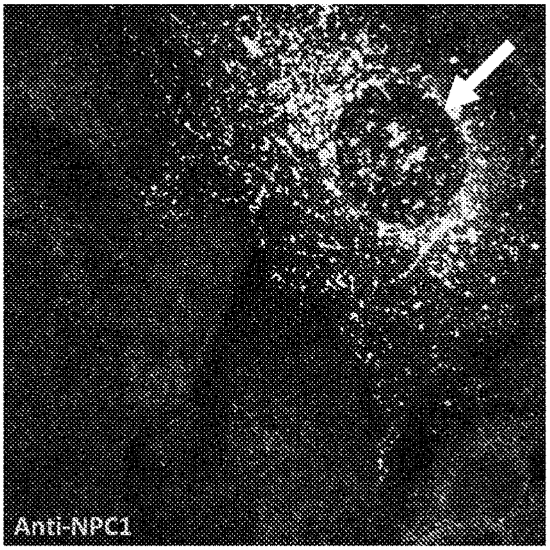
FIG. 7H is an enlarged microscopic image of the area shown in FIG. 7G of U2OS-NPC1-null cells, four days post-transfection with the pAAV-EF1αS-intronS-coNPC1-TAT plasmid. The areas showing white accumulation are NPC1-TAT proteins which were detected by the anti-NPC1 antibody. Arrow indicates cell with NPC1 staining.
Figure 7I:
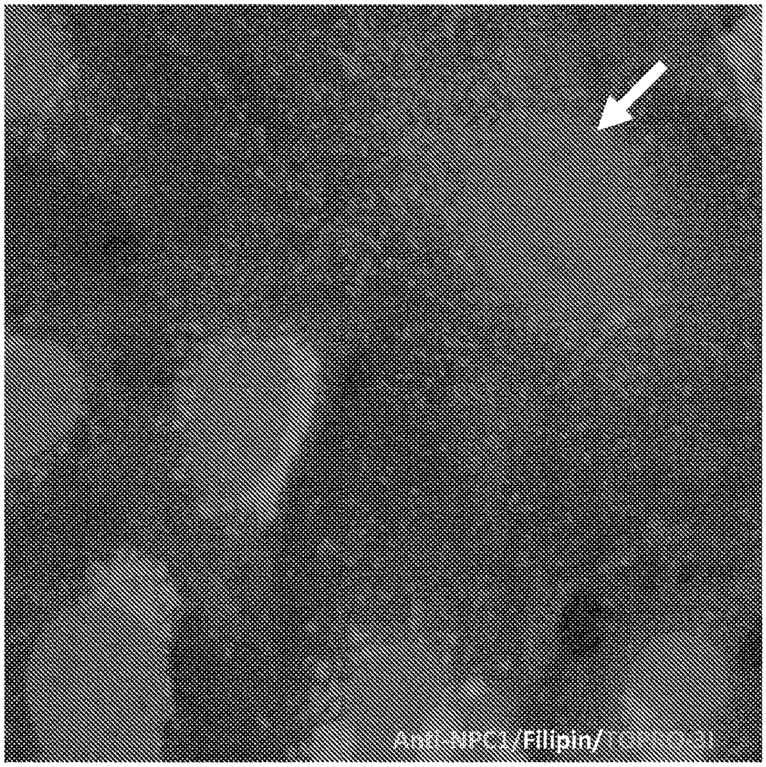
FIG. 7I is an enlarged microscopic image of the same field shown in FIGS. 7G and 7H showing the filipin staining, the anti-NPC1 antibody, and TOPRO-31 (a nuclear maker).

The constructs were synthesized and tested for NPC1 expression in a human mutant NPC1 cell line. The data can be seen in FIGS. 4A-4R ($_{co}$NPC1 expressing construct), FIGS. 5A-5R (hMITF-FLAG tag plasmid control construct), and FIGS. 7A-7I (intron containing $_{co}$NPC1 expressing construct). The cells were stained for filipin and either (1) hMITF-FLAG® tag (control), (2) $_{co}$NPC1-FLAG® tag, or (3) not stained with any FLAG® tag (FIGS. 7A-7C). Anti-NPC1 antibodies were added. The data demonstrates that coNPC1-FLAG® tag expressing cells cleared or significantly reduced the accumulated cellular cholesterol (a cellular hallmark of NPC), as shown by the decrease in filipin staining in cells expressing NPC1 (FIGS. 4A-4R and 7A-7I) as compared to those expressing the control hMITF-FLAG tag plasmid (FIGS. 5A-5R).

Example 2

Figure 6:
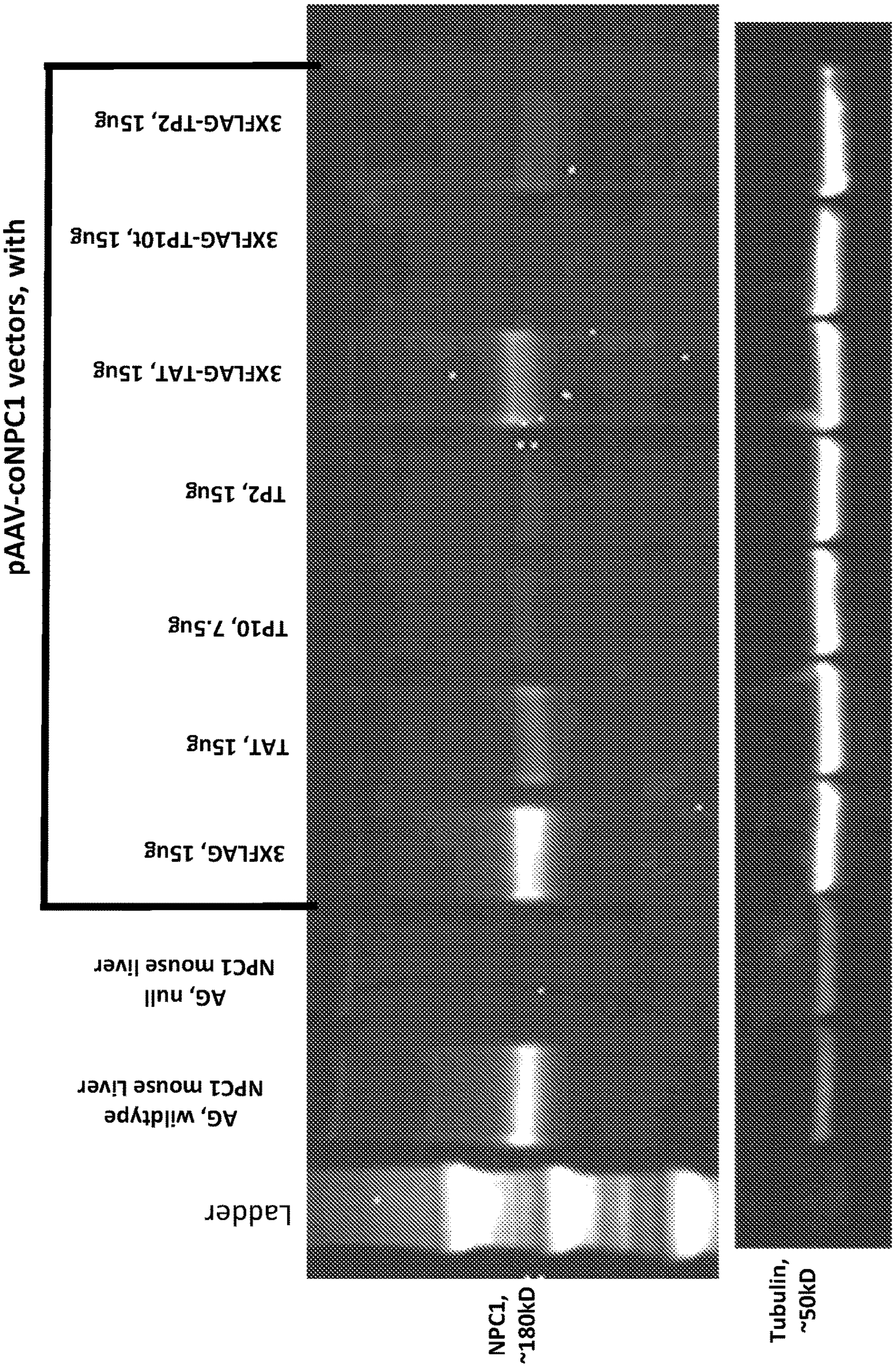
Figure 8A:
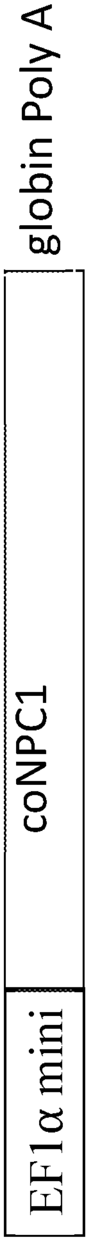
FIG. 8A is a schematic of the experimental design of a "second generation" vector which includes a mini EF1α promoter, a codon-optimized NPC1 gene, and a rabbit beta globin gene polyA signal.
Figure 8B:
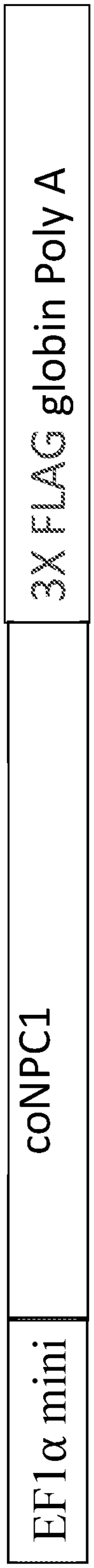
FIG. 8B is a schematic of the experimental design of a "second generation" vector which includes a mini EF1α promoter, a codon-optimized NPC1 gene, a 3×FLAG tag moiety, and a rabbit beta globin gene polyA signal.
Figure 8C:
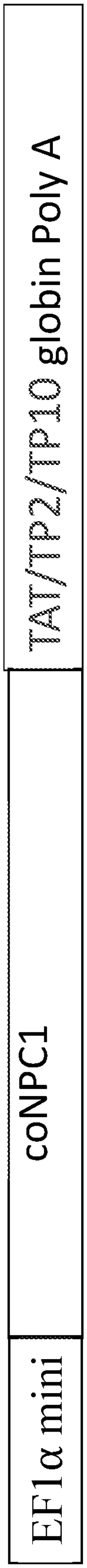
FIG. 8C is a schematic of the experimental design of a "second generation" vector which includes a mini EF1α promoter, a codon-optimized NPC1 gene, a protein transduction domain (either TAT, TP2, or TP10), anda rabbit beta globin gene polyA signal.
Figure 8D:
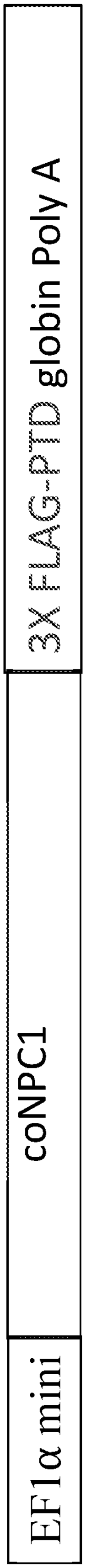
FIG. 8D is a schematic of the experimental design of a "second generation" vector which includes a mini EF1α promoter, a codon-optimized NPC1 gene, a 3×FLAG tag moiety, a protein transduction domain, and a rabbit beta globin gene polyA signal.
Figure 9:
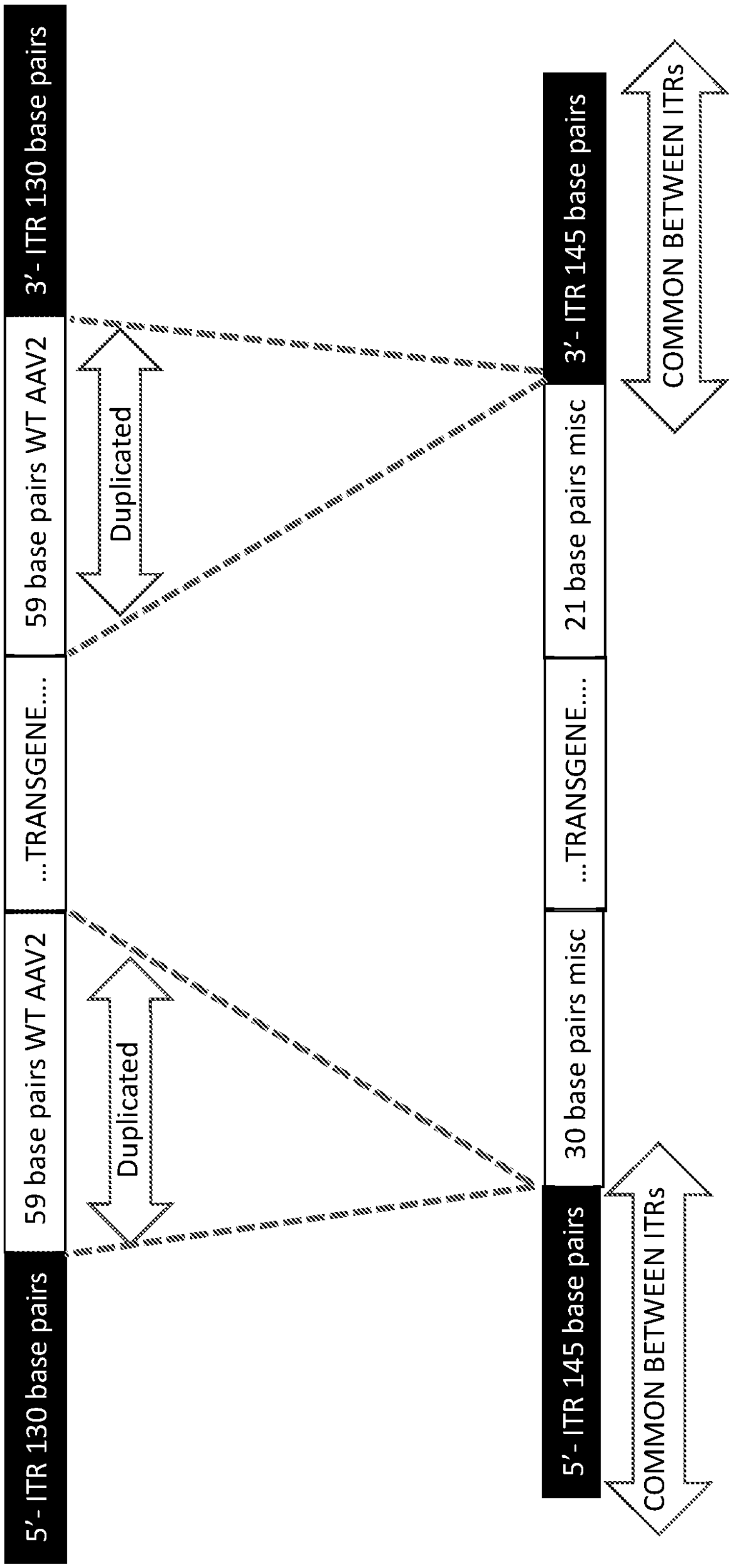

The expression cassettes of the following sequences were prepared as AAV plasmids: AAV mini EF1α-coNPC1 3×FLAG tag (FIG. 8B and SEQ ID NO: 28) AAV mini EF1α-coNPC1-tat (FIG. 8C and SEQ ID NO: 27)), AAV mini EF1α-coNPC1-TP10 (FIG. 8C and SEQ ID NO: 29), AAV mini EF1α-coNPC1-TP2 (FIG. 8C and SEQ ID NO: 30), AAV mini EF1α-coNPC1 3×FLAG tag-tat (FIG. 8D and SEQ ID NO: 31), AAV mini EF1α-coNPC1 3×FLAG tag-TP10 (FIG. 8D and SEQ ID NO: 32), AAV mini EF1α-coNPC1 3×FLAG tag-TP2 (FIG. 8D and SEQ ID NO: 33), AAV short EF1α-intronS-coNPC1 (FIG. 11A and SEQ ID NO: 38), AAV short EF1α-intronS-coNPC1 3×FLAG tag (FIG. 11B and SEQ ID NO: 40), and AAV short EF1α-intronS-coNPC1-tat (FIG. 1C and SEQ ID NO: 39). U2OS-NPC1 knock out cells were transfected with 2 micrograms of each DNA construct using LIPOFECTAMINE (Invitrogen, Carlsbad, California, USA) to deliver the nucleic acid. After 48 hours, total cellular extracts were prepared from the transfected cells and subjected to Western analysis and compared to the expression of Npc1 in wild-type or Npc1 knock-out mouse liver extracts. As can be seen in FIG. 6, all AAV expression constructs tested, except for the AAV mini EF1α-coNPC1 3×FLAG tag-TP10 (FIG. 8C), produced robust expression in the NPC1 knock-out cell line after transfection, comparable to the expression of Npc1 in the wild-type mouse liver. The Western Blot analysis results for the AAV short EF1α-intronS-coNPC1 (FIG. 11A and SEQ ID NO: 38), AAV short EF1α-intronS-coNPC1 3×FLAG tag (FIG. 11B and SEQ ID NO: 40), and AAV short EF1α-intronS-coNPC1-tat (FIG. 11C and sEQ ID NO: 39) constructs are not shown.

DISCUSSION

The vectors (AAV) discussed above represent a new suite of therapeutic agents capable of treating human NPC1 deficiency and related conditions. Due to the genes being synthetic (i.e., codon-optimized), the significant nucleotide sequence divergence also will allow the NPC1 alleles to be easily and uniquely detected in preclinical models, and in patients.

The new codon optimized NPC1 alleles function in vivo as per the demonstration that the expression of NPC1-3× FLAG tag clears filipin from NPC1 null human cells, and localizes to the cytosol in a punctate pattern. Furthermore, the addition of a PTD such as tat, TP2, or TP10, or the combination of PTD and a tag is expressed from the AAV backbone as seen in Example 2.

The vectors of the present disclosure can be used to treat NPC1 deficiency by systemic gene delivery and/or by targeting delivery to an affected organ or tissue, such as to the CSF or deep brain structures, which can be affected in patients with NPC1.

The vectors of the present disclosure may also be used in a generalized fashion for other neurometabolic disorders if the tagged PTD elements are functional, and define a new approach to allow cross-correction of other disorder that have previously been constrained by cellular autonomy.

The vectors of the present disclosure may also be combined with novel AAV serotypes, such as PHP.B or Anc80, in order to allow potent CNS correction after peripheral gene delivery.

Specific Embodiments

According to an aspect, the present disclosure provides a nucleic acid construct for the expression of a therapeutic amount of NPC1 in a cell, the construct comprising: a human codon-optimized NPC1 gene selected from the group consisting of SEQ ID NOs: 1-8.

In any aspect or embodiments described herein, the NPC1 is translationally fused to a protein transduction domain (PTD) to form a NPC1-PTD fusion protein, wherein the fusion protein is capable of cross-correcting non-transformed neighboring cells.

In any aspect or embodiments described herein, the PTD is HIV-Tat, transportin 10 (TP10), or TP2.

In any aspect or embodiments described herein, the NPC1 gene is under the control of a promoter.

In any aspect or embodiments described herein, the promoter is an $EF1_t$ promoter.

In any aspect or embodiments described herein, the NPC1 is translationally fused to a FLAG®-tag moiety.

In any aspect or embodiments described herein, at least one of the cell, the neighboring cells, or both are neuronal cells.

In any aspect or embodiments described herein, the nucleic acid construct comprises a nucleic acid sequence selected from the group consisting of SEQ ID NOS: 1-8.

According to a further aspect, the present disclosure provides an expression vector comprising the nucleic acid construct of the present disclosure, and which is capable of expressing the NPC1 protein, the NPC1-PTD fusion protein, the NPC1-FLAG® tag fusion protein, the NPC1-PTD-FLAG® tag fusion protein, or the NPC1-FLAG® tag-PTD fusion protein in the cell.

According to another aspect, the present disclosure provides a cell comprising the expression vector of the present disclosure.

According to yet another aspect, the present disclosure provides a method of ameliorating, treating, or preventing Niemann-Pick disease, type C in a subject, the method comprising administering a therapeutically effective amount of an expression vector to at least one cell, the expression vector comprising a nucleic acid molecule comprising a human codon-optimized NPC1 gene selected from the group consisting of SEQ ID NOs: 1-8 that encodes an NPC1, wherein the expression vector is effective at ameliorating, treating, or preventing at least one symptom of Niemann-Pick disease, type C1 in the subject.

In any aspect or embodiments described herein, the NPC1 is translationally fused to a PTD to form a NPC1-PTD fusion protein, wherein the NPC1-PTD fusion protein is capable of cross-correcting non-transformed neighboring cells.

In any aspect or embodiments described herein, the PTD protein transduction domain is HIV-Tat, TP10, or TP2.

In any aspect or embodiments described herein, the NPC1 gene is under the control of a promoter.

In any aspect or embodiments described herein, the promoter is an $EF1_t$ promoter.

In any aspect or embodiments described herein, the NPC1 is translationally fused to a FLAG®-tag moiety to form a NPC1-FLAG® tag fusion protein, a NPC1-PTD-FLAG® tag fusion protein, or a NPC1-FLAG® tag-PTD fusion protein.

In any aspect or embodiments described herein, at least one of the cell, the neighboring cells, or both are neuronal cells.

In any aspect or embodiments described herein, the nucleic acid molecule comprises a nucleic acid sequence selected from the group consisting of SEQ ID NO: 1-8.

In any aspect or embodiments described herein, the NPC1 gene may be under the control of a promoter, wherein the promoter is may be a truncated EF1α promoter ($EF1\alpha_t$ promoter) or a mini EF1α promoter (EF1α promoter) or the short EF1α promoter (EF1α S).

In any aspect or embodiments described herein, the nucleic acid construct comprises an expression cassette comprising a nucleotide sequence selected from the group consisting of SEQ ID NOs: 26-38.

In any aspect or embodiments described herein, the gene therapy vector may comprise first and second full-length, wild type AAV inverted terminal repeats (ITRs) that flank the transgene. In any aspect or embodiments described herein, besides the ITRs, the nucleic acid construct may be devoid of any other sequence from the wild-type AAV genome.

In any aspect or embodiments described herein, the first and second AAV ITRs are AAV2 ITRs. In a particular embodiment, the first and second AAV ITRs each comprise the nucleotide sequence of SEQ ID NO: 48. In another particular embodiment, the first and second AAV ITRs each comprise the nucleotide sequence of SEQ ID NO: 49.

In any aspect or embodiments described herein, the NPC1 protein, the $_{co}$NPC1-PTD fusion protein and NPC1-tag fusion protein can be included in a vector, more particularly, in an expression cassette, with a synthetic intron sequence (SEQ ID NO: 25) which may enhance expression by providing more effective splicing of the transgene as compared to the vector which does not comprise the synthetic intron sequence.

In any aspect or embodiments described herein, the NPC1 gene is under the control of a promoter, and the Intron S is positioned between the promoter and the NPC1 gene. In a particular embodiment, the Intron S comprises the nucleotide sequence of SEQ ID NO: 25.

In any aspect or embodiments described herein, the nucleic acid construct may further comprise a nucleotide sequence encoding an antibiotic resistance marker. In an embodiment, the antibiotic resistance marker is an ampicillin resistance marker. In any aspect or embodiments described herein, the antibiotic resistance marker is a kanamycin resistance marker.

In any aspect or embodiments described herein, the nucleic acid construct comprises an expression vector which is capable of expressing the NPC1 protein, the NPC1-PTD fusion protein, or the NPC1 fusion protein, optionally comprising a tag moiety.

In any aspect or embodiments described herein, the invention comprises a cell comprising the expression vector, wherein the cell produces the expression vector and/or the cell expresses the NPC1 protein.

In any aspect or embodiments described herein, the invention comprises a method of ameliorating, treating, or preventing Niemann-Pick disease, type C1 in a subject, the method comprising administering a therapeutically effective amount of an expression vector to at least one cell, the expression vector comprising a nucleic acid molecule comprising a human codon-optimized NPC1 gene, wherein the expression vector is effective at of ameliorating, treating, or preventing at least one symptom of Niemann-Pick disease, type C1 in the subject.

In any aspect or embodiments described herein, the NPC1 of the inventive method is translationally fused to a PTD to form a NPC1-PTD fusion protein, wherein the NPC1-PTD fusion protein is capable of cross-correcting non-transformed neighboring cells. In particular embodiments, the PTD protein transduction domain may be HIV-Tat, TP10, or TP2.

In any aspect or embodiments described herein, the NPC1 gene of the inventive method is under the control of a promoter. In any aspect or embodiments described herein, the promoter may be a truncated EF1α promoter ($EF1\alpha_t$ promoter) or a mini EF1α promoter (EF1α promoter) or the short EF1α promoter (EF1α S).

In any aspect or embodiments described herein, the NPC1 gene of the inventive method may be translationally fused to a tag moiety to form a NPC1-tag fusion protein, a NPC1-PTD-tag fusion protein, or a NPC1-tag-PTD fusion protein.

In any aspect or embodiments described herein, the nucleic acid molecule of the inventive method comprises a nucleic acid sequence selected from the group consisting of SEQ ID NO: 1-8.

In any aspect or embodiments described herein, the expression vector of the inventive method may comprise an expression cassette, with a synthetic intron sequence (SEQ ID NO: 25), which sequence may enhance expression by providing more effective splicing of the transgene as compared to the gene therapy vector which does not comprise the synthetic intron sequence. In any aspect or embodiments described herein, the NPC1 gene of the inventive method is under the control of a promoter, and the Intron S is positioned between the promoter and the NPC1 gene. In a particular embodiment, the Intron S comprises the nucleotide sequence of SEQ ID NO: 25.

In any aspect or embodiments described herein, the inventive method comprises a nucleic acid construct comprising an expression cassette comprising a nucleotide sequence selected from the group consisting of SEQ ID NOs: 26-38.

In any aspect or embodiments described herein, the expression vector of the inventive method may comprise first and second full-length, wild type AAV inverted terminal repeats (ITRs) that flank the transgene. In any aspect or embodiments described herein, besides the ITRs, the nucleic acid construct may be devoid of any other sequence from the wild-type AAV genome. In an embodiment, the first and second AAV ITRs are AAV2 ITRs. In a particular embodiment, the first and second AAV ITRs each comprise the nucleotide sequence of SEQ ID NO: 48. In any aspect or embodiments described herein, the first and second AAV ITRs each comprise the nucleotide sequence of SEQ ID NO: 49.

In any aspect or embodiments described herein, inventive method may further comprise a nucleotide sequence encoding an antibiotic resistance marker. In an embodiment, the antibiotic resistance marker is an ampicillin resistance marker. In another embodiment, the antibiotic resistance marker is a kanamycin resistance marker.

In any aspect or embodiments described herein, the nucleic acid construct may comprise first and second AAV ITRs, the human codon-optimized NPC1 gene, and one or more of a nucleotide sequence encoding a PTD, a promoter, an Intron S, and a nucleotide sequence encoding a tag, wherein the NPC1 gene and all of the one or more of the nucleotide sequence encoding the PTD, the promoter, and the nucleotide sequence encoding the tag are positioned between the first and second AAV ITRs. In any aspect or embodiments described herein, the nucleic acid construct may comprise first and second AAV ITRs, the human codon-optimized NPC1 gene, and all of a nucleotide sequence encoding a PTD, a promoter, an Intron S, and a nucleotide sequence encoding a tag, wherein the NPC1 gene and all of the one or more of the nucleotide sequence encoding the PTD, the promoter, and the nucleotide sequence encoding the tag are positioned between the first and second AAV ITRs.

EQUIVALENTS

Those skilled in the art will recognize, or be able to ascertain using no more than routine experimentation, many equivalents to the specific embodiments of the disclosure described herein. Such equivalents are intended to be encompassed by the following claims.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

Reference for Anc AAVs and AAV Anc80: Zinn E, Pacouret S, Khaychuk V, Turunen H T, Carvalho L S, Andres-Mateos E, Shah S, Shelke R, Maurer A C, Plovic E, Xiao R, Vandenberghe L H. In Silico Reconstruction of the Viral Evolutionary Lineage Yields a Potent Gene Therapy Vector. Cell Rep. 2015 Aug. 11; 12(6):1056-68. doi: 10.1016/j.celrep.2015.07.019. Epub 2015 Jul. 30. PubMed PMID: 26235624; PubMed Central PMCID: PMC4536165

| Vector | Generation | ITR (bases) | Antibiotic | Transgene | Tag or PTD | 5' Intron | Studies | SEQ ID NO. of expression cassette |
|---|---|---|---|---|---|---|---|---|
| AAV-mini EF1α-coNPC1-AMP | Second | 130 | ampicillin | codon optimized NPC1 | none | not present | | mini EF1α-coNPC1 (SEQ ID NO: 26) |
| AAV-mini EF1α-coNPC1-3XFLAG tag AMP | Second | 130 | ampicillin | codon optimized NPC1 | 3xFLAG | not present | Transfection | mini EF1α-coNPC1-3XFLAG tag (SEQ ID NO: 28) |
| AAV-mini EF1α-coNPC1-TAT AMP | Second | 130 | ampicillin | codon optimized NPC1 | TAT | not present | Transfection, IHC, Filipin | mini EF1α-coNPC1-TAT (SEQ ID NO: 27) |
| AAV-mini EF1α-coNPC1-TP2 AMP | Second | 130 | ampicillin | codon optimized NPC1 | TP2 | not present | Transfection | mini EF1α-coNPC1-TP2 (SEQ ID NO: 30) |
| AAV-mini EF1α-coNPC1-TP10 AMP | Second | 130 | ampicillin | codon optimized NPC1 | TP10 | not present | Transfection | mini EF1α-coNPC1-TP10 (SEQ ID NO: 29) |
| AAV-mini EF1α-coNPC1-3XFLAG tag-TAF AMP | Second | 130 | ampicillin | codon optimized NPC1 | 3XFLAG-TAT | not present | Transfection | mini EF1α-CONPC1-3XFLAG tag-TAT (SEQ ID NO: 31) |
| AAV-mini EF1α-coNPC1-3XFLAG tag-TP2 AMP | Second | 130 | ampicillin | codon optimized NPC1 | 3XFLAG-TP2 | not present | Transfection | mini EF1α-coNPC1-3XFLAG tag-TP2 (SEQ ID NO: 33) |
| AAV-mini EF1α-coNPC1-3XFLAG tag-TP10 AMP | Second | 130 | ampicillin | codon optimized NPC1 | 3XFLAG-TP10 | not present | Transfection | mini EF1α-coNPC1-3XFLAG tag-TP10 (SEQ ID NO: 32) |
| AAV- EF1α S-coNPC1-AMP | Third | 145 | ampicillin | codon optimized NPC1 | none | not present | | EF1α S-coNPC1 (SEQ ID NO: 34) |
| AAV-EF1α S_NPC1_3xFLAG tag AMP | Third | 145 | ampicillin | codon optimized NPC1 | 3xFLAG | not present | grown as an AAV9 vector | EF1α S_NPC1_3XFLAG tag (SEQ ID NO: 36) |
| AAV-EF1α S-NPC1_TAT AMP | Third | 145 | ampicillin | codon optimized NPC1 | TAT | not present | | EF1α S-NPC1_TAT (SEQ ID NO: 35) |
| AAV-EF1α-coNPC1-3XFLAG tag-TAT AMP | Third | 145 | ampilcillin | codon optimized NPC1 | 3XFLAG-TAT | not present | | EF1α S-coNPC1-3XFLAG-TAT (SEQ ID NO: 37) |

-continued

| Vector | Generation | ITR (bases) | Antibiotic | Transgene | Tag or PTD | 5' Intron | Studies | SEQ ID NO. of expression cassette |
|---|---|---|---|---|---|---|---|---|
| AAV-EF1α S-intronS-NPC1-KANA | Fourth | 145 | kanamycin | codon optimized NPC1 | none | present | Transfection, IHC, Filipin | EF1α S-intronS-NPC1 (SEQ ID NO: 38) |
| AAV-EF1α S-intronS-BPC1_3XFLAG tag-KANA | Fourth | 145 | kanamycin | codon optimized NPC1 | 3xFLAG | present | Transfection, IHC, Filipin | EF1α S-intronS-NPC1_3XFLAG tag (SEQ ID NO: 40) |
| AAV-EF1α S-intronS-NPC1_TAT-KANA | Fourth | 145 | kanamycin | codon optimized NPC1 | TAT | present | Transfection, IHC, Filipin | EF1α S-intronS-NPC1_TAT (SEQ ID NO: 39) |

The invention claimed is:

1. A nucleic acid construct encoding a Niemann-Pick disease, type C1 (NPC1) fusion protein, the construct comprising a human codon-optimized NPC1 gene, wherein the NPC1 is translationally fused to a protein transduction domain (PTD) to form a NPC1-PTD fusion protein, and the PTD is HIV-Tat, transportin 10 (TP10), or TP2.

2. The nucleic acid construct of claim 1, wherein the NPC1 gene is under the control of a promoter and the promoter is a truncated EF1α promoter ($EF1_t$ promoter) or a mini EF1α promoter (EF1α promoter) or a short EF1α promoter (EF1α S).

3. The nucleic acid construct of claim 1, wherein the nucleic acid construct comprises a nucleic acid sequence selected from SEQ ID NOs: 1-6 and 8.

4. The nucleic acid construct of claim 1, further comprising Intron S.

5. The nucleic acid construct of claim 4, wherein the NPC1 gene is under the control of a promoter, and the Intron S is positioned between the promoter and the NPC1 gene.

6. The nucleic acid construct of claim 4, wherein the Intron S comprises the nucleotide sequence of SEQ ID NO: 25.

7. The nucleic acid construct of claim 1, wherein the nucleic acid construct comprises an expression cassette comprising a nucleotide sequence selected from SEQ ID NOs: 26-31 and 33-38.

8. The nucleic acid construct of claim 1, further comprising first and second adeno-associated virus (AAV) inverted terminal repeats (ITRs).

9. The nucleic acid construct of claim 1, further comprising a nucleotide sequence encoding an antibiotic resistance marker.

10. An expression vector comprising the nucleic acid construct of claim 1.

11. An isolated or purified cell comprising the expression vector of claim 10.

* * * * *

SEQUENCE LISTING

<160> NUMBER OF SEQ ID NOS: 52

<210> SEQ ID NO 1
<211> LENGTH: 3847
<212> TYPE: DNA
<213> ORGANISM: Artificial Sequence
<220> FEATURE:
<223> OTHER INFORMATION: Synthetic

<400> SEQUENCE: 1

```
atgaccgcga ggggactggc cctcgggctg ctcctgctgc tcctttgccc ggcccaagtg      60

ttctcgcaat cgtgcgtgtg gtacggggaa tgcggaattg cctacggcga caagcggtac     120

aactgcgaat actccgggcc tccaaagccg ctgcccaagg acggatacga cctggtccaa     180

gagctctgcc ctggattctt cttcggcaac gtgtcgctgt gttgtgacgt gcggcagctg     240

cagaccctga aggataacct ccagctgccg ctgcaattcc tctcccggtg tccgtcatgc     300

ttctacaact tgctcaacct gttctgcgaa cttacctgtt cgccgagaca gtcccagttt     360

cttaacgtca ccgcaaccga ggactacgtg gaccctgtga ctaaccagac caagactaat     420

gtcaaagaat tgcagtacta cgtgggccag tccttcgcca atgcgatgta caacgcctgt     480

cgggacgtcg aagcgcccag ctccaacgac aaggcactcg gactgctttg cggcaaagat     540

gccgacgcct gcaacgccac caactggatc gagtacatgt tcaataagga caacggacag     600

gcccctttca ccatcacacc tgtgttcagc gacttcccag tccacgggat ggaacctatg     660

aacaacgcga ctaagggatg cgacgagtcc gtggacgaag tgaccgcccc gtgttcctgt     720

caagattgct caatcgtgtg cggtccgaag ccccagcctc ctcctccgcc ggctccatgg     780

accatcctgg gtctggacgc tatgtacgtg attatgtgga tcacttacat ggccttcctc     840

ctggtgttct tcggcgcttt cttcgccgtg tggtgttacc ggaagcgcta cttcgtgtcc     900

gagtatactc ctatcgactc taacatagcg ttctccgtga acgcctccga taagggagag     960

gcatcgtgct gtgatcccgt gtccgccgct ttcgaaggat gcttgaggcg gctgttcacc    1020

cgctggggca gcttctgcgt gagaaatccc ggctgtgtga ttttcttctc gctggtgttc    1080

atcaccgctt gctcgtcggg gctggtgttc gtcagagtca caacgaaccc cgtggacctg    1140

tggagcgcgc ctagcagcca ggcccgcctg gaaaaggaat acttcgacca gcatttcgga    1200

ccctttttcc ggaccgaaca gctgattatc cgcgccccgc tgactgacaa gcatatctac    1260

cagccttacc cgagcggagc ggatgtgccc tttggtccgc cactcgacat ccagatcctg    1320

caccaagtcc tggacttgca aatcgctatt gagaacatta ctgcctccta cgacaacgag    1380

acagtgaccc tgcaggacat ttgtcttgcc ccgctgtccc cctacaacac caactgcacg    1440

atcctgagcg tgctgaacta tttccaaaac tcgcactccg tgctggatca caagaagggc    1500
```

-continued

```
gacgatttct tcgtctacgc cgattaccac acccacttcc tgtactgcgt gcgcgctccg   1560
gcttcactga acgacacttc cctcctccac gacccgtgcc tgggaacgtt cggcggaccc   1620
gtgtttccct ggctggtcct gggcggctac gacgaccaga actacaacaa cgccaccgcc   1680
ctcgtgatca cctttcctgt gaacaactac tacaacgaca ccgaaaagtt gcagagagca   1740
caagcgtggg agaaggagtt catcaacttc gtgaagaact acaaaaaccc taacctgacc   1800
atctccttta cggccgagcg ctcaatcgag gacgaattga acagggaatc ggactccgac   1860
gtgttcactg tcgtcattag ctacgccatc atgttcttgt acattagcct ggcgctgggg   1920
cacatgaagt cctgccgccg gctgctggtc gattcgaagg tgtccctggg aatcgccggc   1980
atcctgatcg tcctgtcgtc cgtggcctgt tccctgggag tgttcagcta cattggactg   2040
ccactgaccc tcattgtgat tgaagtgatc ccttttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
gaccagagcc tctccatgcc ggatgattcc tacatggtgg actacttcaa gagcatctct   2640
cagtacttgc acgctggccc tcccgtgtat ttcgtgctgg aggaagggca cgactacact   2700
agctctaagg gacagaacat ggtctgcggt ggcatgggat gcaacaatga ctcgctggtg   2760
cagcagattt tcaacgccgc gcaactcgat aactacacca ggattggatt cgctccctcc   2820
tcctggatcg acgattattt tgactgggtc aagccgcagt ctagctgctg ccgggtggac   2880
aacatcacgg atcagttctg caatgcttcc gtggtcgacc cggcctgcgt gcggtgccgg   2940
cctcttactc cggagggaaa gcagaggccc cagggtggcg acttcatgcg gtttctgccc   3000
atgttcctga gcgataaccc caaccccaaa tgcgggaagg gaggtcacgc ggcgtactcg   3060
tcagcggtca acatcctgct gggccatgga actagagtgg gagcgaccta cttcatgact   3120
taccatactg tgctgcagac ctcagccgac ttcatcgacg cactcaagaa agcccgcctg   3180
atcgcatcaa acgtgaccga gactatgggg atcaacggat ccgcgtaccg cgtgttccca   3240
tattcggtgt tctacgtgtt ctacgagcaa tacctgacca ttattgacga caccatcttt   3300
aacctggggg tgtcactggg agccatcttc cttgtgacca tggtcctcct gggctgcgaa   3360
ctgtggtccg ccgtgatcat gtgcgctacc atcgcaatgg tcctcgtgaa catgtttggg   3420
gtcatgtggc tgtggggcat ctccctgaac gcggtgtccc tcgtgaacct ggtcatgtca   3480
tgcggcatta gcgtggagtt ctgctcccac attactcgcg ccttcaccgt gtcgatgaag   3540
ggttcccgcg tggagcgggc ggaggaagcc ctggcccaca tgggatcctc ggtgttctcg   3600
ggcatcaccc ttactaagtt cggcggtatc gtggtgctgg ccttcgccaa gtcacagatc   3660
ttccagattt tctacttccg gatgtacctg gcgatggtgc ttctgggagc aacccacggc   3720
ctgatcttcc tgcccgtgct cttgtcctac atcggcccca gcgtgaacaa ggccaagtcc   3780
tgcgccactg aggaacgcta caagggcacc gaaagagaaa ggctgctgaa tttctgatag   3840
```

-continued atgatag 3847

<210> SEQ ID NO 2
<211> LENGTH: 3876
<212> TYPE: DNA
<213> ORGANISM: Artificial Sequence
<220> FEATURE:
<223> OTHER INFORMATION: Synthetic

<400> SEQUENCE: 2
atgaccgcga ggggactggc cctcgggctg ctcctgctgc tcctttgccc ggcccaagtg 60
ttctcgcaat cgtgcgtgtg gtacggggaa tgcggaattg cctacggcga caagcggtac 120
aactgcgaat actccgggcc tccaaagccg ctgcccaagg acggatacga cctggtccaa 180
gagctctgcc ctggattctt cttcggcaac gtgtcgctgt gttgtgacgt gcggcagctg 240
cagaccctga aggataacct ccagctgccg ctgcaattcc tctcccggtg tccgtcatgc 300
ttctacaact tgctcaacct gttctgcgaa cttacctgtt cgccgagaca gtcccagttt 360
cttaacgtca ccgcaaccga ggactacgtg gaccctgtga ctaaccagac caagactaat 420
gtcaaagaat tgcagtacta cgtgggccag tccttcgcca atgcgatgta caacgcctgt 480
cgggacgtcg aagcgcccag ctccaacgac aaggcactcg gactgctttg cggcaaagat 540
gccgacgcct gcaacgccac caactggatc gagtacatgt tcaataagga caacggacag 600 gccccttca ccatcacacc tgtgttcagc gacttcccag tccacgggat ggaacctatg 660
aacaacgcga ctaagggatg cgacgagtcc gtggacgaag tgaccgcccc gtgttcctgt 720
caagattgct caatcgtgtg cggtccgaag ccccagcctc ctcctccgcc ggctccatgg 780
accatcctgg gtctggacgc tatgtacgtg attatgtgga tcacttacat ggccttcctc 840
ctggtgttct tcggcgcttt cttcgccgtg tggtgttacc ggaagcgcta cttcgtgtcc 900
gagtatactc ctatcgactc taacatagcg ttctccgtga acgcctccga taagggagag 960
gcatcgtgct gtgatcccgt gtccgccgct ttcgaaggat gcttgaggcg gctgttcacc 1020
cgctggggca gcttctgcgt gagaaatccc ggctgtgtga ttttcttctc gctggtgttc 1080
atcaccgctt gctcgtcggg gctggtgttc gtcagagtca caacgaaccc cgtggacctg 1140
tggagcgcgc ctagcagcca ggcccgcctg gaaaaggaat acttcgacca gcatttcgga 1200 cccttttcc ggaccgaaca gctgattatc cgcgccccgc tgactgacaa gcatatctac 1260
cagccttacc cgagcggagc ggatgtgccc tttggtccgc cactcgacat ccagatcctg 1320
caccaagtcc tggacttgca aatcgctatt gagaacatta ctgcctccta cgacaacgag 1380
acagtgaccc tgcaggacat ttgtcttgcc ccgctgtccc cctacaacac caactgcacg 1440
atcctgagcg tgctgaacta tttccaaaac tcgcactccg tgctggatca caagaagggc 1500
gacgatttct tcgtctacgc cgattaccac acccacttcc tgtactgcgt gcgcgctccg 1560
gcttcactga acgacacttc cctcctccac gacccgtgcc tgggaacgtt cggcggaccc 1620
gtgtttccct ggctggtcct gggcggctac gacgaccaga actacaacaa cgccaccgcc 1680
ctcgtgatca cctttcctgt gaacaactac tacaacgaca ccgaaaagtt gcagagagca 1740
caagcgtggg agaaggagtt catcaacttc gtgaagaact acaaaaaccc taacctgacc 1800
atctccttta cggccgagcg ctcaatcgag gacgaattga acagggaatc ggactccgac 1860
gtgttcactg tcgtcattag ctacgccatc atgttcttgt acattagcct ggcgctgggg 1920
cacatgaagt cctgccgccg gctgctggtc gattcgaagg tgtccctggg aatcgccggc 1980
atcctgatcg tcctgtcgtc cgtggcctgt tccctgggag tgttcagcta cattggactg 2040

```
ccactgaccc tcattgtgat tgaagtgatc ccttttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
gaccagagcc tctccatgcc ggatgattcc tacatggtgg actacttcaa gagcatctct   2640
cagtacttgc acgctggccc tcccgtgtat ttcgtgctgg aggaagggca cgactacact   2700
agctctaagg gacagaacat ggtctgcggt ggcatgggat gcaacaatga ctcgctggtg   2760
cagcagattt tcaacgccgc gcaactcgat aactacacca ggattggatt cgctccctcc   2820
tcctggatcg acgattattt tgactgggtc aagccgcagt ctagctgctg ccgggtggac   2880
aacatcacgg atcagttctg caatgcttcc gtggtcgacc cggcctgcgt gcggtgccgg   2940
cctcttactc cggagggaaa gcagaggccc cagggtggcg acttcatgcg gtttctgccc   3000
atgttcctga gcgataaccc caaccccaaa tgcgggaagg gaggtcacgc ggcgtactcg   3060
tcagcggtca acatcctgct gggccatgga actagagtgg gagcgaccta cttcatgact   3120
taccatactg tgctgcagac ctcagccgac ttcatcgacg cactcaagaa agcccgcctg   3180
atcgcatcaa acgtgaccga gactatgggg atcaacggat ccgcgtaccg cgtgttccca   3240
tattcggtgt tctacgtgtt ctacgagcaa tacctgacca ttattgacga caccatcttt   3300
aacctggggg tgtcactggg agccatcttc cttgtgacca tggtcctcct gggctgcgaa   3360
ctgtggtccg ccgtgatcat gtgcgctacc atcgcaatgg tcctcgtgaa catgtttggg   3420
gtcatgtggc tgtggggcat ctccctgaac gcggtgtccc tcgtgaacct ggtcatgtca   3480
tgcggcatta gcgtggagtt ctgctcccac attactcgcg ccttcaccgt gtcgatgaag   3540
ggttcccgcg tggagcgggc ggaggaagcc ctggcccaca tgggatcctc ggtgttctcg   3600
ggcatcaccc ttactaagtt cggcggtatc gtggtgctgg ccttcgccaa gtcacagatc   3660
ttccaaattt tctacttcag aatgtacttg gcgatggtcc tgcttggagc cacacacggt   3720
ctgatcttcc tgcctgtgct tctgtcctac atcggcccgt ccgtgaacaa agcgaagtcc   3780
tgtgctactg aggagcggta caagggaact gagcgcgagc gcctgctcaa ctttgggggc   3840
ggccgcaaga agcgccggca gcgcagaagg tgatag                             3876
```

<210> SEQ ID NO 3
<211> LENGTH: 3925
<212> TYPE: DNA
<213> ORGANISM: Artificial Sequence
<220> FEATURE:
<223> OTHER INFORMATION: Synthetic

<400> SEQUENCE: 3

```
atgaccgcga ggggactggc cctcgggctg ctcctgctgc tcctttgccc ggcccaagtg     60
ttctcgcaat cgtgcgtgtg gtacggggaa tgcggaattg cctacggcga caagcggtac    120
aactgcgaat actccgggcc tccaaagccg ctgcccaagg acggatacga cctggtccaa    180
```

-continued

```
gagctctgcc ctggattctt cttcggcaac gtgtcgctgt gttgtgacgt gcggcagctg    240
cagaccctga aggataacct ccagctgccg ctgcaattcc tctcccggtg tccgtcatgc    300
ttctacaact tgctcaacct gttctgcgaa cttacctgtt cgccgagaca gtcccagttt    360
cttaacgtca ccgcaaccga ggactacgtg gaccctgtga ctaaccagac caagactaat    420
gtcaaagaat tgcagtacta cgtgggccag tccttcgcca atgcgatgta caacgcctgt    480
cgggacgtcg aagcgcccag ctccaacgac aaggcactcg gactgctttg cggcaaagat    540
gccgacgcct gcaacgccac caactggatc gagtacatgt tcaataagga caacggacag    600
gcccctttca ccatcacacc tgtgttcagc gacttcccag tccacgggat ggaacctatg    660
aacaacgcga ctaagggatg cgacgagtcc gtggacgaag tgaccgcccc gtgttcctgt    720
caagattgct caatcgtgtg cggtccgaag ccccagcctc ctcctccgcc ggctccatgg    780
accatcctgg gtctggacgc tatgtacgtg attatgtgga tcacttacat ggccttcctc    840
ctggtgttct tcggcgcttt cttcgccgtg tggtgttacc ggaagcgcta cttcgtgtcc    900
gagtatactc ctatcgactc taacatagcg ttctccgtga acgcctccga taagggagag    960
gcatcgtgct gtgatcccgt gtccgccgct ttcgaaggat gcttgaggcg gctgttcacc   1020
cgctggggca gcttctgcgt gagaaatccc ggctgtgtga ttttcttctc gctggtgttc   1080
atcaccgctt gctcgtcggg gctggtgttc gtcagagtca caacgaaccc cgtggacctg   1140
tggagcgcgc ctagcagcca ggcccgcctg gaaaaggaat acttcgacca gcatttcgga   1200
ccctttttcc ggaccgaaca gctgattatc cgcgccccgc tgactgacaa gcatatctac   1260
cagccttacc cgagcggagc ggatgtgccc tttggtccgc cactcgacat ccagatcctg   1320
caccaagtcc tggacttgca aatcgctatt gagaacatta ctgcctccta cgacaacgag   1380
acagtgaccc tgcaggacat ttgtcttgcc ccgctgtccc cctacaacac caactgcacg   1440
atcctgagcg tgctgaacta tttccaaaac tcgcactccg tgctggatca caagaagggc   1500
gacgatttct tcgtctacgc cgattaccac acccacttcc tgtactgcgt gcgcgctccg   1560
gcttcactga acgacacttc cctcctccac gacccgtgcc tgggaacgtt cggcggaccc   1620
gtgtttccct ggctggtcct gggcggctac gacgaccaga actacaacaa cgccaccgcc   1680
ctcgtgatca cctttcctgt gaacaactac tacaacgaca ccgaaaagtt gcagagagca   1740
caagcgtggg agaaggagtt catcaacttc gtgaagaact acaaaaaccc taacctgacc   1800
atctccttta cggccgagcg ctcaatcgag gacgaattga acagggaatc ggactccgac   1860
gtgttcactg tcgtcattag ctacgccatc atgttcttgt acattagcct ggcgctgggg   1920
cacatgaagt cctgccgccg gctgctggtc gattcgaagg tgtccctggg aatcgccggc   1980
atcctgatcg tcctgtcgtc cgtggcctgt tccctgggag tgttcagcta cattggactg   2040
ccactgaccc tcattgtgat tgaagtgatc ccttttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
```

```
gaccagagcc tctccatgcc ggatgattcc tacatggtgg actacttcaa gagcatctct   2640
cagtacttgc acgctggccc tcccgtgtat ttcgtgctgg aggaagggca cgactacact   2700
agctctaagg gacagaacat ggtctgcggt ggcatgggat gcaacaatga ctcgctggtg   2760
cagcagattt tcaacgccgc gcaactcgat aactacacca ggattggatt cgctccctcc   2820
tcctggatcg acgattattt tgactgggtc aagccgcagt ctagctgctg ccgggtggac   2880
aacatcacgg atcagttctg caatgcttcc gtggtcgacc cggcctgcgt gcggtgccgg   2940
cctcttactc cggagggaaa gcagaggccc cagggtggcg acttcatgcg gtttctgccc   3000
atgttcctga gcgataaccc caaccccaaa tgcgggaagg gaggtcacgc ggcgtactcg   3060
tcagcggtca acatcctgct gggccatgga actagagtgg gagcgaccta cttcatgact   3120
taccatactg tgctgcagac ctcagccgac ttcatcgacg cactcaagaa agcccgcctg   3180
atcgcatcaa acgtgaccga gactatgggg atcaacggat ccgcgtaccg cgtgttccca   3240
tattcggtgt tctacgtgtt ctacgagcaa tacctgacca ttattgacga caccatcttt   3300
aacctggggg tgtcactggg agccatcttc cttgtgacca tggtcctcct gggctgcgaa   3360
ctgtggtccg ccgtgatcat gtgcgctacc atcgcaatgg tcctcgtgaa catgtttggg   3420
gtcatgtggc tgtggggcat ctccctgaac gcggtgtccc tcgtgaacct ggtcatgtca   3480
tgcggcatta gcgtggagtt ctgctcccac attactcgcg ccttcaccgt gtcgatgaag   3540
ggttcccgcg tggagcgggc ggaggaagcc ctggcccaca tgggatcctc ggtgttctcg   3600
ggcatcaccc ttactaagtt cggcggtatc gtggtgctgg ccttcgccaa gtcacagatc   3660
ttccaaattt tctacttcag aatgtacttg gcgatggtcc tgcttggagc cacacacggt   3720
ctgatcttcc tgcctgtgct gctgagctac atcggtccca gcgtgaacaa ggctaagtcc   3780
tgcgcgacgg aggaaaggta caagggaacc gagagggagc gccttctcaa cttcggagga   3840
gattataaag acgatgatga caagggggac tacaaggacg acgatgacaa gggcgattac   3900
aaagacgacg acgacaagtt gatag                                         3925
```

<210> SEQ ID NO 4
<211> LENGTH: 3910
<212> TYPE: DNA
<213> ORGANISM: Artificial Sequence
<220> FEATURE:
<223> OTHER INFORMATION: Synthetic

<400> SEQUENCE: 4

```
atgaccgcga ggggactggc cctcgggctg ctcctgctgc tcctttgccc ggcccaagtg     60
ttctcgcaat cgtgcgtgtg gtacggggaa tgcggaattg cctacggcga caagcggtac    120
aactgcgaat actccgggcc tccaaagccg ctgcccaagg acggatacga cctggtccaa    180
gagctctgcc ctggattctt cttcggcaac gtgtcgctgt gttgtgacgt gcggcagctg    240
cagaccctga aggataacct ccagctgccg ctgcaattcc tctcccggtg tccgtcatgc    300
ttctacaact tgctcaacct gttctgcgaa cttacctgtt cgccgagaca gtcccagttt    360
cttaacgtca ccgcaaccga ggactacgtg gaccctgtga ctaaccagac caagactaat    420
gtcaaagaat tgcagtacta cgtgggccag tccttcgcca atgcgatgta caacgcctgt    480
cgggacgtcg aagcgcccag ctccaacgac aaggcactcg gactgctttg cggcaaagat    540
gccgacgcct gcaacgccac caactggatc gagtacatgt tcaataagga caacggacag    600
gcccctttca ccatcacacc tgtgttcagc gacttcccag tccacgggat ggaacctatg    660
```

-continued

```
aacaacgcga ctaagggatg cgacgagtcc gtggacgaag tgaccgcccc gtgttcctgt    720
caagattgct caatcgtgtg cggtccgaag ccccagcctc ctcctccgcc ggctccatgg    780
accatcctgg gtctggacgc tatgtacgtg attatgtgga tcacttacat ggccttcctc    840
ctggtgttct tcggcgcttt cttcgccgtg tggtgttacc ggaagcgcta cttcgtgtcc    900
gagtatactc ctatcgactc taacatagcg ttctccgtga acgcctccga taagggagag    960
gcatcgtgct gtgatcccgt gtccgccgct ttcgaaggat gcttgaggcg gctgttcacc   1020
cgctggggca gcttctgcgt gagaaatccc ggctgtgtga ttttcttctc gctggtgttc   1080
atcaccgctt gctcgtcggg gctggtgttc gtcagagtca caacgaaccc cgtggacctg   1140
tggagcgcgc ctagcagcca ggcccgcctg gaaaaggaat acttcgacca gcatttcgga   1200
cccttttttcc ggaccgaaca gctgattatc cgcgccccgc tgactgacaa gcatatctac   1260
cagccttacc cgagcggagc ggatgtgccc tttggtccgc cactcgacat ccagatcctg   1320
caccaagtcc tggacttgca aatcgctatt gagaacatta ctgcctccta cgacaacgag   1380
acagtgaccc tgcaggacat ttgtcttgcc ccgctgtccc cctacaacac caactgcacg   1440
atcctgagcg tgctgaacta tttccaaaac tcgcactccg tgctggatca caagaagggc   1500
gacgatttct tcgtctacgc cgattaccac acccacttcc tgtactgcgt gcgcgctccg   1560
gcttcactga acgacacttc cctcctccac gacccgtgcc tgggaacgtt cggcggaccc   1620
gtgtttccct ggctggtcct gggcggctac gacgaccaga actacaacaa cgccaccgcc   1680
ctcgtgatca cctttcctgt gaacaactac tacaacgaca ccgaaaagtt gcagagagca   1740
caagcgtggg agaaggagtt catcaacttc gtgaagaact acaaaaaccc taacctgacc   1800
atctccttta cggccgagcg ctcaatcgag gacgaattga acagggaatc ggactccgac   1860
gtgttcactg tcgtcattag ctacgccatc atgttcttgt acattagcct ggcgctgggg   1920
cacatgaagt cctgccgccg gctgctggtc gattcgaagg tgtccctggg aatcgccggc   1980
atcctgatcg tcctgtcgtc cgtggcctgt tccctgggag tgttcagcta cattggactg   2040
ccactgaccc tcattgtgat tgaagtgatc cctttttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
gaccagagcc tctccatgcc ggatgattcc tacatggtgg actacttcaa gagcatctct   2640
cagtacttgc acgctggccc tcccgtgtat ttcgtgctgg aggaagggca cgactacact   2700
agctctaagg gacagaacat ggtctgcggt ggcatgggat gcaacaatga ctcgctggtg   2760
cagcagattt tcaacgccgc gcaactcgat aactacacca ggattggatt cgctccctcc   2820
tcctggatcg acgattattt tgactgggtc aagccgcagt ctagctgctg ccgggtggac   2880
aacatcacgg atcagttctg caatgcttcc gtggtcgacc cggcctgcgt gcggtgccgg   2940
cctcttactc cggagggaaa gcagaggccc cagggtggcg acttcatgcg gtttctgccc   3000
atgttcctga gcgataaccc caaccccaaa tgcgggaagg gaggtcacgc ggcgtactcg   3060
```

```
tcagcggtca acatcctgct gggccatgga actagagtgg gagcgaccta cttcatgact   3120

taccatactg tgctgcagac ctcagccgac ttcatcgacg cactcaagaa agcccgcctg   3180

atcgcatcaa acgtgaccga gactatgggg atcaacggat ccgcgtaccg cgtgttccca   3240

tattcggtgt tctacgtgtt ctacgagcaa tacctgacca ttattgacga caccatcttt   3300

aacctggggg tgtcactggg agccatcttc cttgtgacca tggtcctcct gggctgcgaa   3360

ctgtggtccg ccgtgatcat gtgcgctacc atcgcaatgg tcctcgtgaa catgtttggg   3420

gtcatgtggc tgtggggcat ctccctgaac gcggtgtccc tcgtgaacct ggtcatgtca   3480

tgcggcatta gcgtggagtt ctgctcccac attactcgcg ccttcaccgt gtcgatgaag   3540

ggttcccgcg tggagcgggc ggaggaagcc ctggcccaca tgggatcctc ggtgttctcg   3600

ggcatcaccc ttactaagtt cggcggtatc gtggtgctgg ccttcgccaa gtcacagatc   3660

ttccaaattt tctacttcag aatgtacttg gcgatggtcc tgcttggagc cacacacggt   3720

ctgatcttcc tgcctgtgct gctgagctac atcggtccca gcgtgaacaa ggctaagtcc   3780

tgcgcgacgg aggaaaggta caaggggact gaacgcgaac ggctgctgaa ctttggcggc   3840

gctgggtacc tgctcggaaa gatcaacctc aaagcgctgg cggccctggc caagaagatc   3900

ctgttgatag                                                        3910
```

<210> SEQ ID NO 5
<211> LENGTH: 3883
<212> TYPE: DNA
<213> ORGANISM: Artificial Sequence
<220> FEATURE:
<223> OTHER INFORMATION: Synthetic

<400> SEQUENCE: 5

```
atgaccgcga ggggactggc cctcgggctg ctcctgctgc tcctttgccc ggcccaagtg     60

ttctcgcaat cgtgcgtgtg gtacggggaa tgcggaattg cctacggcga caagcggtac    120

aactgcgaat actccgggcc tccaaagccg ctgcccaagg acggatacga cctggtccaa    180

gagctctgcc ctggattctt cttcggcaac gtgtcgctgt gttgtgacgt gcggcagctg    240

cagaccctga aggataacct ccagctgccg ctgcaattcc tctcccggtg tccgtcatgc    300

ttctacaact tgctcaacct gttctgcgaa cttacctgtt cgccgagaca gtcccagttt    360

cttaacgtca ccgcaaccga ggactacgtg gaccctgtga ctaaccagac caagactaat    420

gtcaaagaat tgcagtacta cgtgggccag tccttcgcca atgcgatgta caacgcctgt    480

cgggacgtcg aagcgcccag ctccaacgac aaggcactcg gactgctttg cggcaaagat    540

gccgacgcct gcaacgccac caactggatc gagtacatgt tcaataagga caacggacag    600

gcccctttca ccatcacacc tgtgttcagc gacttcccag tccacgggat ggaacctatg    660

aacaacgcga ctaagggatg cgacgagtcc gtggacgaag tgaccgcccc gtgttcctgt    720

caagattgct caatcgtgtg cggtccgaag ccccagcctc ctcctccgcc ggctccatgg    780

accatcctgg gtctggacgc tatgtacgtg attatgtgga tcacttacat ggccttcctc    840

ctggtgttct tcggcgcttt cttcgccgtg tggtgttacc ggaagcgcta cttcgtgtcc    900

gagtatactc ctatcgactc taacatagcg ttctccgtga acgcctccga taagggagag    960

gcatcgtgct gtgatcccgt gtccgccgct ttcgaaggat gcttgaggcg gctgttcacc   1020

cgctggggca gcttctgcgt gagaaatccc ggctgtgtga ttttcttctc gctggtgttc   1080

atcaccgctt gctcgtcggg gctggtgttc gtcagagtca caacgaaccc cgtggacctg   1140
```

-continued

```
tggagcgcgc ctagcagcca ggcccgcctg gaaaaggaat acttcgacca gcatttcgga   1200
ccctttttcc ggaccgaaca gctgattatc cgcgccccgc tgactgacaa gcatatctac   1260
cagccttacc cgagcggagc ggatgtgccc tttggtccgc cactcgacat ccagatcctg   1320
caccaagtcc tggacttgca aatcgctatt gagaacatta ctgcctccta cgacaacgag   1380
acagtgaccc tgcaggacat ttgtcttgcc ccgctgtccc cctacaacac caactgcacg   1440
atcctgagcg tgctgaacta tttccaaaac tcgcactccg tgctggatca caagaagggc   1500
gacgatttct tcgtctacgc cgattaccac acccacttcc tgtactgcgt gcgcgctccg   1560
gcttcactga acgacacttc cctcctccac gacccgtgcc tgggaacgtt cggcggaccc   1620
gtgtttccct ggctggtcct gggcggctac gacgaccaga actacaacaa cgccaccgcc   1680
ctcgtgatca cctttcctgt gaacaactac tacaacgaca ccgaaaagtt gcagagagca   1740
caagcgtggg agaaggagtt catcaacttc gtgaagaact acaaaaaccc taacctgacc   1800
atctccttta cggccgagcg ctcaatcgag gacgaattga acagggaatc ggactccgac   1860
gtgttcactg tcgtcattag ctacgccatc atgttcttgt acattagcct ggcgctgggg   1920
cacatgaagt cctgccgccg gctgctggtc gattcgaagg tgtccctggg aatcgccggc   1980
atcctgatcg tcctgtcgtc cgtggcctgt tccctgggag tgttcagcta cattggactg   2040
ccactgaccc tcattgtgat tgaagtgatc ccttttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
gaccagagcc tctccatgcc ggatgattcc tacatggtgg actacttcaa gagcatctct   2640
cagtacttgc acgctggccc tcccgtgtat ttcgtgctgg aggaagggca cgactacact   2700
agctctaagg gacagaacat ggtctgcggt ggcatgggat gcaacaatga ctcgctggtg   2760
cagcagattt tcaacgccgc gcaactcgat aactacacca ggattggatt cgctccctcc   2820
tcctggatcg acgattattt tgactgggtc aagccgcagt ctagctgctg ccgggtggac   2880
aacatcacgg atcagttctg caatgcttcc gtggtcgacc cggcctgcgt gcggtgccgg   2940
cctcttactc cggagggaaa gcagaggccc cagggtggcg acttcatgcg gtttctgccc   3000
atgttcctga gcgataaccc caaccccaaa tgcgggaagg gaggtcacgc ggcgtactcg   3060
tcagcggtca acatcctgct gggccatgga actagagtgg gagcgaccta cttcatgact   3120
taccatactg tgctgcagac ctcagccgac ttcatcgacg cactcaagaa agcccgcctg   3180
atcgcatcaa acgtgaccga gactatgggg atcaacggat ccgcgtaccg cgtgttccca   3240
tattcggtgt tctacgtgtt ctacgagcaa tacctgacca ttattgacga caccatcttt   3300
aacctggggg tgtcactggg agccatcttc cttgtgacca tggtcctcct gggctgcgaa   3360
ctgtggtccg ccgtgatcat gtgcgctacc atcgcaatgg tcctcgtgaa catgtttggg   3420
gtcatgtggc tgtggggcat ctccctgaac gcggtgtccc tcgtgaacct ggtcatgtca   3480
tgcggcatta gcgtggagtt ctgctcccac attactcgcg ccttcaccgt gtcgatgaag   3540
```

-continued ggttcccgcg tggagcgggc ggaggaagcc ctggcccaca tgggatcctc ggtgttctcg 3600
ggcatcaccc ttactaagtt cggcggtatc gtggtgctgg ccttcgccaa gtcacagatc 3660
ttccaaattt tctacttcag aatgtacttg gcgatggtcc tgcttggagc cacacacggt 3720
ctgatcttcc tgcctgtgct gctgagctac atcggtccca gcgtgaacaa ggctaagtcc 3780
tgcgcgacgg aggaaaggta caagggtact gaaagagagc ggctgctcaa cttcggtggc 3840
cccctgatct acctgcgcct cctgcggggt cagttcttga tag 3883

<210> SEQ ID NO 6
<211> LENGTH: 3958
<212> TYPE: DNA
<213> ORGANISM: Artificial Sequence
<220> FEATURE:
<223> OTHER INFORMATION: Synthetic

<400> SEQUENCE: 6
atgaccgcga ggggactggc cctcgggctg ctcctgctgc tcctttgccc ggcccaagtg 60
ttctcgcaat cgtgcgtgtg gtacggggaa tgcggaattg cctacggcga caagcggtac 120
aactgcgaat actccgggcc tccaaagccg ctgcccaagg acggatacga cctggtccaa 180
gagctctgcc ctggattctt cttcggcaac gtgtcgctgt gttgtgacgt gcggcagctg 240
cagaccctga aggataacct ccagctgccg ctgcaattcc tctcccggtg tccgtcatgc 300
ttctacaact tgctcaacct gttctgcgaa cttacctgtt cgccgagaca gtcccagttt 360
cttaacgtca ccgcaaccga ggactacgtg gaccctgtga ctaaccagac caagactaat 420
gtcaaagaat tgcagtacta cgtgggccag tccttcgcca atgcgatgta caacgcctgt 480
cgggacgtcg aagcgcccag ctccaacgac aaggcactcg gactgctttg cggcaaagat 540
gccgacgcct gcaacgccac caactggatc gagtacatgt tcaataagga caacggacag 600
gcccctttca ccatcacacc tgtgttcagc gacttcccag tccacgggat ggaacctatg 660
aacaacgcga ctaagggatg cgacgagtcc gtggacgaag tgaccgcccc gtgttcctgt 720
caagattgct caatcgtgtg cggtccgaag ccccagcctc ctcctccgcc ggctccatgg 780
accatcctgg gtctggacgc tatgtacgtg attatgtgga tcacttacat ggccttcctc 840
ctggtgttct tcggcgcttt cttcgccgtg tggtgttacc ggaagcgcta cttcgtgtcc 900
gagtatactc ctatcgactc taacatagcg ttctccgtga acgcctccga taagggagag 960
gcatcgtgct gtgatcccgt gtccgccgct ttcgaaggat gcttgaggcg gctgttcacc 1020
cgctggggca gcttctgcgt gagaaatccc ggctgtgtga ttttcttctc gctggtgttc 1080
atcaccgctt gctcgtcggg gctggtgttc gtcagagtca caacgaaccc cgtggacctg 1140
tggagcgcgc ctagcagcca ggcccgcctg gaaaaggaat acttcgacca gcatttcgga 1200
ccctttttcc ggaccgaaca gctgattatc cgcgccccgc tgactgacaa gcatatctac 1260
cagccttacc cgagcggagc ggatgtgccc tttggtccgc cactcgacat ccagatcctg 1320
caccaagtcc tggacttgca aatcgctatt gagaacatta ctgcctccta cgacaacgag 1380
acagtgaccc tgcaggacat ttgtcttgcc ccgctgtccc cctacaacac caactgcacg 1440
atcctgagcg tgctgaacta tttccaaaac tcgcactccg tgctggatca caagaagggc 1500
gacgatttct tcgtctacgc cgattaccac acccacttcc tgtactgcgt gcgcgctccg 1560
gcttcactga acgacacttc cctcctccac gacccgtgcc tgggaacgtt cggcggaccc 1620
gtgtttccct ggctggtcct gggcggctac gacgaccaga actacaacaa cgccaccgcc 1680

-continued

```
ctcgtgatca cctttcctgt gaacaactac tacaacgaca ccgaaaagtt gcagagagca   1740
caagcgtggg agaaggagtt catcaacttc gtgaagaact acaaaaaccc taacctgacc   1800
atctccttta cggccgagcg ctcaatcgag gacgaattga acagggaatc ggactccgac   1860
gtgttcactg tcgtcattag ctacgccatc atgttcttgt acattagcct ggcgctgggg   1920
cacatgaagt cctgccgccg gctgctggtc gattcgaagg tgtccctggg aatcgccggc   1980
atcctgatcg tcctgtcgtc cgtggcctgt tccctgggag tgttcagcta cattggactg   2040
ccactgaccc tcattgtgat tgaagtgatc ccttttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
gaccagagcc tctccatgcc ggatgattcc tacatggtgg actacttcaa gagcatctct   2640
cagtacttgc acgctggccc tcccgtgtat ttcgtgctgg aggaagggca cgactacact   2700
agctctaagg gacagaacat ggtctgcggt ggcatgggat gcaacaatga ctcgctggtg   2760
cagcagattt tcaacgccgc gcaactcgat aactacacca ggattggatt cgctccctcc   2820
tcctggatcg acgattattt tgactgggtc aagccgcagt ctagctgctg ccgggtggac   2880
aacatcacgg atcagttctg caatgcttcc gtggtcgacc cggcctgcgt gcggtgccgg   2940
cctcttactc cggagggaaa gcagaggccc cagggtggcg acttcatgcg gtttctgccc   3000
atgttcctga gcgataaccc caaccccaaa tgcgggaagg gaggtcacgc ggcgtactcg   3060
tcagcggtca acatcctgct gggccatgga actagagtgg gagcgaccta cttcatgact   3120
taccatactg tgctgcagac ctcagccgac ttcatcgacg cactcaagaa agcccgcctg   3180
atcgcatcaa acgtgaccga gactatgggg atcaacggat ccgcgtaccg cgtgttccca   3240
tattcggtgt tctacgtgtt ctacgagcaa tacctgacca ttattgacga caccatcttt   3300
aacctggggg tgtcactggg agccatcttc cttgtgacca tggtcctcct gggctgcgaa   3360
ctgtggtccg ccgtgatcat gtgcgctacc atcgcaatgg tcctcgtgaa catgtttggg   3420
gtcatgtggc tgtggggcat ctccctgaac gcggtgtccc tcgtgaacct ggtcatgtca   3480
tgcggcatta gcgtggagtt ctgctcccac attactcgcg ccttcaccgt gtcgatgaag   3540
ggttcccgcg tggagcgggc ggaggaagcc ctggcccaca tgggatcctc ggtgttctcg   3600
ggcatcaccc ttactaagtt cggcggtatc gtggtgctgg ccttcgccaa gtcacagatc   3660
ttccaaattt tctacttcag aatgtacttg gcgatggtcc tgcttggagc cacacacggt   3720
ctgatcttcc tgcctgtgct gctgagctac atcggtccca gcgtgaacaa ggctaagtcc   3780
tgcgcgacgg aggaaaggta caagggaacc gagagggagc gccttctcaa cttcggagga   3840
gattataaag acgatgatga caagggggac tacaaggacg acgatgacaa gggcgattac   3900
aaagacgacg acgacaaggg cggccggaag aagcgccgcc agcggcggag attgatag     3958
```

<210> SEQ ID NO 7
<211> LENGTH: 3994

<212> TYPE: DNA
<213> ORGANISM: Artificial Sequence
<220> FEATURE:
<223> OTHER INFORMATION: Synthetic

<400> SEQUENCE: 7
atgaccgcga ggggactggc cctcgggctg ctcctgctgc tcctttgccc ggcccaagtg 60
ttctcgcaat cgtgcgtgtg gtacggggaa tgcggaattg cctacggcga caagcggtac 120
aactgcgaat actccgggcc tccaaagccg ctgcccaagg acggatacga cctggtccaa 180
gagctctgcc ctggattctt cttcggcaac gtgtcgctgt gttgtgacgt gcggcagctg 240
cagaccctga aggataacct ccagctgccg ctgcaattcc tctcccggtg tccgtcatgc 300
ttctacaact tgctcaacct gttctgcgaa cttacctgtt cgccgagaca gtcccagttt 360
cttaacgtca ccgcaaccga ggactacgtg gaccctgtga ctaaccagac caagactaat 420
gtcaaagaat tgcagtacta cgtgggccag tccttcgcca atgcgatgta caacgcctgt 480
cgggacgtcg aagcgcccag ctccaacgac aaggcactcg gactgctttg cggcaaagat 540
gccgacgcct gcaacgccac caactggatc gagtacatgt tcaataagga caacggacag 600
gcccctttca ccatcacacc tgtgttcagc gacttcccag tccacgggat ggaacctatg 660
aacaacgcga ctaagggatg cgacgagtcc gtggacgaag tgaccgcccc gtgttcctgt 720
caagattgct caatcgtgtg cggtccgaag ccccagcctc ctcctccgcc ggctccatgg 780
accatcctgg gtctggacgc tatgtacgtg attatgtgga tcacttacat ggccttcctc 840
ctggtgttct tcggcgcttt cttcgccgtg tggtgttacc ggaagcgcta cttcgtgtcc 900
gagtatactc ctatcgactc taacatagcg ttctccgtga acgcctccga taagggagag 960
gcatcgtgct gtgatcccgt gtccgccgct ttcgaaggat gcttgaggcg gctgttcacc 1020
cgctggggca gcttctgcgt gagaaatccc ggctgtgtga ttttcttctc gctggtgttc 1080
atcaccgctt gctcgtcggg gctggtgttc gtcagagtca caacgaaccc cgtggacctg 1140
tggagcgcgc ctagcagcca ggcccgcctg gaaaaggaat acttcgacca gcatttcgga 1200 cccttttttcc ggaccgaaca gctgattatc cgcgccccgc tgactgacaa gcatatctac 1260
cagccttacc cgagcggagc ggatgtgccc tttggtccgc cactcgacat ccagatcctg 1320
caccaagtcc tggacttgca aatcgctatt gagaacatta ctgcctccta cgacaacgag 1380
acagtgaccc tgcaggacat ttgtcttgcc ccgctgtccc cctacaacac caactgcacg 1440
atcctgagcg tgctgaacta tttccaaaac tcgcactccg tgctggatca caagaagggc 1500
gacgatttct tcgtctacgc cgattaccac acccacttcc tgtactgcgt gcgcgctccg 1560
gcttcactga acgacacttc cctcctccac gacccgtgcc tgggaacgtt cggcggaccc 1620
gtgtttccct ggctggtcct gggcggctac gacgaccaga actacaacaa cgccaccgcc 1680
ctcgtgatca cctttcctgt gaacaactac tacaacgaca ccgaaaagtt gcagagagca 1740
caagcgtggg agaaggagtt catcaacttc gtgaagaact acaaaaaccc taacctgacc 1800
atctccttta cggccgagcg ctcaatcgag gacgaattga acagggaatc ggactccgac 1860
gtgttcactg tcgtcattag ctacgccatc atgttcttgt acattagcct ggcgctgggg 1920
cacatgaagt cctgccgccg gctgctggtc gattcgaagg tgtccctggg aatcgccggc 1980
atcctgatcg tcctgtcgtc cgtggcctgt tccctgggag tgttcagcta cattggactg 2040
ccactgaccc tcattgtgat tgaagtgatc ccttttcttg tcttggccgt gggagtggat 2100
aatattttta tcctggtgca agcctaccag cgggacgaga ggctgcaggg ggagactctg 2160

```
gaccagcagc tgggccgcgt gctgggcgaa gtcgccccgt ccatgtttct gtcctcattc   2220

tccgaaaccg tggccttctt cctgggcgcg ctcagcgtga tgcctgccgt gcacaccttc   2280

tccctgtttg ccggtctggc tgtgtttatc gatttccttc tccaaattac ttgcttcgtg   2340

tcactgcttg gactcgacat caagcgccag gaaaagaacc ggctggacat tttctgctgc   2400

gtgagaggag cggaggacgg aacctcagtg caggcttccg agtcatgcct gtttcgattc   2460

ttcaagaact cgtattcgcc gctgctcctg aaggattgga tgcggcccat tgtgatcgcc   2520

atctttgtcg gcgtcctgag cttcagcatt gcggtgttga acaaagtgga cattggcctg   2580

gaccagagcc tctccatgcc ggatgattcc tacatggtgg actacttcaa gagcatctct   2640

cagtacttgc acgctggccc tcccgtgtat ttcgtgctgg aggaagggca cgactacact   2700

agctctaagg gacagaacat ggtctgcggt ggcatgggat gcaacaatga ctcgctggtg   2760

cagcagattt tcaacgccgc gcaactcgat aactacacca ggattggatt cgctccctcc   2820

tcctggatcg acgattattt tgactgggtc aagccgcagt ctagctgctg ccgggtggac   2880

aacatcacgg atcagttctg caatgcttcc gtggtcgacc cggcctgcgt gcggtgccgg   2940

cctcttactc cggagggaaa gcagaggccc cagggtggcg acttcatgcg gtttctgccc   3000

atgttcctga gcgataaccc caaccccaaa tgcgggaagg gaggtcacgc ggcgtactcg   3060

tcagcggtca acatcctgct gggccatgga actagagtgg gagcgaccta cttcatgact   3120

taccatactg tgctgcagac ctcagccgac ttcatcgacg cactcaagaa agcccgcctg   3180

atcgcatcaa acgtgaccga gactatgggg atcaacggat ccgcgtaccg cgtgttccca   3240

tattcggtgt tctacgtgtt ctacgagcaa tacctgacca ttattgacga caccatcttt   3300

aacctggggg tgtcactggg agccatcttc cttgtgacca tggtcctcct gggctgcgaa   3360

ctgtggtccg ccgtgatcat gtgcgctacc atcgcaatgg tcctcgtgaa catgtttggg   3420

gtcatgtggc tgtggggcat ctccctgaac gcggtgtccc tcgtgaacct ggtcatgtca   3480

tgcggcatta gcgtggagtt ctgctcccac attactcgcg ccttcaccgt gtcgatgaag   3540

ggttcccgcg tggagcgggc ggaggaagcc ctggcccaca tgggatcctc ggtgttctcg   3600

ggcatcaccc ttactaagtt cggcggtatc gtggtgctgg ccttcgccaa gtcacagatc   3660

ttccaaattt tctacttcag aatgtacttg gcgatggtcc tgcttggagc cacacacggt   3720

ctgatcttcc tgcctgtgct gctgagctac atcggtccca gcgtgaacaa ggctaagtcc   3780

tgcgcgacgg aggaaaggta caagggaacc gagagggagc gccttctcaa cttcggagga   3840

gattataaag acgatgatga caagggggac tacaaggacg acgatgacaa gggcgattac   3900

aaagacgacg acgacaaggg cggcgccggc tacctcctgg ggaagattaa cctgaaggcc   3960

ctggcagccc tcgccaagaa gatcctgttg atag                                3994
```

<210> SEQ ID NO 8
<211> LENGTH: 3967
<212> TYPE: DNA
<213> ORGANISM: Artificial Sequence
<220> FEATURE:
<223> OTHER INFORMATION: Synthetic

<400> SEQUENCE: 8

```
atgaccgcga ggggactggc cctcgggctg ctcctgctgc tcctttgccc ggcccaagtg     60

ttctcgcaat cgtgcgtgtg gtacggggaa tgcggaattg cctacggcga caagcggtac    120

aactgcgaat actccgggcc tccaaagccg ctgcccaagg acggatacga cctggtccaa    180

gagctctgcc ctggattctt cttcggcaac gtgtcgctgt gttgtgacgt gcggcagctg    240
```

-continued

```
cagaccctga aggataacct ccagctgccg ctgcaattcc tctcccggtg tccgtcatgc    300
ttctacaact tgctcaacct gttctgcgaa cttacctgtt cgccgagaca gtcccagttt    360
cttaacgtca ccgcaaccga ggactacgtg gaccctgtga ctaaccagac caagactaat    420
gtcaaagaat tgcagtacta cgtgggccag tccttcgcca atgcgatgta caacgcctgt    480
cgggacgtcg aagcgcccag ctccaacgac aaggcactcg gactgctttg cggcaaagat    540
gccgacgcct gcaacgccac caactggatc gagtacatgt tcaataagga caacggacag    600
gccccttca ccatcacacc tgtgttcagc gacttcccag tccacgggat ggaacctatg    660
aacaacgcga ctaagggatg cgacgagtcc gtggacgaag tgaccgcccc gtgttcctgt    720
caagattgct caatcgtgtg cggtccgaag ccccagcctc ctcctccgcc ggctccatgg    780
accatcctgg gtctggacgc tatgtacgtg attatgtgga tcacttacat ggccttcctc    840
ctggtgttct tcggcgcttt cttcgccgtg tggtgttacc ggaagcgcta cttcgtgtcc    900
gagtatactc ctatcgactc taacatagcg ttctccgtga acgcctccga taagggagag    960
gcatcgtgct gtgatcccgt gtccgccgct ttcgaaggat gcttgaggcg gctgttcacc   1020
cgctggggca gcttctgcgt gagaaatccc ggctgtgtga ttttcttctc gctggtgttc   1080
atcaccgctt gctcgtcggg gctggtgttc gtcagagtca caacgaaccc cgtggacctg   1140
tggagcgcgc ctagcagcca ggcccgcctg gaaaaggaat acttcgacca gcatttcgga   1200
cccttttcc ggaccgaaca gctgattatc cgcgccccgc tgactgacaa gcatatctac   1260
cagccttacc cgagcggagc ggatgtgccc tttggtccgc cactcgacat ccagatcctg   1320
caccaagtcc tggacttgca aatcgctatt gagaacatta ctgcctccta cgacaacgag   1380
acagtgaccc tgcaggacat ttgtcttgcc ccgctgtccc cctacaacac caactgcacg   1440
atcctgagcg tgctgaacta tttccaaaac tcgcactccg tgctggatca caagaagggc   1500
gacgatttct tcgtctacgc cgattaccac acccacttcc tgtactgcgt gcgcgctccg   1560
gcttcactga acgacacttc cctcctccac gacccgtgcc tgggaacgtt cggcggaccc   1620
gtgtttccct ggctggtcct gggcggctac gacgaccaga actacaacaa cgccaccgcc   1680
ctcgtgatca cctttcctgt gaacaactac tacaacgaca ccgaaaagtt gcagagagca   1740
caagcgtggg agaaggagtt catcaacttc gtgaagaact acaaaaaccc taacctgacc   1800
atctccttta cggccgagcg ctcaatcgag gacgaattga acagggaatc ggactccgac   1860
gtgttcactg tcgtcattag ctacgccatc atgttcttgt acattagcct ggcgctgggg   1920
cacatgaagt cctgccgccg gctgctggtc gattcgaagg tgtccctggg aatcgccggc   1980
atcctgatcg tcctgtcgtc cgtggcctgt tccctgggag tgttcagcta cattggactg   2040
ccactgaccc tcattgtgat tgaagtgatc cctttcttg tcttggccgt gggagtggat   2100
aatattttta tcctggtgca agcctaccag cgggacgaga ggctgcaggg ggagactctg   2160
gaccagcagc tgggccgcgt gctgggcgaa gtcgccccgt ccatgtttct gtcctcattc   2220
tccgaaaccg tggccttctt cctgggcgcg ctcagcgtga tgcctgccgt gcacaccttc   2280
tccctgtttg ccggtctggc tgtgtttatc gatttccttc tccaaattac ttgcttcgtg   2340
tcactgcttg gactcgacat caagcgccag gaaaagaacc ggctggacat tttctgctgc   2400
gtgagaggag cggaggacgg aacctcagtg caggcttccg agtcatgcct gtttcgattc   2460
ttcaagaact cgtattcgcc gctgctcctg aaggattgga tgcggcccat tgtgatcgcc   2520
atctttgtcg gcgtcctgag cttcagcatt gcggtgttga acaaagtgga cattggcctg   2580
```

-continued gaccagagcc tctccatgcc ggatgattcc tacatggtgg actacttcaa gagcatctct 2640
cagtacttgc acgctggccc tcccgtgtat ttcgtgctgg aggaagggca cgactacact 2700
agctctaagg gacagaacat ggtctgcggt ggcatgggat gcaacaatga ctcgctggtg 2760
cagcagattt tcaacgccgc gcaactcgat aactacacca ggattggatt cgctccctcc 2820
tcctggatcg acgattattt tgactgggtc aagccgcagt ctagctgctg ccgggtggac 2880
aacatcacgg atcagttctg caatgcttcc gtggtcgacc cggcctgcgt gcggtgccgg 2940
cctcttactc cggagggaaa gcagaggccc cagggtggcg acttcatgcg gtttctgccc 3000
atgttcctga gcgataaccc caaccccaaa tgcgggaagg gaggtcacgc ggcgtactcg 3060
tcagcggtca acatcctgct gggccatgga actagagtgg gagcgaccta cttcatgact 3120
taccatactg tgctgcagac ctcagccgac ttcatcgacg cactcaagaa agcccgcctg 3180
atcgcatcaa acgtgaccga gactatgggg atcaacggat ccgcgtaccg cgtgttccca 3240
tattcggtgt tctacgtgtt ctacgagcaa tacctgacca ttattgacga caccatcttt 3300
aacctggggg tgtcactggg agccatcttc cttgtgacca tggtcctcct gggctgcgaa 3360
ctgtggtccg ccgtgatcat gtgcgctacc atcgcaatgg tcctcgtgaa catgtttggg 3420
gtcatgtggc tgtggggcat ctccctgaac gcggtgtccc tcgtgaacct ggtcatgtca 3480
tgcggcatta gcgtggagtt ctgctcccac attactcgcg ccttcaccgt gtcgatgaag 3540
ggttcccgcg tggagcgggc ggaggaagcc ctggcccaca tgggatcctc ggtgttctcg 3600
ggcatcaccc ttactaagtt cggcggtatc gtggtgctgg ccttcgccaa gtcacagatc 3660
ttccaaattt tctacttcag aatgtacttg gcgatggtcc tgcttggagc cacacacggt 3720
ctgatcttcc tgcctgtgct gctgagctac atcggtccca gcgtgaacaa ggctaagtcc 3780
tgcgcgacgg aggaaaggta caagggaacc gagagggagc gccttctcaa cttcggagga 3840
gattataaag acgatgatga caagggggac tacaaggacg acgatgacaa gggcgattac 3900
aaagacgacg acgacaaggg gggcccgctc atctacctcc ggctgctgcg gggccagttt 3960
ttgatag 3967

<210> SEQ ID NO 9
<211> LENGTH: 3837
<212> TYPE: DNA
<213> ORGANISM: Homo sapiens

<400> SEQUENCE: 9
atgaccgctc gcggcctggc ccttggcctc ctcctgctgc tactgtgtcc agcgcaggtg 60
ttttcacagt cctgtgtttg gtatggagag tgtggaattg catatgggga caagaggtac 120
aattgcgaat attctggccc accaaaacca ttgccaaagg atggatatga cttagtgcag 180
gaactctgtc caggattctt ctttggcaat gtcagtctct gttgtgatgt tcggcagctt 240
cagacactaa aagacaacct gcagctgcct ctacagtttc tgtccagatg tccatcctgt 300
ttttataacc tactgaacct gttttgtgag ctgacatgta gccctcgaca gagtcagttt 360
ttgaatgtta cagctactga agattatgtt gatcctgtta caaaccagac gaaaacaaat 420
gtgaaagagt tacaatacta cgtcggacag agttttgcca atgcaatgta caatgcctgc 480
cgggatgtgg aggccccctc aagtaatgac aaggccctgg gactcctgtg tgggaaggac 540
gctgacgcct gtaatgccac caactggatt gaatacatgt tcaataagga caatggacag 600
gcacctttta ccatcactcc tgtgttttca gattttccag tccatgggat ggagcccatg 660
aacaatgcca ccaaaggctg tgacgagtct gtggatgagg tcacagcacc atgtagctgc 720

-continued

```
caagactgct ctattgtctg tggccccaag ccccagcccc cacctcctcc tgctccctgg    780
acgatccttg gcttggacgc catgtatgtc atcatgtgga tcacctacat ggcgtttttg    840
cttgtgtttt ttggagcatt ttttgcagtg tggtgctaca gaaaacggta ttttgtctcc    900
gagtacactc ccatcgatag caatatagct tttctgttta atgcaagtga caaaggagag    960
gcgtcctgct gtgaccctgt cagcgcagca tttgagggct gcttgaggcg gctgttcaca   1020
cgctgggggt ctttctgcgt ccgaaaccct ggctgtgtca ttttcttctc gctggtcttc   1080
attactgcgt gttcgtcagg cctggtgttt gtccgggtca caaccaatcc agttgacctc   1140
tggtcagccc ccagcagcca ggctcgcctg gaaaaagagt actttgacca gcactttggg   1200
cctttcttcc ggacggagca gctcatcatc cgggcccctc tcactgacaa acacatttac   1260
cagccatacc cttcgggagc tgatgtaccc tttggacctc cgcttgacat acagatactg   1320
caccaggttc ttgacttaca aatagccatc gaaaacatta ctgcctctta tgacaatgag   1380
actgtgacac ttcaagacat ctgcttggcc cctctttcac cgtataacac gaactgcacc   1440
attttgagtg tgttaaatta cttccagaac agccattccg tgctggacca caagaaaggg   1500
gacgacttct ttgtgtatgc cgattaccac acgcactttc tgtactgcgt acgggctcct   1560
gcctctctga atgatacaag tttgctccat gacccttgtc tgggtacgtt tggtggacca   1620
gtgttcccgt ggcttgtgtt gggaggctat gatgatcaaa actacaataa cgccactgcc   1680
cttgtgatta ccttccctgt caataattac tataatgata cagagaagct ccagagggcc   1740
caggcctggg aaaaagagtt tattaatttt gtgaaaaact acaagaatcc caatctgacc   1800
atttccttca ctgctgaacg aagtattgaa gatgaactaa atcgtgaaag tgacagtgat   1860
gtcttcaccg ttgtaattag ctatgccatc atgtttctat atatttccct agccttgggg   1920
cacatcaaaa gctgtcgcag gcttctggtg gattcgaagg tctcactagg catcgcgggc   1980
atcttgatcg tgctgagctc ggtggcttgc tccttgggtg tcttcagcta cattgggttg   2040
cccttgaccc tcattgtgat tgaagtcatc ccgttcctgg tgctggctgt tggagtggac   2100
aacatcttca ttctggtgca ggcctaccag agagatgaac gtcttcaagg ggaaaccctg   2160
gatcagcagc tgggcagggt cctaggagaa gtggctccca gtatgttcct gtcatccttt   2220
tctgagactg tagcattttt cttaggagca ttgtccgtga tgccagccgt gcacaccttc   2280
tctctctttg cgggattggc agtcttcatt gactttcttc tgcagattac ctgtttcgtg   2340
agtctcttgg ggttagacat taaacgtcaa gagaaaaatc ggctagacat cttttgctgt   2400
gtcagaggtg ctgaagatgg aacaagcgtc caggcctcag agagctgttt gtttcgcttc   2460
ttcaaaaact cctattctcc acttctgcta aaggactgga tgagaccaat tgtgatagca   2520
atatttgtgg gtgttctgtc attcagcatc gcagtcctga acaaagtaga tattggattg   2580
gatcagtctc tttcgatgcc agatgactcc tacatggtgg attatttcaa atccatcagt   2640
cagtacctgc atgcgggtcc gcctgtgtac tttgtcctgg aggaagggca cgactacact   2700
tcttccaagg ggcagaacat ggtgtgcggc ggcatgggct gcaacaatga ttccctggtg   2760
cagcagatat ttaacgcggc gcagctggac aactataccc gaataggctt cgcccccctcg   2820
tcctggatcg acgattattt cgactgggtg aagccacagt cgtcttgctg tcgagtggac   2880
aatatcactg accagttctg caatgcttca gtggttgacc ctgcctgcgt tcgctgcagg   2940
cctctgactc cggaaggcaa acagaggcct caggggggag acttcatgag attcctgccc   3000
atgttccttt cggataaccc taaccccaag tgtggcaaag ggggacatgc tgcctatagt   3060
```

```
tctgcagtta acatcctcct tggccatggc accagggtcg gagccacgta cttcatgacc   3120

taccacaccg tgctgcagac ctctgctgac tttattgacg ctctgaagaa agcccgactt   3180

atagccagta atgtcaccga aaccatgggc attaacggca gtgcctaccg agtatttcct   3240

tacagtgtgt tttatgtctt ctacgaacag tacctgacca tcattgacga cactatcttc   3300

aacctcggtg tgtccctggg cgcgatattt ctggtgacca tggtcctcct gggctgtgag   3360

ctctggtctg cagtcatcat gtgtgccacc atcgccatgg tcttggtcaa catgtttgga   3420

gttatgtggc tctggggcat cagtctgaac gctgtatcct tggtcaacct ggtgatgagc   3480

tgtggcatct ccgtggagtt ctgcagccac ataaccagag cgttcacggt gagcatgaaa   3540

ggcagccgcg tggagcgcgc ggaagaggca cttgcccaca tgggcagctc cgtgttcagt   3600

ggaatcacac ttacaaaatt tggagggatt gtggtgttgg cttttgccaa atctcaaatt   3660

ttccagatat tctacttcag gatgtatttg gccatggtct tactgggagc cactcacgga   3720

ttaatatttc tccctgtctt actcagttac atagggccat cagtaaataa agccaaaagt   3780

tgtgccactg aagagcgata caaaggaaca gagcgcgaac ggcttctaaa tttctag      3837
```

<210> SEQ ID NO 10
<211> LENGTH: 247
<212> TYPE: DNA
<213> ORGANISM: Artificial Sequence
<220> FEATURE:
<223> OTHER INFORMATION: Synthetic

<400> SEQUENCE: 10

```
agagctccgg tgcccgtcag tgggcagagc gcacatcgcc cacagtcccc gagaagttgg     60

ggggaggggt cggcaattga accggtgcct agagaaggtg gcgcggggta aactgggaaa    120

gtgatgtcgt gtactggctc cgcctttttc ccgagggtgg gggagaaccg tatataagtg    180

cagtagtcgc cgtgaacgtt ctttttcgca acgggtttgc cgccagaaca cgcgtaaggg    240

cgaattc                                                              247
```

<210> SEQ ID NO 11
<211> LENGTH: 4139
<212> TYPE: DNA
<213> ORGANISM: Homo sapiens

<400> SEQUENCE: 11

```
tggctgttcc tgaggcctgg cctggctccc cgctgacccc ttcccagacc tgggatggcg     60

gaggccggcc tgaggggctg gctgctgtgg gccctgctcc tgcgcttggc ccagagtgag    120

ccttacacaa ccatccacca gcctggctac tgcgccttct atgacgaatg tgggaagaac    180

ccagagctgt ctggaagcct catgacactc tccaacgtgt cctgcctgtc caacacgccg    240

gcccgcaaga tcacaggtga tcacctgatc ctattacaga agatctgccc ccgcctctac    300

accggcccca acacccaagc ctgctgctcc gccaagcagc tggtatcact ggaagcgagt    360

ctgtcgatca ccaaggccct cctcacccgc tgcccagcct gctctgacaa ttttgtgaac    420

ctgcactgcc acaacacgtg cagccccaat cagagcctct tcatcaatgt gacccgcgtg    480

gcccagctag ggctggaca actcccagct gtggtggcct atgaggcctt ctaccagcat    540

agctttgccg agcagagcta tgactcctgc agccgtgtgc gcgtccctgc agctgccacg    600

ctggctgtgg gcaccatgtg tggcgtgtat ggctctgccc tttgcaatgc ccagcgctgg    660

ctcaacttcc agggagacac aggcaatggt ctggccccac tggacatcac cttccacctc    720

ttggagcctg gccaggccgt ggggagtggg attcagcctc tgaatgaggg ggttgcacgt    780
```

-continued

```
tgcaatgagt cccaaggtga cgacgtggcg acctgctcct gccaagactg tgctgcatcc    840
tgtcctgcca tagcccgccc ccaggccctc gactccacct tctacctggg ccagatgccg    900
ggcagtctgg tcctcatcat catcctctgc tctgtcttcg ctgtggtcac catcctgctt    960
gtgggattcc gtgtggcccc cgccagggac aaaagcaaga tggtggaccc caagaagggc   1020
accagcctct ctgacaagct cagcttctcc acccacaccc tccttggcca gttcttccag   1080
ggctggggca cgtgggtggc ttcgtggcct ctgaccatct tggtgctatc tgtcatcccg   1140
gtggtggcct tggcagcggg cctggtcttt acagaactca ctacggaccc cgtggagctg   1200
tggtcggccc ccaacagcca agcccggagt gagaaagctt tccatgacca gcatttcggc   1260
cccttcttcc gaaccaacca ggtgatcctg acggctccta accggtccag ctacaggtat   1320
gactctctgc tgctggggcc caagaacttc agcggaatcc tggacctgga cttgctgctg   1380
gagctgctag agctgcagga gaggctgcgg cacctccagg tatggtcgcc cgaagcacag   1440
cgcaacatct ccctgcagga catctgctac gccccctca atccggacaa taccagtctc    1500
tacgactgct gcatcaacag cctcctgcag tatttccaga acaaccgcac gctcctgctg   1560
ctcacagcca accagacact gatggggcag acctcccaag tcgactggaa ggaccatttt   1620
ctgtactgtg ccaatgcccc gctcaccttc aaggatggca cagccctggc cctgagctgc   1680
atggctgact acggggcccc tgtcttcccc ttccttgcca ttgggggggta caaaggaaag   1740
gactattctg aggcagaggc cctgatcatg acgttctccc tcaacaatta ccctgccggg   1800
gacccccgtc tggcccaggc caagctgtgg gaggaggcct tcttagagga aatgcgagcc   1860
ttccagcgtc ggatggctgg catgttccag gtcacgttca tggctgagcg ctctctggaa   1920
gacgagatca atcgcaccac agctgaagac ctgcccatct ttgccaccag ctacattgtc   1980
atattcctgt acatctctct ggccctgggc agctattcca gctggagccg agtgatggtg   2040
gactccaagg ccacgctggg cctcggcggg gtggccgtgg tcctgggagc agtcatggct   2100
gccatgggct tcttctccta cttgggtatc cgctcctccc tggtcatcct gcaagtggtt   2160
cctttcctgg tgctgtccgt gggggctgat aacatcttca tctttgttct cgagtaccag   2220
aggctgcccc ggaggcctgg ggagccacga gaggtccaca ttgggcgagc cctaggcagg   2280
gtggctccca gcatgctgtt gtgcagcctc tctgaggcca tctgcttctt cctaggggcc   2340
ctgaccccca tgccagctgt gcggaccttt gccctgacct ctggccttgc agtgatcctt   2400
gacttcctcc tgcagatgtc agcctttgtg gccctgctct ccctggacag caagaggcag   2460
gaggcctccc ggttggacgt ctgctgctgt gtcaagcccc aggagctgcc cccgcctggc   2520
cagggagagg ggctcctgct tggcttcttc caaaaggctt atgcccctt cctgctgcac    2580
tggatcactc gaggtgttgt gctgctgctg tttctcgccc tgttcggagt gagcctctac   2640
tccatgtgcc acatcagcgt gggactggac caggagctgg ccctgcccaa ggactcgtac   2700
ctgcttgact atttcctctt tctgaaccgc tacttcgagg tgggggcccc ggtgtacttt   2760
gttaccacct tgggctacaa cttctccagc gaggctggga tgaatgccat ctgctccagt   2820
gcaggctgca acaacttctc cttcacccag aagatccagt atgccacaga gttccctgag   2880
cagtcttacc tggccatccc tgcctcctcc tgggtggatg acttcattga ctggctgacc   2940
ccgtcctcct gctgccgcct ttatatatct ggccccaata aggacaagtt ctgcccctcg   3000
accgtcaact ctctgaactg cctaaagaac tgcatgagca tcacgatggg ctctgtgagg   3060
ccctcggtgg agcagttcca taagtatctt ccctggttcc tgaacgaccg gcccaacatc   3120
```

-continued

```
aaatgtccca aaggcggcct ggcagcatac agcacctctg tgaacttgac ttcagatggc   3180
caggttttag cctccaggtt catggcctat cacaagcccc tgaaaaactc acaggattac   3240
acagaagctc tgcgggcagc tcgagagctg gcagccaaca tcactgctga cctgcggaaa   3300
gtgcctggaa cagacccggc ttttgaggtc ttcccctaca cgatcaccaa tgtgttttat   3360
gagcagtacc tgaccatcct ccctgagggg ctcttcatgc tcagcctctg ccttgtgccc   3420
accttcgctg tctcctgcct cctgctgggc ctggacctgc gctccggcct cctcaacctg   3480
ctctccattg tcatgatcct cgtggacact gtcggcttca tggccctgtg gggcatcagt   3540
tacaatgctg tgtccctcat caacctggtc tcggcggtgg gcatgtctgt ggagtttgtg   3600
tcccacatta cccgctcctt tgccatcagc accaagccca cctggctgga gagggccaaa   3660
gaggccacca tctctatggg aagtgcggtg tttgcaggtg tggccatgac caacctgcct   3720
ggcatccttg tcctgggcct cgccaaggcc cagctcattc agatcttctt cttccgcctc   3780
aacctcctga tcactctgct gggcctgctg catggcttgg tcttcctgcc cgtcatcctc   3840
agctatgtgg ggcctgacgt caacccggct ctggcactgg agcagaagcg ggctgaggag   3900
gcggtggcag cagtcatggt ggcctcttgc ccaaatcacc cctcccgagt ctccacagct   3960
gacaacatct atgtcaacca cagctttgaa ggttctatca aaggtgctgg tgccatcagc   4020
aacttcttgc ccaacaatgg gcggcagttc tgatacagcc agaggccctg tctaggctct   4080
atggccctga accaaagggt tatggggatc ttccttgtga ctgccccttg acacacgcc    4139
```

<210> SEQ ID NO 12
<211> LENGTH: 4001
<212> TYPE: DNA
<213> ORGANISM: Homo sapiens

<400> SEQUENCE: 12

```
tggctgttcc tgaggcctgg cctggctccc cgctgacccc ttcccagacc tgggatggcg     60
gaggccggcc tgaggggctg gctgctgtgg gccctgctcc tgcgcttggc ccagagtgag    120
ccttacacaa ccatccacca gcctggctac tgcgccttct atgacgaatg tgggaagaac    180
ccagagctgt ctggaagcct catgacactc tccaacgtgt cctgcctgtc caacacgccg    240
gcccgcaaga tcacaggtga tcacctgatc ctattacaga agatctgccc ccgcctctac    300
accggcccca acacccaagc ctgctgctcc gccaagcagc tggtatcact ggaagcgagt    360
ctgtcgatca ccaaggccct cctcacccgc tgcccagcct gctctgacaa ttttgtgaac    420
ctgcactgcc acaacacgtg cagccccaat cagagcctct tcatcaatgt gacccgcgtg    480
gcccagctag ggctggaca actcccagct gtggtggcct atgaggcctt ctaccagcat    540
agctttgccg agcagagcta tgactcctgc agccgtgtgc gcgtccctgc agctgccacg    600
ctggctgtgg gcaccatgtg tggcgtgtat ggctctgccc tttgcaatgc ccagcgctgg    660
ctcaacttcc agggagacac aggcaatggt ctggccccac tggacatcac cttccacctc    720
ttggagcctg gccaggccgt ggggagtggg attcagcctc tgaatgaggg ggttgcacgt    780
tgcaatgagt cccaaggtga cgacgtggcg acctgctcct gccaagactg tgctgcatcc    840
tgtcctgcca tagcccgccc ccaggccctg gactccacct tctacctggg ccagatgccg    900
ggcagtctgg tcctcatcat catcctctgc tctgtcttcg ctgtggtcac catcctgctt    960
gtgggattcc gtgtggcccc cgccagggac aaaagcaaga tggtggaccc caagaagggc   1020
accagcctct ctgacaagct cagcttctcc acccacaccc tccttggcca gttcttccag   1080
ggctggggca cgtgggtggc ttcgtggcct ctgaccatct tggtgctatc tgtcatcccg   1140
```

-continued

```
gtggtggcct tggcagcggg cctggtcttt acagaactca ctacggaccc cgtggagctg   1200
tggtcggccc ccaacagcca agcccggagt gagaaagctt tccatgacca gcatttcggc   1260
cccttcttcc gaaccaacca ggtgatcctg acggctccta accggtccag ctacaggtat   1320
gactctctgc tgctggggcc caagaacttc agcggaatcc tggacctgga cttgctgctg   1380
gagctgctag agctgcagga gaggctgcgg cacctccagg tatggtcgcc cgaagcacag   1440
cgcaacatct ccctgcagga catctgctac gccccctca atccggacaa taccagtctc   1500
tacgactgct gcatcaacag cctcctgcag tatttccaga acaaccgcac gctcctgctg   1560
ctcacagcca accagacact gatggggcag acctcccaag tcgactggaa ggaccatttt   1620
ctgtactgtg ccaatgcccc gctcaccttc aaggatggca cagccctggc cctgagctgc   1680
atggctgact acggggcccc tgtcttcccc ttccttgcca ttggggggta caaaggaaag   1740
gactattctg aggcagaggc cctgatcatg acgttctccc tcaacaatta ccctgccggg   1800
gacccccgtc tggcccaggc caagctgtgg gaggaggcct tcttagagga aatgcgagcc   1860
ttccagcgtc ggatggctgg catgttccag gtcacgttca tggctgagcg ctctctggaa   1920
gacgagatca atcgcaccac agctgaagac ctgcccatct ttgccaccag ctacattgtc   1980
atattcctgt acatctctct ggccctgggc agctattcca gctggagccg agtgatggtg   2040
gactccaagg ccacgctggg cctcggcggg gtggccgtgg tcctgggagc agtcatggct   2100
gccatgggct tcttctccta cttgggtatc cgctcctccc tggtcatcct gcaagtggtt   2160
cctttcctgg tgctgtccgt gggggctgat aacatcttca tctttgttct cgagtaccag   2220
aggctgcccc ggaggcctgg ggagccacga gaggtccaca ttgggcgagc cctaggcagg   2280
gtggctccca gcatgctgtt gtgcagcctc tctgaggcca tctgcttctt cctaggggcc   2340
ctgaccccca tgccagctgt gcggaccttt gccctgacct ctggccttgc agtgatcctt   2400
gacttcctcc tgcagatgtc agcctttgtg gccctgctct ccctggacag caagaggcag   2460
gaggcctccc ggttggacgt ctgctgctgt gtcaagcccc aggagctgcc cccgcctggc   2520
cagggagagg ggctcctgct tggcttcttc caaaaggctt atgcccctt cctgctgcac   2580
tggatcactc gaggtgttgt ggtgggggcc ccggtgtact ttgttaccac cttgggctac   2640
aacttctcca gcgaggctgg gatgaatgcc atctgctcca gtgcaggctg caacaacttc   2700
tccttcaccc agaagatcca gtatgccaca gagttccctg agcagtctta cctggccatc   2760
cctgcctcct cctgggtgga tgacttcatt gactggctga ccccgtcctc ctgctgccgc   2820
ctttatatat ctggccccaa taaggacaag ttctgcccct cgaccgtcaa ctctctgaac   2880
tgcctaaaga actgcatgag catcacgatg ggctctgtga ggccctcggt ggagcagttc   2940
cataagtatc ttccctggtt cctgaacgac cggcccaaca tcaaatgtcc caaaggcggc   3000
ctggcagcat acagcacctc tgtgaacttg acttcagatg gccaggtttt agcctccagg   3060
ttcatggcct atcacaagcc cctgaaaaac tcacaggatt acacagaagc tctgcgggca   3120
gctcgagagc tggcagccaa catcactgct gacctgcgga aagtgcctgg aacagacccg   3180
gcttttgagg tcttccccta cacgatcacc aatgtgtttt atgagcagta cctgaccatc   3240
ctccctgagg ggctcttcat gctcagcctc tgccttgtgc ccaccttcgc tgtctcctgc   3300
ctcctgctgg gcctggacct gcgctccggc ctcctcaacc tgctctccat tgtcatgatc   3360
ctcgtggaca ctgtcggctt catggccctg tggggcatca gttacaatgc tgtgtccctc   3420
atcaacctgg tctcggcggt gggcatgtct gtggagtttg tgtcccacat tacccgctcc   3480
```

```
tttgccatca gcaccaagcc cacctggctg gagagggcca aagaggccac catctctatg   3540

ggaagtgcgg tgtttgcagg tgtggccatg accaacctgc ctggcatcct tgtcctgggc   3600

ctcgccaagg cccagctcat tcagatcttc ttcttccgcc tcaacctcct gatcactctg   3660

ctgggcctgc tgcatggctt ggtcttcctg cccgtcatcc tcagctacgt ggggcctgac   3720

gttaacccgg ctctggcact ggagcagaag cgggctgagg aggcggtggc agcagtcatg   3780

gtggcctctt gcccaaatca cccctcccga gtctccacag ctgacaacat ctatgtcaac   3840

cacagctttg aaggttctat caaaggtgct ggtgccatca gcaacttctt gcccaacaat   3900

gggcggcagt tctgatacag ccagaggccc tgtctaggct ctatggccct gaaccaaagg   3960

gttatgggga tcttccttgt gactgcccct tgacacacgc c                       4001


<210> SEQ ID NO 13
<211> LENGTH: 4360
<212> TYPE: DNA
<213> ORGANISM: Felis catus

<400> SEQUENCE: 13

caccaaggca gcatgaccgc gcgcggccca gccctcggcc tccttctgct gctgctgtgt     60

cccgcgcagg tgttggcaca gtcttgcatc tggtatggag agtgtggaat tgcatctgga    120

gataagaggt acaactgcaa atattcaggg ccaccaaaac ccttgccgaa ggatgggtat    180

gacttagtgc aggagctctg tccaggattc ttctttgaca atgtcagtct ttgttgcgat    240

gtgcagcagc tccagacact gaaagacaac ctgcagctgc ctctacagtt tctgtccaga    300

tgtccatcct gtttctataa cctagtgaac ctgttttgcg agctgacgtg tagccctcgg    360

caaagtcagt ttctgaatgt tacagcaact gaagattatg ttgatcctgt tacaaaccag    420

actaaaacaa atgtaaaaga attacagtac tacattggag agagttttgc caatgccatg    480

tacaatgcct gccgggacgt ggaggccccc tccagtaatg acaaagccct gggactgctg    540

tgtgggaagg acgccgaagc ctgcaatgcc actaactgga ttgagtacat gttcagtaag    600

gacaacggcc aggcaccttt caccatcaca cccatttttt cagatcttcc aacccatggg    660

atggagccca tgaacaatgc caccaagggc tgtgacgagt ctgtggacga ggtcaccggg    720

ccgtgcagct gccaggactg ctcaattgtt tgtggcccaa agccccagcc cccaccgcct    780

cctgtgccct ggagaatctt gggcctggac gccatgtatg tcatcatgtg gatcacctac    840

atggcatttt tgcttgtgtt ttttggagct ttttttgctt tgtggtgcta cagaaaacgc    900

tattttgtct ccgagtacac ccccattgat agcaacatag ctttctctgt aaatgccaat    960

gacagagggg aggcgtcctg ctgcgacgcg cttggtgcgg catttgaggg ctgtctgagg   1020

cggctcttct cacagtgggg ctctttctgc gtccgaaacc cgggccccat catcttcttc   1080

tccctggcct tcattgccgc ctgttcttca ggcctggtgt ttgtgcgggt cacgaccaat   1140

ccagttgacc tgtggtcagc tcccagcagc caggcgcgcc tcgagaaaga gtactttgac   1200

acgcactttg ggcctttctt ccgcacggag cagctcatca tccaggcccc ccacaccagt   1260

gcacacactt accagccgta cccctcagga tccgatgtgc ccttcggacc tccgcttgac   1320

ctcgcgatct tgcaccaggt tcttgactta caaactgcca tcgaaaatat cactgcatct   1380

tataacaatg agaccgtgac acttcaagac atctgcgtgg ccccccctgtc accctataac   1440

aagaactgca ccattctgag cgtgttaaat tacttccaga acagccattc catgctggac   1500

catgaaatag gagatgactt ctttgtgtat gcagattacc acacgcactt gctatactgt   1560

gtacgggctc ctgcctctct gaacgatacc agtttgctcc atgatccttg cctgggtaca   1620
```

```
ttcggtgggc cagtgttccc gtggcttgtg ttaggaggct atgatgatca aaattacaat   1680
aatgccacag cccttgtgat tacctttcct gtcaataatt actataatga tacagagagg   1740
ctccagaagg cccacgtctg ggaaaaagag tttattaatt ttgtgaaaaa ctacaagaat   1800
ccaaatctga ccatttcttt cactactgag cgaagtattg aagatgaact aaatcgtgaa   1860
agtaacggtg atattttcac tgttataatc agctatgcca tcatgtttct gtacatttcc   1920
atagccttgg ggcacatcaa aagctgtagc aggcttctag tggactctaa aatctccctc   1980
ggcatcgcgg ggatcctcat tgtgttgagc tcaaaggcgt gctcgttggg catctttagt   2040
tacgttggga tcccccctcac cctcattgtg atcgaagtca tcccattcct ggtgctggct   2100
gttggggtgg acaacatctt cattctggtc cagacctacc agcgagatga acgtcttcat   2160
ggagaaactc tggatcagca gctgggcagg gtcctaggag aagtggctcc tagtatgttc   2220
ctgtcatcct tttcagaggc tgtagcattt ttcttaggag cgctgtcaaa gatgccggct   2280
gttcacacct tctctctgtt tgccgggatg gcagtcctca tcgacttcct tcttcagatt   2340
acctgtttcg tgagtctctt ggggttagac attaagcgtc aagagaaaaa ccgtctggat   2400
gttctttgct gtgtcagagg ctctgaagat ggaaccagtg tccaggcttc agagagctgc   2460
ttgtttcggc tcttcaagca ctcctattct ccacttctgc ttaaggactg gatgagacca   2520
attgtgatag caatatttgt gggtgtcctg tcattcagtg ttgcagtcct gaacaaagtg   2580
gaaatcggat tggatcagtc tctttcaatg ccagatgact cctacgtgat ggattatttc   2640
aagtccctca aatacctgca tgcaggtcca cctgtgtact ttgtcctgga ggaagggcat   2700
gactacacct ctctgaaagg gcagaacatg gtgtgcggag gcatgggctg caataacgac   2760
tccctggtgc agcagatatt caacgcggcc cagctagaca gctatacccg aataggcttt   2820
gctccctctt cctggatcga cgattacttt gattgggtca agcctcagtc ttcttgctgt   2880
agagtctaca acagcaccga tcggttctgc aatgcttcag tggttgaccc tgcctgcatc   2940
cgctgcaggc ccctcaccca ggagggcaaa cagaggcctc aaggtggaga cttcatgaga   3000
ttcctgccca tgttcctttc tgataacccg aaccccaagt gcggcaaagg gggacatgct   3060
gcttacagtt cggcagttaa catcctcggc aatgacacgg gtgtcggagc cacttacttc   3120
atgacctacc acaccgtgct tcagacgtct gctgacttta ctgacgccat gagaaaagcc   3180
aacctcatcg ccagtaacat caccaaaacc atgggccttg aaggaagtaa ttaccgtgtg   3240
ttcccataca gtgtgttcta tgtcttctac gaacagtacc tgaccattat tgatgacacg   3300
atctttaacc tcagcgtgtc cctgggagcc atcttcttag tgaccgtgat tctcctgggc   3360
tgtgatctgt ggtctgcagt gatcatgtgt atcaccatcg ctatgatctt ggtcaacatg   3420
tttggcgtca tgtggctgtg ggcatcagt ctgaatgcag tttccttggt caacttggtt   3480
atgagctgtg gcatttccgt ggagttctgc agccacataa cgagagcatt cacagtgagc   3540
atgaagggca gccgtgcaca acgggcagaa gaggcgctcg ctcacatggg cagttctgtg   3600
ttcagtggaa tcacactaac aaaatttgga gggattgtgg tattggcctt tgccaaatct   3660
cagattttcc agatatttta cttcaggatg tatttggcta tggtcttact gggagccacc   3720
cacggcttga tcttcctccc ggtcttactc agctacatag gcccatcaat aaataaagcc   3780
aaaagcttgg ccactcaaga gcaatacaaa ggtacagagc gagaacaact cctaaatttc   3840
tagccctctt gcaaggtcgg gggactctga actgtgtctg tgggtcgctc agcctaccgc   3900
tcactggaca gtggctgcac cgtcgaggcc gagttggaca ctggacggta ccagacatca   3960
```

-continued ggctacttaa cagcagcagc ttcggccata gtgcttttaa actcaggaat gcaaatgtga 4020
tgcgtgaatc ggaagcatta cggaatcgga aggcagcccc gggacgctgc agggccttcc 4080
agttctccac gaaccagacc taactcttgg gcaggcggaa ggtgacacta gcatggctga 4140
gtgggatctg ctccgtgaca ctttttaaag gccaatcaat gcaatgtttt tccttttgtt 4200
tgggagtaag ccatcacaca gattctatac cgtattttta gtaacatttg aggatggtgt 4260
agatacactt tactataaca ttttgtagtt taaagagctt tattaatgca ataaattaac 4320
tttgtacaca tttttatata tatataaaaa aactagcaag 4360

<210> SEQ ID NO 14
<211> LENGTH: 5016
<212> TYPE: DNA
<213> ORGANISM: Mus musculus

<400> SEQUENCE: 14
ccttcctgcc ttgcgcacac agtccgccgt ctgctcttgc cccctccttg gtcaggcgcc 60
ggttccgaaa ccgcccgcca gtgccgcgac gctcgggtcg cggtgctccg cgagccgaac 120
tgagagctgt agccccgcgc ggcgacagca tgggtgcgca ccacccggcc ctcggcctgc 180
tgctgctgct gctgtgccct gcgcaggtgt tttcgcaatc ctgtgtttgg tatggagagt 240
gtggaattgc gactggagat aagaggtaca actgtaaata ttctggccca ccaaaacccc 300
tcccaaagga cggctatgac ttagtgcagg aactctgtcc aggactcttc tttgacaatg 360
tcagtctctg ctgtgacatt caacagcttc agacgctgaa gagtaacctg cagctgcccc 420
tgcagttcct gtccaggtgt ccgtcatgtt tttataacct aatgaccctg ttttgtgagc 480
taacatgtag cccacaccag agtcagtttc tgaatgtgac agcaactgag gattattttg 540
atcctaagac acaggagaat aaaacaaatg taaaggaatt agagtacttt gtcggacaga 600
gcttcgcgaa tgcgatgtac aatgcctgcc gtgatgtgga ggcgccttcc agtaacgaga 660
aggccttagg actcttgtgt gggagggatg cccgtgcctg caatgccacc aactggattg 720
agtacatgtt caataaagac aacggacaag cgccatttac catcattcct gtgttttcag 780
atctttcaat ccttgggatg gagcccatga gaaatgccac caaaggctgc aatgagtctg 840
tagatgaggt cacggggcca tgtagctgcc aggactgctc catcgtctgc ggccccaagc 900
cccagccccc accccctcct atgccctgga ggatctgggg cttggatgcc atgtatgtca 960
tcatgtgggt cacctacgtg gcatttctgt ttgtgttttt tggagcactg ttggcagtgt 1020
ggtgccacag aaggcggtac tttgtgtctg agtacactcc cattgacagt aacatcgcct 1080
tttctgtgaa tagcagtgac aaaggggaag cctcatgctg tgacccactt ggtgcagcat 1140
ttgatgactg tctgaggcgc atgttcacaa agtggggggc tttctgtgtc cgaaatccca 1200
cctgcatcat tttcttctca ttggccttca tcactgtgtg ctcttctggc ctggtatttg 1260
tccaggtcac caccaatcct gtagagctct ggtcagcccc tcacagtcag gcccgcttgg 1320
aaaaggagta ctttgacaag cactttgggc ctttctttcg cacggagcag cttatcatcc 1380
aggcccccaa caccagtgtt catatctacg aaccgtaccc cgcaggagcc gatgtgccct 1440
tcgggcctcc attgaacaaa gagattctgc accaggttct ggacttacag atcgccattg 1500
aaagcatcac cgcatcttac aacaatgaaa ccgtgacact gcaggacatc tgtgtggccc 1560
ccctctctcc atacaacaag aactgcacca ttatgagtgt gttaaattac ttccagaaca 1620
gccatgcggt gctggacagc caagtaggcg acgacttcta tatctacgct gattaccaca 1680
cacactttct gtactgtgta cgggctcccg cctccttgaa tgatacgagt ttgctccacg 1740

-continued

```
gtccttgcct gggtacattt ggaggaccgg tgttcccgtg gcttgtgttg ggtggctatg   1800
atgatcagaa ctacaacaat gccaccgcgc ttgtgatcac cttccccgtg aataattact   1860
acaatgacac agagaggctc cagagggcct gggcctggga gaaagagttt attagttttg   1920
tgaaaaacta caagaatcca aatctgacca tttctttcac tgctgagcga agcatcgaag   1980
atgagctcaa tcgggaaagt aacagtgacg tgttcaccgt catcatcagc tacgtcgtga   2040
tgtttctgta catttccctc gccctgggtc acatccagag ctgcagcagg ctcctggtgg   2100
attctaagat ctcgctgggc attgcgggga tcctgatcgt gctaagctcg gtggcctgct   2160
ctctgggcat cttcagctac atggggatgc cgctgaccct catcgtcatt gaggtcatcc   2220
cattcctggt gctggctgtc ggggtggaca acatcttcat tctagtgcag acctaccaga   2280
gagatgagcg tcttcaggag gaaacgctgg atcagcagct gggcaggatc cttggagaag   2340
tggccccgac catgttcctt tcatcctttt ctgagacctc agcatttttc tttggggcgc   2400
tgtcctcgat gccagctgtg cacaccttct ctctgtttgc gggaatggcc gtcctcattg   2460
acttcctcct tcagattacc tgctttgtga gcctgttggg gttagatatt aagaggcaag   2520
agaaaaacca tctggacatc ctgtgctgtg tcagaggcgc tgacgacgga caaggtagcc   2580
acgcctccga aagctacctg tttcgcttct tcaaaaacta ctttgccccc cttctgctga   2640
aggactggct gaggccaatt gtggtagcgg tgtttgtggg cgttctgtca ttcagtgttg   2700
cggtggtgaa caaagtagac atcgggttgg atcagtctct ctcaatgcca aacgattcgt   2760
atgtgattga ctatttcaaa tcactcgctc agtacctgca ctcgggccca cccgtgtact   2820
ttgtcctgga ggaaggctat aactacagtt cacgcaaagg gcagaacatg gtgtgcggcg   2880
gcatgggctg tgacaatgac tccctggtgc agcagatatt taacgcagct gagctggaca   2940
cctacacccg agtaggcttc gccccctcgt cctggatcga tgactacttt gactgggtct   3000
cgccacagtc gtcctgctgc agactctaca acgtcactca ccagttctgc aatgcttctg   3060
tgatggaccc aacctgtgtc cgctgcagac ctctgactcc agagggtaaa cagaggcctc   3120
aggggaaaga attcatgaaa ttcctgccca tgttcctttc tgataacccc aaccccaagt   3180
gcggcaaagg gggacatgct gcttacggtt cagctgttaa cattgtggga gatgacactt   3240
acattggggc cacttacttc atgacctacc acaccatact taagacctcc gctgactata   3300
ctgatgccat gaagaaagct cggctaatag ccagtaacat cacggaaacc atgcgttcta   3360
aggggagtga ctaccgcgta ttcccttaca gtgtgttcta cgtcttctat gaacagtacc   3420
tgaccattat tgatgacacc atctttaacc tcagtgtgtc tctgggctcc atatttctgg   3480
tgaccttggt ggttctgggc tgtgagctgt ggtctgcggt catcatgtgt atcaccatag   3540
ccatgatcct ggtcaacatg ttcggtgtca tgtggctgtg ggcatcagt ctgaatgcgg    3600
tctccttggt caacttggtg atgagctgcg gcatttctgt ggagttctgc agccatataa   3660
cgagagcatt caccatgagt accaaaggaa gccgagtgag ccgggcggaa gaggcactgg   3720
cccacatggg tagttctgta ttcagtggaa tcacacttac gaaatttgga gggatcgtgg   3780
tgttagcctt tgccaaatct caaatttttg agatatttta cttcaggatg tacttagcca   3840
tggtcttact cggagccact catggactaa tatttcttcc cgtcttactc agttacatag   3900
ggccgtcggt gaataaagct aaaagacaca ccacttacga gcgctacaga gggacagaga   3960
gaaaacggct cctcaatttt tagccttgta gcaggctttg gtgactgtgt ttatggatag   4020
gtcaagttta ctgcaagaca gctgcgctgt caagactgag ctggcttcag gctgtgtccg   4080
```

agctgtgtca catgcagctc tacccacgct tttaaactca ggaatgcaca cctaacttgt 4140
gaagcagtat taatggatct gaaagcaaca atcgccagcc cctactgtcg taccagtaga 4200
aacctcatct tgggtacaag gaaggatagt tctgtcactt taacttgttt caatgcctac 4260
ttttaatgga ggttattaaa cactttaacc tcccttctag cccaccacca accagagata 4320
gtgggaaaga aaggatacag gggaagtgga cctgtttaga aatggttctt tggagcagat 4380
cctgtctgca ttatcaggaa accagcaatt cagttcacgg gtcagcagtg gcagctcgac 4440
ccactcgcaa acacttcacg gatacaccag cagtgttggg ataggagcag ccaggcctca 4500
gcaggaggga ccagggccga caggaacacc agaggttctt ggctgttcct ctatcagcga 4560
agactggaga ccaacaaaca ttacacagct agctctatat tctctctgtg gagtcccaac 4620
acatggagct caactacaca atataaggca gaccaaccaa tacatgcctg tcattcacgt 4680
gtcctttcat gtgcttgctt tagggaaaca gtccttcaca agtctgcctt tcacctgtgt 4740
ctgcttcagc aaaatgttct ttcacatttg ccccagcaaa accccatcta acacaactga 4800
ctttccaaag aacccttaag tttccatttc ccagtggcaa taactgtgac ctgatcccta 4860
ccccacatgc tgtctccttt tctttgggag ttagcaacat ttgaggatgt tgtaggtact 4920
ttattacatt tttttgtagt ttaaagagct ttattaatgc aataaattaa ctttgtacat 4980
ttttatatta aaaaaaaaaa aaaaaaaaaa aaaaaa 5016

<210> SEQ ID NO 15
<211> LENGTH: 4724
<212> TYPE: DNA
<213> ORGANISM: Bos taurus

<400> SEQUENCE: 15
gagccggcgc ttggtttcct ccctccgcgg gcgcgggagc cggagacagc ccggggtgcc 60
caaccgagcc tgcgagccga gtctctccga catccgccgc ccgtcgccgc ggcagcatga 120
gcgtgcgcgg cccagccttc ggcctcctcc tgctgctgtt ctgcccggcg caggtatttt 180
cacagtcctg catttggtat ggagagtgtg gaattgcatc tggagataag agatacaact 240
gcagatattc tgggccacca gagccattgc cacaggatgg ctatgaccta gtgcaggaac 300
tctgtccagg gttcttcttt ggcaatgtca gtctttgctg tgatgtccag cagcttcaca 360
cactgaagga caacctgcag ctgcctctgc agtttctgtc cagatgtcca tcctgttttt 420
ataacctagt gaacctgttt tgtgagctga catgtagccc tcgacaaagt cagtttctga 480
acgttacagc aactgaagat tatgttgatc ctgctacaaa ccagacgaaa acaaatgtaa 540
aagaattaca gtactatgtt ggagagagtt ttgccaatgc catgtacaat tcctgccggg 600
atgtggaggc cccctcgagc aacgagaagg ccctggggct gctgtgcggg cgtgaggcca 660
gcgcctgcaa tgctactaac tggatcgagt acatgttcaa caaggacaat ggccaggcgc 720
ccttcaccat cacccccgtc ttttcagatc ttccgacgca tgggatggag cccatgaaca 780
atgccaccaa gggctgtgac gagtcggtgg acgaggtcac ggggccgtgc agctgccagg 840
actgctcggc cgtctgcggc cccaagcccc agcccccacc ccctcccgtt ccctggagaa 900
tcctgggtct ggacgccatg tatgtcatca tgtggagcac ctacatggct ttcctgctcg 960
tgttctttgg agcgttcttt gctgtgtggt gctacagaaa acggtatttt gtctctgagt 1020
ttacccccat tgatggcaat ataccttttct ctataaacgc cagtgacaaa ggggggccaa 1080
cctgctgtga ccctctgggt gccgccttcg aggctcatct gcggcggctc ttcgaatggt 1140
ggggctcctt ctgcgtgagg caccccggct gtgtcgtgtt cttctccgtg gccttcatcg 1200

-continued

```
ccgcctgttc ctcaggcctg gtgttcatcc aggtcacaac cgacccggtg gacctctggt   1260
cggcccccgg cagccaggcg cgcctggaga aggagtactt tgacacgcac ttcgggccct   1320
tcttccgcac cgagcagctc atcatcaggg ccccccacac cccgccgcac atatacgagc   1380
cctacccctc gggagccgac gtgccctttg ggcctcccct tgctgtagac attctgcacc   1440
aggtccttga cttacaaacc gccatcgaga gcatcactgc ttcttacaac aacgagactg   1500
tgaccctgcg ggacatctgc gtggcgcccc tctcgccata caaccagaac tgcaccatcc   1560
tgagtgtgct gaactacttc cagaacagcc actctgtgct ggaccatcaa gtcgggggatg  1620
acttcttcgt gtatgcagat taccacacgc acttcctcta ctgtgtccgg gctcctgctt   1680
ccctgaatga caccagtttg ctccacgatc cttgcctggg aacgtttggt ggcccagtgt   1740
tcccatggct tgtgcttgga ggctacgatg atcaaaacta caataacgca acagcccttg   1800
tgatcacctt tcctgtcaat aattactata acgatacaga gaagctccag agggcccagg   1860
cctgggaaag agagttcatt aattttgtgc aaaactacga gaatccaaat ctgaccattt   1920
cttttaaggc tgaacgaagc attgaagatg aactaaaccg tgaaagtaac agtgatgtgt   1980
tcactgttct gatcagctat ggcgtcatgt tttatatat ttccatagcc ttggggcata    2040
tcaaaagctg tcgcaggctt ctggtggatt cgaaaatctc cctgggcatt gccggtgtcc   2100
tgattgtgtt gagctcagtg gcctgctcct tgggcatctt cagctacatc ggggtccccc   2160
tcaccctcat tgtgatagaa gtcatcccat tcctcgtgct ggctgtgggg gtggacaaca   2220
tcttcatcct ggtccagacc taccagagag atgaacgtct tcaaggggaa accctcgacc   2280
aacaggtggg ccgggtcctg ggagaagtgg ctcccagcat gttcctctca tccttcgcag   2340
agacggtagc gtttttctta ggaggcctgt ctgtgatgcc ggccgtgcac acgttctctc   2400
tcttcgcggg catggcagtc ctcattgact tcctcctgca gatcacctgc ttcgtgagcc   2460
tcctgggttt ggacattaag cggcaagaga agaaccagct ggacgttctc tgctgtgtcg   2520
ggggggcggc agacgacgcg ggcatccagg cctccgagag ctgcttgttc cgcttcttca   2580
gaaactccta cgcgccgctt ctgctcaagg actggatgcg gcccctcgtg gtggcagtat   2640
ttgtgggtgt gctgtcgttc agtatcgcag tcctgaacaa agtagagatc ggattggatc   2700
agtctctttc aatgccggat gactcctacg tgacggatta cttccagtcc ctgaatcagt   2760
acctgcacgc aggcccacct gtgtacttcg tgctggagga gggccacgac tacacgtcca   2820
cgaaggggca gaacatggtg tgcgggggcc tcggctgcaa caacgactcg ctggtgcagc   2880
aggtcttcac ggccgcccag ctggacagct acacccggat aggctttgcc ccgtcgtcct   2940
ggattgacga ttactttgac tgggtcaagc ctcaatcttc ttgctgtcgc atctacaaca   3000
gcacggagca gttctgcaat gcatcggtgg tcaaccctac ctgtgtccgc tgccggccgc   3060
tgactccaga gggcaagcag agacctcagg gcgcagactt catgaggttc ctgcccatgt   3120
tcctctccga caacccgaac cccaagtgtg gcaaaggggg acacgctgcc tacagcgcag   3180
ccgtcaacat cctggacaac ggcacgaggg tgggagccac gtacttcatg acctaccaca   3240
cggtgctgca gacctcggct gacttcatcg atgccatgga gaaggcccgc ctcatcgcca   3300
gcaacatcac caggaccatg aaccagcagg ggggtgatca ccgggtgttc ccatacagcg   3360
tgttctatgt cttctatgag cagtacctga ccatgattga cgacaccatc ttcaacctca   3420
gcgtgtccct gggcgccatc ttcctggtgg ccgtggtcct cttgggctgt gagctgtggt   3480
ctgcggtcat catgtgcgcc accatcgcca tgatcttggt caacatgttt ggtgtcatgt   3540
```

-continued ggctgtgggg catcagcctg aacgcggttt ctctggtcaa cctggtcatg agctgtggca 3600
tctccgtgga gttctgtagc cacatcacga gggccttcac ggtgagcacg aagggcagcc 3660
gcgtagagcg ggcggaggag gcgctctccc acatgggcag ctctgtattc agtggaatca 3720
cactaacgaa atttggaggc attatcgtgt tggcttttgc caaatctcaa attttccaga 3780
tattttactt caggatgtat ttagctatgg tcttactggg agccactcat ggactaatat 3840
tcctccctgt cctactcagt tacataggcc cgtcaataaa taaagccaaa agtttgacca 3900
cgcagcagcg atacagaggt acagaacgag aacagctcct caacttctag ctgccccctc 3960
cctgaagtga gactgtgtct gcgggtcggt tggtttacaa cagcaaccgt gttgtcgagg 4020
ctcggttgaa ccctggacgt gagcaagcgt caggctactt aacagcagcc gctttggctg 4080
tagcgctttt aaactcagga atgcagactc tgactggaag cagcattact gaacctggag 4140
gcagccccag ggcgctgggg cacctttccg ttccccagga atgaggcctg gttctcaggc 4200
agccagaagg gggagctagg gagcctgcgg tccgctcact gacacttcct aaaggccaat 4260
caatgcaatg tttctccttt ttcaggagta agccatcaca caagttctac accttatttt 4320
tagtaacatt tgaggatgtg gtagatacat actttattac aacattttgt agtttaaaga 4380
gctttattaa cgcaataaat taactttgta cacattttat atatatatat atatatatat 4440
ataaaaaaaa ctagcaagtg acctcagaac gttgtaggcc tcattagagc ttggtctccg 4500
aaaacttgtt tgaaaaaagc gacatgttct tcacagtgtt ctcctgtaaa ggaaaatgca 4560
gatttcatct gttaaaacga ggcacaaaag gaggaaaaca agggaacact ttgcggctcc 4620
tagatgtgga tactgggttt taacttattt ttctctcata aaatactttg ttttcctaaa 4680
aaaaaaaaaa aaaaaaaaaa aaaaaaagaa aaaaaaaaaa aaaa 4724

<210> SEQ ID NO 16
<211> LENGTH: 1440
<212> TYPE: DNA
<213> ORGANISM: Danio rerio

<400> SEQUENCE: 16
ggggaggagg cgttggcaca tatgggcagc tccgtcttca gtggaatcac cctcaccaag 60
tttggcggga tcctgattct cgctctgtcc aaatcgcaga tcttccagat tttctacttc 120
cgcatgtatc tggcaatcgt gctgctggga gccgctcacg gcctcatctt cctgcctgtc 180
ttactcagtt atgcaggccc gtctgtaaat aaagcaaagg ttctagctgc gcacaacagg 240
tttgtgggca cagagagaga gcggctcatc tactgatcct cagcggacga cgccagcttt 300
tcatattcat gttacacaca tttgtaactc attcagctga cagacttaac tcaggactgc 360
gctttggatg aacagaagac ctttcttcca ctacttctcc tgtctgcgtc caccaaataa 420
acctaacaca cttggtagat cctgacatga tgcagtatat agagtttgtg gagaagaaaa 480
ctcttatttc cattaaacac aaacctgtgg ttctggtaaa gcaacaacga gagcatgagg 540
gcaacgtttg tttcgtttgt atgaatgtat acgtgtaaaa aaaatgtttg actaatcctt 600
tttttattta tttgtatgca attatttact tattgttagc atgtttcaca taacgagtca 660
aattcacaga taatgaaaga accgtgttga caatctcttg atgtattgtg atgctttgac 720
aagaaccgta tgttacacac agctagcgct ttattgctag catgacctga acggtgttgt 780
tttcaagcag gaaaaccacg ttagtcttag ctaattaatg aaattggttg cagtgggacg 840
ttttaaaatt gtttacttac aaagttgtgc tgcgttaatt agcatagaca tgctaataaa 900
gggagtgcca gcattagttt agtgacttaa ggcggcaatt ctaaccaaaa cacaagcaaa 960

-continued

```
tataggttgc agtttggttt aactctcata tgttcagaat ttgcctgtta tttcaattac   1020
taacacagtt tagctttaaa atggctgctc acatggtttt gtaaaccatc aatatggaag   1080
gggaattagc ctactatagt aaacttagca acgtgcaagg cagaaatgtg tttgcataca   1140
aataaatggt tatttttatg ataaaagttt gggattgata gggattgtgg gtatgatgtg   1200
atttttcaaa gtaatgtttg tcattagtca gggactggaa acttggacat ttatgtaaac   1260
atttccatag ctttggtaaa agatagatgc gtgtgcctca tggacataat agcagtctaa   1320
agtttctgct ttgtgcgtaa acgttcttga tttgaagatt tttttttgga ataaatacgg   1380
actaatttgt aataaaaaag attgttttat ttaaaaaaaa aaaaaaaaaa aaaaaaaaaa   1440

<210> SEQ ID NO 17
<211> LENGTH: 4827
<212> TYPE: DNA
<213> ORGANISM: Homo sapiens

<400> SEQUENCE: 17

gaagggcaac acggggacct tgaagcgggg tcgcggcggc gccccagccc gggccaggga     60
gtcccggcag cggcacctcc cagaaagggc ggagccgacg acgccttctt ccttcctgac    120
cggcgcgcgc agcctgctgc cgcggtcagc gcctgctcct gctcctccgc tcctcctgcg    180
cggggtgctg aaacagcccg gggaagtaga gccgcctccg gggagcccaa ccagccgaac    240
gccgccggcg tcagcagcct tgcgcggcca cagcatgacc gctcgcggcc tggcccttgg    300
cctcctcctg ctgctactgt gtccagcgca ggtgttttca cagtcctgtg tttggtatgg    360
agagtgtgga attgcatatg ggacaagagg gtacaattgc gaatattctg gcccaccaaa    420
accattgcca aaggatggat atgacttagt gcaggaactc tgtccaggat tcttctttgg    480
caatgtcagt ctctgttgtg atgttcggca gcttcagaca ctaaaagaca acctgcagct    540
gcctctacag tttctgtcca gatgtccatc ctgtttttat aacctactga acctgttttg    600
tgagctgaca tgtagccctc gacagagtca gtttttgaat gttacagcta ctgaagatta    660
tgttgatcct gttacaaacc agacgaaaac aaatgtgaaa gagttacaat actacgtcgg    720
acagagtttt gccaatgcaa tgtacaatgc ctgccgggat gtggaggccc cctcaagtaa    780
tgacaaggcc ctgggactcc tgtgtgggaa ggacgctgac gcctgtaatg ccaccaactg    840
gattgaatac atgttcaata aggacaatgg acaggcacct tttaccatca ctcctgtgtt    900
ttcagatttt ccagtccatg ggatggagcc catgaacaat gccaccaaag gctgtgacga    960
gtctgtggat gaggtcacag caccatgtag ctgccaagac tgctctattg tctgtggccc   1020
caagccccag cccccacctc ctcctgctcc ctggacgatc cttggcttgg acgccatgta   1080
tgtcatcatg tggatcacct acatggcgtt tttgcttgtg tttttggag catttttgc     1140
agtgtggtgc tacagaaaac ggtattttgt ctccgagtac actcccatcg atagcaatat   1200
agctttttct gttaatgcaa gtgacaaagg agaggcgtcc tgctgtgacc ctgtcagcgc   1260
agcatttgag ggctgcttga ggcggctgtt cacacgctgg gggtctttct gcgtccgaaa   1320
ccctggctgt gtcattttct tctcgctggt cttcattact gcgtgttcgt caggcctggt   1380
gtttgtccgg gtcacaacca atccagttga cctctggtca gcccccagca gccaggctcg   1440
cctggaaaaa gagtactttg accagcactt tgggcctttc ttccggacgg agcagctcat   1500
catccgggcc cctctcactg acaaacacat ttaccagcca tacccttcgg gagctgatgt   1560
accctttgga cctccgcttg acatacagat actgcaccag gttcttgact tacaaatagc   1620
```

-continued

```
catcgaaaac attactgcct cttatgacaa tgagactgtg acacttcaag acatctgctt   1680

ggcccctctt tcaccgtata acacgaactg caccattttg agtgtgttaa attacttcca   1740

gaacagccat tccgtgctgg accacaagaa aggggacgac ttctttgtgt atgccgatta   1800

ccacacgcac tttctgtact gcgtacgggc tcctgcctct ctgaatgata caagtttgct   1860

ccatgaccct tgtctgggta cgtttggtgg accagtgttc ccgtggcttg tgttgggagg   1920

ctatgatgat caaaactaca ataacgccac tgcccttgtg attaccttcc ctgtcaataa   1980

ttactataat gatacagaga agctccagag ggcccaggcc tgggaaaaag agtttattaa   2040

ttttgtgaaa aactacaaga atcccaatct gaccatttcc ttcactgctg aacgaagtat   2100

tgaagatgaa ctaaatcgtg aaagtgacag tgatgtcttc accgttgtaa ttagctatgc   2160

catcatgttt ctatatattt ccctagcctt ggggcacatg aaaagctgtc gcaggcttct   2220

ggtggattcg aaggtctcac taggcatcgc gggcatcttg atcgtgctga gctcggtggc   2280

ttgctccttg ggtgtcttca gctacattgg gttgcccttg accctcattg tgattgaagt   2340

catcccgttc ctggtgctgg ctgttggagt ggacaacatc ttcattctgg tgcaggccta   2400

ccagagagat gaacgtcttc aaggggaaac cctggatcag cagctgggca gggtcctagg   2460

agaagtggct cccagtatgt tcctgtcatc cttttctgag actgtagcat ttttcttagg   2520

agcattgtcc gtgatgccag ccgtgcacac cttctctctc tttgcgggat tggcagtctt   2580

cattgacttt cttctgcaga ttacctgttt cgtgagtctc ttggggttag acattaaacg   2640

tcaagagaaa aatcggctag acatcttttg ctgtgtcaga ggtgctgaag atggaacaag   2700

cgtccaggcc tcagagagct gtttgtttcg cttcttcaaa aactcctatt ctccacttct   2760

gctaaaggac tggatgagac caattgtgat agcaatattt gtgggtgttc tgtcattcag   2820

catcgcagtc ctgaacaaag tagatattgg attggatcag tctctttcga tgccagatga   2880

ctcctacatg gtggattatt tcaaatccat cagtcagtac ctgcatgcgg gtccgcctgt   2940

gtactttgtc ctggaggaag ggcacgacta cacttcttcc aaggggcaga acatggtgtg   3000

cggcggcatg ggctgcaaca atgattccct ggtgcagcag atatttaacg cggcgcagct   3060

ggacaactat acccgaatag gcttcgcccc ctcgtcctgg atcgacgatt atttcgactg   3120

ggtgaagcca cagtcgtctt gctgtcgagt ggacaatatc actgaccagt tctgcaatgc   3180

ttcagtggtt gaccctgcct gcgttcgctg caggcctctg actccggaag gcaaacagag   3240

gcctcagggg ggagacttca tgagattcct gcccatgttc ctttcggata accctaaccc   3300

caagtgtggc aaagggggac atgctgccta tagttctgca gttaacatcc tccttggcca   3360

tggcaccagg gtcggagcca cgtacttcat gacctaccac accgtgctgc agacctctgc   3420

tgactttatt gacgctctga agaaagcccg acttatagcc agtaatgtca ccgaaaccat   3480

gggcattaac ggcagtgcct accgagtatt tccttacagt gtgttttatg tcttctacga   3540

acagtacctg accatcattg acgacactat cttcaacctc ggtgtgtccc tgggcgcgat   3600

atttctggtg accatggtcc tcctgggctg tgagctctgg tctgcagtca tcatgtgtgc   3660

caccatcgcc atggtcttgg tcaacatgtt tggagttatg tggctctggg gcatcagtct   3720

gaacgctgta tccttggtca acctggtgat gagctgtggc atctccgtgg agttctgcag   3780

ccacataacc agagcgttca cggtgagcat gaaaggcagc cgcgtggagc gcgcggaaga   3840

ggcacttgcc cacatgggca gctccgtgtt cagtggaatc acacttacaa aatttggagg   3900

gattgtggtg ttggcttttg ccaaatctca aattttccag atattctact tcaggatgta   3960

tttggccatg gtcttactgg gagccactca cggattaata tttctccctg tcttactcag   4020
```

-continued ttacataggg ccatcagtaa ataaagccaa aagttgtgcc actgaagagc gatacaaagg 4080
aacagagcgc gaacggcttc taaatttcta gccctctcgc agggcatcct gactgaactg 4140
tgtctaaggg tcggtcggtt taccactgga cgggtgctgc atcggcaagg ccaagttgaa 4200
caccggatgg tgccaaccat cggttgtttg gcagcagctt tgaacgtagc gcctgtgaac 4260
tcaggaatgc acagttgact tgggaagcag tattactaga tctggaggca accacaggac 4320
actaaacttc tcccagcctc ttcaggaaag aaacctcatt ctttggcaag caggaggtga 4380
cactagatgg ctgtgaatgt gatccgctca ctgacactct gtaaaggcca atcaatgcac 4440
tgtctgtctc tccttttagg agtaagccat cccacaagtt ctataccata tttttagtga 4500
cagttgaggt tgtagataca ctttataaca ttttatagtt taaagagctt tattaatgca 4560
ataaattaac tttgtacaca tttttatata aaaaaacagc aagtgatttc agaatgttgt 4620
aggcctcatt agagcttggt ctccaaaaat ctgtttgaaa aaagcaacat gttcttcaca 4680
gtgttcccct agaaaggaag agatttaatt gccagttaga tgtggcatga aatgagggac 4740
aaagaaagca tctcgtaggt gtgtctactg ggttttaact tatttttctt taataaaata 4800
cattgttttc ctaaaaaaaa aaaaaaa 4827

<210> SEQ ID NO 18
<211> LENGTH: 5209
<212> TYPE: DNA
<213> ORGANISM: Mus musculus

<400> SEQUENCE: 18
ccttcctgcc ttgcgcacac agtccgccgt ctgctcttgc cccctccttg gtcaggcgcc 60
ggttccgaaa ccgcccgcca gtgccgcgac gctcgggtcg cggtgctccg cgagccgaac 120
tgagagctgt agccccgcgc ggcgacagca tgggtgcgca ccacccggcc ctcggcctgc 180
tgctgctgct gctgtgccct gcgcaggtgt tttcgcaatc ctgtgtttgg tatggagagt 240
gtggaattgc gactggagat aagaggtaca actgtaaata ttctggccca ccaaaacccc 300
tcccaaagga cggctatgac ttagtgcagg aactctgtcc aggactcttc tttgacaatg 360
tcagtctctg ctgtgacatt caacagcttc agacgctgaa gagtaacctg cagctgcccc 420
tgcagttcct gtccaggtgt ccgtcatgtt tttataacct aatgaccctg ttttgtgagc 480
taacatgtag cccacaccag agtcagtttc tgaatgtgac agcaactgag gattattttg 540
atcctaagac acaggagaat aaaacaaatg taaaggaatt agagtacttt gtcggacaga 600
gcttcgcgaa tgcgatgtac aatgcctgcc gtgatgtgga ggcgccttcc agtaacgaga 660
aggccttagg actcttgtgt gggagggatg cccgtgcctg caatgccacc aactggattg 720
agtacatgtt caataaagac aacggacaag cgccatttac catcattcct gtgttttcag 780
atctttcaat ccttgggatg gagcccatga gaaatgccac caaaggctgc aatgagtctg 840
tagatgaggt cacggggcca tgtagctgcc aggactgctc catcgtctgc ggccccaagc 900
cccagccccc accccctcct atgccctgga ggatctgggg cttggatgcc atgtatgtca 960
tcatgtgggt cacctacgtg gcatttctgt ttgtgttttt tggagcactg ttggcagtgt 1020
ggtgccacag aaggcggtac tttgtgtctg agtacactcc cattgacagt aacatcgcct 1080
tttctgtgaa tagcagtgac aaaggggaag cctcatgctg tgacccactt ggtgcagcat 1140
ttgatgactg tctgaggcgc atgttcacaa agtggggggc tttctgtgtc cgaaatccca 1200
cctgcatcat tttcttctca ttggccttca tcactgtgtg ctcttctggc ctggtatttg 1260

-continued

```
tccaggtcac caccaatcct gtagagctct ggtcagcccc tcacagtcag gcccgcttgg   1320
aaaaggagta ctttgacaag cactttgggc ctttctttcg cacggagcag cttatcatcc   1380
aggcccccaa caccagtgtt catatctacg aaccgtaccc cgcaggagcc gatgtgccct   1440
tcgggcctcc attgaacaaa gagattctgc accaggttct ggacttacag atcgccattg   1500
aaagcatcac cgcatcttac aacaatgaaa ccgtgacact gcaggacatc tgtgtggccc   1560
ccctctctcc atacaacaag aactgcacca ttatgagtgt gttaaattac ttccagaaca   1620
gccatgcggt gctggacagc caagtaggcg acgacttcta tatctacgct gattaccaca   1680
cacactttct gtactgtgta cgggctcccg cctccttgaa tgatacgagt ttgctccacg   1740
gtccttgcct gggtacattt ggaggaccgg tgttcccgtg gcttgtgttg ggtggctatg   1800
atgatcagaa ctacaacaat gccaccgcgc ttgtgatcac cttccccgtg aataattact   1860
acaatgacac agagaggctc cagagggcct gggcctggga gaaagagttt attagttttg   1920
tgaaaaacta caagaatcca aatctgacca tttctttcac tgctgagcga agcatcgaag   1980
atgagctcaa tcgggaaagt aacagtgacg tgttcaccgt catcatcagc tacgtcgtga   2040
tgtttctgta catttccctc gccctgggtc acatccagag ctgcagcagg ctcctggtgg   2100
attctaagat ctcgctgggc attgcgggga tcctgatcgt gctaagctcg gtggcctgct   2160
ctctgggcat cttcagctac atggggatgc cgctgaccct catcgtcatt gaggtcatcc   2220
cattcctggt gctggctgtc ggggtggaca acatcttcat tctagtgcag acctaccaga   2280
gagatgagcg tcttcaggag gaaacgctgg atcagcagct gggcaggatc cttggagaag   2340
tggccccgac catgttcctt tcatcctttt ctgagacctc agcatttttc tttggggcgc   2400
tgtcctcgat gccagctgtg cacaccttct ctctgtttgc gggaatggcc gtcctcattg   2460
acttcctcct tcagattacc tgctttgtga gcctgttggg gttagatatt aagaggcaag   2520
agaaaaacca tctggacatc ctgtgctgtg tcagaggcgc tgacgacgga caaggtagcc   2580
acgcctccga aagctacctg tttcgcttct tcaaaaacta ctttgccccc cttctgctga   2640
aggactggct gaggccaatt gtggtagcgg tgtttgtggg cgttctgtca ttcagtgttg   2700
cggtggtgaa caaagtagac atcgggttgg atcagtctct ctcaatgcca aacgattcgt   2760
atgtgattga ctatttcaaa tcactcgctc agtacctgca ctcgggccca cccgtgtact   2820
ttgtcctgga ggaaggctat aactacagtt cacgcaaagg gcagaacatg gtgtgcggcg   2880
gcatgggctg tgacaatgac tccctggtgc agcagatatt taacgcagct gagctggaca   2940
cctacacccg agtaggcttc gccccctcgt cctggatcga tgactacttt gactgggtct   3000
cgccacagtc gtcctgctgc agactctaca acgtcactca ccagttctgc aatgcttctg   3060
tgatggaccc aacctgtgtc cgctgcagac ctctgactcc agagggtaaa cagaggcctc   3120
aggggaaaga attcatgaaa ttcctgccca tgttcctttc tgataacccc aaccccaagt   3180
gcggcaaagg gggacatgct gcttacggtt cagctgttaa cattgtggga gatgacactt   3240
acattggggc cacttacttc atgacctacc acaccatact taagacctcc gctgactata   3300
ctgatgccat gaagaaagct cggctaatag ccagtaacat cacggaaacc atgcgttcta   3360
aggggagtga ctaccgcgta ttcccttaca gtgtgttcta cgtcttctat gaacagtacc   3420
tgaccattat tgatgacacc atctttaacc tcagtgtgtc tctgggctcc atatttctgg   3480
tgaccttggt ggttctgggc tgtgagctgt ggtctgcggt catcatgtgt atcaccatag   3540
ccatgatcct ggtcaacatg ttcggtgtca tgtggctgtg ggcatcagt ctgaatgcgg   3600
tctccttggt caacttggtg atgagctgcg gcatttctgt ggagttctgc agccatataa   3660
```

-continued

```
cgagagcatt caccatgagt accaaaggaa gccgagtgag ccgggcggaa gaggcactgg   3720
cccacatggg tagttctgta ttcagtggaa tcacacttac gaaatttgga gggatcgtgg   3780
tgttagcctt tgccaaatct caaatttttg agatatttta cttcaggatg tacttagcca   3840
tggtcttact cggagccact catggactaa tatttcttcc cgtcttactc agttacatag   3900
ggccgtcggt gaataaagct aaaagacaca ccacttacga gcgctacaga gggacagaga   3960
gagaacggct cctcaatttt tagccttgta gcaggctttg gtgactgtgt ttatggatag   4020
gtcaagttta ctgcaagaca gctgcgctgt caagactgag ctggcttcag gctgtgtccg   4080
agctgtgtca catgcagctc tacccacgct tttaaactca ggaatgcaca cctaacttgt   4140
gaagcagtat taatggatct gaaagcaaca atcgccagcc cctactgtcg taccagtaga   4200
aacctcatct tgggtacaag gaaggatagt tctgtcactt taacttgttt caatgcctac   4260
ttttaatgga ggttattaaa cactttaacc tcccttctag cccaccacca accagagata   4320
gtgggaaaga aaggatacag ggaagtgga cctgtttaga aatggttctt tggagcagat    4380
cctgtctgca ttatcaggaa accagcaatt cagttcacgg gtcagcagtg gcagctcgac   4440
ccactcgcaa acacttcacg gatacaccag cagtgttggg ataggagcag ccaggcctca   4500
gcaggaggga ccagggccga caggaacacc agaggttctt ggctgttcct ctatcagcga   4560
agactggaga ccaacaaaca ttacacagct agctctatat tctctctgtg gagtcccaac   4620
acatggagct caactacaca atataaggca gaccaaccaa tacatgcctg tcattcacgt   4680
gtcctttcat gtgcttgctt tagggaaaca gtccttcaca agtctgcctt tcacctgtgt   4740
ctgcttcagc aaaatgttct ttcacatttg ccccagcaaa accccatcta acacaactga   4800
ctttccaaag aaccccttaag tttccatttc ccagtggcaa taactgtgac ctgatcccta   4860
ccccacatgc tgtctccttt tctttgggag ttagcaacat ttgaggatgt tgtaggtact   4920
ttattacatt tttttgtagt ttaaagagct ttattaatgc aataaattaa ctttgtacat   4980
ttttatatta aaaaaaaaaa aagactatta agggacttca gaatgttgta ggcctcatta   5040
gagcttgttc tccaaaaacc tgcttgaaaa aggcaacgtg ttcttcacag tgctctcctg   5100
taaggacaac gcggctcagt cagcagctgg ttatggcccg ggaagacagg atgcagacaa   5160
cgctcatggg ttttaactta tttttcttta ataaaatacc tcctcctcc              5209
```

<210> SEQ ID NO 19
<211> LENGTH: 1033
<212> TYPE: DNA
<213> ORGANISM: Homo sapiens

<400> SEQUENCE: 19

```
ggtccgggcg ggtcaggcct ctgaggggat ggcatgggcg gagactgcag gcttctgggc     60
ctgagagggc tggagctggc tttccggagc cgggggcggg gcgcgggcgg gcctcagctg    120
tggttactgg tgacaggtcg cctgactggg ctcctccccg ggcccgcccc gacaggtttg    180
tcttgtgacc gcgggcggcc gctgcttctt tcccgagctt ggaacttcgt tatccgcgat    240
gcgtttcctg gcagctacat tcctgctcct ggcgctcagc accgctgccc aggccgaacc    300
ggtgcagttc aaggactgcg gttctgtgga tggagttata aaggaagtga atgtgagccc    360
atgccccacc caaccctgcc agctgagcaa aggacagtct tacagcgtca atgtcacctt    420
caccagcaat attcagtcta aaagcagcaa ggccgtggtg catggcatcc tgatgggcgt    480
cccagttccc tttcccattc ctgagcctga tggttgtaag agtggaatta actgccctat    540
```

```
ccaaaaagac aagacctata gctacctgaa taaactacca gtgaaaagcg aatatccctc    600

tataaaactg gtggtggagt ggcaacttca ggatgacaaa aaccaaagtc tcttctgctg    660

ggaaatccca gtacagatcg tttctcatct ctaagtgcct cattgagttc ggtgcatctg    720

gccaatgagt ctgctgagac tcttgacagc acctccagct ctgctgcttc aacaacagtg    780

acttgctctc caatggtatc cagtgattcg ttgaagagga ggtgctctgt agcagaaact    840

gagctccggg tggctggttc tcagtggttg tctcatgtct ctttttctgt cttaggtggt    900

ttcattaaat gcagcacttg gttagcagat gtttaatttt ttttttaaca acattaactt    960

gtggcctctt tctacacctg gaaatttact cttgaataaa taaaaactcg tttgtcttgt   1020

cttctgcatg tgg                                                      1033
```

<210> SEQ ID NO 20
<211> LENGTH: 3278
<212> TYPE: DNA
<213> ORGANISM: Mus musculus

<400> SEQUENCE: 20

```
gagcggggcg aacgcaaaga gcgagttctc cgtaggccct gcctggaagc ggaagagatg     60

ggcggagata aagggcgagc tgcaggccag gcggccccgg agcccagggc ggggcgcggg    120

cgggccttcg ctggttactg ctcacaagtg gcctgatctg gctccaccct cggtccggga    180

caagtttatc ttgtgactgc tcgggctgct tttccttcct agattgcaga gctttcatat    240

ccacgatgcg ttttctggcc gccacgatcc tgctgctggc gctggtcgct gccagccagg    300

cggagcccct gcacttcaag gactgcggct ctaaggtggg agttataaag gaggtgaatg    360

tgagcccatg tcccaccgat ccctgtcagc tgcacaaagg ccagtcctac agtgtcaaca    420

tcacctttac cagcggcact cagtcccaga acagcacggc cttggtccac ggcatcctgg    480

aagggatccg ggtccccttc cctattcctg agcctgacgg ttgtaagagt ggaatcaact    540

gccccatcca gaaagacaag gtctacagct acctgaataa gcttccggtg aagaatgaat    600

acccctctat aaaactggtg gtggaatgga aacttgaaga tgacaaaaag aataatctct    660

tctgctggga gatcccagtt cagatcacaa gctaggctcc ttggcgcctg tgtctgtgtg    720

ggctgagagg ccatggacgg agtggggggg aagaaacaga aatcagaccc gaaatggaat    780

cagtgccata tgatgaacag aatttcaaga atgctgtttt atgcctttta acctccaaag    840

cagtaactgc aagcctacta ctcttgagag cgcgctcaga gccattgtcc cccgagatag    900

cctctgggga ggcttcggga gggaaagggg aaactggaaa gattagattg gtgtccatgg    960

ctgtttgctg ttggattaca ggcaggttcc accagacagg atgggacggg gttgcttagg   1020

gatgtcagat aacttgaccc agggctatgg atccactgtg aaggatggct tcccagagtc   1080

ttctggctgc ctgggggtgt tacctcccct gtttctaagt gcctcctgag tccccagccc   1140

ctggcttatc agtcagatga gtctccttgg tagcctctgc cccatcgctt cagcagtagc   1200

gactagctct cctcggtatc cagactggct gaggggcagt ctgccgcaga aatttgtctc   1260

tgagtggctg tgtctttgtg gttagctctc gttctttggt agttttcatt aaagccaata   1320

cttggttgca ggtgcttggt tttgtttttt aacggtattt gtctgtatcc tctctctgca   1380

tgtaagattg agcctcccca taaattctaa cttgccactc ctgcgtgtgt gttcagtctg   1440

tggttgccta cttcttccag atggcagcct cctaggtcca tagcaggcag ccacccagtt   1500

ccgaagctct agagaagatg tgactcacag gactcacggg caccgcctct ttcctcgttt   1560

ttatttatac cagctagact ttatccatag aaagtggcct tgttctgcat tgctgtcagt   1620
```

```
gtgcctgaag cagcaaccac cacctagcac cacttgagga ggcgtggtga cggggacact   1680

acgcgccctc atggggaagc ctagaaagga gagggaggaa gaggctgtgg ctctatggag   1740

gcaggaggga tgtgagttcc aggccagtcc gagtggcagc atagtgagat ccatttaaat   1800

aaagaagtag gcccaagccg acaaggggca gaagggtcgt gagttccaca ccagcctgga   1860

cttaaccact ctgccgtccc acccttccct gactcaattt cagttctaga aggcaacaga   1920

ggcatgaaga ctgctgcaag ttggagacca accccgtcta caaaatgagc tcaaggccag   1980

cctgagctaa aggagaccta gtctcagatg ggagagagaa acatcatagc agataacagt   2040

tccctttact atatctcaag atgactgaca ggtatggtca tggatcatag tttttggtag   2100

ggaatgcaca cgctgttttt gagatgaggt ctgacgtatc tcaggctggc tttgaactag   2160

ccatgtatcg gagaaccttg actttctgag cctcctgctt ctacctcaag tgctgagatt   2220

gccagtgtag gcccccattc ataaaatccg aatagcatag gactggaggc ttgcgggttt   2280

tttttacct gtgagtttcc caggcaaacc accagggggc agcaatgggt caataatgaa   2340

gttcttaccg gtgacctgtt cacccactgt acagaggtct tttgtgtatc ctttcaccct   2400

gagcccaccc tatcttccca tatgagtcag aatcatgtga actccaaaag tagttacctg   2460

ctgaggtcgt tgcttccagc tgcccgtggt taaattttgg ctcctccagt tattcagctg   2520

tgaatgtgag ctgtaagtga ttccatctct ccgtgcttca atttggattt tcctaatcca   2580

ttgaccaggg acaatggtag cgccatgtga agtgaaatga ggcatgtaaa acacgagtca   2640

gggcgtgcgg tatacacgct gtcggtgtga gccattgtgc taggctgctc tttttgtcta   2700

gaaataggaa aatccggagg ctcaatctca tgtgtaatgt gtctcagaaa aacatagcta   2760

tcgtctgtgt gggagcttgc tgaggggcca ggagaaactc acttctgtgt ttgctgactc   2820

ccttttccca acagattctt cttgcctttt tagctctgca actaacagct ctcaaacccg   2880

aaaaaatggg gggtgggagg aggaagctct gttagtgccc ttgtgtcctc atcagaacag   2940

gaggtgaccc aacagcttag gactgtttgc ttacgggcca ctgggaggct cagtggagcc   3000

tgcagttgtg agataggtag tctcccatgg gaggattagt ttgaaaggtc atccctacaa   3060

gaaagttcac agtcattaac acagaagcct tgaatcctaa gcatacaaag ggccccgtgt   3120

tttctactgc ctgtctctgt gcaaaccttg agtcttagac ccactcttcc cttacaggaa   3180

tctgaggcag gtaaatctca agatccccaa tgctatggtc tgatcttcat actaataaaa   3240

atcaaggggt ggaatcattt caaaaaaaaa aaaaaaaa                          3278
```

<210> SEQ ID NO 21
<211> LENGTH: 1278
<212> TYPE: PRT
<213> ORGANISM: Homo sapiens

<400> SEQUENCE: 21

```
Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80
```

-continued

```
Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495
```

-continued

```
His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640

His Met Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
            660                 665                 670

Gly Val Phe Ser Tyr Ile Gly Leu Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
            740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
    850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
```

-continued

```
        915                 920                 925

Leu Asp Asn Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990

Gly Asp Phe Met Arg Phe Leu Pro  Met Phe Leu Ser Asp  Asn Pro Asn
        995                 1000                 1005

Pro Lys  Cys Gly Lys Gly Gly  His Ala Ala Tyr Ser  Ser Ala Val
    1010                 1015                 1020

Asn Ile  Leu Leu Gly His Gly  Thr Arg Val Gly Ala  Thr Tyr Phe
    1025                 1030                 1035

Met Thr  Tyr His Thr Val Leu  Gln Thr Ser Ala Asp  Phe Ile Asp
    1040                 1045                 1050

Ala Leu  Lys Lys Ala Arg Leu  Ile Ala Ser Asn Val  Thr Glu Thr
    1055                 1060                 1065

Met Gly  Ile Asn Gly Ser Ala  Tyr Arg Val Phe Pro  Tyr Ser Val
    1070                 1075                 1080

Phe Tyr  Val Phe Tyr Glu Gln  Tyr Leu Thr Ile Ile  Asp Asp Thr
    1085                 1090                 1095

Ile Phe  Asn Leu Gly Val Ser  Leu Gly Ala Ile Phe  Leu Val Thr
    1100                 1105                 1110

Met Val  Leu Leu Gly Cys Glu  Leu Trp Ser Ala Val  Ile Met Cys
    1115                 1120                 1125

Ala Thr  Ile Ala Met Val Leu  Val Asn Met Phe Gly  Val Met Trp
    1130                 1135                 1140

Leu Trp  Gly Ile Ser Leu Asn  Ala Val Ser Leu Val  Asn Leu Val
    1145                 1150                 1155

Met Ser  Cys Gly Ile Ser Val  Glu Phe Cys Ser His  Ile Thr Arg
    1160                 1165                 1170

Ala Phe  Thr Val Ser Met Lys  Gly Ser Arg Val Glu  Arg Ala Glu
    1175                 1180                 1185

Glu Ala  Leu Ala His Met Gly  Ser Ser Val Phe Ser  Gly Ile Thr
    1190                 1195                 1200

Leu Thr  Lys Phe Gly Gly Ile  Val Val Leu Ala Phe  Ala Lys Ser
    1205                 1210                 1215

Gln Ile  Phe Gln Ile Phe Tyr  Phe Arg Met Tyr Leu  Ala Met Val
    1220                 1225                 1230

Leu Leu  Gly Ala Thr His Gly  Leu Ile Phe Leu Pro  Val Leu Leu
    1235                 1240                 1245

Ser Tyr  Ile Gly Pro Ser Val  Asn Lys Ala Lys Ser  Cys Ala Thr
    1250                 1255                 1260

Glu Glu  Arg Tyr Lys Gly Thr  Glu Arg Glu Arg Leu  Leu Asn Phe
    1265                 1270                 1275
```

<210> SEQ ID NO 22
<211> LENGTH: 1277
<212> TYPE: PRT
<213> ORGANISM: Mus musculus

<400> SEQUENCE: 22

-continued

```
Met Gly Ala His His Pro Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Thr Gly Asp Lys Arg Tyr Asn Cys Lys Tyr Ser Gly Pro Pro
        35                  40                  45

Lys Pro Leu Pro Lys Asp Gly Tyr Asp Leu Val Gln Glu Leu Cys Pro
    50                  55                  60

Gly Leu Phe Phe Asp Asn Val Ser Leu Cys Cys Asp Ile Gln Gln Leu
65                  70                  75                  80

Gln Thr Leu Lys Ser Asn Leu Gln Leu Pro Leu Gln Phe Leu Ser Arg
                85                  90                  95

Cys Pro Ser Cys Phe Tyr Asn Leu Met Thr Leu Phe Cys Glu Leu Thr
            100                 105                 110

Cys Ser Pro His Gln Ser Gln Phe Leu Asn Val Thr Ala Thr Glu Asp
        115                 120                 125

Tyr Phe Asp Pro Lys Thr Gln Glu Asn Lys Thr Asn Val Lys Glu Leu
    130                 135                 140

Glu Tyr Phe Val Gly Gln Ser Phe Ala Asn Ala Met Tyr Asn Ala Cys
145                 150                 155                 160

Arg Asp Val Glu Ala Pro Ser Ser Asn Glu Lys Ala Leu Gly Leu Leu
                165                 170                 175

Cys Gly Arg Asp Ala Arg Ala Cys Asn Ala Thr Asn Trp Ile Glu Tyr
            180                 185                 190

Met Phe Asn Lys Asp Asn Gly Gln Ala Pro Phe Thr Ile Ile Pro Val
        195                 200                 205

Phe Ser Asp Leu Ser Ile Leu Gly Met Glu Pro Met Arg Asn Ala Thr
    210                 215                 220

Lys Gly Cys Asn Glu Ser Val Asp Glu Val Thr Gly Pro Cys Ser Cys
225                 230                 235                 240

Gln Asp Cys Ser Ile Val Cys Gly Pro Lys Pro Gln Pro Pro Pro Pro
                245                 250                 255

Pro Met Pro Trp Arg Ile Trp Gly Leu Asp Ala Met Tyr Val Ile Met
            260                 265                 270

Trp Val Thr Tyr Val Ala Phe Leu Phe Val Phe Phe Gly Ala Leu Leu
        275                 280                 285

Ala Val Trp Cys His Arg Arg Arg Tyr Phe Val Ser Glu Tyr Thr Pro
    290                 295                 300

Ile Asp Ser Asn Ile Ala Phe Ser Val Asn Ser Ser Asp Lys Gly Glu
305                 310                 315                 320

Ala Ser Cys Cys Asp Pro Leu Gly Ala Ala Phe Asp Asp Cys Leu Arg
                325                 330                 335

Arg Met Phe Thr Lys Trp Gly Ala Phe Cys Val Arg Asn Pro Thr Cys
            340                 345                 350

Ile Ile Phe Phe Ser Leu Ala Phe Ile Thr Val Cys Ser Ser Gly Leu
        355                 360                 365

Val Phe Val Gln Val Thr Thr Asn Pro Val Glu Leu Trp Ser Ala Pro
    370                 375                 380

His Ser Gln Ala Arg Leu Glu Lys Glu Tyr Phe Asp Lys His Phe Gly
385                 390                 395                 400

Pro Phe Phe Arg Thr Glu Gln Leu Ile Ile Gln Ala Pro Asn Thr Ser
                405                 410                 415

Val His Ile Tyr Glu Pro Tyr Pro Ala Gly Ala Asp Val Pro Phe Gly
```

```
            420                 425                 430

Pro Pro Leu Asn Lys Glu Ile Leu His Gln Val Leu Asp Leu Gln Ile
        435                 440                 445

Ala Ile Glu Ser Ile Thr Ala Ser Tyr Asn Asn Glu Thr Val Thr Leu
    450                 455                 460

Gln Asp Ile Cys Val Ala Pro Leu Ser Pro Tyr Asn Lys Asn Cys Thr
465                 470                 475                 480

Ile Met Ser Val Leu Asn Tyr Phe Gln Asn Ser His Ala Val Leu Asp
                485                 490                 495

Ser Gln Val Gly Asp Asp Phe Tyr Ile Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Gly Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Arg
                565                 570                 575

Leu Gln Arg Ala Trp Ala Trp Glu Lys Glu Phe Ile Ser Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asn Ser Asp Val Phe Thr Val
    610                 615                 620

Ile Ile Ser Tyr Val Val Met Phe Leu Tyr Ile Ser Leu Ala Leu Gly
625                 630                 635                 640

His Ile Gln Ser Cys Ser Arg Leu Leu Val Asp Ser Lys Ile Ser Leu
                645                 650                 655

Gly Ile Ala Gly Ile Leu Ile Val Leu Ser Ser Val Ala Cys Ser Leu
            660                 665                 670

Gly Ile Phe Ser Tyr Met Gly Met Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Thr Tyr Gln Arg Asp Glu Arg Leu Gln Glu Glu Thr Leu
705                 710                 715                 720

Asp Gln Gln Leu Gly Arg Ile Leu Gly Glu Val Ala Pro Thr Met Phe
                725                 730                 735

Leu Ser Ser Phe Ser Glu Thr Ser Ala Phe Phe Phe Gly Ala Leu Ser
            740                 745                 750

Ser Met Pro Ala Val His Thr Phe Ser Leu Phe Ala Gly Met Ala Val
        755                 760                 765

Leu Ile Asp Phe Leu Leu Gln Ile Thr Cys Phe Val Ser Leu Leu Gly
    770                 775                 780

Leu Asp Ile Lys Arg Gln Glu Lys Asn His Leu Asp Ile Leu Cys Cys
785                 790                 795                 800

Val Arg Gly Ala Asp Asp Gly Gln Gly Ser His Ala Ser Glu Ser Tyr
                805                 810                 815

Leu Phe Arg Phe Phe Lys Asn Tyr Phe Ala Pro Leu Leu Leu Lys Asp
            820                 825                 830

Trp Leu Arg Pro Ile Val Val Ala Val Phe Val Gly Val Leu Ser Phe
        835                 840                 845
```

Ser Val Ala Val Val Asn Lys Val Asp Ile Gly Leu Asp Gln Ser Leu
    850                 855                 860

Ser Met Pro Asn Asp Ser Tyr Val Ile Asp Tyr Phe Lys Ser Leu Ala
865                 870                 875                 880

Gln Tyr Leu His Ser Gly Pro Pro Val Tyr Phe Val Leu Glu Glu Gly
                885                 890                 895

Tyr Asn Tyr Ser Ser Arg Lys Gly Gln Asn Met Val Cys Gly Gly Met
            900                 905                 910

Gly Cys Asp Asn Asp Ser Leu Val Gln Gln Ile Phe Asn Ala Ala Glu
        915                 920                 925

Leu Asp Thr Tyr Thr Arg Val Gly Phe Ala Pro Ser Ser Trp Ile Asp
    930                 935                 940

Asp Tyr Phe Asp Trp Val Ser Pro Gln Ser Ser Cys Cys Arg Leu Tyr
945                 950                 955                 960

Asn Val Thr His Gln Phe Cys Asn Ala Ser Val Met Asp Pro Thr Cys
                965                 970                 975

Val Arg Cys Arg Pro Leu Thr Pro Glu Gly Lys Gln Arg Pro Gln Gly
            980                 985                 990

Lys Glu Phe Met Lys Phe Leu Pro  Met Phe Leu Ser Asp  Asn Pro Asn
        995                 1000                1005

Pro Lys  Cys Gly Lys Gly Gly  His Ala Ala Tyr Gly  Ser Ala Val
    1010                1015                1020

Asn Ile  Val Gly Asp Asp Thr  Tyr Ile Gly Ala Thr  Tyr Phe Met
    1025                1030                1035

Thr Tyr  His Thr Ile Leu Lys  Thr Ser Ala Asp Tyr  Thr Asp Ala
    1040                1045                1050

Met Lys  Lys Ala Arg Leu Ile  Ala Ser Asn Ile Thr  Glu Thr Met
    1055                1060                1065

Arg Ser  Lys Gly Ser Asp Tyr  Arg Val Phe Pro Tyr  Ser Val Phe
    1070                1075                1080

Tyr Val  Phe Tyr Glu Gln Tyr  Leu Thr Ile Ile Asp  Asp Thr Ile
    1085                1090                1095

Phe Asn  Leu Ser Val Ser Leu  Gly Ser Ile Phe Leu  Val Thr Leu
    1100                1105                1110

Val Val  Leu Gly Cys Glu Leu  Trp Ser Ala Val Ile  Met Cys Ile
    1115                1120                1125

Thr Ile  Ala Met Ile Leu Val  Asn Met Phe Gly Val  Met Trp Leu
    1130                1135                1140

Trp Gly  Ile Ser Leu Asn Ala  Val Ser Leu Val Asn  Leu Val Met
    1145                1150                1155

Ser Cys  Gly Ile Ser Val Glu  Phe Cys Ser His Ile  Thr Arg Ala
    1160                1165                1170

Phe Thr  Met Ser Thr Lys Gly  Ser Arg Val Ser Arg  Ala Glu Glu
    1175                1180                1185

Ala Leu  Ala His Met Gly Ser  Ser Val Phe Ser Gly  Ile Thr Leu
    1190                1195                1200

Thr Lys  Phe Gly Gly Ile Val  Val Leu Ala Phe Ala  Lys Ser Gln
    1205                1210                1215

Ile Phe  Glu Ile Phe Tyr Phe  Arg Met Tyr Leu Ala  Met Val Leu
    1220                1225                1230

Leu Gly  Ala Thr His Gly Leu  Ile Phe Leu Pro Val  Leu Leu Ser
    1235                1240                1245

```
Tyr Ile  Gly Pro Ser Val Asn  Lys Ala Lys Arg His  Thr Thr Tyr
    1250                1255                1260

Glu Arg  Tyr Arg Gly Thr Glu  Arg Glu Arg Leu Leu  Asn Phe
    1265                1270                1275


<210> SEQ ID NO 23
<211> LENGTH: 151
<212> TYPE: PRT
<213> ORGANISM: Homo sapiens

<400> SEQUENCE: 23

Met Arg Phe Leu Ala Ala Thr Phe Leu Leu Leu Ala Leu Ser Thr Ala
1               5                   10                  15

Ala Gln Ala Glu Pro Val Gln Phe Lys Asp Cys Gly Ser Val Asp Gly
            20                  25                  30

Val Ile Lys Glu Val Asn Val Ser Pro Cys Pro Thr Gln Pro Cys Gln
        35                  40                  45

Leu Ser Lys Gly Gln Ser Tyr Ser Val Asn Val Thr Phe Thr Ser Asn
    50                  55                  60

Ile Gln Ser Lys Ser Ser Lys Ala Val Val His Gly Ile Leu Met Gly
65                  70                  75                  80

Val Pro Val Pro Phe Pro Ile Pro Glu Pro Asp Gly Cys Lys Ser Gly
                85                  90                  95

Ile Asn Cys Pro Ile Gln Lys Asp Lys Thr Tyr Ser Tyr Leu Asn Lys
            100                 105                 110

Leu Pro Val Lys Ser Glu Tyr Pro Ser Ile Lys Leu Val Val Glu Trp
        115                 120                 125

Gln Leu Gln Asp Asp Lys Asn Gln Ser Leu Phe Cys Trp Glu Ile Pro
    130                 135                 140

Val Gln Ile Val Ser His Leu
145                 150


<210> SEQ ID NO 24
<211> LENGTH: 149
<212> TYPE: PRT
<213> ORGANISM: Mus musculus

<400> SEQUENCE: 24

Met Arg Phe Leu Ala Ala Thr Ile Leu Leu Leu Ala Leu Val Ala Ala
1               5                   10                  15

Ser Gln Ala Glu Pro Leu His Phe Lys Asp Cys Gly Ser Lys Val Gly
            20                  25                  30

Val Ile Lys Glu Val Asn Val Ser Pro Cys Pro Thr Asp Pro Cys Gln
        35                  40                  45

Leu His Lys Gly Gln Ser Tyr Ser Val Asn Ile Thr Phe Thr Ser Gly
    50                  55                  60

Thr Gln Ser Gln Asn Ser Thr Ala Leu Val His Gly Ile Leu Glu Gly
65                  70                  75                  80

Ile Arg Val Pro Phe Pro Ile Pro Glu Pro Asp Gly Cys Lys Ser Gly
                85                  90                  95

Ile Asn Cys Pro Ile Gln Lys Asp Lys Val Tyr Ser Tyr Leu Asn Lys
            100                 105                 110

Leu Pro Val Lys Asn Glu Tyr Pro Ser Ile Lys Leu Val Val Glu Trp
        115                 120                 125

Lys Leu Glu Asp Asp Lys Lys Asn Asn Leu Phe Cys Trp Glu Ile Pro
    130                 135                 140
```

Val Gln Ile Thr Ser
145

<210> SEQ ID NO 25
<211> LENGTH: 183
<212> TYPE: DNA
<213> ORGANISM: Artificial Sequence
<220> FEATURE:
<223> OTHER INFORMATION: Synthetic

<400> SEQUENCE: 25
ttgtcgatcc taccatccac tcgacacacc cgccagcggc cgcgttggta tcaaggttac 60
aagacaggtt taaggagacc aatagaaact gggcatgtgg agacagagaa gactcttggg 120
tttctgatag gcactgactc tcttcctttg tcctgttccc atttcagaag cttccgagct 180
ctc 183

<210> SEQ ID NO 26
<211> LENGTH: 4276
<212> TYPE: DNA
<213> ORGANISM: Artificial Sequence
<220> FEATURE:
<223> OTHER INFORMATION: Synthetic

<400> SEQUENCE: 26
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440

-continued

```
aatacttcga ccagcatttc ggaccctttt tccggaccga acagctgatt atccgcgccc   1500
cgctgactga caagcatatc taccagcctt acccgagcgg agcggatgtg ccctttggtc   1560
cgccactcga catccagatc ctgcaccaag tcctggactt gcaaatcgct attgagaaca   1620
ttactgcctc ctacgacaac gagacagtga ccctgcagga catttgtctt gccccgctgt   1680
ccccctacaa caccaactgc acgatcctga gcgtgctgaa ctatttccaa aactcgcact   1740
ccgtgctgga tcacaagaag ggcgacgatt tcttcgtcta cgccgattac cacacccact   1800
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg ggcacatgaa agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg ggatcaacg    3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
```

acatgggatc ctcggtgttc tcgggcatca cccttactaa gttcggcggt atcgtggtgc 3900
tggccttcgc caagtcacag atcttccaga ttttctactt ccggatgtac ctggcgatgg 3960
tgcttctggg agcaacccac ggcctgatct tcctgcccgt gctcttgtcc tacatcggcc 4020
ccagcgtgaa caaggccaag tcctgcgcca ctgaggaacg ctacaagggc accgaaagag 4080
aaaggctgct gaatttctga tagatgatag aagcttctcg aggacggggt gaactacgcc 4140
tgaggatccg atctttttcc ctctgccaaa aattatgggg acatcatgaa gccccttgag 4200
catctgactt ctggctaata aaggaaattt attttcattg caatagtgtg ttggaatttt 4260
ttgtgtctct cactcg 4276

<210> SEQ ID NO 27
<211> LENGTH: 4305
<212> TYPE: DNA
<213> ORGANISM: Artificial Sequence
<220> FEATURE:
<223> OTHER INFORMATION: Synthetic

<400> SEQUENCE: 27
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560

-continued

```
cgccactcga catccagatc ctgcaccaag tcctggactt gcaaatcgct attgagaaca   1620
ttactgcctc ctacgacaac gagacagtga ccctgcagga catttgtctt gccccgctgt   1680
cccccctacaa caccaactgc acgatcctga gcgtgctgaa ctatttccaa aactcgcact   1740
ccgtgctgga tcacaagaag ggcgacgatt tcttcgtcta cgccgattac cacacccact   1800
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg ggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg ggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
```

tcctgcttgg agccacacac ggtctgatct tcctgcctgt gcttctgtcc tacatcggcc 4020
cgtccgtgaa caaagcgaag tcctgtgcta ctgaggagcg gtacaaggga actgagcgcg 4080
agcgcctgct caactttggg ggcggccgca agaagcgccg gcagcgcaga aggtgataga 4140
agcttctcga ggacggggtg aactacgcct gaggatccga tctttttccc tctgccaaaa 4200
attatgggga catcatgaag ccccttgagc atctgacttc tggctaataa aggaaattta 4260
ttttcattgc aatagtgtgt tggaattttt tgtgtctctc actcg 4305

<210> SEQ ID NO 28
<211> LENGTH: 4354
<212> TYPE: DNA
<213> ORGANISM: Artificial Sequence
<220> FEATURE:
<223> OTHER INFORMATION: Synthetic

<400> SEQUENCE: 28
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680

-continued

```
cccccctacaa caccaactgc acgatcctga gcgtgctgaa ctatttccaa aactcgcact   1740
ccgtgctgga tcacaagaag ggcgacgatt tcttcgtcta cgccgattac cacacccact   1800
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg ggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga catttttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg ggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gctgctgagc tacatcggtc   4020
ccagcgtgaa caaggctaag tcctgcgcga cggaggaaag gtacaaggga accgagaggg   4080
```

agcgccttct caacttcgga ggagattata aagacgatga tgacaagggg gactacaagg 4140
acgacgatga caagggcgat tacaaagacg acgacgacaa gttgatagaa gcttctcgag 4200
gacggggtga actacgcctg aggatccgat ctttttccct ctgccaaaaa ttatggggac 4260
atcatgaagc cccttgagca tctgacttct ggctaataaa ggaaatttat tttcattgca 4320
atagtgtgtt ggaatttttt gtgtctctca ctcg 4354

<210> SEQ ID NO 29
<211> LENGTH: 4339
<212> TYPE: DNA
<213> ORGANISM: Artificial Sequence
<220> FEATURE:
<223> OTHER INFORMATION: Synthetic

<400> SEQUENCE: 29
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680 cccccctacaa caccaactgc acgatcctga gcgtgctgaa ctatttccaa aactcgcact 1740

-continued

```
ccgtgctgga tcacaagaag ggcgacgatt tcttcgtcta cgccgattac cacacccact   1800
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atccctttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg ggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gctgctgagc tacatcggtc   4020
ccagcgtgaa caaggctaag tcctgcgcga cggaggaaag gtacaagggg actgaacgcg   4080
aacggctgct gaactttggc ggcgctgggt acctgctcgg aaagatcaac ctcaaagcgc   4140
```

tggcggccct ggccaagaag atcctgttga tagaagcttc tcgaggacgg ggtgaactac 4200
gcctgaggat ccgatctttt tccctctgcc aaaaattatg gggacatcat gaagcccctt 4260
gagcatctga cttctggcta ataaaggaaa tttattttca ttgcaatagt gtgttggaat 4320
tttttgtgtc tctcactcg 4339

<210> SEQ ID NO 30
<211> LENGTH: 4312
<212> TYPE: DNA
<213> ORGANISM: Artificial Sequence
<220> FEATURE:
<223> OTHER INFORMATION: Synthetic

<400> SEQUENCE: 30
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800

-continued

```
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atccctttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg ggatcaacg    3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca ccccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gctgctgagc tacatcggtc   4020
ccagcgtgaa caaggctaag tcctgcgcga cggaggaaag gtacaagggt actgaaagag   4080
agcggctgct caacttcggt ggccccctga tctacctgcg cctcctgcgg ggtcagttct   4140
tgatagaagc ttctcgagga cggggtgaac tacgcctgag gatccgatct ttttccctct   4200
```

gccaaaaatt atggggacat catgaagccc cttgagcatc tgacttctgg ctaataaagg 4260
aaatttattt tcattgcaat agtgtgttgg aattttttgt gtctctcact cg 4312

<210> SEQ ID NO 31
<211> LENGTH: 4387
<212> TYPE: DNA
<213> ORGANISM: Artificial Sequence
<220> FEATURE:
<223> OTHER INFORMATION: Synthetic

<400> SEQUENCE: 31
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920

-continued

```
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga catttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg gggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gctgctgagc tacatcggtc   4020
ccagcgtgaa caaggctaag tcctgcgcga cggaggaaag gtacaaggga accgagaggg   4080
agcgccttct caacttcgga ggagattata aagacgatga tgacaagggg gactacaagg   4140
acgacgatga caagggcgat tacaaagacg acgacgacaa gggcggccgg aagaagcgcc   4200
gccagcggcg gagattgata gaagcttctc gaggacgggg tgaactacgc ctgaggatcc   4260
gatctttttc cctctgccaa aaattatggg gacatcatga agccccttga gcatctgact   4320
```

-continued tctggctaat aaaggaaatt tattttcatt gcaatagtgt gttggaattt tttgtgtctc 4380
tcactcg 4387

<210> SEQ ID NO 32
<211> LENGTH: 4423
<212> TYPE: DNA
<213> ORGANISM: Artificial Sequence
<220> FEATURE:
<223> OTHER INFORMATION: Synthetic

<400> SEQUENCE: 32
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920

-continued

```
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga catttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg gggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gctgctgagc tacatcggtc   4020
ccagcgtgaa caaggctaag tcctgcgcga cggaggaaag gtacaaggga accgagaggg   4080
agcgccttct caacttcgga ggagattata aagacgatga tgacaagggg gactacaagg   4140
acgacgatga caagggcgat tacaaagacg acgacgacaa gggcggcgcc ggctacctcc   4200
tggggaagat taacctgaag gccctggcag ccctcgccaa gaagatcctg ttgatagaag   4260
cttctcgagg acggggtgaa ctacgcctga ggatccgatc tttttccctc tgccaaaaat   4320
```

tatggggaca tcatgaagcc ccttgagcat ctgacttctg gctaataaag gaaatttatt 4380
ttcattgcaa tagtgtgttg gaattttttg tgtctctcac tcg 4423

<210> SEQ ID NO 33
<211> LENGTH: 4396
<212> TYPE: DNA
<213> ORGANISM: Artificial Sequence
<220> FEATURE:
<223> OTHER INFORMATION: Synthetic

<400> SEQUENCE: 33
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920
agaactacaa caacgccacc gccctcgtga tcacctttcc tgtgaacaac tactacaacg 1980
acaccgaaaa gttgcagaga gcacaagcgt gggagaagga gttcatcaac ttcgtgaaga 2040
actacaaaaa ccctaacctg accatctcct ttacggccga gcgctcaatc gaggacgaat 2100
tgaacaggga atcggactcc gacgtgttca ctgtcgtcat tagctacgcc atcatgttct 2160
tgtacattag cctggcgctg ggcacatga agtcctgccg ccggctgctg gtcgattcga 2220
aggtgtccct gggaatcgcc ggcatcctga tcgtcctgtc gtccgtggcc tgttccctgg 2280
gagtgttcag ctacattgga ctgccactga ccctcattgt gattgaagtg atcccttttc 2340
ttgtcttggc cgtgggagtg gataatattt ttatcctggt gcaagcctac cagcgggacg 2400
agaggctgca gggggagact ctggaccagc agctgggccg cgtgctgggc gaagtcgccc 2460
cgtccatgtt tctgtcctca ttctccgaaa ccgtggcctt cttcctgggc gcgctcagcg 2520
tgatgcctgc cgtgcacacc ttctccctgt ttgccggtct ggctgtgttt atcgatttcc 2580
ttctccaaat tacttgcttc gtgtcactgc ttggactcga catcaagcgc caggaaaaga 2640
accggctgga catttctgc tgcgtgagag gagcggagga cggaacctca gtgcaggctt 2700
ccgagtcatg cctgtttcga ttcttcaaga actcgtattc gccgctgctc ctgaaggatt 2760
ggatgcggcc cattgtgatc gccatctttg tcggcgtcct gagcttcagc attgcggtgt 2820
tgaacaaagt ggacattggc ctggaccaga gcctctccat gccggatgat tcctacatgg 2880
tggactactt caagagcatc tctcagtact tgcacgctgg ccctcccgtg tatttcgtgc 2940
tggaggaagg gcacgactac actagctcta agggacagaa catggtctgc ggtggcatgg 3000
gatgcaacaa tgactcgctg gtgcagcaga ttttcaacgc cgcgcaactc gataactaca 3060
ccaggattgg attcgctccc tcctcctgga tcgacgatta ttttgactgg gtcaagccgc 3120
agtctagctg ctgccgggtg gacaacatca cggatcagtt ctgcaatgct tccgtggtcg 3180
acccggcctg cgtgcggtgc cggcctctta ctccggaggg aaagcagagg ccccagggtg 3240
gcgacttcat gcggtttctg cccatgttcc tgagcgataa ccccaacccc aaatgcggga 3300
agggaggtca cgcggcgtac tcgtcagcgg tcaacatcct gctgggccat ggaactagag 3360
tgggagcgac ctacttcatg acttaccata ctgtgctgca gacctcagcc gacttcatcg 3420
acgcactcaa gaaagcccgc ctgatcgcat caaacgtgac cgagactatg gggatcaacg 3480
gatccgcgta ccgcgtgttc ccatattcgg tgttctacgt gttctacgag caatacctga 3540
ccattattga cgacaccatc tttaacctgg gggtgtcact gggagccatc ttccttgtga 3600
ccatggtcct cctgggctgc gaactgtggt ccgccgtgat catgtgcgct accatcgcaa 3660
tggtcctcgt gaacatgttt ggggtcatgt ggctgtgggg catctccctg aacgcggtgt 3720
ccctcgtgaa cctggtcatg tcatgcggca ttagcgtgga gttctgctcc cacattactc 3780
gcgccttcac cgtgtcgatg aagggttccc gcgtggagcg ggcggaggaa gccctggccc 3840
acatgggatc ctcggtgttc tcgggcatca cccttactaa gttcggcggt atcgtggtgc 3900
tggccttcgc caagtcacag atcttccaaa ttttctactt cagaatgtac ttggcgatgg 3960
tcctgcttgg agccacacac ggtctgatct tcctgcctgt gctgctgagc tacatcggtc 4020
ccagcgtgaa caaggctaag tcctgcgcga cggaggaaag gtacaaggga accgagaggg 4080
agcgccttct caacttcgga ggagattata aagacgatga tgacaagggg gactacaagg 4140
acgacgatga caagggcgat tacaaagacg acgacgacaa gggggggcccg ctcatctacc 4200
tccggctgct gcggggccag tttttgatag aagcttctcg aggacggggt gaactacgcc 4260
tgaggatccg atctttttcc ctctgccaaa aattatgggg acatcatgaa gccccttgag 4320
catctgactt ctggctaata aaggaaattt attttcattg caatagtgtg ttggaatttt 4380
ttgtgtctct cactcg 4396

<210> SEQ ID NO 34
<211> LENGTH: 4276
<212> TYPE: DNA
<213> ORGANISM: Artificial Sequence
<220> FEATURE:
<223> OTHER INFORMATION: Synthetic

<400> SEQUENCE: 34
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggccccct tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920

-continued

```
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga catttttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg gggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaga ttttctactt ccggatgtac ctggcgatgg   3960
tgcttctggg agcaacccac ggcctgatct tcctgcccgt gctcttgtcc tacatcggcc   4020
ccagcgtgaa caaggccaag tcctgcgcca ctgaggaacg ctacaagggc accgaaagag   4080
aaaggctgct gaatttctga tagatgatag aagcttctcg aggacggggt gaactacgcc   4140
tgaggatccg atctttttcc ctctgccaaa aattatgggg acatcatgaa gccccttgag   4200
catctgactt ctggctaata aaggaaattt attttcattg caatagtgtg ttggaatttt   4260
ttgtgtctct cactcg                                                   4276
```

<210> SEQ ID NO 35
<211> LENGTH: 4305
<212> TYPE: DNA
<213> ORGANISM: Artificial Sequence
<220> FEATURE:
<223> OTHER INFORMATION: Synthetic

<400> SEQUENCE: 35
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680 cccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920
agaactacaa caacgccacc gccctcgtga tcacctttcc tgtgaacaac tactacaacg 1980
acaccgaaaa gttgcagaga gcacaagcgt gggagaagga gttcatcaac ttcgtgaaga 2040

-continued

```
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg gggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gcttctgtcc tacatcggcc   4020
cgtccgtgaa caaagcgaag tcctgtgcta ctgaggagcg gtacaaggga actgagcgcg   4080
agcgcctgct caactttggg ggcggccgca agaagcgccg gcagcgcaga aggtgataga   4140
agcttctcga ggacggggtg aactacgcct gaggatccga tctttttccc tctgccaaaa   4200
attatgggga catcatgaag ccccttgagc atctgacttc tggctaataa aggaaattta   4260
ttttcattgc aatagtgtgt tggaattttt tgtgtctctc actcg                   4305
```

<210> SEQ ID NO 36
<211> LENGTH: 4354

<212> TYPE: DNA
<213> ORGANISM: Artificial Sequence
<220> FEATURE:
<223> OTHER INFORMATION: Synthetic

<400> SEQUENCE: 36
aagagctccg gtgcccgtca gtgggcagag cgcacatcgc ccacagtccc cgagaagttg 60
gggggagggg tcggcaattg aaccggtgcc tagagaaggt ggcgcggggt aaactgggaa 120
agtgatgtcg tgtactggct ccgccttttt cccgagggtg ggggagaacc gtatataagt 180
gcagtagtcg ccgtgaacgt tctttttcgc aacgggtttg ccgccagaac acgcgtaagg 240
gcgaattcga tatcgccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680 cccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920
agaactacaa caacgccacc gccctcgtga tcacctttcc tgtgaacaac tactacaacg 1980
acaccgaaaa gttgcagaga gcacaagcgt gggagaagga gttcatcaac ttcgtgaaga 2040
actacaaaaa ccctaacctg accatctcct ttacggccga gcgctcaatc gaggacgaat 2100
tgaacaggga atcggactcc gacgtgttca ctgtcgtcat tagctacgcc atcatgttct 2160

-continued

```
tgtacattag cctggcgctg gggcacatga agtcctgccg ccggctgctg gtcgattcga   2220

aggtgtccct gggaatcgcc ggcatcctga tcgtcctgtc gtccgtggcc tgttccctgg   2280

gagtgttcag ctacattgga ctgccactga ccctcattgt gattgaagtg atcccttttc   2340

ttgtcttggc cgtgggagtg gataatattt ttatcctggt gcaagcctac cagcgggacg   2400

agaggctgca gggggagact ctggaccagc agctgggccg cgtgctgggc gaagtcgccc   2460

cgtccatgtt tctgtcctca ttctccgaaa ccgtggcctt cttcctgggc gcgctcagcg   2520

tgatgcctgc cgtgcacacc ttctccctgt ttgccggtct ggctgtgttt atcgatttcc   2580

ttctccaaat tacttgcttc gtgtcactgc ttggactcga catcaagcgc caggaaaaga   2640

accggctgga cattttctgc tgcgtgagag gagcggagga cggaacctca gtgcaggctt   2700

ccgagtcatg cctgtttcga ttcttcaaga actcgtattc gccgctgctc ctgaaggatt   2760

ggatgcggcc cattgtgatc gccatctttg tcggcgtcct gagcttcagc attgcggtgt   2820

tgaacaaagt ggacattggc ctggaccaga gcctctccat gccggatgat tcctacatgg   2880

tggactactt caagagcatc tctcagtact tgcacgctgg ccctcccgtg tatttcgtgc   2940

tggaggaagg gcacgactac actagctcta agggacagaa catggtctgc ggtggcatgg   3000

gatgcaacaa tgactcgctg gtgcagcaga ttttcaacgc cgcgcaactc gataactaca   3060

ccaggattgg attcgctccc tcctcctgga tcgacgatta ttttgactgg gtcaagccgc   3120

agtctagctg ctgccgggtg gacaacatca cggatcagtt ctgcaatgct tccgtggtcg   3180

acccggcctg cgtgcggtgc cggcctctta ctccggaggg aaagcagagg ccccagggtg   3240

gcgacttcat gcggtttctg cccatgttcc tgagcgataa ccccaacccc aaatgcggga   3300

agggaggtca cgcggcgtac tcgtcagcgg tcaacatcct gctgggccat ggaactagag   3360

tgggagcgac ctacttcatg acttaccata ctgtgctgca gacctcagcc gacttcatcg   3420

acgcactcaa gaaagcccgc ctgatcgcat caaacgtgac cgagactatg ggatcaacg   3480

gatccgcgta ccgcgtgttc ccatattcgg tgttctacgt gttctacgag caatacctga   3540

ccattattga cgacaccatc tttaacctgg gggtgtcact gggagccatc ttccttgtga   3600

ccatggtcct cctgggctgc gaactgtggt ccgccgtgat catgtgcgct accatcgcaa   3660

tggtcctcgt gaacatgttt ggggtcatgt ggctgtgggg catctccctg aacgcggtgt   3720

ccctcgtgaa cctggtcatg tcatgcggca ttagcgtgga gttctgctcc cacattactc   3780

gcgccttcac cgtgtcgatg aagggttccc gcgtggagcg ggcggaggaa gccctggccc   3840

acatgggatc ctcggtgttc tcgggcatca cccttactaa gttcggcggt atcgtggtgc   3900

tggccttcgc caagtcacag atcttccaaa ttttctactt cagaatgtac ttggcgatgg   3960

tcctgcttgg agccacacac ggtctgatct tcctgcctgt gctgctgagc tacatcggtc   4020

ccagcgtgaa caaggctaag tcctgcgcga cggaggaaag gtacaaggga accgagaggg   4080

agcgccttct caacttcgga ggagattata aagacgatga tgacaagggg gactacaagg   4140

acgacgatga caagggcgat tacaaagacg acgacgacaa gttgatagaa gcttctcgag   4200

gacggggtga actacgcctg aggatccgat ctttttccct ctgccaaaaa ttatggggac   4260

atcatgaagc cccttgagca tctgacttct ggctaataaa ggaaatttat tttcattgca   4320

atagtgtgtt ggaatttttt gtgtctctca ctcg                               4354
```

<210> SEQ ID NO 37
<211> LENGTH: 4387
<212> TYPE: DNA
<213> ORGANISM: Artificial Sequence
<220> FEATURE:
<223> OTHER INFORMATION: Synthetic

<400> SEQUENCE: 37

```
aagagctccg gtgcccgtca gtgggcagag cgcacatcgc ccacagtccc cgagaagttg     60
gggggagggg tcggcaattg aaccggtgcc tagagaaggt ggcgcggggt aaactgggaa    120
agtgatgtcg tgtactggct ccgccttttt cccgagggtg ggggagaacc gtatataagt    180
gcagtagtcg ccgtgaacgt tctttttcgc aacgggtttg ccgccagaac acgcgtaagg    240
gcgaattcga tatcgccgcc accatgaccg cgaggggact ggccctcggg ctgctcctgc    300
tgctcctttg cccggcccaa gtgttctcgc aatcgtgcgt gtggtacggg gaatgcggaa    360
ttgcctacgg cgacaagcgg tacaactgcg aatactccgg gcctccaaag ccgctgccca    420
aggacggata cgacctggtc caagagctct gccctggatt cttcttcggc aacgtgtcgc    480
tgtgttgtga cgtgcggcag ctgcagaccc tgaaggataa cctccagctg ccgctgcaat    540
tcctctcccg gtgtccgtca tgcttctaca acttgctcaa cctgttctgc gaacttacct    600
gttcgccgag acagtcccag tttcttaacg tcaccgcaac cgaggactac gtggaccctg    660
tgactaacca gaccaagact aatgtcaaag aattgcagta ctacgtgggc cagtccttcg    720
ccaatgcgat gtacaacgcc tgtcgggacg tcgaagcgcc cagctccaac gacaaggcac    780
tcggactgct ttgcggcaaa gatgccgacg cctgcaacgc caccaactgg atcgagtaca    840
tgttcaataa ggacaacgga caggcccctt tcaccatcac acctgtgttc agcgacttcc    900
cagtccacgg gatggaacct atgaacaacg cgactaaggg atgcgacgag tccgtggacg    960
aagtgaccgc cccgtgttcc tgtcaagatt gctcaatcgt gtgcggtccg aagccccagc   1020
ctcctcctcc gccggctcca tggaccatcc tgggtctgga cgctatgtac gtgattatgt   1080
ggatcactta catggccttc ctcctggtgt tcttcggcgc tttcttcgcc gtgtggtgtt   1140
accggaagcg ctacttcgtg tccgagtata ctcctatcga ctctaacata gcgttctccg   1200
tgaacgcctc cgataaggga gaggcatcgt gctgtgatcc cgtgtccgcc gctttcgaag   1260
gatgcttgag gcggctgttc acccgctggg gcagcttctg cgtgagaaat cccggctgtg   1320
tgattttctt ctcgctggtg ttcatcaccg cttgctcgtc ggggctggtg ttcgtcagag   1380
tcacaacgaa ccccgtggac ctgtggagcg cgcctagcag ccaggcccgc ctggaaaagg   1440
aatacttcga ccagcatttc ggaccctttt tccggaccga acagctgatt atccgcgccc   1500
cgctgactga caagcatatc taccagcctt acccgagcgg agcggatgtg ccctttggtc   1560
cgccactcga catccagatc ctgcaccaag tcctggactt gcaaatcgct attgagaaca   1620
ttactgcctc ctacgacaac gagacagtga ccctgcagga catttgtctt gccccgctgt   1680
cccccctacaa caccaactgc acgatcctga gcgtgctgaa ctatttccaa aactcgcact   1740
ccgtgctgga tcacaagaag ggcgacgatt tcttcgtcta cgccgattac cacacccact   1800
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg ggcacatga agtcctgccg ccggctgctg gtcgattcga   2220
```

-continued

```
aggtgtccct gggaatcgcc ggcatcctga tcgtcctgtc gtccgtggcc tgttccctgg   2280
gagtgttcag ctacattgga ctgccactga ccctcattgt gattgaagtg atccctttc    2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg gggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca cccttactaa gttcggcggt atcgtggtgc   3900
tggccttcgc caagtcacag atcttccaaa ttttctactt cagaatgtac ttggcgatgg   3960
tcctgcttgg agccacacac ggtctgatct tcctgcctgt gctgctgagc tacatcggtc   4020
ccagcgtgaa caaggctaag tcctgcgcga cggaggaaag gtacaaggga accgagaggg   4080
agcgccttct caacttcgga ggagattata aagacgatga tgacaagggg gactacaagg   4140
acgacgatga caagggcgat tacaaagacg acgacgacaa gggcggccgg aagaagcgcc   4200
gccagcggcg gagattgata gaagcttctc gaggacgggg tgaactacgc ctgaggatcc   4260
gatctttttc cctctgccaa aaattatggg gacatcatga agccccttga gcatctgact   4320
tctggctaat aaaggaaatt tattttcatt gcaatagtgt gttggaattt tttgtgtctc   4380
tcactcg                                                             4387
```

<210> SEQ ID NO 38
<211> LENGTH: 4276
<212> TYPE: DNA
<213> ORGANISM: Artificial Sequence
<220> FEATURE:
<223> OTHER INFORMATION: Synthetic

<400> SEQUENCE: 38
cggctccggt gcccgtcagt gggcagagcg cacatcgccc acagtccccg agaagttggg 60
gggaggggtc ggcaattgaa ccggtgccta gagaaggtgg cgcggggtaa actgggaaag 120
tgatgtcgtg tactggctcc gcctttttcc cgagggtggg ggagaaccgt atataagtgc 180
agtagtcgcc gtgaacgttc tttttcgcaa cgggtttgcc gccagaacac aggtcagatc 240
agatctttgt cgatcccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920
agaactacaa caacgccacc gccctcgtga tcacctttcc tgtgaacaac tactacaacg 1980
acaccgaaaa gttgcagaga gcacaagcgt gggagaagga gttcatcaac ttcgtgaaga 2040
actacaaaaa ccctaacctg accatctcct ttacggccga gcgctcaatc gaggacgaat 2100
tgaacaggga atcggactcc gacgtgttca ctgtcgtcat tagctacgcc atcatgttct 2160
tgtacattag cctggcgctg ggcacatga agtcctgccg ccggctgctg gtcgattcga 2220

-continued

```
aggtgtccct gggaatcgcc ggcatcctga tcgtcctgtc gtccgtggcc tgttccctgg   2280
gagtgttcag ctacattgga ctgccactga ccctcattgt gattgaagtg atcccttttc   2340
ttgtcttggc cgtgggagtg gataatattt ttatcctggt gcaagcctac cagcgggacg   2400
agaggctgca gggggagact ctggaccagc agctgggccg cgtgctgggc gaagtcgccc   2460
cgtccatgtt tctgtcctca ttctccgaaa ccgtggcctt cttcctgggc gcgctcagcg   2520
tgatgcctgc cgtgcacacc ttctccctgt ttgccggtct ggctgtgttt atcgatttcc   2580
ttctccaaat tacttgcttc gtgtcactgc ttggactcga catcaagcgc caggaaaaga   2640
accggctgga cattttctgc tgcgtgagag gagcggagga cggaacctca gtgcaggctt   2700
ccgagtcatg cctgtttcga ttcttcaaga actcgtattc gccgctgctc ctgaaggatt   2760
ggatgcggcc cattgtgatc gccatctttg tcggcgtcct gagcttcagc attgcggtgt   2820
tgaacaaagt ggacattggc ctggaccaga gcctctccat gccggatgat tcctacatgg   2880
tggactactt caagagcatc tctcagtact tgcacgctgg ccctcccgtg tatttcgtgc   2940
tggaggaagg gcacgactac actagctcta agggacagaa catggtctgc ggtggcatgg   3000
gatgcaacaa tgactcgctg gtgcagcaga ttttcaacgc cgcgcaactc gataactaca   3060
ccaggattgg attcgctccc tcctcctgga tcgacgatta ttttgactgg gtcaagccgc   3120
agtctagctg ctgccgggtg gacaacatca cggatcagtt ctgcaatgct tccgtggtcg   3180
acccggcctg cgtgcggtgc cggcctctta ctccggaggg aaagcagagg ccccagggtg   3240
gcgacttcat gcggtttctg cccatgttcc tgagcgataa ccccaacccc aaatgcggga   3300
agggaggtca cgcggcgtac tcgtcagcgg tcaacatcct gctgggccat ggaactagag   3360
tgggagcgac ctacttcatg acttaccata ctgtgctgca gacctcagcc gacttcatcg   3420
acgcactcaa gaaagcccgc ctgatcgcat caaacgtgac cgagactatg gggatcaacg   3480
gatccgcgta ccgcgtgttc ccatattcgg tgttctacgt gttctacgag caatacctga   3540
ccattattga cgacaccatc tttaacctgg gggtgtcact gggagccatc ttccttgtga   3600
ccatggtcct cctgggctgc gaactgtggt ccgccgtgat catgtgcgct accatcgcaa   3660
tggtcctcgt gaacatgttt ggggtcatgt ggctgtgggg catctccctg aacgcggtgt   3720
ccctcgtgaa cctggtcatg tcatgcggca ttagcgtgga gttctgctcc cacattactc   3780
gcgccttcac cgtgtcgatg aagggttccc gcgtggagcg ggcggaggaa gccctggccc   3840
acatgggatc ctcggtgttc tcgggcatca ccettactaa gttcggcggt atcgtggtgc   3900
tggccttcgc caagtcacag atcttccaga ttttctactt ccggatgtac ctggcgatgg   3960
tgcttctggg agcaacccac ggcctgatct tcctgcccgt gctcttgtcc tacatcggcc   4020
ccagcgtgaa caaggccaag tcctgcgcca ctgaggaacg ctacaagggc accgaaagag   4080
aaaggctgct gaatttctga tagatgatag aagcttctcg aggacggggt gaactacgcc   4140
tgaggatccg atctttttcc ctctgccaaa aattatgggg acatcatgaa gccccttgag   4200
catctgactt ctggctaata aaggaaattt attttcattg caatagtgtg ttggaatttt   4260
ttgtgtctct cactcg                                                   4276
```

<210> SEQ ID NO 39
<211> LENGTH: 4305
<212> TYPE: DNA
<213> ORGANISM: Artificial Sequence
<220> FEATURE:
<223> OTHER INFORMATION: Synthetic

<400> SEQUENCE: 39

-continued

```
cggctccggt gcccgtcagt gggcagagcg cacatcgccc acagtccccg agaagttggg     60
gggaggggtc ggcaattgaa ccggtgccta gagaaggtgg cgcggggtaa actgggaaag    120
tgatgtcgtg tactggctcc gcctttttcc cgagggtggg ggagaaccgt atataagtgc    180
agtagtcgcc gtgaacgttc tttttcgcaa cgggtttgcc gccagaacac aggtcagatc    240
agatctttgt cgatcccgcc accatgaccg cgaggggact ggccctcggg ctgctcctgc    300
tgctcctttg cccggcccaa gtgttctcgc aatcgtgcgt gtggtacggg gaatgcggaa    360
ttgcctacgg cgacaagcgg tacaactgcg aatactccgg gcctccaaag ccgctgccca    420
aggacggata cgacctggtc caagagctct gccctggatt cttcttcggc aacgtgtcgc    480
tgtgttgtga cgtgcggcag ctgcagaccc tgaaggataa cctccagctg ccgctgcaat    540
tcctctcccg gtgtccgtca tgcttctaca acttgctcaa cctgttctgc gaacttacct    600
gttcgccgag acagtcccag tttcttaacg tcaccgcaac cgaggactac gtggaccctg    660
tgactaacca gaccaagact aatgtcaaag aattgcagta ctacgtgggc cagtccttcg    720
ccaatgcgat gtacaacgcc tgtcgggacg tcgaagcgcc cagctccaac gacaaggcac    780
tcggactgct ttgcggcaaa gatgccgacg cctgcaacgc caccaactgg atcgagtaca    840
tgttcaataa ggacaacgga caggcccctt tcaccatcac acctgtgttc agcgacttcc    900
cagtccacgg gatggaacct atgaacaacg cgactaaggg atgcgacgag tccgtggacg    960
aagtgaccgc cccgtgttcc tgtcaagatt gctcaatcgt gtgcggtccg aagccccagc   1020
ctcctcctcc gccggctcca tggaccatcc tgggtctgga cgctatgtac gtgattatgt   1080
ggatcactta catggccttc ctcctggtgt tcttcggcgc tttcttcgcc gtgtggtgtt   1140
accggaagcg ctacttcgtg tccgagtata ctcctatcga ctctaacata gcgttctccg   1200
tgaacgcctc cgataaggga gaggcatcgt gctgtgatcc cgtgtccgcc gctttcgaag   1260
gatgcttgag gcggctgttc acccgctggg gcagcttctg cgtgagaaat cccggctgtg   1320
tgattttctt ctcgctggtg ttcatcaccg cttgctcgtc ggggctggtg ttcgtcagag   1380
tcacaacgaa ccccgtggac ctgtggagcg cgcctagcag ccaggcccgc ctggaaaagg   1440
aatacttcga ccagcatttc ggaccctttt tccggaccga acagctgatt atccgcgccc   1500
cgctgactga caagcatatc taccagcctt acccgagcgg agcggatgtg ccctttggtc   1560
cgccactcga catccagatc ctgcaccaag tcctggactt gcaaatcgct attgagaaca   1620
ttactgcctc ctacgacaac gagacagtga ccctgcagga catttgtctt gccccgctgt   1680
cccccctacaa caccaactgc acgatcctga gcgtgctgaa ctatttccaa aactcgcact   1740
ccgtgctgga tcacaagaag ggcgacgatt tcttcgtcta cgccgattac cacacccact   1800
tcctgtactg cgtgcgcgct ccggcttcac tgaacgacac ttccctcctc cacgacccgt   1860
gcctgggaac gttcggcgga cccgtgtttc cctggctggt cctgggcggc tacgacgacc   1920
agaactacaa caacgccacc gccctcgtga tcacctttcc tgtgaacaac tactacaacg   1980
acaccgaaaa gttgcagaga gcacaagcgt gggagaagga gttcatcaac ttcgtgaaga   2040
actacaaaaa ccctaacctg accatctcct ttacggccga gcgctcaatc gaggacgaat   2100
tgaacaggga atcggactcc gacgtgttca ctgtcgtcat tagctacgcc atcatgttct   2160
tgtacattag cctggcgctg gggcacatga agtcctgccg ccggctgctg gtcgattcga   2220
aggtgtccct gggaatcgcc ggcatcctga tcgtcctgtc gtccgtggcc tgttccctgg   2280
gagtgttcag ctacattgga ctgccactga ccctcattgt gattgaagtg atccctttc    2340
```

ttgtcttggc cgtgggagtg gataatattt ttatcctggt gcaagcctac cagcgggacg 2400
agaggctgca gggggagact ctggaccagc agctgggccg cgtgctgggc gaagtcgccc 2460
cgtccatgtt tctgtcctca ttctccgaaa ccgtggcctt cttcctgggc gcgctcagcg 2520
tgatgcctgc cgtgcacacc ttctccctgt ttgccggtct ggctgtgttt atcgatttcc 2580
ttctccaaat tacttgcttc gtgtcactgc ttggactcga catcaagcgc caggaaaaga 2640
accggctgga cattttctgc tgcgtgagag gagcggagga cggaacctca gtgcaggctt 2700
ccgagtcatg cctgtttcga ttcttcaaga actcgtattc gccgctgctc ctgaaggatt 2760
ggatgcggcc cattgtgatc gccatctttg tcggcgtcct gagcttcagc attgcggtgt 2820
tgaacaaagt ggacattggc ctggaccaga gcctctccat gccggatgat tcctacatgg 2880
tggactactt caagagcatc tctcagtact tgcacgctgg ccctcccgtg tatttcgtgc 2940
tggaggaagg gcacgactac actagctcta agggacagaa catggtctgc ggtggcatgg 3000
gatgcaacaa tgactcgctg gtgcagcaga ttttcaacgc cgcgcaactc gataactaca 3060
ccaggattgg attcgctccc tcctcctgga tcgacgatta ttttgactgg gtcaagccgc 3120
agtctagctg ctgccgggtg gacaacatca cggatcagtt ctgcaatgct tccgtggtcg 3180
acccggcctg cgtgcggtgc cggcctctta ctccggaggg aaagcagagg ccccagggtg 3240
gcgacttcat gcggtttctg cccatgttcc tgagcgataa ccccaacccc aaatgcggga 3300
agggaggtca cgcggcgtac tcgtcagcgg tcaacatcct gctgggccat ggaactagag 3360
tgggagcgac ctacttcatg acttaccata ctgtgctgca gacctcagcc gacttcatcg 3420
acgcactcaa gaaagcccgc ctgatcgcat caaacgtgac cgagactatg gggatcaacg 3480
gatccgcgta ccgcgtgttc ccatattcgg tgttctacgt gttctacgag caatacctga 3540
ccattattga cgacaccatc tttaacctgg gggtgtcact gggagccatc ttccttgtga 3600
ccatggtcct cctgggctgc gaactgtggt ccgccgtgat catgtgcgct accatcgcaa 3660
tggtcctcgt gaacatgttt ggggtcatgt ggctgtgggg catctccctg aacgcggtgt 3720
ccctcgtgaa cctggtcatg tcatgcggca ttagcgtgga gttctgctcc cacattactc 3780
gcgccttcac cgtgtcgatg aagggttccc gcgtggagcg ggcggaggaa gccctggccc 3840
acatgggatc ctcggtgttc tcgggcatca cccttactaa gttcggcggt atcgtggtgc 3900
tggccttcgc caagtcacag atcttccaaa ttttctactt cagaatgtac ttggcgatgg 3960
tcctgcttgg agccacacac ggtctgatct tcctgcctgt gcttctgtcc tacatcggcc 4020
cgtccgtgaa caaagcgaag tcctgtgcta ctgaggagcg gtacaaggga actgagcgcg 4080
agcgcctgct caactttggg ggcggccgca agaagcgccg gcagcgcaga aggtgataga 4140
agcttctcga ggacggggtg aactacgcct gaggatccga tctttttccc tctgccaaaa 4200
attatgggga catcatgaag ccccttgagc atctgacttc tggctaataa aggaaattta 4260
ttttcattgc aatagtgtgt tggaattttt tgtgtctctc actcg 4305

<210> SEQ ID NO 40
<211> LENGTH: 4354
<212> TYPE: DNA
<213> ORGANISM: Artificial Sequence
<220> FEATURE:
<223> OTHER INFORMATION: Synthetic

<400> SEQUENCE: 40
cggctccggt gcccgtcagt gggcagagcg cacatcgccc acagtccccg agaagttggg 60
gggaggggtc ggcaattgaa ccggtgccta gagaaggtgg cgcggggtaa actgggaaag 120

-continued tgatgtcgtg tactggctcc gcctttttcc cgagggtggg ggagaaccgt atataagtgc 180
agtagtcgcc gtgaacgttc tttttcgcaa cgggtttgcc gccagaacac aggtcagatc 240
agatctttgt cgatcccgcc accatgaccg cgaggggact ggccctcggg ctgctcctgc 300
tgctcctttg cccggcccaa gtgttctcgc aatcgtgcgt gtggtacggg gaatgcggaa 360
ttgcctacgg cgacaagcgg tacaactgcg aatactccgg gcctccaaag ccgctgccca 420
aggacggata cgacctggtc caagagctct gccctggatt cttcttcggc aacgtgtcgc 480
tgtgttgtga cgtgcggcag ctgcagaccc tgaaggataa cctccagctg ccgctgcaat 540
tcctctcccg gtgtccgtca tgcttctaca acttgctcaa cctgttctgc gaacttacct 600
gttcgccgag acagtcccag tttcttaacg tcaccgcaac cgaggactac gtggaccctg 660
tgactaacca gaccaagact aatgtcaaag aattgcagta ctacgtgggc cagtccttcg 720
ccaatgcgat gtacaacgcc tgtcgggacg tcgaagcgcc cagctccaac gacaaggcac 780
tcggactgct ttgcggcaaa gatgccgacg cctgcaacgc caccaactgg atcgagtaca 840
tgttcaataa ggacaacgga caggcccctt tcaccatcac acctgtgttc agcgacttcc 900
cagtccacgg gatggaacct atgaacaacg cgactaaggg atgcgacgag tccgtggacg 960
aagtgaccgc cccgtgttcc tgtcaagatt gctcaatcgt gtgcggtccg aagccccagc 1020
ctcctcctcc gccggctcca tggaccatcc tgggtctgga cgctatgtac gtgattatgt 1080
ggatcactta catggccttc ctcctggtgt tcttcggcgc tttcttcgcc gtgtggtgtt 1140
accggaagcg ctacttcgtg tccgagtata ctcctatcga ctctaacata gcgttctccg 1200
tgaacgcctc cgataaggga gaggcatcgt gctgtgatcc cgtgtccgcc gctttcgaag 1260
gatgcttgag gcggctgttc acccgctggg gcagcttctg cgtgagaaat cccggctgtg 1320
tgattttctt ctcgctggtg ttcatcaccg cttgctcgtc ggggctggtg ttcgtcagag 1380
tcacaacgaa ccccgtggac ctgtggagcg cgcctagcag ccaggcccgc ctggaaaagg 1440
aatacttcga ccagcatttc ggaccctttt tccggaccga acagctgatt atccgcgccc 1500
cgctgactga caagcatatc taccagcctt acccgagcgg agcggatgtg ccctttggtc 1560
cgccactcga catccagatc ctgcaccaag tcctggactt gcaaatcgct attgagaaca 1620
ttactgcctc ctacgacaac gagacagtga ccctgcagga catttgtctt gccccgctgt 1680
ccccctacaa caccaactgc acgatcctga gcgtgctgaa ctatttccaa aactcgcact 1740
ccgtgctgga tcacaagaag ggcgacgatt tcttcgtcta cgccgattac cacacccact 1800
tcctgtactg cgtgcgcgct ccggcttcac tgaacgacac ttccctcctc cacgacccgt 1860
gcctgggaac gttcggcgga cccgtgtttc cctggctggt cctgggcggc tacgacgacc 1920
agaactacaa caacgccacc gccctcgtga tcacctttcc tgtgaacaac tactacaacg 1980
acaccgaaaa gttgcagaga gcacaagcgt gggagaagga gttcatcaac ttcgtgaaga 2040
actacaaaaa ccctaacctg accatctcct ttacggccga gcgctcaatc gaggacgaat 2100
tgaacaggga atcggactcc gacgtgttca ctgtcgtcat tagctacgcc atcatgttct 2160
tgtacattag cctggcgctg gggcacatga agtcctgccg ccggctgctg gtcgattcga 2220
aggtgtccct gggaatcgcc ggcatcctga tcgtcctgtc gtccgtggcc tgttccctgg 2280
gagtgttcag ctacattgga ctgccactga ccctcattgt gattgaagtg atcccttttc 2340
ttgtcttggc cgtgggagtg gataatattt ttatcctggt gcaagcctac cagcgggacg 2400
agaggctgca gggggagact ctggaccagc agctgggccg cgtgctgggc gaagtcgccc 2460

-continued

```
cgtccatgtt tctgtcctca ttctccgaaa ccgtggcctt cttcctgggc gcgctcagcg   2520

tgatgcctgc cgtgcacacc ttctccctgt ttgccggtct ggctgtgttt atcgatttcc   2580

ttctccaaat tacttgcttc gtgtcactgc ttggactcga catcaagcgc caggaaaaga   2640

accggctgga cattttctgc tgcgtgagag gagcggagga cggaacctca gtgcaggctt   2700

ccgagtcatg cctgtttcga ttcttcaaga actcgtattc gccgctgctc ctgaaggatt   2760

ggatgcggcc cattgtgatc gccatctttg tcggcgtcct gagcttcagc attgcggtgt   2820

tgaacaaagt ggacattggc ctggaccaga gcctctccat gccggatgat tcctacatgg   2880

tggactactt caagagcatc tctcagtact tgcacgctgg ccctcccgtg tatttcgtgc   2940

tggaggaagg gcacgactac actagctcta agggacagaa catggtctgc ggtggcatgg   3000

gatgcaacaa tgactcgctg gtgcagcaga ttttcaacgc cgcgcaactc gataactaca   3060

ccaggattgg attcgctccc tcctcctgga tcgacgatta ttttgactgg gtcaagccgc   3120

agtctagctg ctgccgggtg gacaacatca cggatcagtt ctgcaatgct tccgtggtcg   3180

acccggcctg cgtgcggtgc cggcctctta ctccggaggg aaagcagagg ccccagggtg   3240

gcgacttcat gcggtttctg cccatgttcc tgagcgataa ccccaacccc aaatgcggga   3300

agggaggtca cgcggcgtac tcgtcagcgg tcaacatcct gctgggccat ggaactagag   3360

tgggagcgac ctacttcatg acttaccata ctgtgctgca gacctcagcc gacttcatcg   3420

acgcactcaa gaaagcccgc ctgatcgcat caaacgtgac cgagactatg ggatcaacg   3480

gatccgcgta ccgcgtgttc ccatattcgg tgttctacgt gttctacgag caatacctga   3540

ccattattga cgacaccatc tttaacctgg gggtgtcact gggagccatc ttccttgtga   3600

ccatggtcct cctgggctgc gaactgtggt ccgccgtgat catgtgcgct accatcgcaa   3660

tggtcctcgt gaacatgttt ggggtcatgt ggctgtgggg catctccctg aacgcggtgt   3720

ccctcgtgaa cctggtcatg tcatgcggca ttagcgtgga gttctgctcc cacattactc   3780

gcgccttcac cgtgtcgatg aagggttccc gcgtggagcg ggcggaggaa gccctggccc   3840

acatgggatc ctcggtgttc tcgggcatca cccttactaa gttcggcggt atcgtggtgc   3900

tggccttcgc caagtcacag atcttccaaa ttttctactt cagaatgtac ttggcgatgg   3960

tcctgcttgg agccacacac ggtctgatct tcctgcctgt gctgctgagc tacatcggtc   4020

ccagcgtgaa caaggctaag tcctgcgcga cggaggaaag gtacaaggga accgagaggg   4080

agcgccttct caacttcgga ggagattata aagacgatga tgacaagggg gactacaagg   4140

acgacgatga caagggcgat tacaaagacg acgacgacaa gttgatagaa gcttctcgag   4200

gacggggtga actacgcctg aggatccgat ctttttccct ctgccaaaaa ttatggggac   4260

atcatgaagc cccttgagca tctgacttct ggctaataaa ggaaatttat tttcattgca   4320

atagtgtgtt ggaatttttt gtgtctctca ctcg                              4354
```

<210> SEQ ID NO 41
<211> LENGTH: 1278
<212> TYPE: PRT
<213> ORGANISM: Homo sapiens

<400> SEQUENCE: 41

```
Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
```

-continued

```
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460
```

Gln Asp Ile Cys Leu Ala Pro Leu Ser Pro Tyr Asn Thr Asn Cys Thr
465 470 475 480

Ile Leu Ser Val Leu Asn Tyr Phe Gln Asn Ser His Ser Val Leu Asp
485 490 495

His Lys Lys Gly Asp Asp Phe Phe Val Tyr Ala Asp Tyr His Thr His
500 505 510

Phe Leu Tyr Cys Val Arg Ala Pro Ala Ser Leu Asn Asp Thr Ser Leu
515 520 525

Leu His Asp Pro Cys Leu Gly Thr Phe Gly Gly Pro Val Phe Pro Trp
530 535 540

Leu Val Leu Gly Gly Tyr Asp Asp Gln Asn Tyr Asn Asn Ala Thr Ala
545 550 555 560

Leu Val Ile Thr Phe Pro Val Asn Asn Tyr Tyr Asn Asp Thr Glu Lys
565 570 575

Leu Gln Arg Ala Gln Ala Trp Glu Lys Glu Phe Ile Asn Phe Val Lys
580 585 590

Asn Tyr Lys Asn Pro Asn Leu Thr Ile Ser Phe Thr Ala Glu Arg Ser
595 600 605

Ile Glu Asp Glu Leu Asn Arg Glu Ser Asp Ser Asp Val Phe Thr Val
610 615 620

Val Ile Ser Tyr Ala Ile Met Phe Leu Tyr Ile Ser Leu Ala Leu Gly
625 630 635 640

His Ile Lys Ser Cys Arg Arg Leu Leu Val Asp Ser Lys Val Ser Leu
645 650 655

Gly Ile Ala Gly Ile Leu Ile Val Leu Ser Ser Val Ala Cys Ser Leu
660 665 670

Gly Val Phe Ser Tyr Ile Gly Leu Pro Leu Thr Leu Ile Val Ile Glu
675 680 685

Val Ile Pro Phe Leu Val Leu Ala Val Gly Val Asp Asn Ile Phe Ile
690 695 700

Leu Val Gln Ala Tyr Gln Arg Asp Glu Arg Leu Gln Gly Glu Thr Leu
705 710 715 720

Asp Gln Gln Leu Gly Arg Val Leu Gly Glu Val Ala Pro Ser Met Phe
725 730 735

Leu Ser Ser Phe Ser Glu Thr Val Ala Phe Phe Leu Gly Ala Leu Ser
740 745 750

Val Met Pro Ala Val His Thr Phe Ser Leu Phe Ala Gly Leu Ala Val
755 760 765

Phe Ile Asp Phe Leu Leu Gln Ile Thr Cys Phe Val Ser Leu Leu Gly
770 775 780

Leu Asp Ile Lys Arg Gln Glu Lys Asn Arg Leu Asp Ile Phe Cys Cys
785 790 795 800

Val Arg Gly Ala Glu Asp Gly Thr Ser Val Gln Ala Ser Glu Ser Cys
805 810 815

Leu Phe Arg Phe Phe Lys Asn Ser Tyr Ser Pro Leu Leu Leu Lys Asp
820 825 830

Trp Met Arg Pro Ile Val Ile Ala Ile Phe Val Gly Val Leu Ser Phe
835 840 845

Ser Ile Ala Val Leu Asn Lys Val Asp Ile Gly Leu Asp Gln Ser Leu
850 855 860

Ser Met Pro Asp Asp Ser Tyr Met Val Asp Tyr Phe Lys Ser Ile Ser
865 870 875 880

-continued

```
Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
        915                 920                 925

Leu Asp Asn Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990

Gly Asp Phe Met Arg Phe Leu Pro  Met Phe Leu Ser Asp  Asn Pro Asn
        995                 1000                1005

Pro Lys  Cys Gly Lys Gly Gly  His Ala Ala Tyr Ser  Ser Ala Val
    1010                 1015                 1020

Asn Ile  Leu Leu Gly His Gly  Thr Arg Val Gly Ala  Thr Tyr Phe
    1025                 1030                 1035

Met Thr  Tyr His Thr Val Leu  Gln Thr Ser Ala Asp  Phe Ile Asp
    1040                 1045                 1050

Ala Leu  Lys Lys Ala Arg Leu  Ile Ala Ser Asn Val  Thr Glu Thr
    1055                 1060                 1065

Met Gly  Ile Asn Gly Ser Ala  Tyr Arg Val Phe Pro  Tyr Ser Val
    1070                 1075                 1080

Phe Tyr  Val Phe Tyr Glu Gln  Tyr Leu Thr Ile Ile  Asp Asp Thr
    1085                 1090                 1095

Ile Phe  Asn Leu Gly Val Ser  Leu Gly Ala Ile Phe  Leu Val Thr
    1100                 1105                 1110

Met Val  Leu Leu Gly Cys Glu  Leu Trp Ser Ala Val  Ile Met Cys
    1115                 1120                 1125

Ala Thr  Ile Ala Met Val Leu  Val Asn Met Phe Gly  Val Met Trp
    1130                 1135                 1140

Leu Trp  Gly Ile Ser Leu Asn  Ala Val Ser Leu Val  Asn Leu Val
    1145                 1150                 1155

Met Ser  Cys Gly Ile Ser Val  Glu Phe Cys Ser His  Ile Thr Arg
    1160                 1165                 1170

Ala Phe  Thr Val Ser Met Lys  Gly Ser Arg Val Glu  Arg Ala Glu
    1175                 1180                 1185

Glu Ala  Leu Ala His Met Gly  Ser Ser Val Phe Ser  Gly Ile Thr
    1190                 1195                 1200

Leu Thr  Lys Phe Gly Gly Ile  Val Val Leu Ala Phe  Ala Lys Ser
    1205                 1210                 1215

Gln Ile  Phe Gln Ile Phe Tyr  Phe Arg Met Tyr Leu  Ala Met Val
    1220                 1225                 1230

Leu Leu  Gly Ala Thr His Gly  Leu Ile Phe Leu Pro  Val Leu Leu
    1235                 1240                 1245

Ser Tyr  Ile Gly Pro Ser Val  Asn Lys Ala Lys Ser  Cys Ala Thr
    1250                 1255                 1260

Glu Glu  Arg Tyr Lys Gly Thr  Glu Arg Glu Arg Leu  Leu Asn Phe
    1265                 1270                 1275
```

<210> SEQ ID NO 42
<211> LENGTH: 1332
<212> TYPE: PRT
<213> ORGANISM: Homo sapiens

<400> SEQUENCE: 42

Met Ala Glu Ala Gly Leu Arg Gly Trp Leu Leu Trp Ala Leu Leu Leu
1 5 10 15

Arg Leu Ala Gln Ser Glu Pro Tyr Thr Thr Ile His Gln Pro Gly Tyr
20 25 30

Cys Ala Phe Tyr Asp Glu Cys Gly Lys Asn Pro Glu Leu Ser Gly Ser
35 40 45

Leu Met Thr Leu Ser Asn Val Ser Cys Leu Ser Asn Thr Pro Ala Arg
50 55 60

Lys Ile Thr Gly Asp His Leu Ile Leu Leu Gln Lys Ile Cys Pro Arg
65 70 75 80

Leu Tyr Thr Gly Pro Asn Thr Gln Ala Cys Cys Ser Ala Lys Gln Leu
85 90 95

Val Ser Leu Glu Ala Ser Leu Ser Ile Thr Lys Ala Leu Leu Thr Arg
100 105 110

Cys Pro Ala Cys Ser Asp Asn Phe Val Asn Leu His Cys His Asn Thr
115 120 125

Cys Ser Pro Asn Gln Ser Leu Phe Ile Asn Val Thr Arg Val Ala Gln
130 135 140

Leu Gly Ala Gly Gln Leu Pro Ala Val Val Ala Tyr Glu Ala Phe Tyr
145 150 155 160

Gln His Ser Phe Ala Glu Gln Ser Tyr Asp Ser Cys Ser Arg Val Arg
165 170 175

Val Pro Ala Ala Ala Thr Leu Ala Val Gly Thr Met Cys Gly Val Tyr
180 185 190

Gly Ser Ala Leu Cys Asn Ala Gln Arg Trp Leu Asn Phe Gln Gly Asp
195 200 205

Thr Gly Asn Gly Leu Ala Pro Leu Asp Ile Thr Phe His Leu Leu Glu
210 215 220

Pro Gly Gln Ala Val Gly Ser Gly Ile Gln Pro Leu Asn Glu Gly Val
225 230 235 240

Ala Arg Cys Asn Glu Ser Gln Gly Asp Asp Val Ala Thr Cys Ser Cys
245 250 255

Gln Asp Cys Ala Ala Ser Cys Pro Ala Ile Ala Arg Pro Gln Ala Leu
260 265 270

Asp Ser Thr Phe Tyr Leu Gly Gln Met Pro Gly Ser Leu Val Leu Ile
275 280 285

Ile Ile Leu Cys Ser Val Phe Ala Val Val Thr Ile Leu Leu Val Gly
290 295 300

Phe Arg Val Ala Pro Ala Arg Asp Lys Ser Lys Met Val Asp Pro Lys
305 310 315 320

Lys Gly Thr Ser Leu Ser Asp Lys Leu Ser Phe Ser Thr His Thr Leu
325 330 335

Leu Gly Gln Phe Phe Gln Gly Trp Gly Thr Trp Val Ala Ser Trp Pro
340 345 350

Leu Thr Ile Leu Val Leu Ser Val Ile Pro Val Val Ala Leu Ala Ala
355 360 365

Gly Leu Val Phe Thr Glu Leu Thr Thr Asp Pro Val Glu Leu Trp Ser
370 375 380

-continued

```
Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Leu Gly Pro Lys Asn Phe
            420                 425                 430

Ser Gly Ile Leu Asp Leu Asp Leu Leu Leu Glu Leu Leu Glu Leu Gln
        435                 440                 445

Glu Arg Leu Arg His Leu Gln Val Trp Ser Pro Glu Ala Gln Arg Asn
    450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Lys Asp His Phe Leu Tyr Cys Ala Asn Ala
        515                 520                 525

Pro Leu Thr Phe Lys Asp Gly Thr Ala Leu Ala Leu Ser Cys Met Ala
    530                 535                 540

Asp Tyr Gly Ala Pro Val Phe Pro Phe Leu Ala Ile Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Lys Leu Trp
            580                 585                 590

Glu Glu Ala Phe Leu Glu Glu Met Arg Ala Phe Gln Arg Arg Met Ala
        595                 600                 605

Gly Met Phe Gln Val Thr Phe Met Ala Glu Arg Ser Leu Glu Asp Glu
    610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
            660                 665                 670

Val Ala Val Val Leu Gly Ala Val Met Ala Ala Met Gly Phe Phe Ser
        675                 680                 685

Tyr Leu Gly Ile Arg Ser Ser Leu Val Ile Leu Gln Val Val Pro Phe
    690                 695                 700

Leu Val Leu Ser Val Gly Ala Asp Asn Ile Phe Ile Phe Val Leu Glu
705                 710                 715                 720

Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
            740                 745                 750

Ser Glu Ala Ile Cys Phe Phe Leu Gly Ala Leu Thr Pro Met Pro Ala
        755                 760                 765

Val Arg Thr Phe Ala Leu Thr Ser Gly Leu Ala Val Ile Leu Asp Phe
    770                 775                 780

Leu Leu Gln Met Ser Ala Phe Val Ala Leu Leu Ser Leu Asp Ser Lys
785                 790                 795                 800

Arg Gln Glu Ala Ser Arg Leu Asp Val Cys Cys Cys Val Lys Pro Gln
```

-continued

```
                805                 810                 815

Glu Leu Pro Pro Pro Gly Gln Gly Glu Gly Leu Leu Leu Gly Phe Phe
            820                 825                 830

Gln Lys Ala Tyr Ala Pro Phe Leu Leu His Trp Ile Thr Arg Gly Val
        835                 840                 845

Val Leu Leu Leu Phe Leu Ala Leu Phe Gly Val Ser Leu Tyr Ser Met
    850                 855                 860

Cys His Ile Ser Val Gly Leu Asp Gln Glu Leu Ala Leu Pro Lys Asp
865                 870                 875                 880

Ser Tyr Leu Leu Asp Tyr Phe Leu Phe Leu Asn Arg Tyr Phe Glu Val
                885                 890                 895

Gly Ala Pro Val Tyr Phe Val Thr Thr Leu Gly Tyr Asn Phe Ser Ser
            900                 905                 910

Glu Ala Gly Met Asn Ala Ile Cys Ser Ser Ala Gly Cys Asn Asn Phe
        915                 920                 925

Ser Phe Thr Gln Lys Ile Gln Tyr Ala Thr Glu Phe Pro Glu Gln Ser
    930                 935                 940

Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
                965                 970                 975

Asp Lys Phe Cys Pro Ser Thr Val Asn Ser Leu Asn Cys Leu Lys Asn
            980                 985                 990

Cys Met Ser Ile Thr Met Gly Ser  Val Arg Pro Ser Val  Glu Gln Phe
        995                 1000                1005

His Lys  Tyr Leu Pro Trp Phe  Leu Asn Asp Arg Pro  Asn Ile Lys
    1010                1015                1020

Cys Pro  Lys Gly Gly Leu Ala  Ala Tyr Ser Thr Ser  Val Asn Leu
    1025                1030                1035

Thr Ser  Asp Gly Gln Val Leu  Ala Ser Arg Phe Met  Ala Tyr His
    1040                1045                1050

Lys Pro  Leu Lys Asn Ser Gln  Asp Tyr Thr Glu Ala  Leu Arg Ala
    1055                1060                1065

Ala Arg  Glu Leu Ala Ala Asn  Ile Thr Ala Asp Leu  Arg Lys Val
    1070                1075                1080

Pro Gly  Thr Asp Pro Ala Phe  Glu Val Phe Pro Tyr  Thr Ile Thr
    1085                1090                1095

Asn Val  Phe Tyr Glu Gln Tyr  Leu Thr Ile Leu Pro  Glu Gly Leu
    1100                1105                1110

Phe Met  Leu Ser Leu Cys Leu  Val Pro Thr Phe Ala  Val Ser Cys
    1115                1120                1125

Leu Leu  Leu Gly Leu Asp Leu  Arg Ser Gly Leu Leu  Asn Leu Leu
    1130                1135                1140

Ser Ile  Val Met Ile Leu Val  Asp Thr Val Gly Phe  Met Ala Leu
    1145                1150                1155

Trp Gly  Ile Ser Tyr Asn Ala  Val Ser Leu Ile Asn  Leu Val Ser
    1160                1165                1170

Ala Val  Gly Met Ser Val Glu  Phe Val Ser His Ile  Thr Arg Ser
    1175                1180                1185

Phe Ala  Ile Ser Thr Lys Pro  Thr Trp Leu Glu Arg  Ala Lys Glu
    1190                1195                1200

Ala Thr  Ile Ser Met Gly Ser  Ala Val Phe Ala Gly  Val Ala Met
    1205                1210                1215
```

```
Thr Asn  Leu Pro Gly Ile Leu  Val Leu Gly Leu Ala  Lys Ala Gln
    1220                 1225                 1230

Leu Ile  Gln Ile Phe Phe Phe  Arg Leu Asn Leu Leu  Ile Thr Leu
    1235                 1240                 1245

Leu Gly  Leu Leu His Gly Leu  Val Phe Leu Pro Val  Ile Leu Ser
    1250                 1255                 1260

Tyr Val  Gly Pro Asp Val Asn  Pro Ala Leu Ala Leu  Glu Gln Lys
    1265                 1270                 1275

Arg Ala  Glu Glu Ala Val Ala  Ala Val Met Val Ala  Ser Cys Pro
    1280                 1285                 1290

Asn His  Pro Ser Arg Val Ser  Thr Ala Asp Asn Ile  Tyr Val Asn
    1295                 1300                 1305

His Ser  Phe Glu Gly Ser Ile  Lys Gly Ala Gly Ala  Ile Ser Asn
    1310                 1315                 1320

Phe Leu  Pro Asn Asn Gly Arg  Gln Phe
    1325                 1330


<210> SEQ ID NO 43
<211> LENGTH: 1286
<212> TYPE: PRT
<213> ORGANISM: Homo sapiens

<400> SEQUENCE: 43

Met Ala Glu Ala Gly Leu Arg Gly Trp Leu Leu Trp Ala Leu Leu Leu
1               5                   10                  15

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
        35                  40                  45

Leu Met Thr Leu Ser Asn Val Ser Cys Leu Ser Asn Thr Pro Ala Arg
    50                  55                  60

Lys Ile Thr Gly Asp His Leu Ile Leu Leu Gln Lys Ile Cys Pro Arg
65                  70                  75                  80

Leu Tyr Thr Gly Pro Asn Thr Gln Ala Cys Cys Ser Ala Lys Gln Leu
                85                  90                  95

Val Ser Leu Glu Ala Ser Leu Ser Ile Thr Lys Ala Leu Leu Thr Arg
            100                 105                 110

Cys Pro Ala Cys Ser Asp Asn Phe Val Asn Leu His Cys His Asn Thr
        115                 120                 125

Cys Ser Pro Asn Gln Ser Leu Phe Ile Asn Val Thr Arg Val Ala Gln
    130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val Arg
                165                 170                 175

Val Pro Ala Ala Ala Thr Leu Ala Val Gly Thr Met Cys Gly Val Tyr
            180                 185                 190

Gly Ser Ala Leu Cys Asn Ala Gln Arg Trp Leu Asn Phe Gln Gly Asp
        195                 200                 205

Thr Gly Asn Gly Leu Ala Pro Leu Asp Ile Thr Phe His Leu Leu Glu
    210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Asp Val Ala Thr Cys Ser Cys
```

-continued

```
                245                 250                 255

Gln Asp Cys Ala Ala Ser Cys Pro Ala Ile Ala Arg Pro Gln Ala Leu
            260                 265                 270

Asp Ser Thr Phe Tyr Leu Gly Gln Met Pro Gly Ser Leu Val Leu Ile
        275                 280                 285

Ile Ile Leu Cys Ser Val Phe Ala Val Val Thr Ile Leu Leu Val Gly
    290                 295                 300

Phe Arg Val Ala Pro Ala Arg Asp Lys Ser Lys Met Val Asp Pro Lys
305                 310                 315                 320

Lys Gly Thr Ser Leu Ser Asp Lys Leu Ser Phe Ser Thr His Thr Leu
                325                 330                 335

Leu Gly Gln Phe Phe Gln Gly Trp Gly Thr Trp Val Ala Ser Trp Pro
            340                 345                 350

Leu Thr Ile Leu Val Leu Ser Val Ile Pro Val Val Ala Leu Ala Ala
        355                 360                 365

Gly Leu Val Phe Thr Glu Leu Thr Thr Asp Pro Val Glu Leu Trp Ser
    370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Leu Gly Pro Lys Asn Phe
            420                 425                 430

Ser Gly Ile Leu Asp Leu Asp Leu Leu Leu Glu Leu Leu Glu Leu Gln
        435                 440                 445

Glu Arg Leu Arg His Leu Gln Val Trp Ser Pro Glu Ala Gln Arg Asn
    450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Lys Asp His Phe Leu Tyr Cys Ala Asn Ala
        515                 520                 525

Pro Leu Thr Phe Lys Asp Gly Thr Ala Leu Ala Leu Ser Cys Met Ala
    530                 535                 540

Asp Tyr Gly Ala Pro Val Phe Pro Phe Leu Ala Ile Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Lys Leu Trp
            580                 585                 590

Glu Glu Ala Phe Leu Glu Glu Met Arg Ala Phe Gln Arg Arg Met Ala
        595                 600                 605

Gly Met Phe Gln Val Thr Phe Met Ala Glu Arg Ser Leu Glu Asp Glu
    610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
            660                 665                 670
```

-continued

```
Val Ala Val Val Leu Gly Ala Val Met Ala Ala Met Gly Phe Phe Ser
        675                 680                 685

Tyr Leu Gly Ile Arg Ser Ser Leu Val Ile Leu Gln Val Val Pro Phe
    690                 695                 700

Leu Val Leu Ser Val Gly Ala Asp Asn Ile Phe Ile Phe Val Leu Glu
705                 710                 715                 720

Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
            740                 745                 750

Ser Glu Ala Ile Cys Phe Phe Leu Gly Ala Leu Thr Pro Met Pro Ala
        755                 760                 765

Val Arg Thr Phe Ala Leu Thr Ser Gly Leu Ala Val Ile Leu Asp Phe
    770                 775                 780

Leu Leu Gln Met Ser Ala Phe Val Ala Leu Leu Ser Leu Asp Ser Lys
785                 790                 795                 800

Arg Gln Glu Ala Ser Arg Leu Asp Val Cys Cys Cys Val Lys Pro Gln
                805                 810                 815

Glu Leu Pro Pro Pro Gly Gln Gly Glu Gly Leu Leu Leu Gly Phe Phe
            820                 825                 830

Gln Lys Ala Tyr Ala Pro Phe Leu Leu His Trp Ile Thr Arg Gly Val
        835                 840                 845

Val Val Gly Ala Pro Val Tyr Phe Val Thr Thr Leu Gly Tyr Asn Phe
    850                 855                 860

Ser Ser Glu Ala Gly Met Asn Ala Ile Cys Ser Ser Ala Gly Cys Asn
865                 870                 875                 880

Asn Phe Ser Phe Thr Gln Lys Ile Gln Tyr Ala Thr Glu Phe Pro Glu
                885                 890                 895

Gln Ser Tyr Leu Ala Ile Pro Ala Ser Ser Trp Val Asp Asp Phe Ile
            900                 905                 910

Asp Trp Leu Thr Pro Ser Ser Cys Cys Arg Leu Tyr Ile Ser Gly Pro
        915                 920                 925

Asn Lys Asp Lys Phe Cys Pro Ser Thr Val Asn Ser Leu Asn Cys Leu
    930                 935                 940

Lys Asn Cys Met Ser Ile Thr Met Gly Ser Val Arg Pro Ser Val Glu
945                 950                 955                 960

Gln Phe His Lys Tyr Leu Pro Trp Phe Leu Asn Asp Arg Pro Asn Ile
                965                 970                 975

Lys Cys Pro Lys Gly Gly Leu Ala Ala Tyr Ser Thr Ser Val Asn Leu
            980                 985                 990

Thr Ser Asp Gly Gln Val Leu Ala  Ser Arg Phe Met Ala  Tyr His Lys
        995                 1000                 1005

Pro Leu  Lys Asn Ser Gln Asp  Tyr Thr Glu Ala Leu  Arg Ala Ala
    1010                 1015                 1020

Arg Glu  Leu Ala Ala Asn Ile  Thr Ala Asp Leu Arg  Lys Val Pro
    1025                 1030                 1035

Gly Thr  Asp Pro Ala Phe Glu  Val Phe Pro Tyr Thr  Ile Thr Asn
    1040                 1045                 1050

Val Phe  Tyr Glu Gln Tyr Leu  Thr Ile Leu Pro Glu  Gly Leu Phe
    1055                 1060                 1065

Met Leu  Ser Leu Cys Leu Val  Pro Thr Phe Ala Val  Ser Cys Leu
    1070                 1075                 1080
```

```
Leu Leu  Gly Leu Asp Leu Arg  Ser Gly Leu Leu Asn  Leu Leu Ser
    1085                 1090                 1095

Ile Val  Met Ile Leu Val Asp  Thr Val Gly Phe Met  Ala Leu Trp
    1100                 1105                 1110

Gly Ile  Ser Tyr Asn Ala Val  Ser Leu Ile Asn Leu  Val Ser Ala
    1115                 1120                 1125

Val Gly  Met Ser Val Glu Phe  Val Ser His Ile Thr  Arg Ser Phe
    1130                 1135                 1140

Ala Ile  Ser Thr Lys Pro Thr  Trp Leu Glu Arg Ala  Lys Glu Ala
    1145                 1150                 1155

Thr Ile  Ser Met Gly Ser Ala  Val Phe Ala Gly Val  Ala Met Thr
    1160                 1165                 1170

Asn Leu  Pro Gly Ile Leu Val  Leu Gly Leu Ala Lys  Ala Gln Leu
    1175                 1180                 1185

Ile Gln  Ile Phe Phe Phe Arg  Leu Asn Leu Leu Ile  Thr Leu Leu
    1190                 1195                 1200

Gly Leu  Leu His Gly Leu Val  Phe Leu Pro Val Ile  Leu Ser Tyr
    1205                 1210                 1215

Val Gly  Pro Asp Val Asn Pro  Ala Leu Ala Leu Glu  Gln Lys Arg
    1220                 1225                 1230

Ala Glu  Glu Ala Val Ala Ala  Val Met Val Ala Ser  Cys Pro Asn
    1235                 1240                 1245

His Pro  Ser Arg Val Ser Thr  Ala Asp Asn Ile Tyr  Val Asn His
    1250                 1255                 1260

Ser Phe  Glu Gly Ser Ile Lys  Gly Ala Gly Ala Ile  Ser Asn Phe
    1265                 1270                 1275

Leu Pro  Asn Asn Gly Arg Gln  Phe
    1280                 1285
```

<210> SEQ ID NO 44
<211> LENGTH: 1276
<212> TYPE: PRT
<213> ORGANISM: Felis catus

<400> SEQUENCE: 44

```
Met Thr Ala Arg Gly Pro Ala Leu Gly Leu Leu Leu Leu Leu Leu Cys
1               5                   10                  15

Pro Ala Gln Val Leu Ala Gln Ser Cys Ile Trp Tyr Gly Glu Cys Gly
            20                  25                  30

Ile Ala Ser Gly Asp Lys Arg Tyr Asn Cys Lys Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Asp Asn Val Ser Leu Cys Cys Asp Val Gln Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Val Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140

Gln Tyr Tyr Ile Gly Glu Ser Phe Ala Asn Ala Met Tyr Asn Ala Cys
145                 150                 155                 160
```

```
Arg Asp Val Glu Ala Pro Ser Ser Asn Asp Lys Ala Leu Gly Leu Leu
                165                 170                 175

Cys Gly Lys Asp Ala Glu Ala Cys Asn Ala Thr Asn Trp Ile Glu Tyr
            180                 185                 190

Met Phe Ser Lys Asp Asn Gly Gln Ala Pro Phe Thr Ile Thr Pro Ile
        195                 200                 205

Phe Ser Asp Leu Pro Thr His Gly Met Glu Pro Met Asn Asn Ala Thr
    210                 215                 220

Lys Gly Cys Asp Glu Ser Val Asp Glu Val Thr Gly Pro Cys Ser Cys
225                 230                 235                 240

Gln Asp Cys Ser Ile Val Cys Gly Pro Lys Pro Gln Pro Pro Pro Pro
                245                 250                 255

Pro Val Pro Trp Arg Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Leu Trp Cys Tyr Arg Lys Arg Tyr Phe Val Ser Glu Tyr Thr Pro
    290                 295                 300

Ile Asp Ser Asn Ile Ala Phe Ser Val Asn Ala Asn Asp Arg Gly Glu
305                 310                 315                 320

Ala Ser Cys Cys Asp Ala Leu Gly Ala Ala Phe Glu Gly Cys Leu Arg
                325                 330                 335

Arg Leu Phe Ser Gln Trp Gly Ser Phe Cys Val Arg Asn Pro Gly Pro
            340                 345                 350

Ile Ile Phe Phe Ser Leu Ala Phe Ile Ala Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Thr His Phe Gly
385                 390                 395                 400

Pro Phe Phe Arg Thr Glu Gln Leu Ile Ile Gln Ala Pro His Thr Ser
                405                 410                 415

Ala His Thr Tyr Gln Pro Tyr Pro Ser Gly Ser Asp Val Pro Phe Gly
            420                 425                 430

Pro Pro Leu Asp Leu Ala Ile Leu His Gln Val Leu Asp Leu Gln Thr
        435                 440                 445

Ala Ile Glu Asn Ile Thr Ala Ser Tyr Asn Asn Glu Thr Val Thr Leu
    450                 455                 460

Gln Asp Ile Cys Val Ala Pro Leu Ser Pro Tyr Asn Lys Asn Cys Thr
465                 470                 475                 480

Ile Leu Ser Val Leu Asn Tyr Phe Gln Asn Ser His Ser Met Leu Asp
                485                 490                 495

His Glu Ile Gly Asp Asp Phe Phe Val Tyr Ala Asp Tyr His Thr His
            500                 505                 510

Leu Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Arg
                565                 570                 575
```

-continued

```
Leu Gln Lys Ala His Val Trp Glu Lys Glu Phe Ile Asn Phe Val Lys
            580                 585                 590

Asn Tyr Lys Asn Pro Asn Leu Thr Ile Ser Phe Thr Thr Glu Arg Ser
        595                 600                 605

Ile Glu Asp Glu Leu Asn Arg Glu Ser Asn Gly Asp Ile Phe Thr Val
    610                 615                 620

Ile Ile Ser Tyr Ala Ile Met Phe Leu Tyr Ile Ser Ile Ala Leu Gly
625                 630                 635                 640

His Ile Lys Ser Cys Ser Arg Leu Leu Val Asp Ser Lys Ile Ser Leu
                645                 650                 655

Gly Ile Ala Gly Ile Leu Ile Val Leu Ser Ser Lys Ala Cys Ser Leu
            660                 665                 670

Gly Ile Phe Ser Tyr Val Gly Ile Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Thr Tyr Gln Arg Asp Glu Arg Leu His Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Ala Val Ala Phe Phe Leu Gly Ala Leu Ser
            740                 745                 750

Lys Met Pro Ala Val His Thr Phe Ser Leu Phe Ala Gly Met Ala Val
        755                 760                 765

Leu Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Val Leu Cys Cys
785                 790                 795                 800

Val Arg Gly Ser Glu Asp Gly Thr Ser Val Gln Ala Ser Glu Ser Cys
                805                 810                 815

Leu Phe Arg Leu Phe Lys His Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Val Ala Val Leu Asn Lys Val Glu Ile Gly Leu Asp Gln Ser Leu
    850                 855                 860

Ser Met Pro Asp Asp Ser Tyr Val Met Asp Tyr Phe Lys Ser Leu Lys
865                 870                 875                 880

Tyr Leu His Ala Gly Pro Pro Val Tyr Phe Val Leu Glu Glu Gly His
                885                 890                 895

Asp Tyr Thr Ser Leu Lys Gly Gln Asn Met Val Cys Gly Gly Met Gly
            900                 905                 910

Cys Asn Asn Asp Ser Leu Val Gln Gln Ile Phe Asn Ala Ala Gln Leu
        915                 920                 925

Asp Ser Tyr Thr Arg Ile Gly Phe Ala Pro Ser Ser Trp Ile Asp Asp
    930                 935                 940

Tyr Phe Asp Trp Val Lys Pro Gln Ser Ser Cys Cys Arg Val Tyr Asn
945                 950                 955                 960

Ser Thr Asp Arg Phe Cys Asn Ala Ser Val Val Asp Pro Ala Cys Ile
                965                 970                 975

Arg Cys Arg Pro Leu Thr Gln Glu Gly Lys Gln Arg Pro Gln Gly Gly
            980                 985                 990

Asp Phe Met Arg Phe Leu Pro Met  Phe Leu Ser Asp Asn  Pro Asn Pro
```

```
        995                 1000                1005

Lys Cys  Gly Lys Gly Gly His  Ala Ala Tyr Ser Ser  Ala Val Asn
    1010                 1015                 1020

Ile Leu  Gly Asn Asp Thr Gly  Val Gly Ala Thr Tyr  Phe Met Thr
    1025                 1030                 1035

Tyr His  Thr Val Leu Gln Thr  Ser Ala Asp Phe Thr  Asp Ala Met
    1040                 1045                 1050

Arg Lys  Ala Asn Leu Ile Ala  Ser Asn Ile Thr Lys  Thr Met Gly
    1055                 1060                 1065

Leu Glu  Gly Ser Asn Tyr Arg  Val Phe Pro Tyr Ser  Val Phe Tyr
    1070                 1075                 1080

Val Phe  Tyr Glu Gln Tyr Leu  Thr Ile Ile Asp Asp  Thr Ile Phe
    1085                 1090                 1095

Asn Leu  Ser Val Ser Leu Gly  Ala Ile Phe Leu Val  Thr Val Ile
    1100                 1105                 1110

Leu Leu  Gly Cys Asp Leu Trp  Ser Ala Val Ile Met  Cys Ile Thr
    1115                 1120                 1125

Ile Ala  Met Ile Leu Val Asn  Met Phe Gly Val Met  Trp Leu Trp
    1130                 1135                 1140

Gly Ile  Ser Leu Asn Ala Val  Ser Leu Val Asn Leu  Val Met Ser
    1145                 1150                 1155

Cys Gly  Ile Ser Val Glu Phe  Cys Ser His Ile Thr  Arg Ala Phe
    1160                 1165                 1170

Thr Val  Ser Met Lys Gly Ser  Arg Ala Gln Arg Ala  Glu Glu Ala
    1175                 1180                 1185

Leu Ala  His Met Gly Ser Ser  Val Phe Ser Gly Ile  Thr Leu Thr
    1190                 1195                 1200

Lys Phe  Gly Gly Ile Val Val  Leu Ala Phe Ala Lys  Ser Gln Ile
    1205                 1210                 1215

Phe Gln  Ile Phe Tyr Phe Arg  Met Tyr Leu Ala Met  Val Leu Leu
    1220                 1225                 1230

Gly Ala  Thr His Gly Leu Ile  Phe Leu Pro Val Leu  Leu Ser Tyr
    1235                 1240                 1245

Ile Gly  Pro Ser Ile Asn Lys  Ala Lys Ser Leu Ala  Thr Gln Glu
    1250                 1255                 1260

Gln Tyr  Lys Gly Thr Glu Arg  Glu Gln Leu Leu Asn  Phe
    1265                 1270                 1275


<210> SEQ ID NO 45
<211> LENGTH: 1277
<212> TYPE: PRT
<213> ORGANISM: Mus musculus

<400> SEQUENCE: 45

Met Gly Ala His His Pro Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Thr Gly Asp Lys Arg Tyr Asn Cys Lys Tyr Ser Gly Pro Pro
        35                  40                  45

Lys Pro Leu Pro Lys Asp Gly Tyr Asp Leu Val Gln Glu Leu Cys Pro
    50                  55                  60

Gly Leu Phe Phe Asp Asn Val Ser Leu Cys Cys Asp Ile Gln Gln Leu
65                  70                  75                  80
```

-continued

```
Gln Thr Leu Lys Ser Asn Leu Gln Leu Pro Leu Gln Phe Leu Ser Arg
                85                  90                  95

Cys Pro Ser Cys Phe Tyr Asn Leu Met Thr Leu Phe Cys Glu Leu Thr
            100                 105                 110

Cys Ser Pro His Gln Ser Gln Phe Leu Asn Val Thr Ala Thr Glu Asp
        115                 120                 125

Tyr Phe Asp Pro Lys Thr Gln Glu Asn Lys Thr Asn Val Lys Glu Leu
    130                 135                 140

Glu Tyr Phe Val Gly Gln Ser Phe Ala Asn Ala Met Tyr Asn Ala Cys
145                 150                 155                 160

Arg Asp Val Glu Ala Pro Ser Ser Asn Glu Lys Ala Leu Gly Leu Leu
                165                 170                 175

Cys Gly Arg Asp Ala Arg Ala Cys Asn Ala Thr Asn Trp Ile Glu Tyr
            180                 185                 190

Met Phe Asn Lys Asp Asn Gly Gln Ala Pro Phe Thr Ile Ile Pro Val
        195                 200                 205

Phe Ser Asp Leu Ser Ile Leu Gly Met Glu Pro Met Arg Asn Ala Thr
    210                 215                 220

Lys Gly Cys Asn Glu Ser Val Asp Glu Val Thr Gly Pro Cys Ser Cys
225                 230                 235                 240

Gln Asp Cys Ser Ile Val Cys Gly Pro Lys Pro Gln Pro Pro Pro Pro
                245                 250                 255

Pro Met Pro Trp Arg Ile Trp Gly Leu Asp Ala Met Tyr Val Ile Met
            260                 265                 270

Trp Val Thr Tyr Val Ala Phe Leu Phe Val Phe Phe Gly Ala Leu Leu
        275                 280                 285

Ala Val Trp Cys His Arg Arg Arg Tyr Phe Val Ser Glu Tyr Thr Pro
    290                 295                 300

Ile Asp Ser Asn Ile Ala Phe Ser Val Asn Ser Ser Asp Lys Gly Glu
305                 310                 315                 320

Ala Ser Cys Cys Asp Pro Leu Gly Ala Ala Phe Asp Asp Cys Leu Arg
                325                 330                 335

Arg Met Phe Thr Lys Trp Gly Ala Phe Cys Val Arg Asn Pro Thr Cys
            340                 345                 350

Ile Ile Phe Phe Ser Leu Ala Phe Ile Thr Val Cys Ser Ser Gly Leu
        355                 360                 365

Val Phe Val Gln Val Thr Thr Asn Pro Val Glu Leu Trp Ser Ala Pro
    370                 375                 380

His Ser Gln Ala Arg Leu Glu Lys Glu Tyr Phe Asp Lys His Phe Gly
385                 390                 395                 400

Pro Phe Phe Arg Thr Glu Gln Leu Ile Ile Gln Ala Pro Asn Thr Ser
                405                 410                 415

Val His Ile Tyr Glu Pro Tyr Pro Ala Gly Ala Asp Val Pro Phe Gly
            420                 425                 430

Pro Pro Leu Asn Lys Glu Ile Leu His Gln Val Leu Asp Leu Gln Ile
        435                 440                 445

Ala Ile Glu Ser Ile Thr Ala Ser Tyr Asn Asn Glu Thr Val Thr Leu
    450                 455                 460

Gln Asp Ile Cys Val Ala Pro Leu Ser Pro Tyr Asn Lys Asn Cys Thr
465                 470                 475                 480

Ile Met Ser Val Leu Asn Tyr Phe Gln Asn Ser His Ala Val Leu Asp
                485                 490                 495

Ser Gln Val Gly Asp Asp Phe Tyr Ile Tyr Ala Asp Tyr His Thr His
```

-continued

```
            500                 505                 510

Phe Leu Tyr Cys Val Arg Ala Pro Ala Ser Leu Asn Asp Thr Ser Leu
        515                 520                 525

Leu His Gly Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Arg
                565                 570                 575

Leu Gln Arg Ala Trp Ala Trp Glu Lys Glu Phe Ile Ser Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asn Ser Asp Val Phe Thr Val
    610                 615                 620

Ile Ile Ser Tyr Val Val Met Phe Leu Tyr Ile Ser Leu Ala Leu Gly
625                 630                 635                 640

His Ile Gln Ser Cys Ser Arg Leu Leu Val Asp Ser Lys Ile Ser Leu
                645                 650                 655

Gly Ile Ala Gly Ile Leu Ile Val Leu Ser Ser Val Ala Cys Ser Leu
            660                 665                 670

Gly Ile Phe Ser Tyr Met Gly Met Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Thr Tyr Gln Arg Asp Glu Arg Leu Gln Glu Glu Thr Leu
705                 710                 715                 720

Asp Gln Gln Leu Gly Arg Ile Leu Gly Glu Val Ala Pro Thr Met Phe
                725                 730                 735

Leu Ser Ser Phe Ser Glu Thr Ser Ala Phe Phe Phe Gly Ala Leu Ser
            740                 745                 750

Ser Met Pro Ala Val His Thr Phe Ser Leu Phe Ala Gly Met Ala Val
        755                 760                 765

Leu Ile Asp Phe Leu Leu Gln Ile Thr Cys Phe Val Ser Leu Leu Gly
    770                 775                 780

Leu Asp Ile Lys Arg Gln Glu Lys Asn His Leu Asp Ile Leu Cys Cys
785                 790                 795                 800

Val Arg Gly Ala Asp Asp Gly Gln Gly Ser His Ala Ser Glu Ser Tyr
                805                 810                 815

Leu Phe Arg Phe Phe Lys Asn Tyr Phe Ala Pro Leu Leu Leu Lys Asp
            820                 825                 830

Trp Leu Arg Pro Ile Val Val Ala Val Phe Val Gly Val Leu Ser Phe
        835                 840                 845

Ser Val Ala Val Val Asn Lys Val Asp Ile Gly Leu Asp Gln Ser Leu
    850                 855                 860

Ser Met Pro Asn Asp Ser Tyr Val Ile Asp Tyr Phe Lys Ser Leu Ala
865                 870                 875                 880

Gln Tyr Leu His Ser Gly Pro Pro Val Tyr Phe Val Leu Glu Glu Gly
                885                 890                 895

Tyr Asn Tyr Ser Ser Arg Lys Gly Gln Asn Met Val Cys Gly Gly Met
            900                 905                 910

Gly Cys Asp Asn Asp Ser Leu Val Gln Gln Ile Phe Asn Ala Ala Glu
        915                 920                 925
```

-continued

```
Leu Asp Thr Tyr Thr Arg Val Gly Phe Ala Pro Ser Ser Trp Ile Asp
    930                 935                 940

Asp Tyr Phe Asp Trp Val Ser Pro Gln Ser Ser Cys Cys Arg Leu Tyr
945                 950                 955                 960

Asn Val Thr His Gln Phe Cys Asn Ala Ser Val Met Asp Pro Thr Cys
                965                 970                 975

Val Arg Cys Arg Pro Leu Thr Pro Glu Gly Lys Gln Arg Pro Gln Gly
            980                 985                 990

Lys Glu Phe Met Lys Phe Leu Pro  Met Phe Leu Ser Asp  Asn Pro Asn
        995                 1000                 1005

Pro Lys  Cys Gly Lys Gly Gly  His Ala Ala Tyr Gly  Ser Ala Val
    1010                 1015                 1020

Asn Ile  Val Gly Asp Asp Thr  Tyr Ile Gly Ala Thr  Tyr Phe Met
    1025                 1030                 1035

Thr Tyr  His Thr Ile Leu Lys  Thr Ser Ala Asp Tyr  Thr Asp Ala
    1040                 1045                 1050

Met Lys  Lys Ala Arg Leu Ile  Ala Ser Asn Ile Thr  Glu Thr Met
    1055                 1060                 1065

Arg Ser  Lys Gly Ser Asp Tyr  Arg Val Phe Pro Tyr  Ser Val Phe
    1070                 1075                 1080

Tyr Val  Phe Tyr Glu Gln Tyr  Leu Thr Ile Ile Asp  Asp Thr Ile
    1085                 1090                 1095

Phe Asn  Leu Ser Val Ser Leu  Gly Ser Ile Phe Leu  Val Thr Leu
    1100                 1105                 1110

Val Val  Leu Gly Cys Glu Leu  Trp Ser Ala Val Ile  Met Cys Ile
    1115                 1120                 1125

Thr Ile  Ala Met Ile Leu Val  Asn Met Phe Gly Val  Met Trp Leu
    1130                 1135                 1140

Trp Gly  Ile Ser Leu Asn Ala  Val Ser Leu Val Asn  Leu Val Met
    1145                 1150                 1155

Ser Cys  Gly Ile Ser Val Glu  Phe Cys Ser His Ile  Thr Arg Ala
    1160                 1165                 1170

Phe Thr  Met Ser Thr Lys Gly  Ser Arg Val Ser Arg  Ala Glu Glu
    1175                 1180                 1185

Ala Leu  Ala His Met Gly Ser  Ser Val Phe Ser Gly  Ile Thr Leu
    1190                 1195                 1200

Thr Lys  Phe Gly Gly Ile Val  Val Leu Ala Phe Ala  Lys Ser Gln
    1205                 1210                 1215

Ile Phe  Glu Ile Phe Tyr Phe  Arg Met Tyr Leu Ala  Met Val Leu
    1220                 1225                 1230

Leu Gly  Ala Thr His Gly Leu  Ile Phe Leu Pro Val  Leu Leu Ser
    1235                 1240                 1245

Tyr Ile  Gly Pro Ser Val Asn  Lys Ala Lys Arg His  Thr Thr Tyr
    1250                 1255                 1260

Glu Arg  Tyr Arg Gly Thr Glu  Arg Lys Arg Leu Leu  Asn Phe
    1265                 1270                 1275


<210> SEQ ID NO 46
<211> LENGTH: 1277
<212> TYPE: PRT
<213> ORGANISM: Bos taurus

<400> SEQUENCE: 46

Met Ser Val Arg Gly Pro Ala Phe Gly Leu Leu Leu Leu Leu Phe Cys
```

-continued

```
1               5                   10                  15

Pro Ala Gln Val Phe Ser Gln Ser Cys Ile Trp Tyr Gly Glu Cys Gly
            20                  25                  30

Ile Ala Ser Gly Asp Lys Arg Tyr Asn Cys Arg Tyr Ser Gly Pro Pro
        35                  40                  45

Glu Pro Leu Pro Gln Asp Gly Tyr Asp Leu Val Gln Glu Leu Cys Pro
    50                  55                  60

Gly Phe Phe Phe Gly Asn Val Ser Leu Cys Cys Asp Val Gln Gln Leu
65                  70                  75                  80

His Thr Leu Lys Asp Asn Leu Gln Leu Pro Leu Gln Phe Leu Ser Arg
                85                  90                  95

Cys Pro Ser Cys Phe Tyr Asn Leu Val Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Ala Thr Asn Gln Thr Lys Thr Asn Val Lys Glu Leu
    130                 135                 140

Gln Tyr Tyr Val Gly Glu Ser Phe Ala Asn Ala Met Tyr Asn Ser Cys
145                 150                 155                 160

Arg Asp Val Glu Ala Pro Ser Ser Asn Glu Lys Ala Leu Gly Leu Leu
                165                 170                 175

Cys Gly Arg Glu Ala Ser Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Leu Pro Thr His Gly Met Glu Pro Met Asn Asn Ala Thr
    210                 215                 220

Lys Gly Cys Asp Glu Ser Val Asp Glu Val Thr Gly Pro Cys Ser Cys
225                 230                 235                 240

Gln Asp Cys Ser Ala Val Cys Gly Pro Lys Pro Gln Pro Pro Pro Pro
                245                 250                 255

Pro Val Pro Trp Arg Ile Leu Gly Leu Asp Ala Met Tyr Val Ile Met
            260                 265                 270

Trp Ser Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Phe Thr Pro
    290                 295                 300

Ile Asp Gly Asn Ile Pro Phe Ser Ile Asn Ala Ser Asp Lys Gly Gly
305                 310                 315                 320

Pro Thr Cys Cys Asp Pro Leu Gly Ala Ala Phe Glu Ala His Leu Arg
                325                 330                 335

Arg Leu Phe Glu Trp Trp Gly Ser Phe Cys Val Arg His Pro Gly Cys
            340                 345                 350

Val Val Phe Phe Ser Val Ala Phe Ile Ala Ala Cys Ser Ser Gly Leu
        355                 360                 365

Val Phe Ile Gln Val Thr Thr Asp Pro Val Asp Leu Trp Ser Ala Pro
    370                 375                 380

Gly Ser Gln Ala Arg Leu Glu Lys Glu Tyr Phe Asp Thr His Phe Gly
385                 390                 395                 400

Pro Phe Phe Arg Thr Glu Gln Leu Ile Ile Arg Ala Pro His Thr Pro
                405                 410                 415

Pro His Ile Tyr Glu Pro Tyr Pro Ser Gly Ala Asp Val Pro Phe Gly
            420                 425                 430
```

-continued

```
Pro Pro Leu Ala Val Asp Ile Leu His Gln Val Leu Asp Leu Gln Thr
        435                 440                 445

Ala Ile Glu Ser Ile Thr Ala Ser Tyr Asn Asn Glu Thr Val Thr Leu
    450                 455                 460

Arg Asp Ile Cys Val Ala Pro Leu Ser Pro Tyr Asn Gln Asn Cys Thr
465                 470                 475                 480

Ile Leu Ser Val Leu Asn Tyr Phe Gln Asn Ser His Ser Val Leu Asp
                485                 490                 495

His Gln Val Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Arg Glu Phe Ile Asn Phe Val Gln
            580                 585                 590

Asn Tyr Glu Asn Pro Asn Leu Thr Ile Ser Phe Lys Ala Glu Arg Ser
        595                 600                 605

Ile Glu Asp Glu Leu Asn Arg Glu Ser Asn Ser Asp Val Phe Thr Val
    610                 615                 620

Leu Ile Ser Tyr Gly Val Met Phe Leu Tyr Ile Ser Ile Ala Leu Gly
625                 630                 635                 640

His Ile Lys Ser Cys Arg Arg Leu Leu Val Asp Ser Lys Ile Ser Leu
                645                 650                 655

Gly Ile Ala Gly Val Leu Ile Val Leu Ser Ser Val Ala Cys Ser Leu
            660                 665                 670

Gly Ile Phe Ser Tyr Ile Gly Val Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Thr Tyr Gln Arg Asp Glu Arg Leu Gln Gly Glu Thr Leu
705                 710                 715                 720

Asp Gln Gln Val Gly Arg Val Leu Gly Glu Val Ala Pro Ser Met Phe
                725                 730                 735

Leu Ser Ser Phe Ala Glu Thr Val Ala Phe Phe Leu Gly Gly Leu Ser
            740                 745                 750

Val Met Pro Ala Val His Thr Phe Ser Leu Phe Ala Gly Met Ala Val
        755                 760                 765

Leu Ile Asp Phe Leu Leu Gln Ile Thr Cys Phe Val Ser Leu Leu Gly
    770                 775                 780

Leu Asp Ile Lys Arg Gln Glu Lys Asn Gln Leu Asp Val Leu Cys Cys
785                 790                 795                 800

Val Gly Gly Ala Ala Asp Asp Ala Gly Ile Gln Ala Ser Glu Ser Cys
                805                 810                 815

Leu Phe Arg Phe Phe Arg Asn Ser Tyr Ala Pro Leu Leu Leu Lys Asp
            820                 825                 830

Trp Met Arg Pro Leu Val Val Ala Val Phe Val Gly Val Leu Ser Phe
        835                 840                 845
```

-continued

```
Ser Ile Ala Val Leu Asn Lys Val Glu Ile Gly Leu Asp Gln Ser Leu
    850                 855                 860

Ser Met Pro Asp Asp Ser Tyr Val Thr Asp Tyr Phe Gln Ser Leu Asn
865                 870                 875                 880

Gln Tyr Leu His Ala Gly Pro Pro Val Tyr Phe Val Leu Glu Glu Gly
                885                 890                 895

His Asp Tyr Thr Ser Thr Lys Gly Gln Asn Met Val Cys Gly Gly Leu
            900                 905                 910

Gly Cys Asn Asn Asp Ser Leu Val Gln Gln Val Phe Thr Ala Ala Gln
        915                 920                 925

Leu Asp Ser Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Ile Tyr
945                 950                 955                 960

Asn Ser Thr Glu Gln Phe Cys Asn Ala Ser Val Val Asn Pro Thr Cys
                965                 970                 975

Val Arg Cys Arg Pro Leu Thr Pro Glu Gly Lys Gln Arg Pro Gln Gly
            980                 985                 990

Ala Asp Phe Met Arg Phe Leu Pro  Met Phe Leu Ser Asp  Asn Pro Asn
        995                 1000                1005

Pro Lys  Cys Gly Lys Gly Gly  His Ala Ala Tyr Ser  Ala Ala Val
    1010                1015                1020

Asn Ile  Leu Asp Asn Gly Thr  Arg Val Gly Ala Thr  Tyr Phe Met
    1025                1030                1035

Thr Tyr  His Thr Val Leu Gln  Thr Ser Ala Asp Phe  Ile Asp Ala
    1040                1045                1050

Met Glu  Lys Ala Arg Leu Ile  Ala Ser Asn Ile Thr  Arg Thr Met
    1055                1060                1065

Asn Gln  Gln Gly Gly Asp His  Arg Val Phe Pro Tyr  Ser Val Phe
    1070                1075                1080

Tyr Val  Phe Tyr Glu Gln Tyr  Leu Thr Met Ile Asp  Asp Thr Ile
    1085                1090                1095

Phe Asn  Leu Ser Val Ser Leu  Gly Ala Ile Phe Leu  Val Ala Val
    1100                1105                1110

Val Leu  Leu Gly Cys Glu Leu  Trp Ser Ala Val Ile  Met Cys Ala
    1115                1120                1125

Thr Ile  Ala Met Ile Leu Val  Asn Met Phe Gly Val  Met Trp Leu
    1130                1135                1140

Trp Gly  Ile Ser Leu Asn Ala  Val Ser Leu Val Asn  Leu Val Met
    1145                1150                1155

Ser Cys  Gly Ile Ser Val Glu  Phe Cys Ser His Ile  Thr Arg Ala
    1160                1165                1170

Phe Thr  Val Ser Thr Lys Gly  Ser Arg Val Glu Arg  Ala Glu Glu
    1175                1180                1185

Ala Leu  Ser His Met Gly Ser  Ser Val Phe Ser Gly  Ile Thr Leu
    1190                1195                1200

Thr Lys  Phe Gly Gly Ile Ile  Val Leu Ala Phe Ala  Lys Ser Gln
    1205                1210                1215

Ile Phe  Gln Ile Phe Tyr Phe  Arg Met Tyr Leu Ala  Met Val Leu
    1220                1225                1230

Leu Gly  Ala Thr His Gly Leu  Ile Phe Leu Pro Val  Leu Leu Ser
    1235                1240                1245

Tyr Ile  Gly Pro Ser Ile Asn  Lys Ala Lys Ser Leu  Thr Thr Gln
```

1250 1255 1260

Gln Arg Tyr Arg Gly Thr Glu Arg Glu Gln Leu Leu Asn Phe
1265 1270 1275

<210> SEQ ID NO 47
<211> LENGTH: 91
<212> TYPE: PRT
<213> ORGANISM: Danio rerio

<400> SEQUENCE: 47

Gly Glu Glu Ala Leu Ala His Met Gly Ser Ser Val Phe Ser Gly Ile
1 5 10 15

Thr Leu Thr Lys Phe Gly Gly Ile Leu Ile Leu Ala Leu Ser Lys Ser
20 25 30

Gln Ile Phe Gln Ile Phe Tyr Phe Arg Met Tyr Leu Ala Ile Val Leu
35 40 45

Leu Gly Ala Ala His Gly Leu Ile Phe Leu Pro Val Leu Leu Ser Tyr
50 55 60

Ala Gly Pro Ser Val Asn Lys Ala Lys Val Leu Ala Ala His Asn Arg
65 70 75 80

Phe Val Gly Thr Glu Arg Glu Arg Leu Ile Tyr
85 90

<210> SEQ ID NO 48
<211> LENGTH: 130
<212> TYPE: DNA
<213> ORGANISM: Artificial Sequence
<220> FEATURE:
<223> OTHER INFORMATION: Synthetic

<400> SEQUENCE: 48
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag 130

<210> SEQ ID NO 49
<211> LENGTH: 145
<212> TYPE: DNA
<213> ORGANISM: Artificial Sequence
<220> FEATURE:
<223> OTHER INFORMATION: Synthetic

<400> SEQUENCE: 49
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcct 145

<210> SEQ ID NO 50
<211> LENGTH: 59
<212> TYPE: DNA
<213> ORGANISM: Artificial Sequence
<220> FEATURE:
<223> OTHER INFORMATION: Synthetic

<400> SEQUENCE: 50
tgtagttaat gattaacccg ccatgctact tatctaccag ggtaatgggg atcctctag 59

<210> SEQ ID NO 51
<211> LENGTH: 230
<212> TYPE: DNA

-continued

<213> ORGANISM: Artificial Sequence
<220> FEATURE:
<223> OTHER INFORMATION: Synthetic

<400> SEQUENCE: 51
agagctccgg tgcccgtcag tgggcagagc gcacatcgcc cacagtcccc gagaagttgg 60
ggggaggggt cggcaattga accggtgcct agagaaggtg gcgcggggta aactgggaaa 120
gtgatgtcgt gtactggctc cgcctttttc ccgagggtgg gggagaaccg tatataagtg 180
cagtagtcgc cgtgaacgtt ctttttcgca acgggtttgc cgccagaaca 230

<210> SEQ ID NO 52
<211> LENGTH: 231
<212> TYPE: DNA
<213> ORGANISM: Artificial Sequence
<220> FEATURE:
<223> OTHER INFORMATION: Synthetic

<400> SEQUENCE: 52
ggctccggtg cccgtcagtg ggcagagcgc acatcgccca cagtccccga gaagttgggg 60
ggaggggtcg gcaattgaac cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca g 231